(12) United States Patent
Zhang et al.

(10) Patent No.: US 11,680,256 B2
(45) Date of Patent: Jun. 20, 2023

(54) METHODS FOR TERPENOID PRODUCTION

(71) Applicants: AGENCY FOR SCIENCE, TECHNOLOGY AND RESEARCH, Singapore (SG); JUSTUS-LIEBIG-UNIVERSITAET GIESSEN, Giessen (DE)

(72) Inventors: Congqiang Zhang, Singapore (SG); Xixian Chen, Singapore (SG); Ruehl Martin, Giessen (DE); Heng-Phon Too, Singapore (SG)

(73) Assignees: AGENCY FOR SCIENCE, TECHNOLOGY AND RESEARCH, Singapore (SG); JUSTUS-LIEBIG-UNIVERSITAET GIESSEN, Giessen (DE)

(*) Notice: Subject to any disclaimer, the term of this patent is extended or adjusted under 35 U.S.C. 154(b) by 0 days.

(21) Appl. No.: 17/272,375

(22) PCT Filed: Sep. 2, 2019

(86) PCT No.: PCT/SG2019/050438
§ 371 (c)(1),
(2) Date: Mar. 1, 2021

(87) PCT Pub. No.: WO2020/046215
PCT Pub. Date: Mar. 5, 2020

(65) Prior Publication Data
US 2021/0332345 A1 Oct. 28, 2021

(30) Foreign Application Priority Data
Aug. 31, 2018 (SG) .............................. 10201807514P

(51) Int. Cl.
C12N 9/88 (2006.01)
C12N 9/10 (2006.01)
C12N 9/90 (2006.01)
C12P 5/00 (2006.01)
C12N 1/21 (2006.01)

(52) U.S. Cl.
CPC ............. *C12N 9/88* (2013.01); *C12N 9/1022* (2013.01); *C12N 9/90* (2013.01); *C12P 5/002* (2013.01); *C12Y 202/01007* (2013.01); *C12Y 503/03002* (2013.01)

(58) Field of Classification Search
None
See application file for complete search history.

(56) References Cited

U.S. PATENT DOCUMENTS

| | | | |
|---|---|---|---|
| 6,806,076 B1 | 10/2004 | Miyake et al. | |
| 2013/0102038 A1* | 4/2013 | Schalk | C12N 15/8243 435/127 |
| 2013/0276166 A1* | 10/2013 | Hugueney | C12N 9/1022 800/278 |

FOREIGN PATENT DOCUMENTS

| | | |
|---|---|---|
| CN | 105154423 A | 12/2015 |
| WO | WO-2018/094110 A2 | 5/2018 |

OTHER PUBLICATIONS

Banerjee et al., Engineering of Recombinant Poplar Deoxy-Xylulose-5-Phosphate Synthase (PtDXS) by Site-Directed Mutagenesis Improves Its Activity, PLoS One 11(8), 2016, e016153. (Year: 2016).*
Peralta-Yahya et al., Identification and microbial production of a terpene-based advanced biofuel, Nature Comm., Feb. 2011, 483. (Year: 2011).*
Genbank, Accession No. WP_113654933, 2018, www.ncbi.nlm.nih.gov. (Year: 2018).*
Wawrzyn et al., Discovery and Characterization of Terpenoid Biosynthetic Pathways of Fungi, Methods Enz. 515, 2012, 83-105. (Year: 2012).*
Uniprot, Accession No. A0A0D2NH86, 2017, www.uniprot.org. (Year: 2017).*
Al-Salihi et al., Improved vectors for Agrobacterium mediated genetic manipulation of *Hypholoma* spp. and other homobasidiomycetes, J. Microbiol. Methods 142, Apr. 9, 2017. (Year: 2017).*
Ajikumar et al., Isoprenoid pathway optimization fortaxol precursor overproduction in *Escherichia coli*, Science 330, 2010, 70-74. (Year: 2010).*
Novagen, pET System Manual, 1999. (Year: 1999).*
Wang et al., Transcriptome and Proteome Exploration to Provide a Resource for the Study of Agrocybe aegerita, PLoS One, Aug. 2013, e56686. (Year: 2013).*
Brehert et al., Monoterpenes in the Aromas of Fresh Wild Mushrooms, J. Agric. Food Chem. 45, 1997, 831-836. (Year: 1997).*
Gupta et al., The genome sequence of the commercially cultivated mushroom Agrocybe aegerita reveals a conserved repertoire of fruiting related genes and a versatile suite of biopolymer-degrading enzymes, GMC Genomics 19, 2018, 48. (Year: 2018).*
Genbank, Accession No. CAA7271863, 2020, www.ncbi.nlm.nih.gov. (Year: 2020).*
Agger et al., "Diversity of Sesquiterpene Synthases in the Basidiomycete *Coprinus cinereus*", Mol Microbiol, vol. 72, No. 5, May 7, 2009, pp. 1181-1195.
Engels et al., "Cloning and Characterization of an *Armillaria gallica* cDNA Encoding Protoilludene Synthase, Which Catalyzes the First Committed Step in the Synthesis of Antimicrobial Melleolides", J Biol Chem, vol. 286, No. 9, Mar. 4, 2011, pp. 6871-6878.
Quin et al., "Mushroom Hunting Using Bioinformatics: Application of a Predictive Framework Facilitates the Selective Identification of Sesquiterpene Synthases in Basidiomycota", Chembiochem, vol. 14, No. 18, Oct. 24, 2013, pp. 2480-2491.

(Continued)

*Primary Examiner* — Robert B Mondesi
*Assistant Examiner* — Todd M Epstein
(74) *Attorney, Agent, or Firm* — Marshall, Gerstein & Borun LLP

(57) ABSTRACT

A bacterial strain comprising one or more vectors encoding a) one or more enzymes to produce one or more terpene precursors; and b) a fungal terpene synthase (FTPS). The present invention also relates to a method of producing a terpenoid comprising a) culturing the bacterial strain described herein in an expression medium; and b) isolating the terpenoid from said expression medium.

20 Claims, 76 Drawing Sheets
Specification includes a Sequence Listing.

(56) References Cited

OTHER PUBLICATIONS

Shaw et al., "Identification of a Fungal 1,8-cineole Synthase from *Hypoxylon* sp. with Common Specificity Determinants to the Plant Synthases", J Biol Chem, vol. 290, No. 13, Mar. 27, 2015, pp. 8511-8526.
Martin et al., "Engineering a Mevalonate Pathway in *Escherichia coli* for Production of Terpenoids", Nat Biotechnol, vol. 21, No. 7, Jun. 1, 2003, pp. 796-802.
Quin et al., "Traversing the Fungal Terpenome", Nat Prod Rep, vol. 31, No. 10, Aug. 29, 2014, pp. 1449-1473.
Wang et al., "Transcriptome and Proteome Exploration to Provide a Resource for the Study of *Agrocybe aegerita*", PLOS One, vol. 8, No. 2, Feb. 13, 2013, 20 pages.
Search Report and Written Opinion in International Application No. PCT/SG2019/050438 dated Nov. 11, 2019, 14 pages.

\* cited by examiner

FIG. 1 (cont'd)

| No. | Compound | $RI^{exp}$ | $RI^{lit}$ |
|---|---|---|---|
| 1 | trans-.beta.-Ocimene | 1231 | 1232 |
| 2 | alpha-Cubebene | 1453 | 1455 |
| 3 | Delta(6)-protoilludene | 1496 | |
| 4 | α-Isocomene | 1516 | 1511 |
| 5 | β-Cubebene | 1531 | 1531 |
| 6 | Longifolene | 1568 | 1562 |
| 7 | β-Copaene | 1581 | 1585 |
| 8 | Caryophyllene | 1585 | 1587 |
| 9 | Cadina-3,5-diene | 1621 | 1626 |
| 10 | α-Humulene | 1657 | 1653 |
| 11 | γ-Muurolene | 1679 | 1679 |
| 12 | Germacrene D | 1696 | 1694 |
| 13 | β-Selinene | 1705 | 1705 |
| 14 | α-Selinene | 1711 | 1713 |
| 15 | α-Muurolene | 1714 | 1715 |
| 16 | δ-Cadinene | 1747 | 1742 |
| 17 | Cubenene | 1770 | 1773 |
| 18 | Calamenene | 1819 | 1822 |
| 19 | Epicubenol | 2039 | 2035 |
| 20 | Cubenol | 2046 | 2043 |

| Abbreviations | Sequences |
|---|---|
| S0 | Wild type |
| SL3 | H105T |
| SL5 | E210D / Q459L/ L415T |

FIG. 5
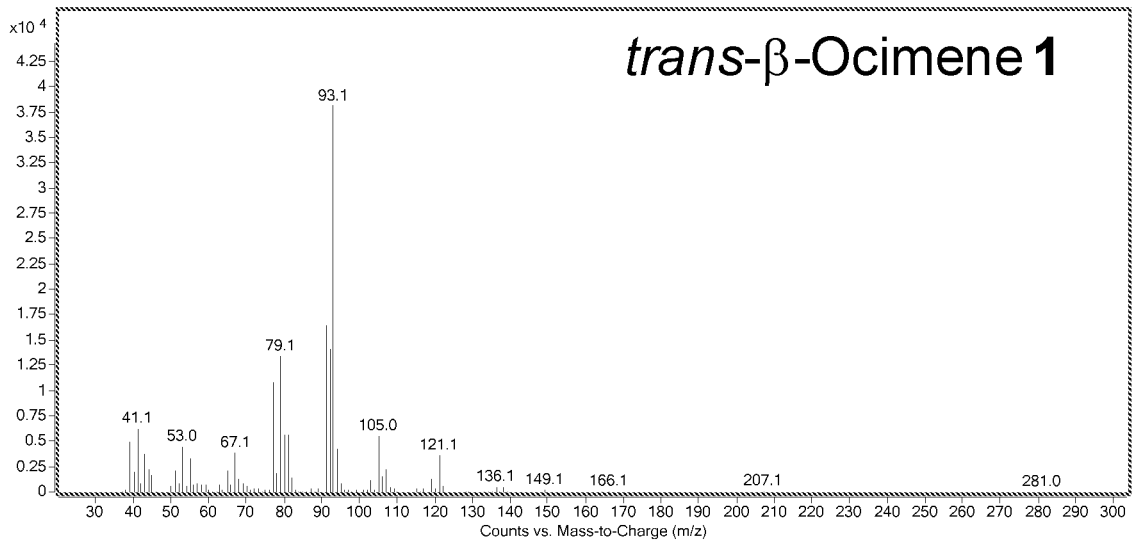
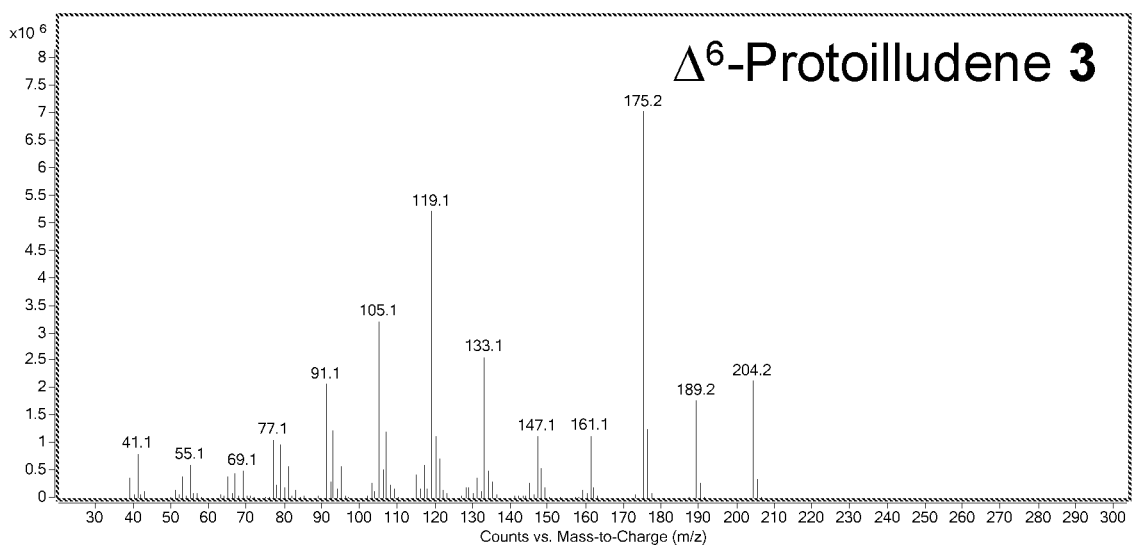
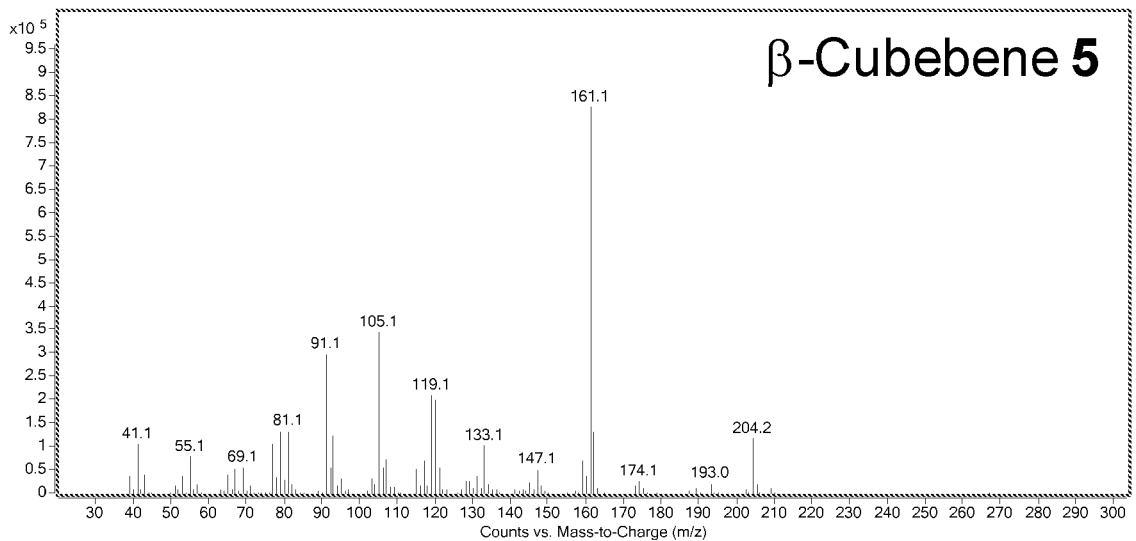

FIG. 5 (cont'd)
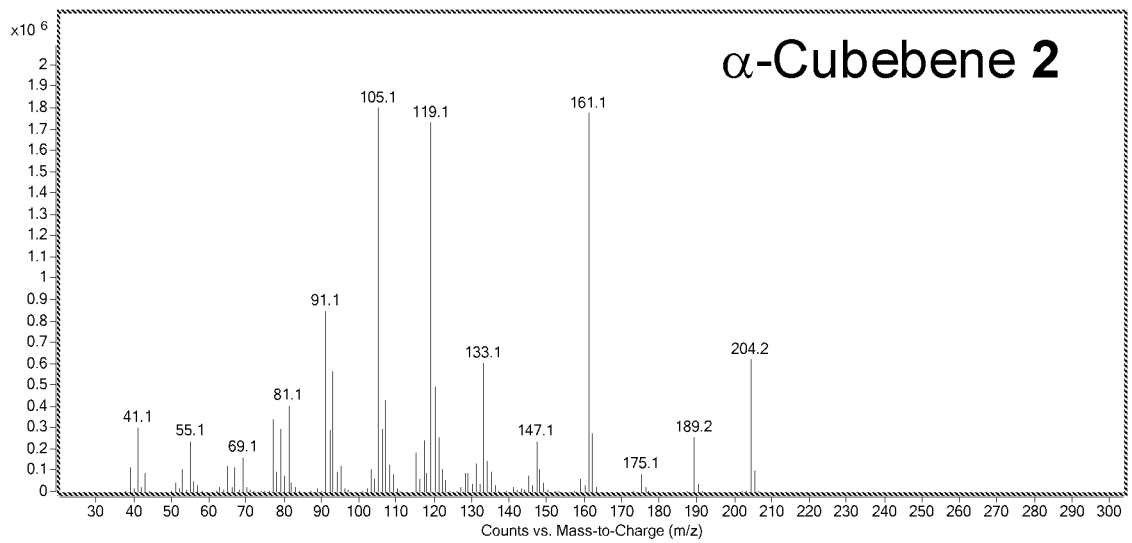
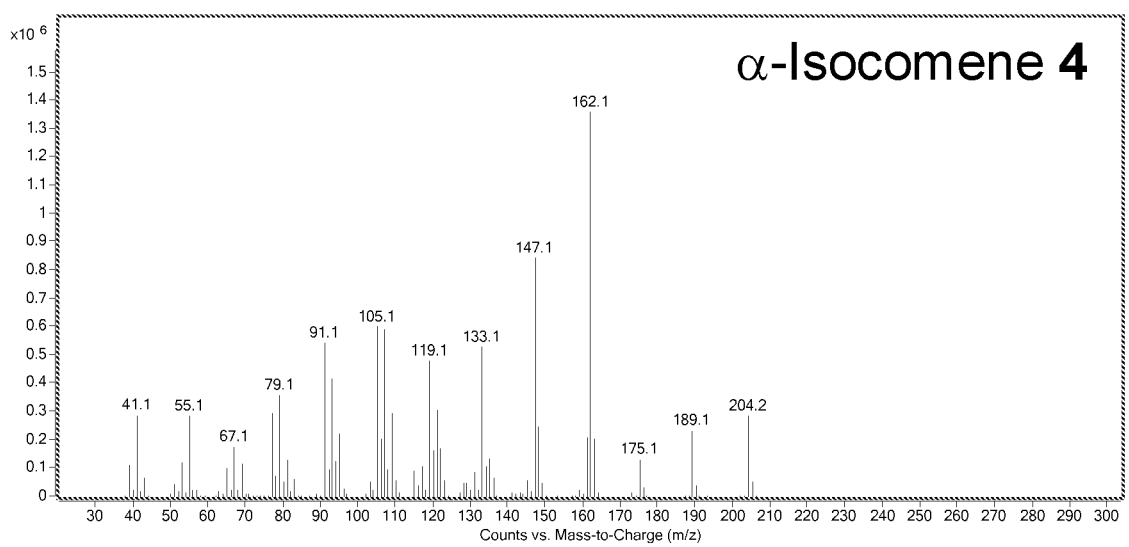
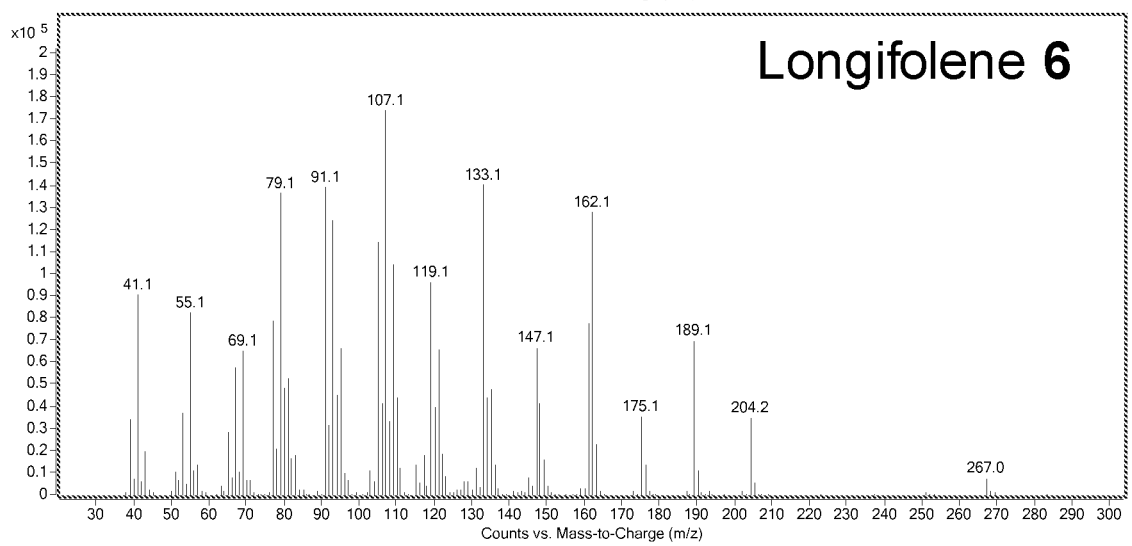

FIG. 5 (cont'd)
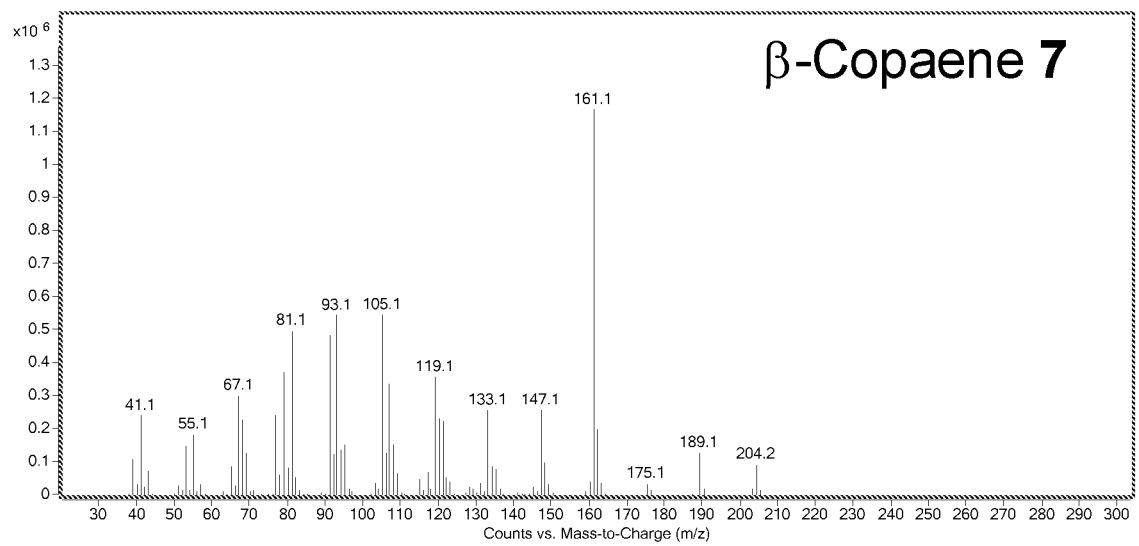
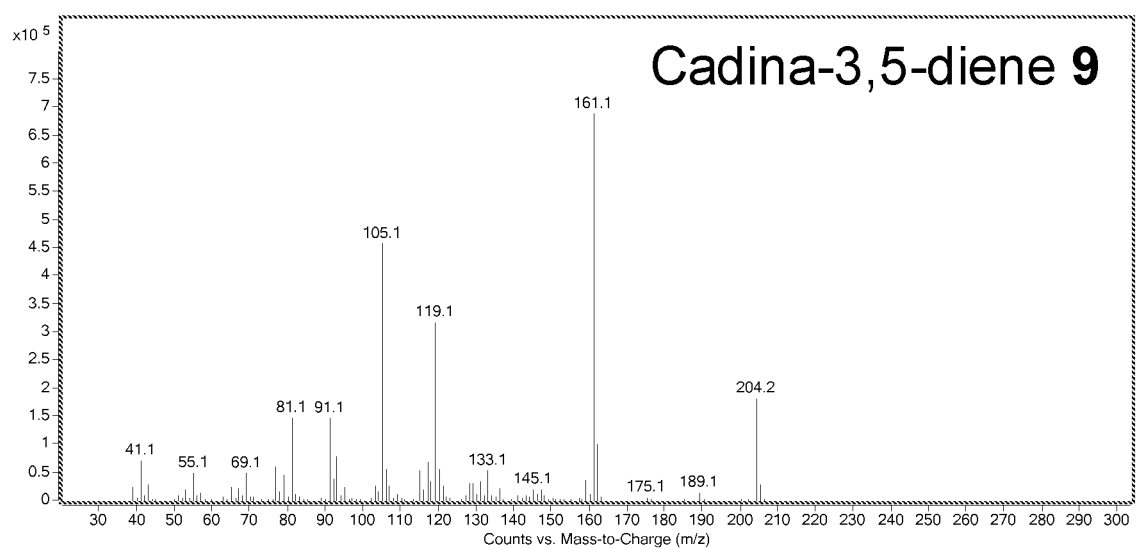
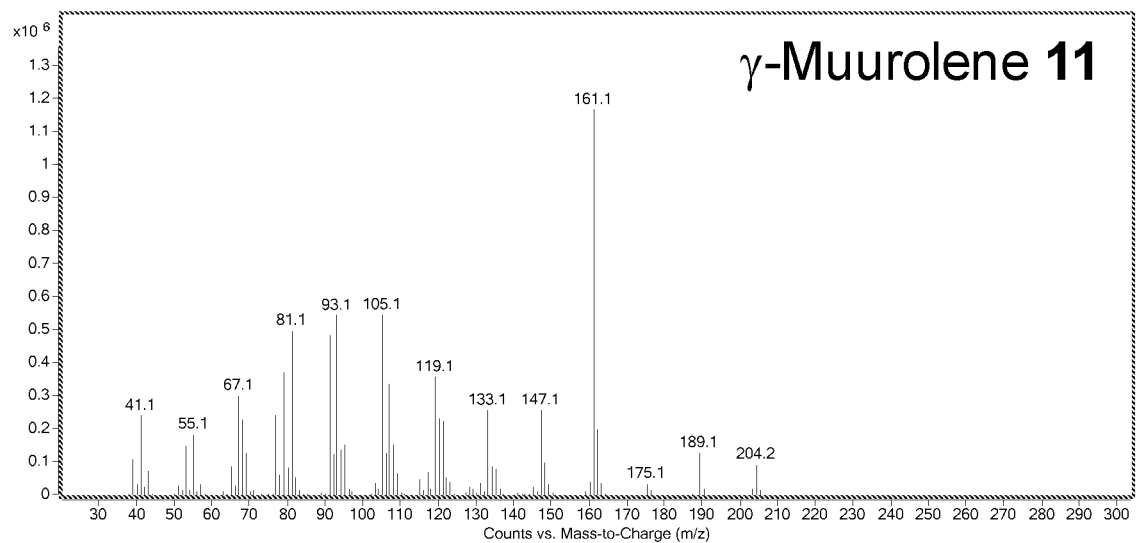

FIG. 5 (cont'd)
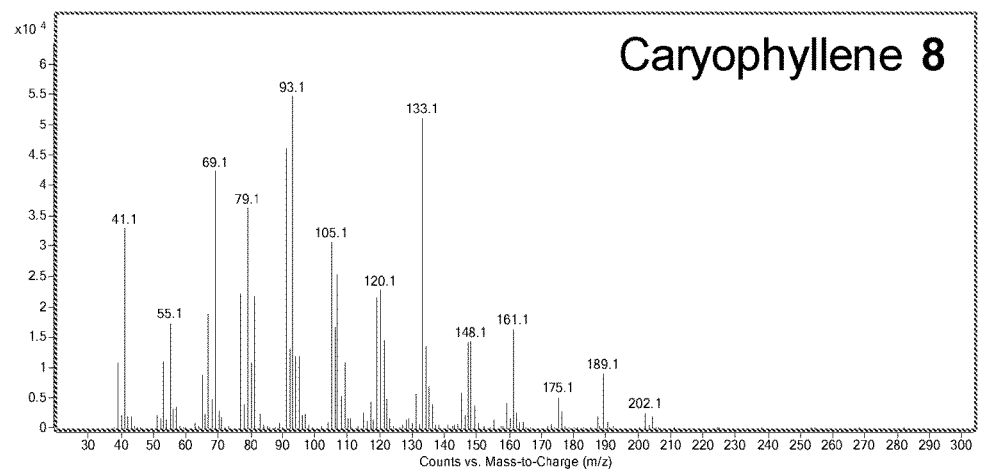
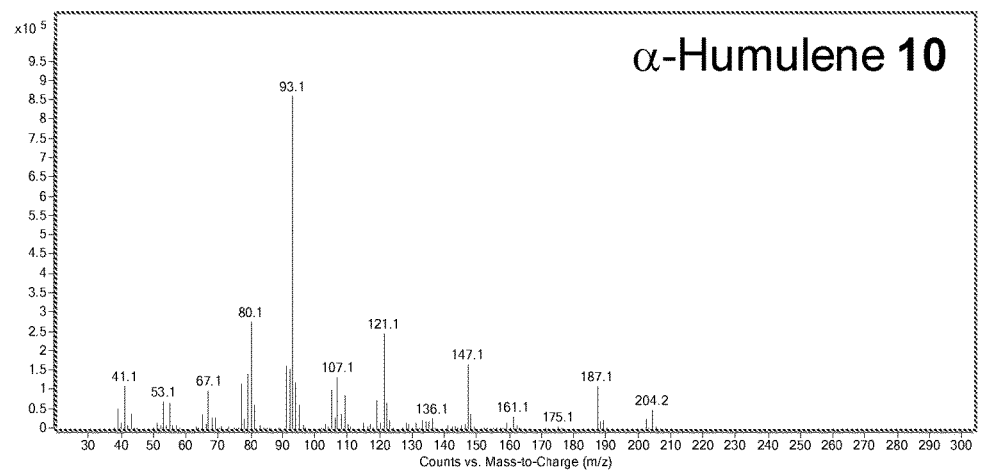
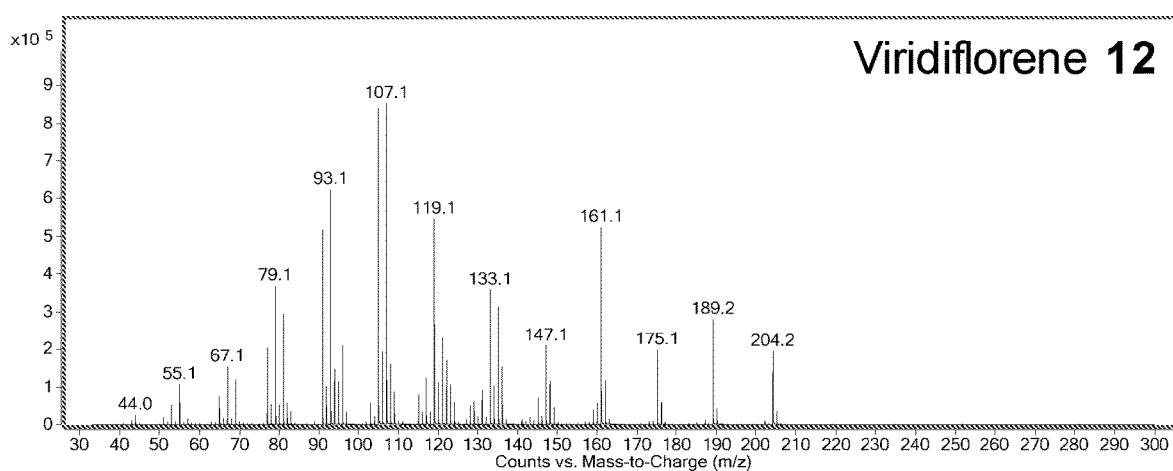

FIG. 5 (cont'd)
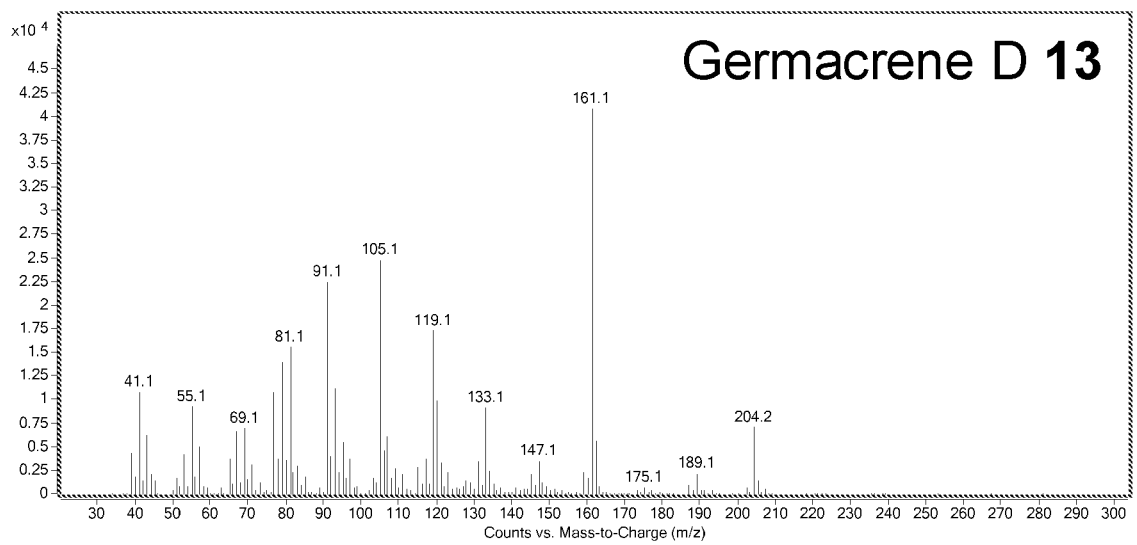
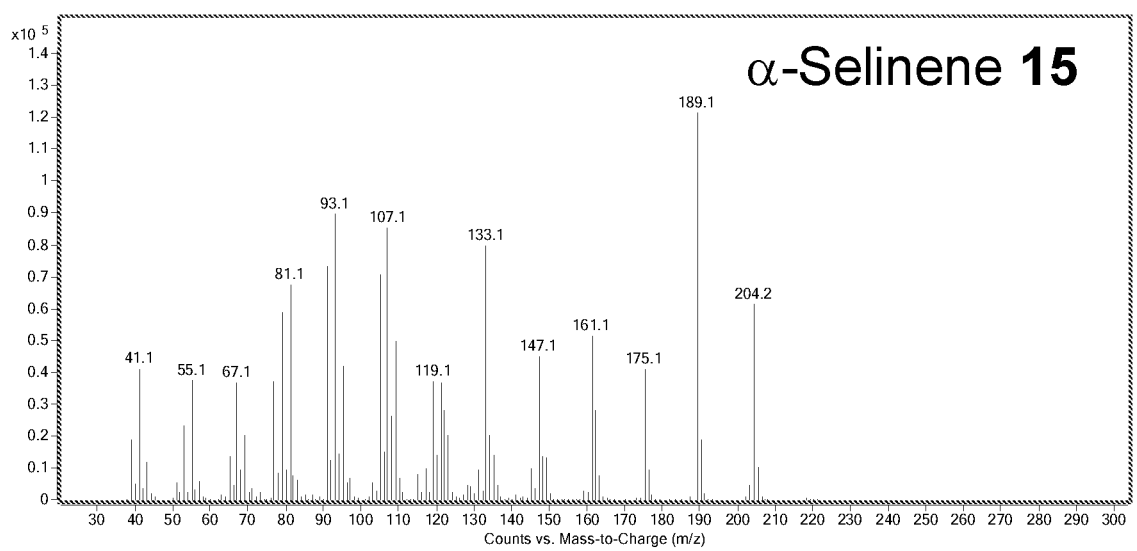
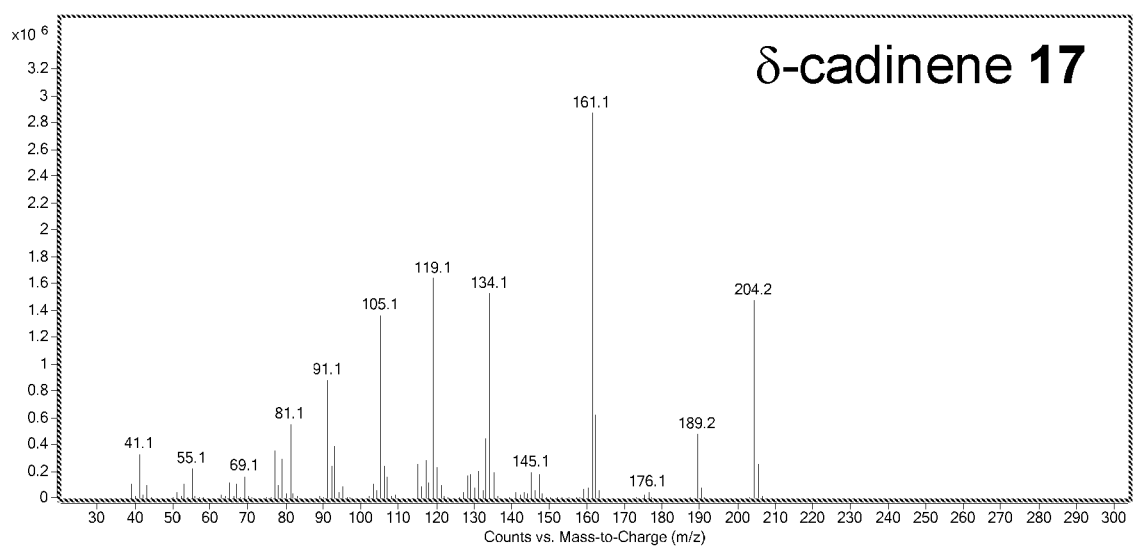

FIG. 5 (cont'd)
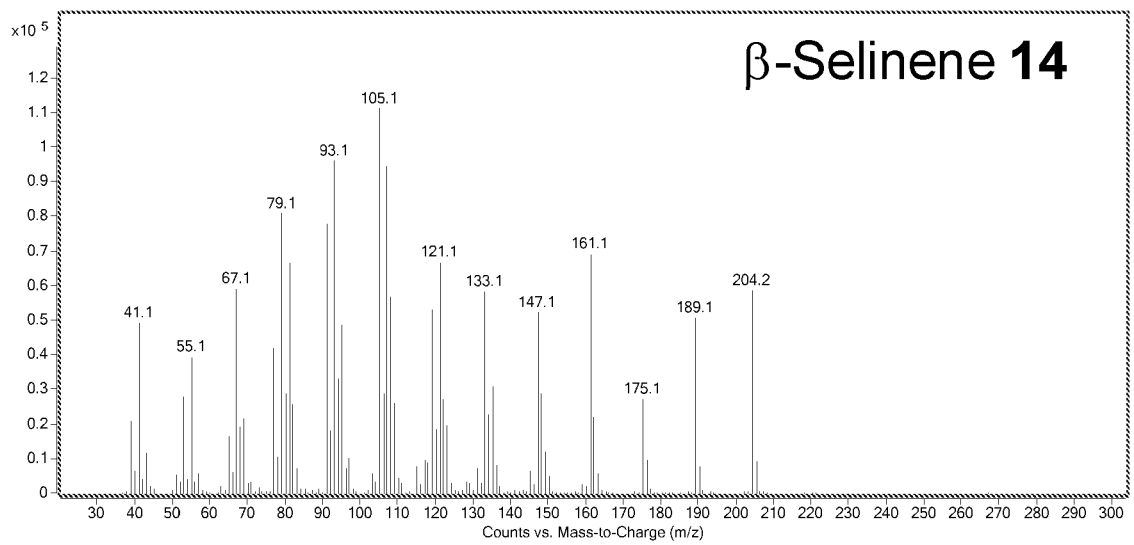
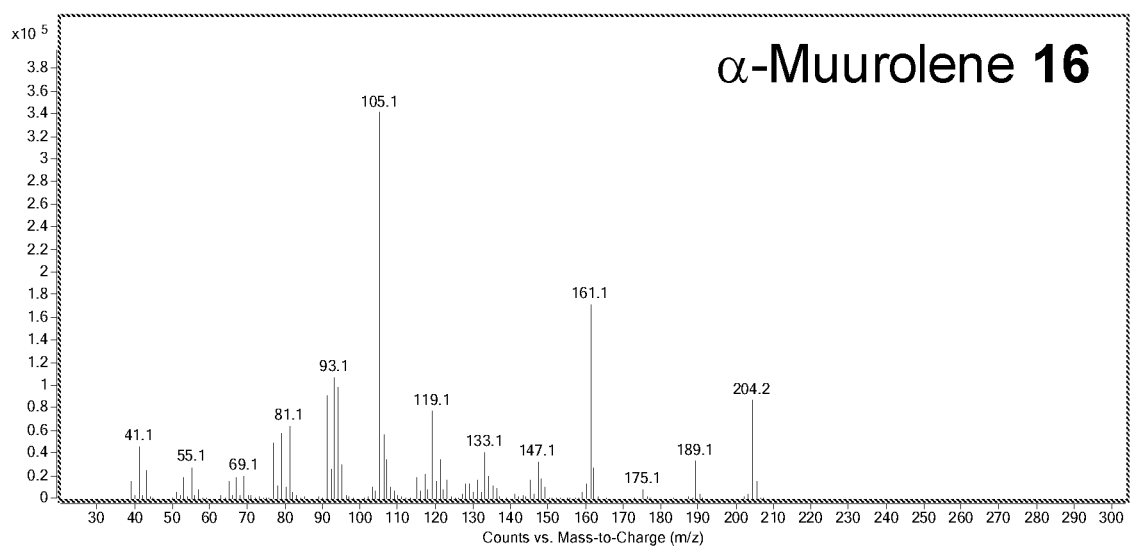
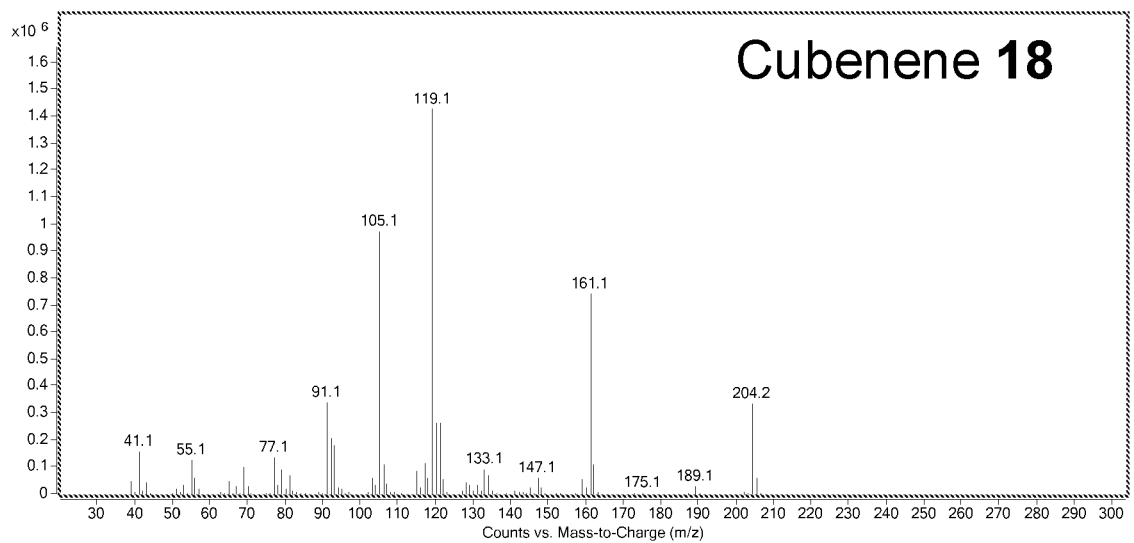

FIG. 5 (cont'd)
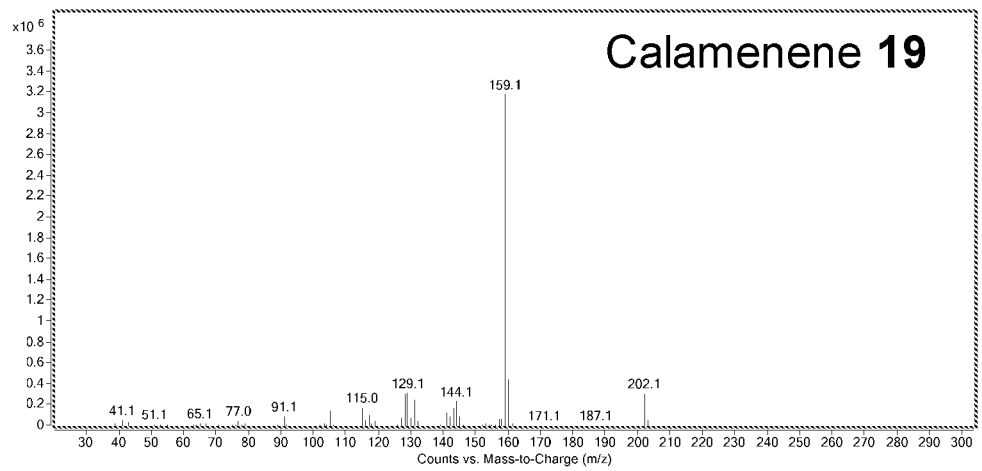
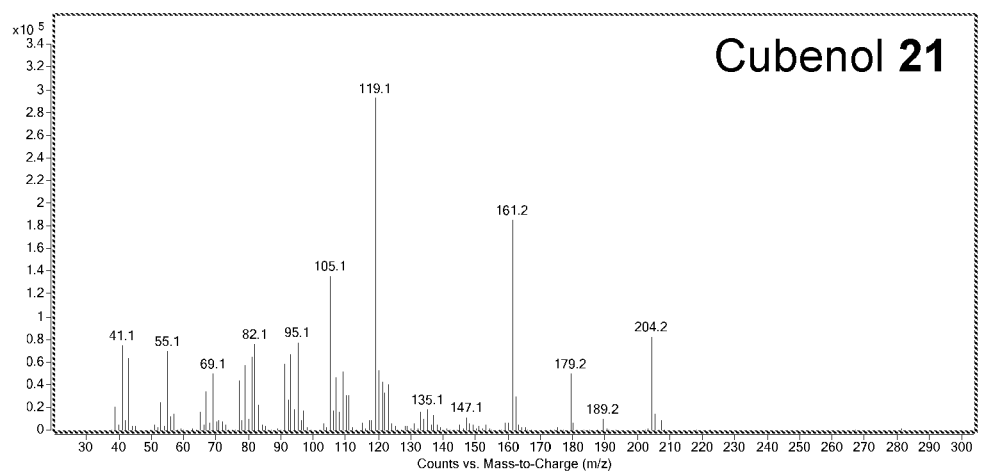
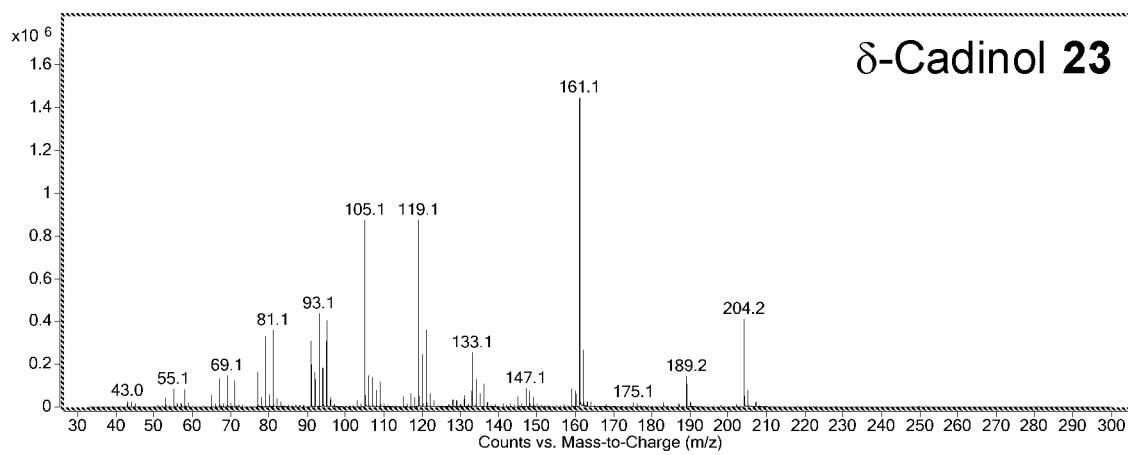

FIG. 5 (cont'd)
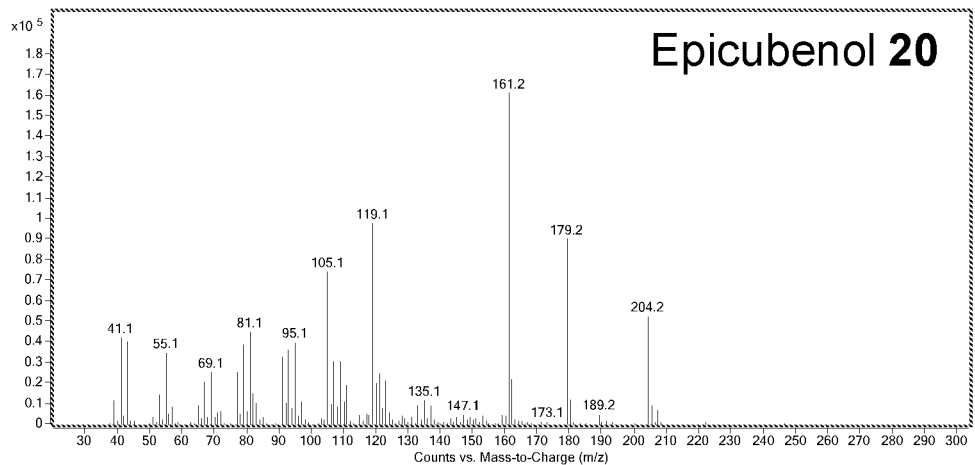
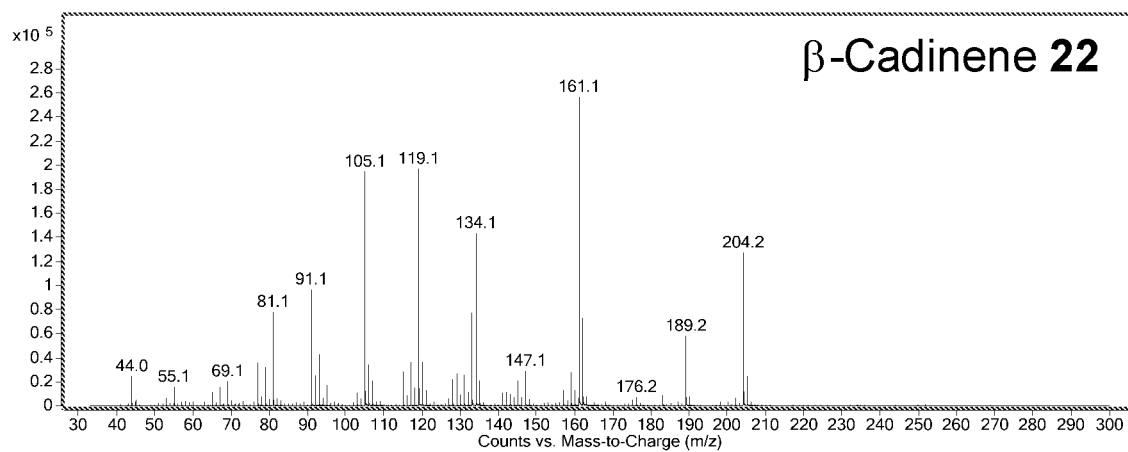
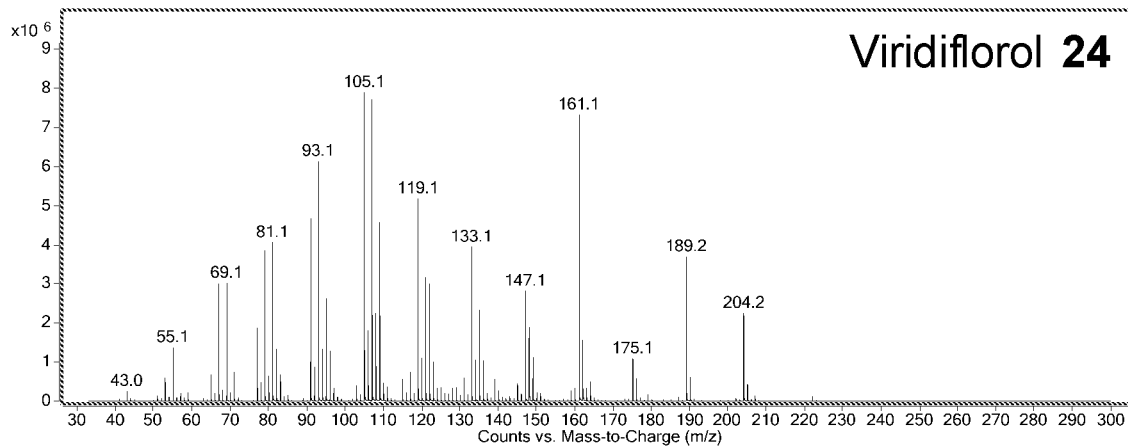

FIG. 5 (cont'd)
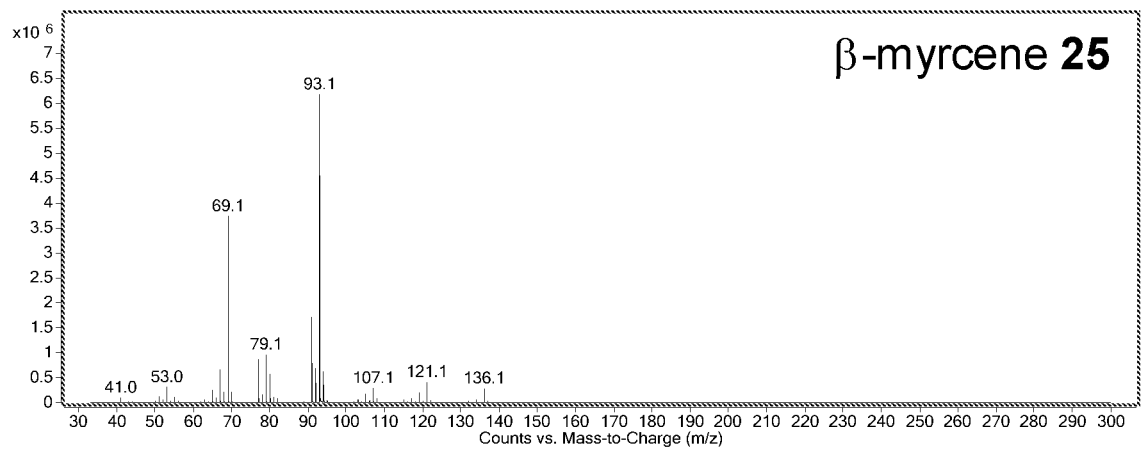
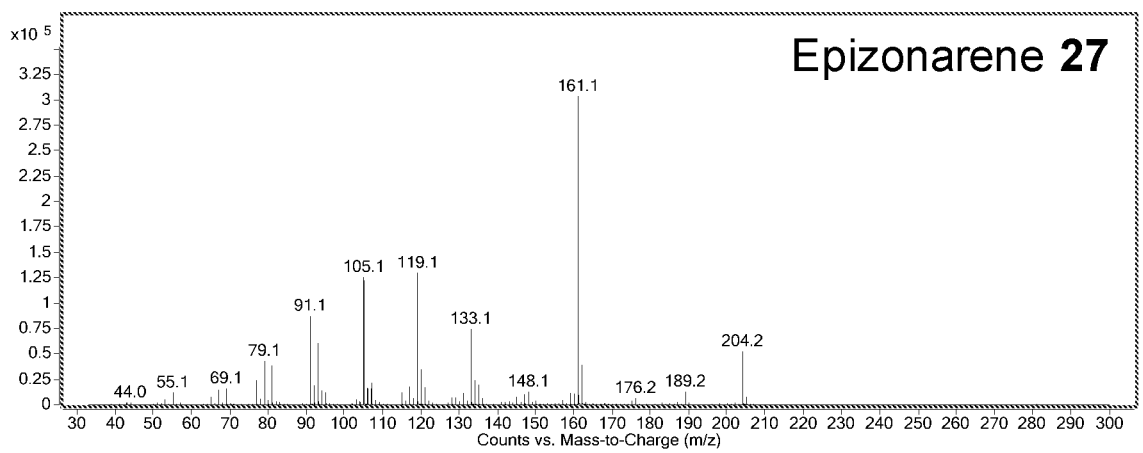
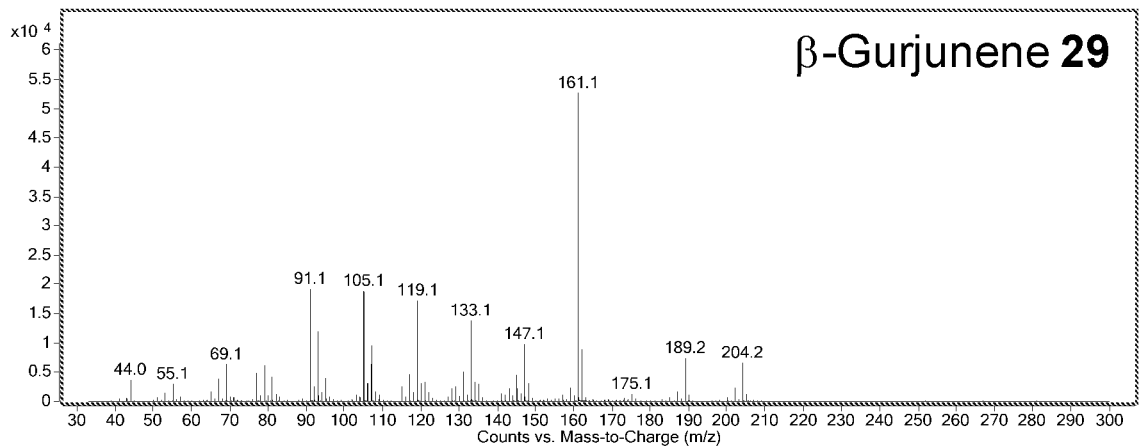

FIG. 5 (cont'd)
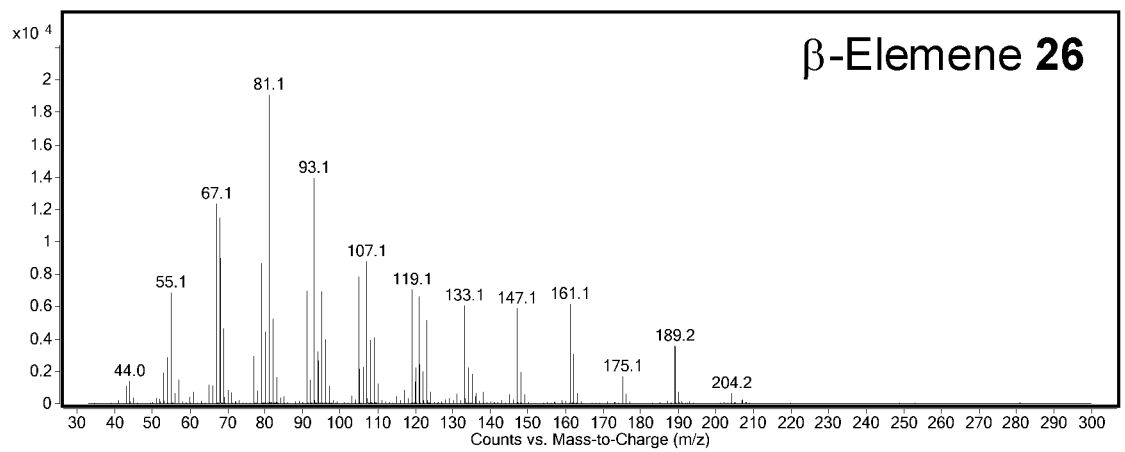
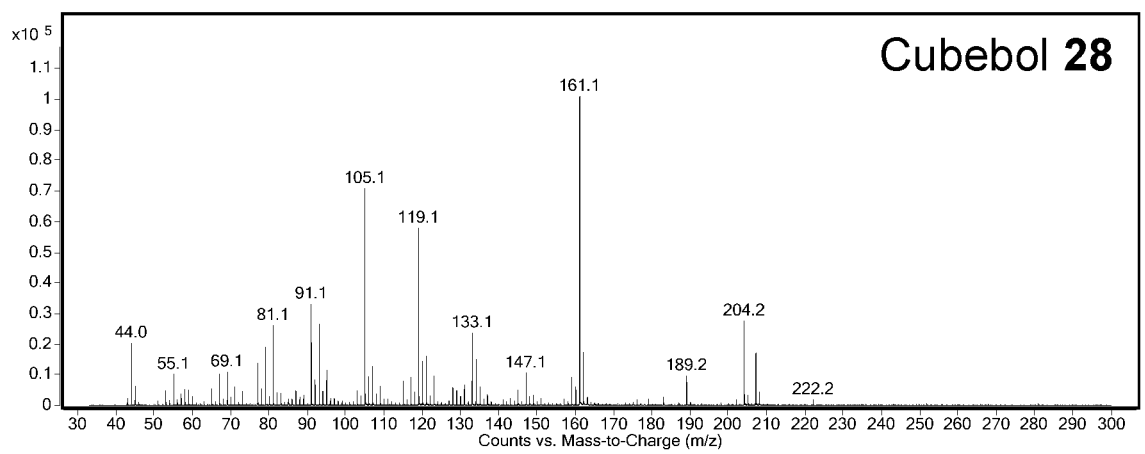
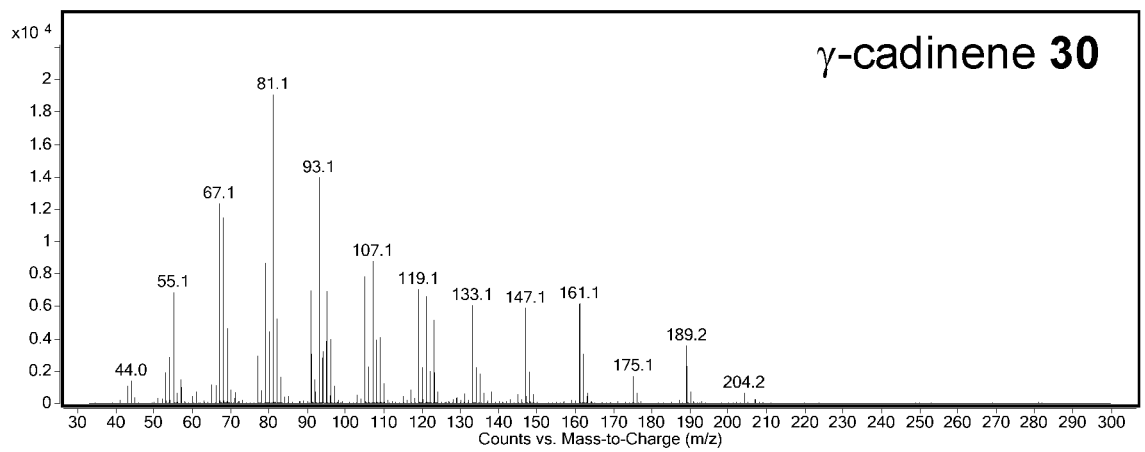

FIG. 5 (cont'd)
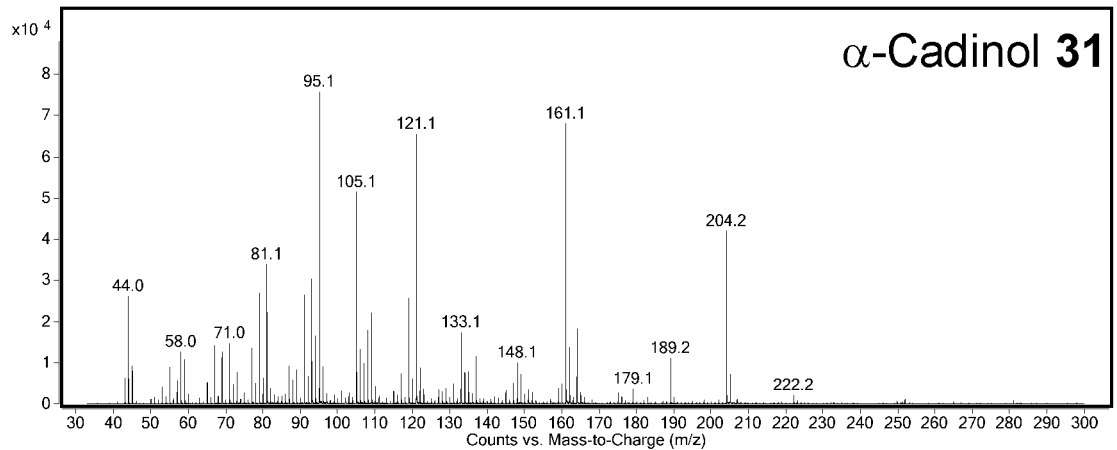
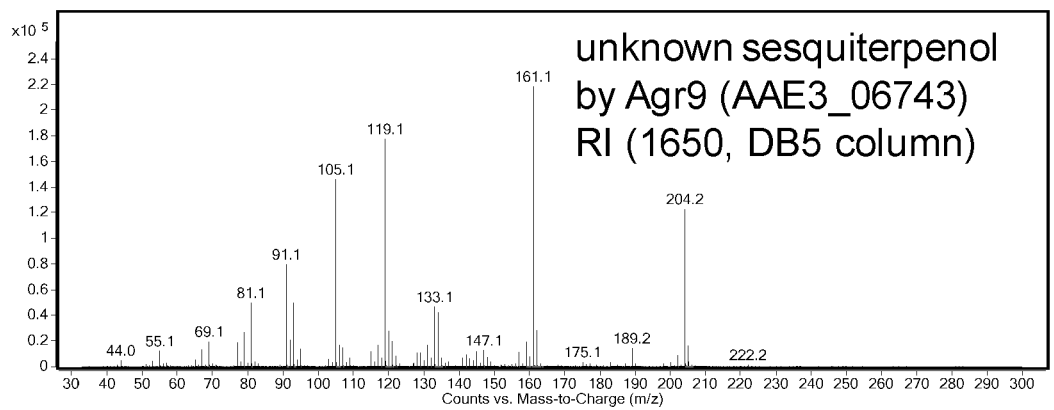
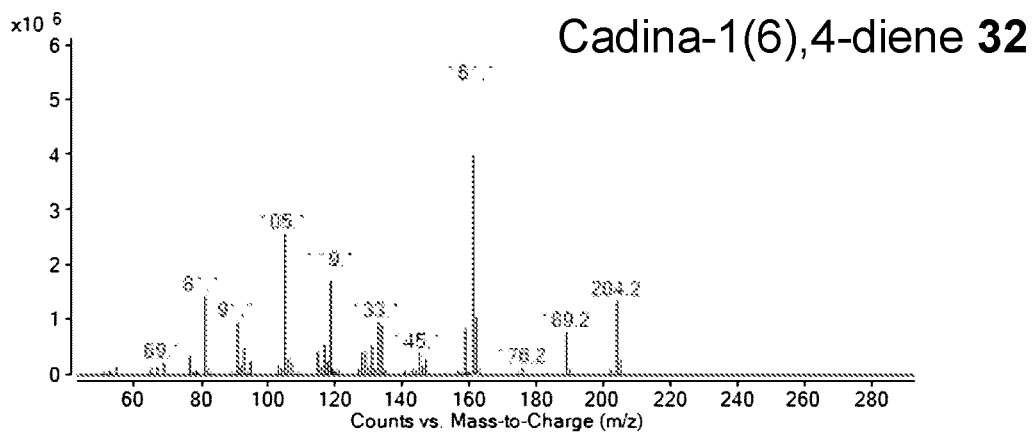

FIG. 10 (cont'd)
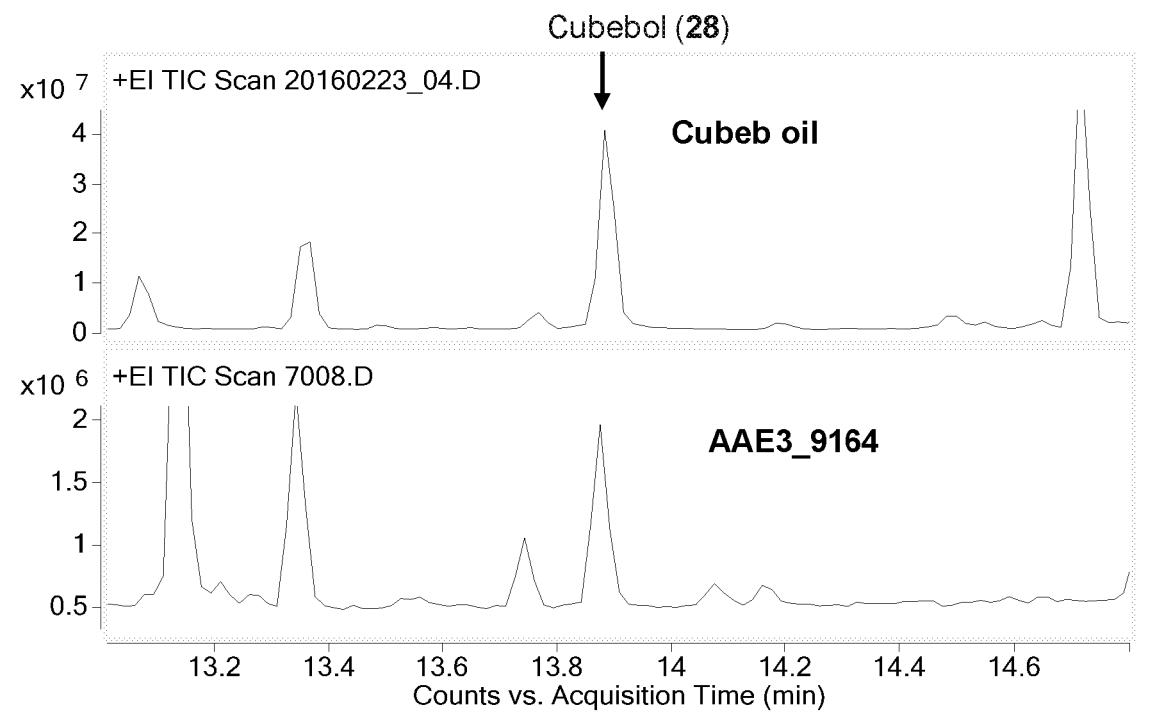
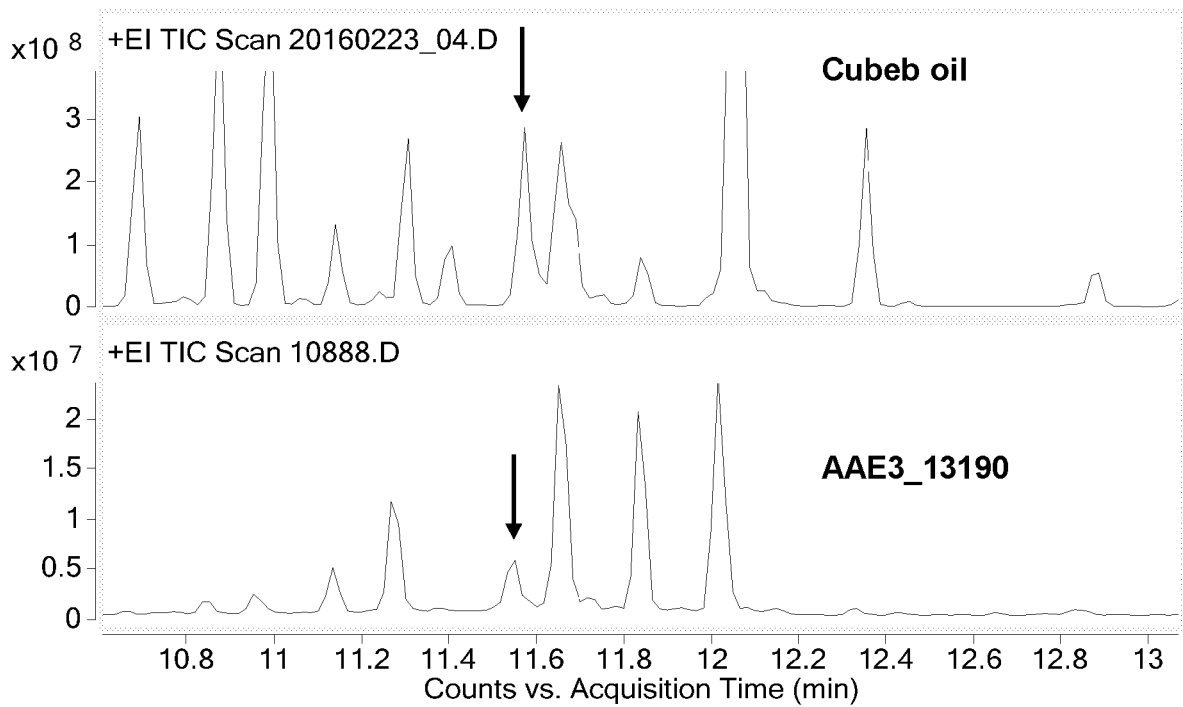

FIG. 15

```
SEQ ID NO: 75 TPS31       1   MAPAAALMSKCQEEEEIVRPLASSPXXGXRXHXXLDNQVAEXXVEEIETLKEQTRSM    60
SEQ ID NO: 34 AAE3_12839  1   -------------------MXWXXVLXXHXLAXX-----XLTXX------------    23
                                                 * **  **:  . : :*.    . .:

SEQ ID NO: 75 TPS31       61  LXXXRTLAEKLNLIDIVERLGIXXHXXXXDDMLNHIFNIDXXFEARRYRDLCTLSLQPR  120
SEQ ID NO: 34 AAE3_12839  24  -XXX------------------XFLXXXXAP--------AXX----------------   39
                              ::*                   :: *::::               **

SEQ ID NO: 75 TPS31       121 ILRQHGYYISPKIFSRFQDANGKFKESLCDDIRGILNLYEASEVRTHGRDTLEEAXXST  180
SEQ ID NO: 34 AAE3_12839  40  -------------------------------------------------PAPXXI-    46
                                                                               ::*

SEQ ID NO: 75 TPS31       181 ARLESAAXXXXPXXQVTXXEQXLXXXPRXXYXXIXXXXKNXXFLRXAKLX         240
SEQ ID NO: 34 AAE3_12839  47  -------LXXXXTXXSLFDXXX--NPXXVACAXXXNXXKXXXVXGAXXQEFXRRCX    98
                                     *.*:  :.:    .  *.:  .*:* ::: *:::  *  ::   * : .*

SEQ ID NO: 75 TPS31       241 XXQ-----MXXXQPXSEVSRXWXDXDXXTTXPYXX----QXXVXCYXWXXGXYAXXXX   293
SEQ ID NO: 34 AAE3_12839  99  XXTSYTYPYXXXGLRAXMDXHNIXWXXDXXTDXXTGXDXHXXAXIXXRXLRXXXXX    158
                              ::*:          :.*: *  . * :.   :.   . *   *:    **::.*:.

SEQ ID NO: 75 TPS31       294 RVXLAKTIAMISIVDDTFDAYGXVRELEVYTDAXQRXDXXXIXXLP---------XNXX  345
SEQ ID NO: 34 AAE3_12839  159 SSXC--------------------RX--------XDXRXXXAGPECTRRFLXXCXX    191
                              :                    :           :: : :*::.*          *: .:

SEQ ID NO: 75 TPS31       346 XXLLDLYRDYXXSXXXX-----------------SDVXQYXXERXXEIXRXYXVXAK   388
SEQ ID NO: 34 AAE3_12839  192 XX------GAVXXRXXXXVLSIEGYLKLRRETSGARTCXXXMXYLXXIDXPXDNYXDP  246
                              ::*     . *:** :.*.                 .:  *:  *.   : : :

SEQ ID NO: 75 TPS31       389 WXIXXXPFXXEYLSNALATSTYYLLFTTSYLGMKSATRKDFEWLAKNPKILEANVTXCR  448
SEQ ID NO: 34 AAE3_12839  247 VXQXXXAAX------------------------------------------XIF    260
                              * :**:  :.                                          *

SEQ ID NO: 75 TPS31       449 YIXXAXXXXXXXCRXXIXXXXE-CYXXXY-----------XXSTXVAXXXXMAXXAW   496
SEQ ID NO: 34 AAE3_12839  261 AXXXYXXXXARXXGXXXLTVVXXTKLNLQSAADYVXXLCXKLXXXXAKXXLEX    320
                              : :** :*::*:*:.:** :.:.:    *::         **    :.:***  .* :

SEQ ID NO: 75 TPS31       497 DXXEGILXPIXXXKIXXR----XXLAXII--XXTXXXQXGXT-XPXXVXXPEIXALX  549
SEQ ID NO: 34 AAE3_12839  321 RLA---KXKXXAXXAAXXDAIRSXXXYXXWXRGXXENXXXTERXFGKXXEXXKSRXXT  377
                              :       .:*.. * :    ::.  :: :  : : *:..:  * * .:* :*     :.  *

SEQ ID NO: 75 TPS31       550 VDXIXX-------                                             555
SEQ ID NO: 34 AAE3_12839  378 TPXMXXNRALKA                                              389
                              . : .:
```

| | |
|---|---|
| Identical positions | 64 |
| Identity | 10.458% |
| Similar positions | 145 |
| Program | CLUSTALO |

FIG. 16

| SEQ ID NO: 76 MqTPS1    | 1   | ------------AIP--S-NKGTGDVIERRSAGYRP----V-LKY-S-         | 42  |
| SEQ ID NO: 32 AAE3_13291 | 1   | MASSLLEPSLAAIALVIL---LSR--R-AAP---------SPQGL-I--L----I- | 48  |

| SEQ ID NO: 76 MqTPS1    | 43  | --VKFEFLGRVEEQIEELKGEVR---AG-----HLIDQIQRLGIEYSFERELDEH | 102 |
| SEQ ID NO: 32 AAE3_13291 | 49  | K--S-------------------------VL-----T------------------ | 67  |

| SEQ ID NO: 76 MqTPS1    | 103 | LERIH-SFS-LT--FK--RMI-LLP---QQ-YISS-V--K-SB-C-PGESLATD | 162 |
| SEQ ID NO: 32 AAE3_13291 | 68  | ------RAV-QL--TP---DAT-HSP---LP-L----V-P-RGL-P--------- | 112 |

| SEQ ID NO: 76 MqTPS1    | 163 | LRGLLSL-EACHLRCHGDIILDEALPFAISHLESIDESRAGANLAKQVNHALKQPLRRGL | 222 |
| SEQ ID NO: 32 AAE3_13291 | 113 | -------N---------------------------------------------TS     | 116 |

| SEQ ID NO: 76 MqTPS1    | 223 | -L--R--PL-E-BP-HD--LA-A-L---L-EQHQKELGNVSRWWKDIDVP-K-- | 282 |
| SEQ ID NO: 32 AAE3_13291 | 117 | A-T--A--NQ-T-VV-GP--AF-N-C---S-------------------S-C-- | 157 |

| SEQ ID NO: 76 MqTPS1    | 283 | RD-------IAEL--AC-V-P-PEF-VAR--I--KA--MT----DVYGTLESLVLLT | 336 |
| SEQ ID NO: 32 AAE3_13291 | 158 | GY-GLRATMDL-N---LX----TGS-EA---AC-VAR--RPD-------------- | 203 |

| SEQ ID NO: 76 MqTPS1    | 337 | EAIE--DVDA--K--------L-EYMQA-YK--LL--Y-E---YAA-GK-YR-VYA-E- | 387 |
| SEQ ID NO: 32 AAE3_13291 | 204 | -DDG-VCR---FKQNHIDKAG-GVAR-ID--C--V-V---AEL-E--EV-DIP-Y- | 262 |

| SEQ ID NO: 76 MqTPS1    | 388 | M------K-L--Y--EA--FRTNYTPT-E--PL-Q--T--MMATTSLV--DVVPKHV | 442 |
| SEQ ID NO: 32 AAE3_13291 | 263 | TFRRE-SA---CL-LV--CLD----LD-P---HDDP--I-S---A---------    | 305 |

| SEQ ID NO: 76 MqTPS1    | 443 | FENSIGDCKIVKAAQT-CRLM---S-----LV--E------BR-------       | 496 |
| SEQ ID NO: 32 AAE3_13291 | 306 | ----------------VFW---------SGG--VT---Q-LQT-VDFLG        | 349 |

| SEQ ID NO: 76 MqTPS1    | 497 | -----------EEL----G--A-------KDT--RPTAVP                 | 522 |
| SEQ ID NO: 32 AAE3_13291 | 350 | GYCEALTAQLLEAKRILQARS-AAY-DVVRLM--DWVRGNVA-FE--GKE----   | 405 |

| SEQ ID NO: 76 MqTPS1    | 523 | MKILTRVLNLSRAMDVLYSDGDNYTHS---P-----L--P-P-*-           | 568 |
| SEQ ID NO: 32 AAE3_13291 | 407 | ---------------------------T-LVEL--P--A-ALKE            | 430 |

| Identical positions | 74 |
|---|---|
| Identity | 11.367% |
| Similar positions | 126 |
| Program | CLUSTALO |

FIG. 19 (Cont'd)
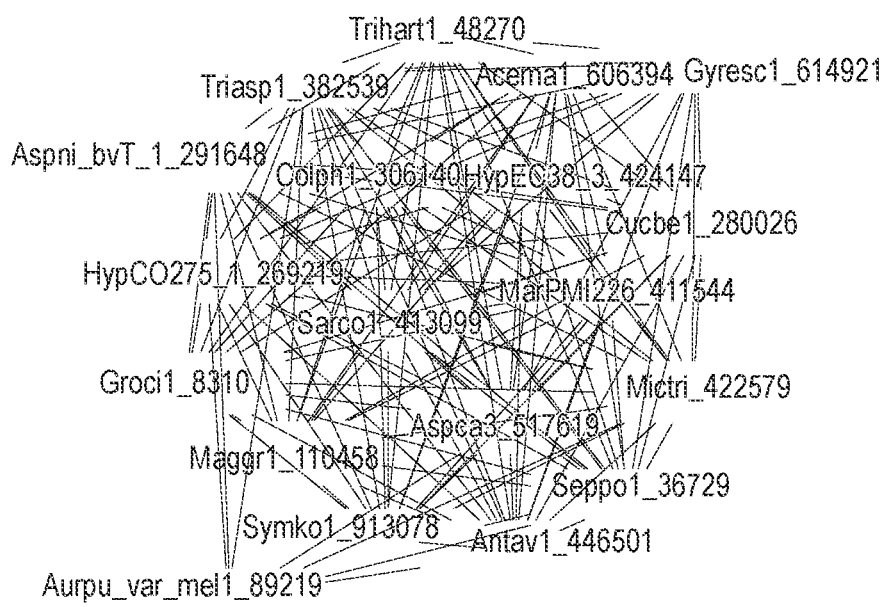
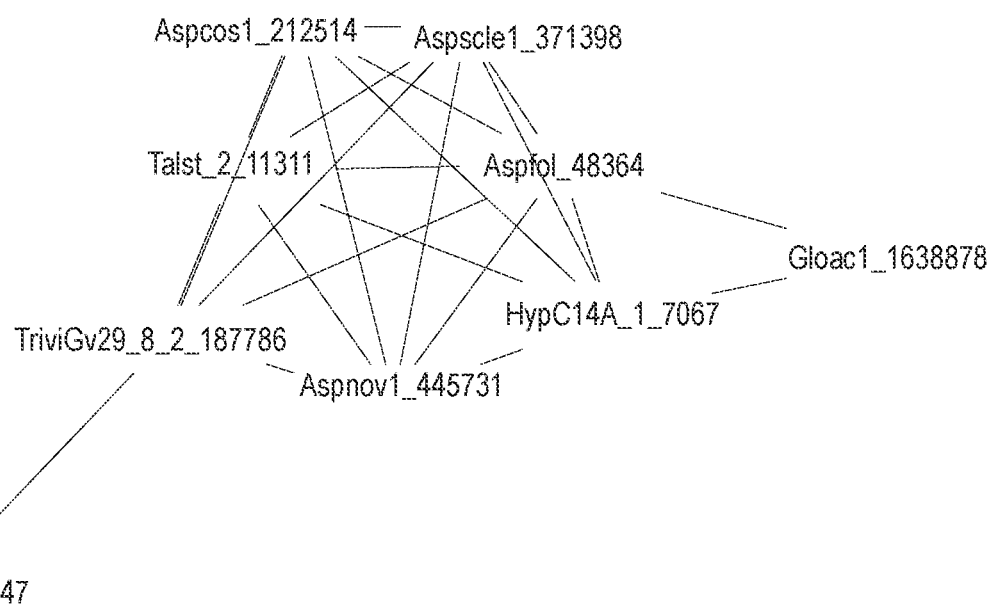

| Identical positions | 84 |
|---|---|
| Identity | 21.429% |
| Similar positions | 107 |
| Program | CLUSTALO |

Agrped1_689675
- F204A
- F204V
- F204I
- F204D
- F204E
- F204H

FIG. 23B
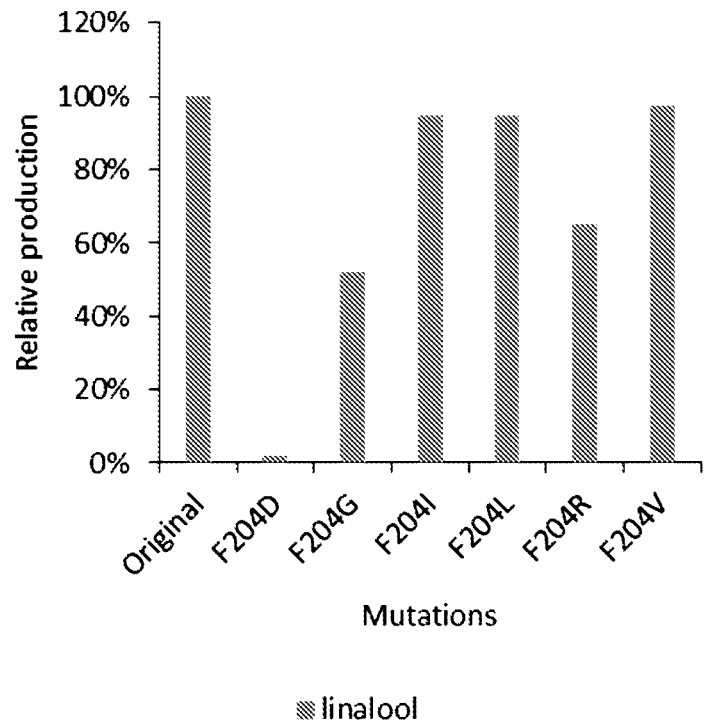
linalool
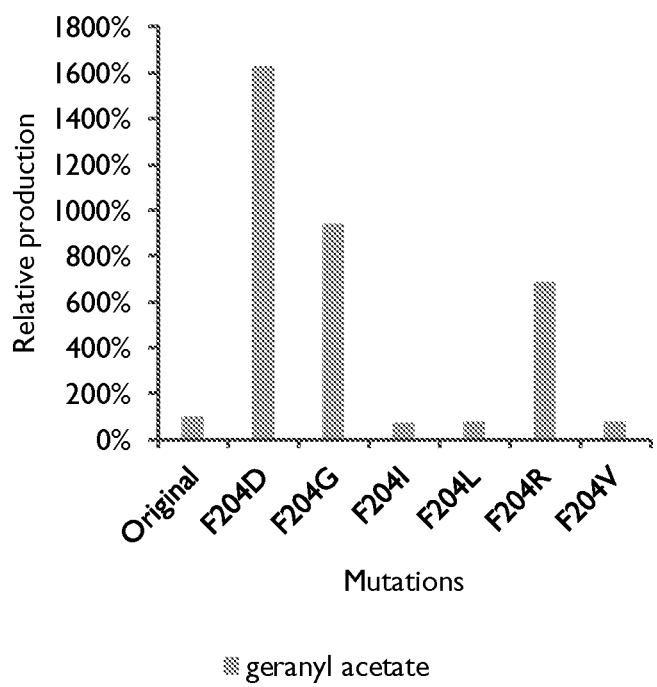
geranyl acetate

FIG. 25

FIG. 26
Agrped1_689671
Swiss with template 5nx6
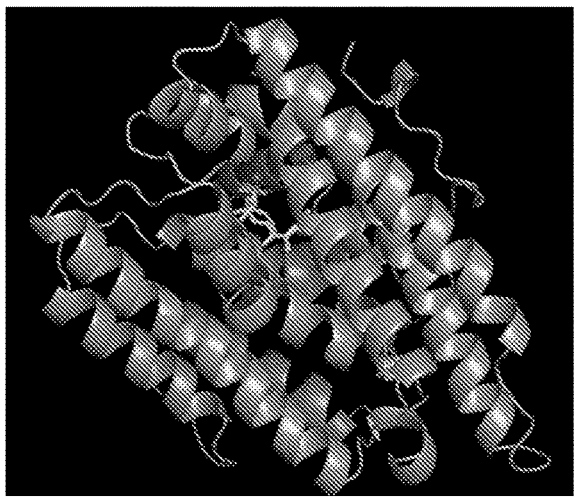
Agrped1_689675
Swiss with template 5nx6
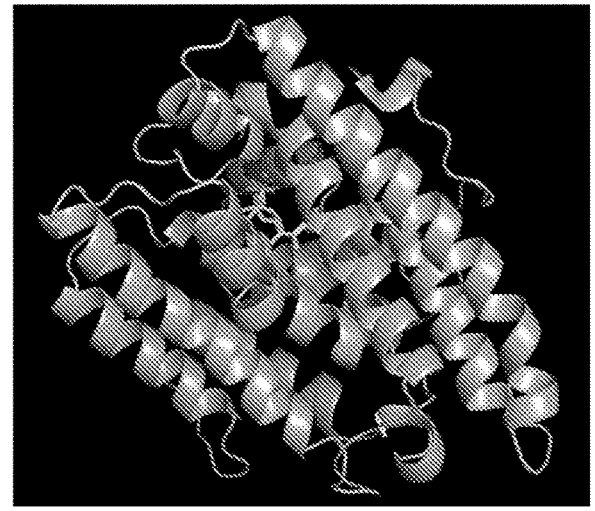

FIG. 26 (cont'd)

Agrped1_689671
Swiss with template 5nx6

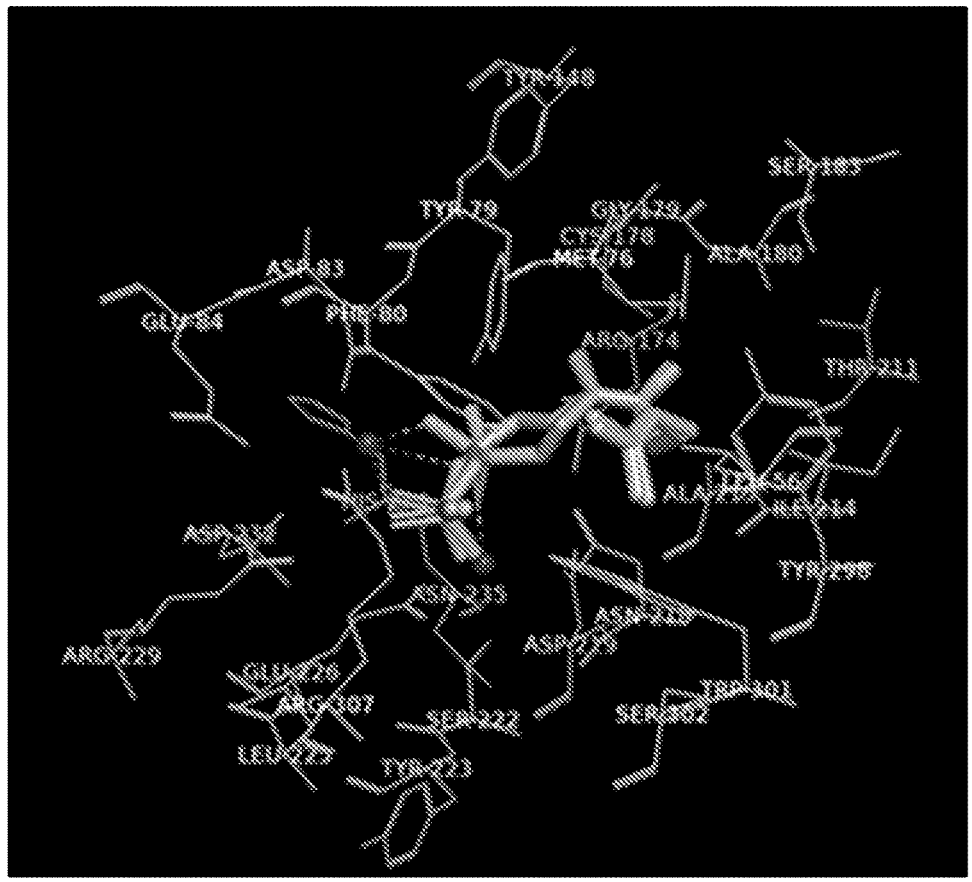

>Agrped1_689671 (Agr3)
MSQFIIPDLLSTWPWQRVSNPMWREIDEEANAWVQSFDLFEPSQFEKFKM
CDFNLLGSMIGTVETKDHLRISCDLMNFYFAFDEYTDMASKDEARKIARD
VMDAFRNTEKPAHNQITEMARQFFKRTIDTVGKDLPGVERFIADFDAYTH
SVIQEADDRATGHIRSVNDYFTLRRDTCGAKPSFSFFGLGLNIPDEVFHH
PVVISMIEGATDLIAVTNDMHSYNLEHSRGLDGHNVITAIMHEYQLDLQG
ALYWLSGYATHTIANFLSNRRNLPSWGPAVDKAVEEFFDRVGRCVRGYDA
WSYETKRYYGKNGLQVQKTRRITLRPRDASYITKEQLQVSIKA
*Red labelled sites are the residues within 6A of ligand.

(SEQ ID NO: 2)

FIG. 26 (cont'd)

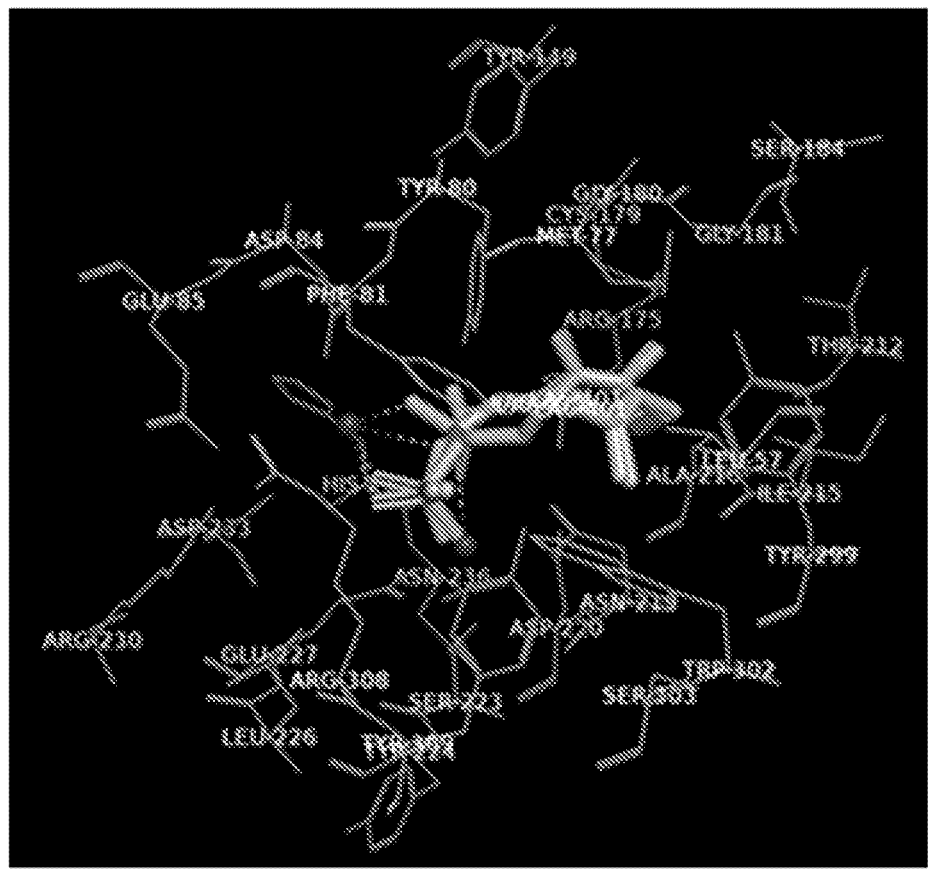

Agrped1_689675
Swiss with template 5nx6

Agrped1_689675 (Agr1)
MSSQIYIPDLLITWPWQKVRNPLLQEVQDEANEWVKSFVLFEPEQFEKFK
ACDFNLLGALVGPLGTKEELRISCDLVNFYFAFDEYTDLASADEAKVIAR
DVWESFRHTDKPSHNKITEMARQFFERTINTVGNDPTGIEQFIADFDAYT
TSIIQEADDRASGHIRSVEDYFILRRDTCGGKPSFSFFGLGLNIPKEVFA
HPWFISWTESATDLIAITNDVHSYNLEQSRGLDGHWVITAIVHEYKINLQ
GALYWLSGYATKTIAKFISDRKNLPSWGPVVDRAVEQYFDRVGRCVRGYD
AWSYETKRYYGKNGLEIQKTRQITLRPLDPAYVTKEQLQVSWKA*
*Red labelled sites are the residues within 6A of ligand.

(SEQ ID NO: 3)

SEQUENCE LISTING

```
<160> NUMBER OF SEQ ID NOS: 180

<210> SEQ ID NO 1
<211> LENGTH: 384
<212> TYPE: PRT
<213> ORGANISM: Agrocybe aegerita

<400> SEQUENCE: 1

Met His Ser Ser Thr Gln Leu Phe Thr His Ser Pro Thr Lys Met Gln
1               5                   10                  15

Ile Ile Leu Pro Asp Leu Leu Cys Ser Trp Gly Tyr Lys Gly Phe Leu
                20                  25                  30

Asn Pro His Tyr Glu Gly Ala Lys Ala Glu Ser Asn Thr Trp Ile Arg
            35                  40                  45

Pro Leu Val Val Lys Leu Phe Asp Glu Arg Gly Gln Lys Ala Phe Ala
        50                  55                  60

Lys Asp Tyr Thr Gly Leu Leu Ala Ser Met Thr Tyr Pro His His Asn
65                  70                  75                  80

Lys Glu Phe Leu Cys Val Ala Cys Asp Met Met Asn Leu Phe Phe Val
                85                  90                  95

Tyr Asp Glu Tyr Thr Asp Ile Thr Pro Pro Glu Thr Ala Gln Arg Leu
                100                 105                 110

Ala Lys Ile Val Val Asn Ala Met Arg Asn Pro Asp Glu Ile Ala Ala
            115                 120                 125

Leu Gly Glu Asp Ser Ile Gly Thr Met Thr Lys Gln Phe Trp Arg Arg
        130                 135                 140

Ala Met Thr Leu Leu Pro Pro Asn Gly Cys Asn Ser Glu Ser Cys Ile
145                 150                 155                 160

Gln His Phe Ile Asp Tyr Thr Glu Glu Tyr Leu Thr Ala Val Thr Arg
                165                 170                 175

Glu Ala Cys Asp Arg Ser Ser Gly Ser Val His Ala Val Lys Asp Tyr
            180                 185                 190

Leu Ala Met Arg Arg Ala Thr Ser Gly Ala Gly Leu Met Val Gly Leu
        195                 200                 205

Leu Glu Phe Gly Leu Asp Leu Pro Glu Glu Val Met Lys His Glu Val
    210                 215                 220

Ile Gln Glu Leu Ser Thr Gly Ala Ile Asp Met Tyr Cys Leu Leu Asn
225                 230                 235                 240

Asp Met His Ser Tyr Ala Ser Glu Leu Ser Ser Gly Gln Ala Ser His
                245                 250                 255

Asn Val Ile Thr Val Val Met His Glu Arg Asn Leu Ser Leu Gln Glu
            260                 265                 270

Ala Phe Asp Trp Leu Ala Ser Tyr Ala Ala Gly Val Val Lys Gly Phe
        275                 280                 285

Lys Thr Asn Leu Asn Arg Val Pro Ser Phe Ser Glu Leu Glu Asp His
    290                 295                 300

Ser Leu His Gly Glu Gly Met Leu Arg Asp Arg Ile Gln Arg Tyr Ile
305                 310                 315                 320

Asp Gly Leu Gly Gln Ala Val Arg Ala Glu Asp Asp Trp Ala Phe Glu
```

```
                325                 330                 335
Thr Thr Arg Tyr His Gly Gln Asn Gly Pro Gln Ile Lys Leu Thr Arg
            340                 345                 350

Met Leu Thr Ile Arg Pro Gln Val Lys Asp Asn Tyr Ala Lys Gln Ala
            355                 360                 365

Pro Arg Val Glu Ala Pro Glu Arg Pro Met Leu Leu Glu Val Arg Ser
370                 375                 380

<210> SEQ ID NO 2
<211> LENGTH: 343
<212> TYPE: PRT
<213> ORGANISM: Agrocybe pediades

<400> SEQUENCE: 2

Met Ser Gln Phe Ile Ile Pro Asp Leu Leu Ser Thr Trp Pro Trp Gln
1               5                   10                  15

Arg Val Ser Asn Pro Met Trp Arg Glu Ile Asp Glu Glu Ala Asn Ala
            20                  25                  30

Trp Val Gln Ser Phe Asp Leu Phe Glu Pro Ser Gln Phe Glu Lys Phe
        35                  40                  45

Lys Met Cys Asp Phe Asn Leu Leu Gly Ser Met Ile Gly Thr Val Glu
    50                  55                  60

Thr Lys Asp His Leu Arg Ile Ser Cys Asp Leu Met Asn Phe Tyr Phe
65                  70                  75                  80

Ala Phe Asp Glu Tyr Thr Asp Met Ala Ser Lys Asp Glu Ala Arg Lys
                85                  90                  95

Ile Ala Arg Asp Val Met Asp Ala Phe Arg Asn Thr Glu Lys Pro Ala
            100                 105                 110

His Asn Gln Ile Thr Glu Met Ala Arg Gln Phe Phe Lys Arg Thr Ile
        115                 120                 125

Asp Thr Val Gly Lys Asp Leu Pro Gly Val Glu Arg Phe Ile Ala Asp
    130                 135                 140

Phe Asp Ala Tyr Thr His Ser Val Ile Gln Glu Ala Asp Asp Arg Ala
145                 150                 155                 160

Thr Gly His Ile Arg Ser Val Asn Asp Tyr Phe Thr Leu Arg Arg Asp
                165                 170                 175

Thr Cys Gly Ala Lys Pro Ser Phe Ser Phe Phe Gly Leu Gly Leu Asn
            180                 185                 190

Ile Pro Asp Glu Val Phe His His Pro Val Val Ile Ser Met Ile Glu
        195                 200                 205

Gly Ala Thr Asp Leu Ile Ala Val Thr Asn Asp Met His Ser Tyr Asn
    210                 215                 220

Leu Glu His Ser Arg Gly Leu Asp Gly His Asn Val Ile Thr Ala Ile
225                 230                 235                 240

Met His Glu Tyr Gln Leu Asp Leu Gln Gly Ala Leu Tyr Trp Leu Ser
                245                 250                 255

Gly Tyr Ala Thr His Thr Ile Ala Asn Phe Leu Ser Asn Arg Arg Asn
            260                 265                 270

Leu Pro Ser Trp Gly Pro Ala Val Asp Lys Ala Val Glu Glu Phe Phe
        275                 280                 285

Asp Arg Val Gly Arg Cys Val Arg Gly Tyr Asp Ala Trp Ser Tyr Glu
    290                 295                 300

Thr Lys Arg Tyr Tyr Gly Lys Asn Gly Leu Gln Val Gln Lys Thr Arg
305                 310                 315                 320
```

```
Arg Ile Thr Leu Arg Pro Arg Asp Ala Ser Tyr Ile Thr Lys Glu Gln
                325                 330                 335

Leu Gln Val Ser Ile Lys Ala
            340

<210> SEQ ID NO 3
<211> LENGTH: 344
<212> TYPE: PRT
<213> ORGANISM: Agrocybe pediades

<400> SEQUENCE: 3

Met Ser Ser Gln Ile Tyr Ile Pro Asp Leu Ile Thr Trp Pro Trp
1               5                   10                  15

Gln Lys Val Arg Asn Pro Leu Leu Gln Glu Val Gln Asp Glu Ala Asn
                20                  25                  30

Glu Trp Val Lys Ser Phe Val Leu Phe Glu Pro Glu Gln Phe Glu Lys
            35                  40                  45

Phe Lys Ala Cys Asp Phe Asn Leu Leu Gly Ala Leu Val Gly Pro Leu
        50                  55                  60

Gly Thr Lys Glu Glu Leu Arg Ile Ser Cys Asp Leu Met Asn Phe Tyr
65                  70                  75                  80

Phe Ala Phe Asp Glu Tyr Thr Asp Leu Ala Ser Ala Asp Glu Ala Lys
                85                  90                  95

Val Ile Ala Arg Asp Val Met Glu Ser Phe Arg His Thr Asp Lys Pro
            100                 105                 110

Ser His Asn Lys Ile Thr Glu Met Ala Arg Gln Phe Phe Glu Arg Thr
        115                 120                 125

Ile Asn Thr Val Gly Asn Asp Pro Thr Gly Ile Glu Gln Phe Ile Ala
130                 135                 140

Asp Phe Asp Ala Tyr Thr Thr Ser Ile Ile Gln Glu Ala Asp Asp Arg
145                 150                 155                 160

Ala Ser Gly His Ile Arg Ser Val Glu Asp Tyr Phe Ile Leu Arg Arg
                165                 170                 175

Asp Thr Cys Gly Gly Lys Pro Ser Phe Ser Phe Phe Gly Leu Gly Leu
            180                 185                 190

Asn Ile Pro Lys Glu Val Phe Ala His Pro Met Phe Ile Ser Met Thr
        195                 200                 205

Glu Ser Ala Thr Asp Leu Ile Ala Ile Thr Asn Asp Met His Ser Tyr
210                 215                 220

Asn Leu Glu Gln Ser Arg Gly Leu Asp Gly His Asn Val Ile Thr Ala
225                 230                 235                 240

Ile Met His Glu Tyr Lys Ile Asn Leu Gln Gly Ala Leu Tyr Trp Leu
                245                 250                 255

Ser Gly Tyr Ala Thr Lys Thr Ile Ala Lys Phe Ile Ser Asp Arg Lys
            260                 265                 270

Asn Leu Pro Ser Trp Gly Pro Val Asp Arg Ala Val Glu Gln Tyr
        275                 280                 285

Phe Asp Arg Val Gly Arg Cys Val Arg Gly Tyr Asp Ala Trp Ser Tyr
290                 295                 300

Glu Thr Lys Arg Tyr Tyr Gly Lys Asn Gly Leu Glu Ile Gln Lys Thr
305                 310                 315                 320

Arg Gln Ile Thr Leu Arg Pro Leu Asp Pro Ala Tyr Val Thr Lys Glu
                325                 330                 335

Gln Leu Gln Val Ser Met Lys Ala
            340
```

<210> SEQ ID NO 4
<211> LENGTH: 343
<212> TYPE: PRT
<213> ORGANISM: Galerina marginata

<400> SEQUENCE: 4

```
Met Pro Ser Gln Phe Thr Ile Pro Asp Leu Ile Thr Trp Pro Trp
1               5                   10                  15

Gln Glu Ile Thr Asn Pro Met Leu His Glu Val Asp Ala Glu Ala Asn
            20                  25                  30

Glu Trp Val Gln Ser Leu Asn Leu Phe Glu Pro Lys Gln Phe Glu Lys
        35                  40                  45

Phe Lys Ala Cys Asn Phe Asn Leu Leu Gly Ser Leu Val Gly Pro Leu
    50                  55                  60

Pro Ser Arg Asp His Leu Arg Val Ser Cys Asp Leu Met Asn Phe Tyr
65                  70                  75                  80

Phe Ala Phe Asp Glu Tyr Thr Asp Met Ala Asn Lys Asp Glu Ala Met
                85                  90                  95

Arg Ile Ala Arg Asp Val Met Gln Ala Phe Arg Asn Thr Asp Thr Pro
            100                 105                 110

Ser Asn Ser Lys Ile Thr Glu Met Ala Arg Gln Phe Phe Lys Arg Thr
        115                 120                 125

Ile Glu Val Val Gly Glu Asp Leu Pro Gly Ile Glu Arg Phe Ile Ala
    130                 135                 140

Asp Phe Asp Ala Tyr Thr Arg Ser Val Ile Gln Glu Ala Asp Asp Arg
145                 150                 155                 160

Val Ala Gly His Ile Arg Asn Val Glu Asp Tyr Phe Ile Leu Arg Arg
                165                 170                 175

Asp Thr Cys Gly Ala Lys Pro Ser Phe Ser Phe Tyr Gly Leu Gly Leu
            180                 185                 190

Asn Ile Pro Thr Glu Val Phe Glu His Pro Leu Leu Ile Ser Met Val
        195                 200                 205

Glu Ser Ala Thr Asp Leu Ile Ala Val Thr Asn Asp Met His Ser Tyr
    210                 215                 220

Gly Leu Glu His Ser Arg Gly Leu Asp Gly His Asn Val Ile Thr Ala
225                 230                 235                 240

Ile Met His Glu Tyr Gln Leu Asp Leu Gln Gly Ala Leu Tyr Trp Leu
                245                 250                 255

Ser Gly Tyr Ala Thr Lys Thr Ile Ser Lys Phe Leu Thr Asp Arg Lys
            260                 265                 270

Asn Leu Pro Ser Trp Gly Pro Thr Ile Asp Lys Ala Leu Glu Ile Tyr
        275                 280                 285

Leu Asp Arg Leu Gly Arg Cys Val Arg Gly Tyr Asp Ala Trp Ser Tyr
    290                 295                 300

Ser Thr Lys Arg Tyr Tyr Gly Lys Asn Gly Leu Lys Val Gln Lys Thr
305                 310                 315                 320

Arg Arg Ile Thr Leu Lys Pro Arg Asp Ala Ala Tyr Ile Thr Lys Asp
                325                 330                 335

Gln Leu Gln Val Ser Ile Ala
            340
```

<210> SEQ ID NO 5
<211> LENGTH: 344
<212> TYPE: PRT

<213> ORGANISM: Hypholoma sublateritium

<400> SEQUENCE: 5

Met Ser Ala Gln Tyr Thr Ile Pro Asp Leu Leu Ala Asn Trp Pro Trp
1               5                   10                  15

Gln Arg Val Thr Asn Ser Met Leu Asp Glu Val Arg Asp Glu Ala Asn
            20                  25                  30

Glu Trp Val Met Ser Leu Gly Leu Phe Glu Pro Ala Gln Phe Lys Lys
        35                  40                  45

Phe Lys Ala Cys Asp Phe Asn Leu Leu Ala Ser Phe Ile Gly Pro Leu
    50                  55                  60

Glu Ser Lys Glu His Leu Arg Val Ala Cys Asp Leu Met Asn Phe Tyr
65                  70                  75                  80

Phe Ala Phe Asp Glu Tyr Thr Asp Val Ala Asn Arg Glu Glu Ala Lys
                85                  90                  95

Lys Ile Ser Gln Gly Val Met His Ala Phe Lys Thr Arg Ser Ala Glu
            100                 105                 110

Pro Ser Ser Ser Lys Ile Thr Glu Met Ala Arg Gln Phe Phe Arg Arg
        115                 120                 125

Thr Val Asp Val Val Gly Glu Asp Ser Pro Ala Ile Asn Gln Phe Ile
130                 135                 140

Thr Asp Phe Asp Thr Tyr Thr Thr Ala Val Ile Gln Glu Ala Asp Asp
145                 150                 155                 160

Arg Thr Glu Gly Thr Ile Arg Asn Val Glu Asp Tyr Phe Thr Leu Arg
                165                 170                 175

Arg Asp Thr Cys Gly Ala Lys Pro Ser Phe Ser Phe Ala Leu Gly
            180                 185                 190

Leu Asn Met Pro Thr Glu Val Phe Glu His Pro Leu Ile Met Ser Leu
        195                 200                 205

Val Glu Arg Ala Thr Asp Leu Ile Ala Ile Val Asn Asp Met His Ser
210                 215                 220

Tyr Gly Leu Glu Arg Ala Arg Gly Leu Asp Gly His Asn Val Val Thr
225                 230                 235                 240

Ser Ile Met Tyr Glu His Gln Leu Asp Leu Gln Gly Ala Leu His Trp
                245                 250                 255

Leu Ala Gly Tyr Ala Glu Asp Thr Ile Ala Lys Phe Leu Ser Glu Lys
            260                 265                 270

Glu Arg Leu Pro Ser Trp Gly Pro Ala Val Asp Val Ser Val Gln Glu
        275                 280                 285

Phe Val Asp Arg Leu Gly Arg Cys Val Arg Gly Tyr Asp Ala Trp Ser
290                 295                 300

Tyr Glu Thr Asn Arg Tyr Tyr Gly Ser His Gly Leu Gln Ile Arg Gln
305                 310                 315                 320

Thr Arg Gln Ile Thr Leu Pro Ser Asn Asp Ser Gly Tyr Ile Thr Arg
                325                 330                 335

Lys Gln Met Gly Val Ser Ile Ala
            340

<210> SEQ ID NO 6
<211> LENGTH: 620
<212> TYPE: PRT
<213> ORGANISM: Escherichia coli

<400> SEQUENCE: 6

Met Ser Phe Asp Ile Ala Lys Tyr Pro Thr Leu Ala Leu Val Asp Ser

-continued

```
1               5                   10                  15
Thr Gln Glu Leu Arg Leu Leu Pro Lys Glu Ser Leu Pro Lys Leu Cys
            20                  25                  30

Asp Glu Leu Arg Arg Tyr Leu Leu Asp Ser Val Ser Arg Ser Ser Gly
            35                  40                  45

His Phe Ala Ser Gly Leu Gly Thr Val Glu Leu Thr Val Ala Leu His
            50                  55                  60

Tyr Val Tyr Asn Thr Pro Phe Asp Gln Leu Ile Trp Asp Val Gly His
 65                 70                  75                  80

Gln Ala Tyr Pro His Lys Ile Leu Thr Gly Arg Arg Asp Lys Ile Gly
                    85                  90                  95

Thr Ile Arg Gln Lys Gly Gly Leu His Pro Phe Pro Trp Arg Gly Glu
            100                 105                 110

Ser Glu Tyr Asp Val Leu Ser Val Gly His Ser Ser Thr Ser Ile Ser
            115                 120                 125

Ala Gly Ile Gly Ile Ala Val Ala Ala Glu Lys Glu Gly Lys Asn Arg
            130                 135                 140

Arg Thr Val Cys Val Ile Gly Asp Gly Ala Ile Thr Ala Gly Met Ala
145                 150                 155                 160

Phe Glu Ala Met Asn His Ala Gly Asp Ile Arg Pro Asp Met Leu Val
                    165                 170                 175

Ile Leu Asn Asp Asn Glu Met Ser Ile Ser Glu Asn Val Gly Ala Leu
            180                 185                 190

Asn Asn His Leu Ala Gln Leu Leu Ser Gly Lys Leu Tyr Ser Ser Leu
            195                 200                 205

Arg Glu Gly Gly Lys Lys Val Phe Ser Gly Val Pro Pro Ile Lys Glu
            210                 215                 220

Leu Leu Lys Arg Thr Glu Glu His Ile Lys Gly Met Val Val Pro Gly
225                 230                 235                 240

Thr Leu Phe Glu Glu Leu Gly Phe Asn Tyr Ile Gly Pro Val Asp Gly
                    245                 250                 255

His Asp Val Leu Gly Leu Ile Thr Thr Leu Lys Asn Met Arg Asp Leu
            260                 265                 270

Lys Gly Pro Gln Phe Leu His Ile Met Thr Lys Lys Gly Arg Gly Tyr
            275                 280                 285

Glu Pro Ala Glu Lys Asp Pro Ile Thr Phe His Ala Val Pro Lys Phe
            290                 295                 300

Asp Pro Ser Ser Gly Cys Leu Pro Lys Ser Ser Gly Gly Leu Pro Ser
305                 310                 315                 320

Tyr Ser Lys Ile Phe Gly Asp Trp Leu Cys Glu Thr Ala Ala Lys Asp
                    325                 330                 335

Asn Lys Leu Met Ala Ile Thr Pro Ala Met Arg Glu Gly Ser Gly Met
            340                 345                 350

Val Glu Phe Ser Arg Lys Phe Pro Asp Arg Tyr Phe Asp Val Ala Ile
            355                 360                 365

Ala Glu Gln His Ala Val Thr Phe Ala Ala Gly Leu Ala Ile Gly Gly
            370                 375                 380

Tyr Lys Pro Ile Val Ala Ile Tyr Ser Thr Phe Leu Gln Arg Ala Tyr
385                 390                 395                 400

Asp Gln Val Leu His Asp Val Ala Ile Gln Lys Leu Pro Val Leu Phe
                    405                 410                 415

Ala Ile Asp Arg Ala Gly Ile Val Gly Ala Asp Gly Gln Thr His Gln
            420                 425                 430
```

Gly Ala Phe Asp Leu Ser Tyr Leu Arg Cys Ile Pro Glu Met Val Ile
                435                 440                 445

Met Thr Pro Ser Asp Glu Asn Glu Cys Arg Gln Met Leu Tyr Thr Gly
450                 455                 460

Tyr His Tyr Asn Asp Gly Pro Ser Ala Val Arg Tyr Pro Arg Gly Asn
465                 470                 475                 480

Ala Val Gly Val Glu Leu Thr Pro Leu Glu Lys Leu Pro Ile Gly Lys
                485                 490                 495

Gly Ile Val Lys Arg Arg Gly Glu Lys Leu Ala Ile Leu Asn Phe Gly
                500                 505                 510

Thr Leu Met Pro Glu Ala Ala Lys Val Ala Glu Ser Leu Asn Ala Thr
            515                 520                 525

Leu Val Asp Met Arg Phe Val Lys Pro Leu Asp Glu Ala Leu Ile Leu
        530                 535                 540

Glu Met Ala Ala Ser His Glu Ala Leu Val Thr Val Glu Glu Asn Ala
545                 550                 555                 560

Ile Met Gly Gly Ala Gly Ser Gly Val Asn Glu Val Leu Met Ala His
                565                 570                 575

Arg Lys Pro Val Pro Val Leu Asn Ile Gly Leu Pro Asp Phe Phe Ile
                580                 585                 590

Pro Gln Gly Thr Gln Glu Glu Met Arg Ala Glu Leu Gly Leu Asp Ala
            595                 600                 605

Ala Gly Met Glu Ala Lys Ile Lys Ala Trp Leu Ala
610                 615                 620

<210> SEQ ID NO 7
<211> LENGTH: 336
<212> TYPE: PRT
<213> ORGANISM: Artificial Sequence
<220> FEATURE:
<223> OTHER INFORMATION: Agrped1_689675_mut1

<400> SEQUENCE: 7

Met Ser Ser Gln Ile Tyr Ile Pro Asp Leu Leu Ile Thr Trp Pro Trp
1               5                   10                  15

Gln Lys Val Arg Asn Pro Leu Leu Gln Glu Val Gln Asp Glu Ala Asn
                20                  25                  30

Glu Trp Val Lys Ser Phe Val Leu Phe Glu Pro Glu Gln Phe Glu Lys
            35                  40                  45

Phe Lys Ala Cys Asp Phe Asn Leu Leu Gly Ala Leu Val Gly Pro Leu
        50                  55                  60

Gly Thr Lys Glu Glu Leu Arg Ile Ser Cys Asp Leu Met Asn Phe Tyr
65                  70                  75                  80

Phe Ala Phe Asp Glu Tyr Thr Asp Leu Ala Ser Ala Asp Glu Ala Lys
                85                  90                  95

Val Ile Ala Arg Asp Val Met Glu Ser Phe Arg His Thr Asp Lys Pro
                100                 105                 110

Ser His Asn Lys Ile Thr Glu Met Ala Arg Gln Phe Glu Arg Thr
            115                 120                 125

Ile Asn Thr Val Gly Asn Asp Pro Thr Gly Ile Glu Gln Phe Ile Ala
        130                 135                 140

Asp Phe Asp Ala Tyr Thr Thr Ser Ile Ile Gln Glu Ala Asp Arg
145                 150                 155                 160

Ala Ser Gly His Ile Arg Ser Val Glu Asp Tyr Phe Ile Leu Arg Arg
                165                 170                 175

Asp Thr Cys Gly Gly Lys Pro Ser Phe Ser Phe Phe Gly Leu Gly Leu
            180                 185                 190

Asn Ile Pro Lys Glu Val Phe Ala His Pro Met Phe Ile Ser Met Thr
        195                 200                 205

Glu Ser Ala Thr Asp Leu Ile Ala Ile Thr Asn Asp Met His Ser Tyr
210                 215                 220

Asn Leu Glu Gln Ser Arg Gly Leu Asp Gly His Asn Val Ile Thr Ala
225                 230                 235                 240

Ile Met His Glu Tyr Lys Ile Asn Leu Gln Gly Ala Leu Tyr Trp Leu
                245                 250                 255

Ser Gly Tyr Ala Thr Lys Thr Ile Ala Lys Phe Ile Ser Asp Arg Lys
            260                 265                 270

Asn Leu Pro Ser Trp Gly Pro Val Asp Arg Ala Val Glu Gln Tyr
        275                 280                 285

Phe Asp Arg Val Gly Arg Cys Val Arg Gly Tyr Asp Ala Trp Ser Tyr
    290                 295                 300

Glu Thr Lys Arg Tyr Tyr Gly Lys Asn Gly Leu Glu Ile Gln Lys Thr
305                 310                 315                 320

Arg Gln Ile Thr Leu Arg Pro Leu Asp Pro Ala Tyr Val Thr Lys Glu
                325                 330                 335

<210> SEQ ID NO 8
<211> LENGTH: 325
<212> TYPE: PRT
<213> ORGANISM: Artificial Sequence
<220> FEATURE:
<223> OTHER INFORMATION: Agrped1_689675_mut2

<400> SEQUENCE: 8

Met Ser Ser Gln Ile Tyr Ile Pro Asp Leu Leu Ile Thr Trp Pro Trp
1               5                   10                  15

Gln Lys Val Arg Asn Pro Leu Leu Gln Glu Val Gln Asp Glu Ala Asn
            20                  25                  30

Glu Trp Val Lys Ser Phe Val Leu Phe Glu Pro Glu Gln Phe Glu Lys
        35                  40                  45

Phe Lys Ala Cys Asp Phe Asn Leu Leu Gly Ala Leu Val Gly Pro Leu
    50                  55                  60

Gly Thr Lys Glu Glu Leu Arg Ile Ser Cys Asp Leu Met Asn Phe Tyr
65                  70                  75                  80

Phe Ala Phe Asp Glu Tyr Thr Asp Leu Ala Ser Ala Asp Glu Ala Lys
                85                  90                  95

Val Ile Ala Arg Asp Val Met Glu Ser Phe Arg His Thr Asp Lys Pro
            100                 105                 110

Ser His Asn Lys Ile Thr Glu Met Ala Arg Gln Phe Phe Glu Arg Thr
        115                 120                 125

Ile Asn Thr Val Gly Asn Asp Pro Thr Gly Ile Glu Gln Phe Ile Ala
    130                 135                 140

Asp Phe Asp Ala Tyr Thr Thr Ser Ile Ile Gln Glu Ala Asp Asp Arg
145                 150                 155                 160

Ala Ser Gly His Ile Arg Ser Val Glu Asp Tyr Phe Ile Leu Arg Arg
                165                 170                 175

Asp Thr Cys Gly Gly Lys Pro Ser Phe Ser Phe Phe Gly Leu Gly Leu
            180                 185                 190

Asn Ile Pro Lys Glu Val Phe Ala His Pro Met Phe Ile Ser Met Thr
        195                 200                 205

```
Glu Ser Ala Thr Asp Leu Ile Ala Ile Thr Asn Asp Met His Ser Tyr
    210                 215                 220

Asn Leu Glu Gln Ser Arg Gly Leu Asp Gly His Asn Val Ile Thr Ala
225                 230                 235                 240

Ile Met His Glu Tyr Lys Ile Asn Leu Gln Gly Ala Leu Tyr Trp Leu
                245                 250                 255

Ser Gly Tyr Ala Thr Lys Thr Ile Ala Lys Phe Ile Ser Asp Arg Lys
                260                 265                 270

Asn Leu Pro Ser Trp Gly Pro Val Asp Arg Ala Val Glu Gln Tyr
            275                 280                 285

Phe Asp Arg Val Gly Arg Cys Val Arg Gly Tyr Asp Ala Trp Ser Tyr
    290                 295                 300

Glu Thr Lys Arg Tyr Tyr Gly Lys Asn Gly Leu Glu Ile Gln Lys Thr
305                 310                 315                 320

Arg Gln Ile Thr Leu
                325

<210> SEQ ID NO 9
<211> LENGTH: 303
<212> TYPE: PRT
<213> ORGANISM: Artificial Sequence
<220> FEATURE:
<223> OTHER INFORMATION: Agrped1_689675_mut3

<400> SEQUENCE: 9

Met Ser Ser Gln Ile Tyr Ile Pro Asp Leu Leu Ile Thr Trp Pro Trp
1               5                   10                  15

Gln Lys Val Arg Asn Pro Leu Leu Gln Glu Val Gln Asp Glu Ala Asn
                20                  25                  30

Glu Trp Val Lys Ser Phe Val Leu Phe Glu Pro Glu Gln Phe Glu Lys
            35                  40                  45

Phe Lys Ala Cys Asp Phe Asn Leu Leu Gly Ala Leu Val Gly Pro Leu
        50                  55                  60

Gly Thr Lys Glu Glu Leu Arg Ile Ser Cys Asp Leu Met Asn Phe Tyr
65                  70                  75                  80

Phe Ala Phe Asp Glu Tyr Thr Asp Leu Ala Ser Ala Asp Glu Ala Lys
                85                  90                  95

Val Ile Ala Arg Asp Val Met Glu Ser Phe Arg His Thr Asp Lys Pro
                100                 105                 110

Ser His Asn Lys Ile Thr Glu Met Ala Arg Gln Phe Phe Glu Arg Thr
            115                 120                 125

Ile Asn Thr Val Gly Asn Asp Pro Thr Gly Ile Glu Gln Phe Ile Ala
        130                 135                 140

Asp Phe Asp Ala Tyr Thr Thr Ser Ile Ile Gln Glu Ala Asp Asp Arg
145                 150                 155                 160

Ala Ser Gly His Ile Arg Ser Val Glu Asp Tyr Phe Ile Leu Arg Arg
                165                 170                 175

Asp Thr Cys Gly Gly Lys Pro Ser Phe Ser Phe Gly Leu Gly Leu
                180                 185                 190

Asn Ile Pro Lys Glu Val Phe Ala His Pro Met Phe Ile Ser Met Thr
        195                 200                 205

Glu Ser Ala Thr Asp Leu Ile Ala Ile Thr Asn Asp Met His Ser Tyr
    210                 215                 220

Asn Leu Glu Gln Ser Arg Gly Leu Asp Gly His Asn Val Ile Thr Ala
225                 230                 235                 240
```

```
Ile Met His Glu Tyr Lys Ile Asn Leu Gln Gly Ala Leu Tyr Trp Leu
            245                 250                 255

Ser Gly Tyr Ala Thr Lys Thr Ile Ala Lys Phe Ile Ser Asp Arg Lys
        260                 265                 270

Asn Leu Pro Ser Trp Gly Pro Val Val Asp Arg Ala Val Glu Gln Tyr
        275                 280                 285

Phe Asp Arg Val Gly Arg Cys Val Arg Gly Tyr Asp Ala Trp Ser
290                 295                 300

<210> SEQ ID NO 10
<211> LENGTH: 332
<212> TYPE: PRT
<213> ORGANISM: Artificial Sequence
<220> FEATURE:
<223> OTHER INFORMATION: Agrped1_689675_mut4

<400> SEQUENCE: 10

Met Trp Pro Trp Gln Lys Val Arg Asn Pro Leu Leu Gln Glu Val Gln
1               5                   10                  15

Asp Glu Ala Asn Glu Trp Val Lys Ser Phe Val Leu Phe Glu Pro Glu
            20                  25                  30

Gln Phe Glu Lys Phe Lys Ala Cys Asp Phe Asn Leu Leu Gly Ala Leu
        35                  40                  45

Val Gly Pro Leu Gly Thr Lys Glu Glu Leu Arg Ile Ser Cys Asp Leu
    50                  55                  60

Met Asn Phe Tyr Phe Ala Phe Asp Glu Tyr Thr Asp Leu Ala Ser Ala
65                  70                  75                  80

Asp Glu Ala Lys Val Ile Ala Arg Asp Val Met Glu Ser Phe Arg His
                85                  90                  95

Thr Asp Lys Pro Ser His Asn Lys Ile Thr Glu Met Ala Arg Gln Phe
            100                 105                 110

Phe Glu Arg Thr Ile Asn Thr Val Gly Asn Asp Pro Thr Gly Ile Glu
        115                 120                 125

Gln Phe Ile Ala Asp Phe Asp Ala Tyr Thr Thr Ser Ile Ile Gln Glu
    130                 135                 140

Ala Asp Asp Arg Ala Ser Gly His Ile Arg Ser Val Glu Asp Tyr Phe
145                 150                 155                 160

Ile Leu Arg Arg Asp Thr Cys Gly Gly Lys Pro Ser Phe Ser Phe Phe
                165                 170                 175

Gly Leu Gly Leu Asn Ile Pro Lys Glu Val Phe Ala His Pro Met Phe
            180                 185                 190

Ile Ser Met Thr Glu Ser Ala Thr Asp Leu Ile Ala Ile Thr Asn Asp
        195                 200                 205

Met His Ser Tyr Asn Leu Glu Gln Ser Arg Gly Leu Asp Gly His Asn
    210                 215                 220

Val Ile Thr Ala Ile Met His Glu Tyr Lys Ile Asn Leu Gln Gly Ala
225                 230                 235                 240

Leu Tyr Trp Leu Ser Gly Tyr Ala Thr Lys Thr Ile Ala Lys Phe Ile
                245                 250                 255

Ser Asp Arg Lys Asn Leu Pro Ser Trp Gly Pro Val Val Asp Arg Ala
            260                 265                 270

Val Glu Gln Tyr Phe Asp Arg Val Gly Arg Cys Val Arg Gly Tyr Asp
        275                 280                 285

Ala Trp Ser Tyr Glu Thr Lys Arg Tyr Tyr Gly Lys Asn Gly Leu Glu
    290                 295                 300
```

Ile Gln Lys Thr Arg Gln Ile Thr Leu Arg Pro Leu Asp Pro Ala Tyr
305                 310                 315                 320

Val Thr Lys Glu Gln Leu Gln Val Ser Met Lys Ala
                325                 330

<210> SEQ ID NO 11
<211> LENGTH: 316
<212> TYPE: PRT
<213> ORGANISM: Artificial Sequence
<220> FEATURE:
<223> OTHER INFORMATION: Agrped1_689675_mut5

<400> SEQUENCE: 11

Met Glu Ala Asn Glu Trp Val Lys Ser Phe Val Leu Phe Glu Pro Glu
1               5                   10                  15

Gln Phe Glu Lys Phe Lys Ala Cys Asp Phe Asn Leu Leu Gly Ala Leu
            20                  25                  30

Val Gly Pro Leu Gly Thr Lys Glu Glu Leu Arg Ile Ser Cys Asp Leu
        35                  40                  45

Met Asn Phe Tyr Phe Ala Phe Asp Glu Tyr Thr Asp Leu Ala Ser Ala
    50                  55                  60

Asp Glu Ala Lys Val Ile Ala Arg Asp Val Met Glu Ser Phe Arg His
65                  70                  75                  80

Thr Asp Lys Pro Ser His Asn Lys Ile Thr Glu Met Ala Arg Gln Phe
                85                  90                  95

Phe Glu Arg Thr Ile Asn Thr Val Gly Asn Asp Pro Thr Gly Ile Glu
            100                 105                 110

Gln Phe Ile Ala Asp Phe Asp Ala Tyr Thr Thr Ser Ile Ile Gln Glu
        115                 120                 125

Ala Asp Asp Arg Ala Ser Gly His Ile Arg Ser Val Glu Asp Tyr Phe
    130                 135                 140

Ile Leu Arg Arg Asp Thr Cys Gly Gly Lys Pro Ser Phe Ser Phe Phe
145                 150                 155                 160

Gly Leu Gly Leu Asn Ile Pro Lys Glu Val Phe Ala His Pro Met Phe
                165                 170                 175

Ile Ser Met Thr Glu Ser Ala Thr Asp Leu Ile Ala Ile Thr Asn Asp
            180                 185                 190

Met His Ser Tyr Asn Leu Glu Gln Ser Arg Gly Leu Asp Gly His Asn
        195                 200                 205

Val Ile Thr Ala Ile Met His Glu Tyr Lys Ile Asn Leu Gln Gly Ala
    210                 215                 220

Leu Tyr Trp Leu Ser Gly Tyr Ala Thr Lys Thr Ile Ala Lys Phe Ile
225                 230                 235                 240

Ser Asp Arg Lys Asn Leu Pro Ser Trp Gly Pro Val Val Asp Arg Ala
                245                 250                 255

Val Glu Gln Tyr Phe Asp Arg Val Gly Arg Cys Val Arg Gly Tyr Asp
            260                 265                 270

Ala Trp Ser Tyr Glu Thr Lys Arg Tyr Tyr Gly Lys Asn Gly Leu Glu
        275                 280                 285

Ile Gln Lys Thr Arg Gln Ile Thr Leu Arg Pro Leu Asp Pro Ala Tyr
    290                 295                 300

Val Thr Lys Glu Gln Leu Gln Val Ser Met Lys Ala
305                 310                 315

<210> SEQ ID NO 12

<211> LENGTH: 344
<212> TYPE: PRT
<213> ORGANISM: Artificial Sequence
<220> FEATURE:
<223> OTHER INFORMATION: Agrped1_689675_mut6

<400> SEQUENCE: 12

```
Met Ser Ser Gln Ile Tyr Ile Pro Asp Leu Leu Ile Thr Trp Pro Trp
1               5                   10                  15

Gln Lys Val Arg Asn Pro Leu Leu Gln Glu Val Gln Asp Glu Ala Asn
            20                  25                  30

Glu Trp Val Lys Ser Phe Val Leu Phe Glu Pro Glu Gln Phe Glu Lys
        35                  40                  45

Phe Lys Ala Cys Asp Phe Asn Leu Leu Gly Ala Leu Val Gly Pro Leu
    50                  55                  60

Gly Thr Lys Glu Glu Leu Arg Ile Ser Cys Asp Leu Met Asn Phe Tyr
65                  70                  75                  80

Phe Ala Phe Asp Glu Tyr Thr Asp Leu Ala Ser Ala Asp Glu Ala Lys
                85                  90                  95

Val Ile Ala Arg Asp Val Met Glu Ser Phe Arg His Thr Asp Lys Pro
            100                 105                 110

Ser His Asn Lys Ile Thr Glu Met Ala Arg Gln Phe Phe Glu Arg Thr
        115                 120                 125

Ile Asn Thr Val Gly Asn Asp Pro Thr Gly Ile Glu Gln Phe Ile Ala
    130                 135                 140

Asp Phe Asp Ala Tyr Thr Thr Ser Ile Ile Gln Glu Ala Asp Asp Arg
145                 150                 155                 160

Ala Ser Gly His Ile Arg Ser Val Glu Asp Tyr Phe Ile Leu Arg Arg
                165                 170                 175

Asp Thr Cys Gly Gly Lys Pro Ser Phe Ser Phe Phe Gly Leu Gly Leu
            180                 185                 190

Asn Ile Pro Lys Glu Val Phe Ala His Pro Met Gly Ile Ser Met Thr
        195                 200                 205

Glu Ser Ala Thr Asp Leu Ile Ala Ile Thr Asn Asp Met His Ser Tyr
    210                 215                 220

Asn Leu Glu Gln Ser Arg Gly Leu Asp Gly His Asn Val Ile Thr Ala
225                 230                 235                 240

Ile Met His Glu Tyr Lys Ile Asn Leu Gln Gly Ala Leu Tyr Trp Leu
                245                 250                 255

Ser Gly Tyr Ala Thr Lys Thr Ile Ala Lys Phe Ile Ser Asp Arg Lys
            260                 265                 270

Asn Leu Pro Ser Trp Gly Pro Val Val Asp Arg Ala Val Glu Gln Tyr
        275                 280                 285

Phe Asp Arg Val Gly Arg Cys Val Arg Gly Tyr Asp Ala Trp Ser Tyr
    290                 295                 300

Glu Thr Lys Arg Tyr Tyr Gly Lys Asn Gly Leu Glu Ile Gln Lys Thr
305                 310                 315                 320

Arg Gln Ile Thr Leu Arg Pro Leu Asp Pro Ala Tyr Val Thr Lys Glu
                325                 330                 335

Gln Leu Gln Val Ser Met Lys Ala
            340
```

<210> SEQ ID NO 13
<211> LENGTH: 344
<212> TYPE: PRT
<213> ORGANISM: Artificial Sequence
<220> FEATURE:
<223> OTHER INFORMATION: Agrped1_689675_mut7

<400> SEQUENCE: 13

```
Met Ser Ser Gln Ile Tyr Ile Pro Asp Leu Leu Ile Thr Trp Pro Trp
1               5                   10                  15

Gln Lys Val Arg Asn Pro Leu Leu Gln Glu Val Gln Asp Glu Ala Asn
            20                  25                  30

Glu Trp Val Lys Ser Phe Val Leu Phe Glu Pro Glu Gln Phe Glu Lys
        35                  40                  45

Phe Lys Ala Cys Asp Phe Asn Leu Leu Gly Ala Leu Val Gly Pro Leu
    50                  55                  60

Gly Thr Lys Glu Glu Leu Arg Ile Ser Cys Asp Leu Met Asn Phe Tyr
65                  70                  75                  80

Phe Ala Phe Asp Glu Tyr Thr Asp Leu Ala Ser Ala Glu Ala Lys
                85                  90                  95

Val Ile Ala Arg Asp Val Met Glu Ser Phe Arg His Thr Asp Lys Pro
            100                 105                 110

Ser His Asn Lys Ile Thr Glu Met Ala Arg Gln Phe Phe Glu Arg Thr
        115                 120                 125

Ile Asn Thr Val Gly Asn Asp Pro Thr Gly Ile Glu Gln Phe Ile Ala
    130                 135                 140

Asp Phe Asp Ala Tyr Thr Thr Ser Ile Ile Gln Glu Ala Asp Asp Arg
145                 150                 155                 160

Ala Ser Gly His Ile Arg Ser Val Glu Asp Tyr Phe Ile Leu Arg Arg
                165                 170                 175

Asp Thr Cys Gly Gly Lys Pro Ser Phe Ser Phe Phe Gly Leu Gly Leu
            180                 185                 190

Asn Ile Pro Lys Glu Val Phe Ala His Pro Met Val Ile Ser Met Thr
        195                 200                 205

Glu Ser Ala Thr Asp Leu Ile Ala Ile Thr Asn Asp Met His Ser Tyr
    210                 215                 220

Asn Leu Glu Gln Ser Arg Gly Leu Asp Gly His Asn Val Ile Thr Ala
225                 230                 235                 240

Ile Met His Glu Tyr Lys Ile Asn Leu Gln Gly Ala Leu Tyr Trp Leu
                245                 250                 255

Ser Gly Tyr Ala Thr Lys Thr Ile Ala Lys Phe Ile Ser Asp Arg Lys
            260                 265                 270

Asn Leu Pro Ser Trp Gly Pro Val Val Asp Arg Ala Val Glu Gln Tyr
        275                 280                 285

Phe Asp Arg Val Gly Arg Cys Val Arg Gly Tyr Asp Ala Trp Ser Tyr
    290                 295                 300

Glu Thr Lys Arg Tyr Tyr Gly Lys Asn Gly Leu Glu Ile Gln Lys Thr
305                 310                 315                 320

Arg Gln Ile Thr Leu Arg Pro Leu Asp Pro Ala Tyr Val Thr Lys Glu
                325                 330                 335

Gln Leu Gln Val Ser Met Lys Ala
            340
```

<210> SEQ ID NO 14
<211> LENGTH: 344
<212> TYPE: PRT
<213> ORGANISM: Artificial Sequence
<220> FEATURE:
<223> OTHER INFORMATION: Agrped1_689675_mut8

<400> SEQUENCE: 14

```
Met Ser Ser Gln Ile Tyr Ile Pro Asp Leu Leu Ile Thr Trp Pro Trp
1               5                   10                  15

Gln Lys Val Arg Asn Pro Leu Leu Gln Glu Val Gln Asp Glu Ala Asn
            20                  25                  30

Glu Trp Val Lys Ser Phe Val Leu Phe Glu Pro Glu Gln Phe Glu Lys
        35                  40                  45

Phe Lys Ala Cys Asp Phe Asn Leu Leu Gly Ala Leu Val Gly Pro Leu
    50                  55                  60

Gly Thr Lys Glu Glu Leu Arg Ile Ser Cys Asp Leu Met Asn Phe Tyr
65                  70                  75                  80

Phe Ala Phe Asp Glu Tyr Thr Asp Leu Ala Ser Ala Asp Glu Ala Lys
                85                  90                  95

Val Ile Ala Arg Asp Val Met Glu Ser Phe Arg His Thr Asp Lys Pro
            100                 105                 110

Ser His Asn Lys Ile Thr Glu Met Ala Arg Gln Phe Phe Glu Arg Thr
        115                 120                 125

Ile Asn Thr Val Gly Asn Asp Pro Thr Gly Ile Glu Gln Phe Ile Ala
    130                 135                 140

Asp Phe Asp Ala Tyr Thr Thr Ser Ile Ile Gln Glu Ala Asp Asp Arg
145                 150                 155                 160

Ala Ser Gly His Ile Arg Ser Val Glu Asp Tyr Phe Ile Leu Arg Arg
                165                 170                 175

Asp Thr Cys Gly Gly Lys Pro Ser Phe Ser Phe Gly Leu Gly Leu
            180                 185                 190

Asn Ile Pro Lys Glu Val Phe Ala His Pro Met Ile Ile Ser Met Thr
        195                 200                 205

Glu Ser Ala Thr Asp Leu Ile Ala Ile Thr Asn Asp Met His Ser Tyr
    210                 215                 220

Asn Leu Glu Gln Ser Arg Gly Leu Asp Gly His Asn Val Ile Thr Ala
225                 230                 235                 240

Ile Met His Glu Tyr Lys Ile Asn Leu Gln Gly Ala Leu Tyr Trp Leu
                245                 250                 255

Ser Gly Tyr Ala Thr Lys Thr Ile Ala Lys Phe Ile Ser Asp Arg Lys
            260                 265                 270

Asn Leu Pro Ser Trp Gly Pro Val Val Asp Arg Ala Val Glu Gln Tyr
        275                 280                 285

Phe Asp Arg Val Gly Arg Cys Val Arg Gly Tyr Asp Ala Trp Ser Tyr
    290                 295                 300

Glu Thr Lys Arg Tyr Tyr Gly Lys Asn Gly Leu Glu Ile Gln Lys Thr
305                 310                 315                 320

Arg Gln Ile Thr Leu Arg Pro Leu Asp Pro Ala Tyr Val Thr Lys Glu
                325                 330                 335

Gln Leu Gln Val Ser Met Lys Ala
            340
```

<210> SEQ ID NO 15
<211> LENGTH: 344
<212> TYPE: PRT
<213> ORGANISM: Artificial Sequence
<220> FEATURE:
<223> OTHER INFORMATION: Agrped1_689675_mut9

<400> SEQUENCE: 15

```
Met Ser Ser Gln Ile Tyr Ile Pro Asp Leu Leu Ile Thr Trp Pro Trp
```

```
            1               5                  10                 15
        Gln Lys Val Arg Asn Pro Leu Leu Gln Glu Val Gln Asp Glu Ala Asn
                        20                  25                  30

Glu Trp Val Lys Ser Phe Val Leu Phe Glu Pro Glu Gln Phe Glu Lys
                        35                  40                  45

Phe Lys Ala Cys Asp Phe Asn Leu Leu Gly Ala Leu Val Gly Pro Leu
                    50                  55                  60

Gly Thr Lys Glu Glu Leu Arg Ile Ser Cys Asp Leu Met Asn Phe Tyr
         65                  70                  75                  80

Phe Ala Phe Asp Glu Tyr Thr Asp Leu Ala Ser Ala Asp Glu Ala Lys
                            85                  90                  95

Val Ile Ala Arg Asp Val Met Glu Ser Phe Arg His Thr Asp Lys Pro
                        100                 105                 110

Ser His Asn Lys Ile Thr Glu Met Ala Arg Gln Phe Phe Glu Arg Thr
                        115                 120                 125

Ile Asn Thr Val Gly Asn Asp Pro Thr Gly Ile Glu Gln Phe Ile Ala
                    130                 135                 140

Asp Phe Asp Ala Tyr Thr Thr Ser Ile Ile Gln Glu Ala Asp Asp Arg
        145                 150                 155                 160

Ala Ser Gly His Ile Arg Ser Val Glu Asp Tyr Phe Ile Leu Arg Arg
                            165                 170                 175

Asp Thr Cys Gly Gly Lys Pro Ser Phe Ser Phe Phe Gly Leu Gly Leu
                        180                 185                 190

Asn Ile Pro Lys Glu Val Phe Ala His Pro Met Asp Ile Ser Met Thr
                        195                 200                 205

Glu Ser Ala Thr Asp Leu Ile Ala Ile Thr Asn Asp Met His Ser Tyr
                    210                 215                 220

Asn Leu Glu Gln Ser Arg Gly Leu Asp Gly His Asn Val Ile Thr Ala
        225                 230                 235                 240

Ile Met His Glu Tyr Lys Ile Asn Leu Gln Gly Ala Leu Tyr Trp Leu
                            245                 250                 255

Ser Gly Tyr Ala Thr Lys Thr Ile Ala Lys Phe Ile Ser Asp Arg Lys
                        260                 265                 270

Asn Leu Pro Ser Trp Gly Pro Val Val Asp Arg Ala Val Glu Gln Tyr
                        275                 280                 285

Phe Asp Arg Val Gly Arg Cys Val Arg Gly Tyr Asp Ala Trp Ser Tyr
                    290                 295                 300

Glu Thr Lys Arg Tyr Tyr Gly Lys Asn Gly Leu Glu Ile Gln Lys Thr
        305                 310                 315                 320

Arg Gln Ile Thr Leu Arg Pro Leu Asp Pro Ala Tyr Val Thr Lys Glu
                            325                 330                 335

Gln Leu Gln Val Ser Met Lys Ala
                        340
```

<210> SEQ ID NO 16
<211> LENGTH: 344
<212> TYPE: PRT
<213> ORGANISM: Artificial Sequence
<220> FEATURE:
<223> OTHER INFORMATION: Agrped1_689675_mut10

<400> SEQUENCE: 16

```
        Met Ser Ser Gln Ile Tyr Ile Pro Asp Leu Leu Ile Thr Trp Pro Trp
        1               5                   10                  15

Gln Lys Val Arg Asn Pro Leu Leu Gln Glu Val Gln Asp Glu Ala Asn
```

```
                20                  25                  30
Glu Trp Val Lys Ser Phe Val Leu Phe Glu Pro Glu Gln Phe Glu Lys
                35                  40                  45
Phe Lys Ala Cys Asp Phe Asn Leu Leu Gly Ala Leu Val Gly Pro Leu
 50                  55                  60
Gly Thr Lys Glu Glu Leu Arg Ile Ser Cys Asp Leu Met Asn Phe Tyr
 65                  70                  75                  80
Phe Ala Phe Asp Glu Tyr Thr Asp Leu Ala Ser Ala Asp Glu Ala Lys
                 85                  90                  95
Val Ile Ala Arg Asp Val Met Glu Ser Phe Arg His Thr Asp Lys Pro
                100                 105                 110
Ser His Asn Lys Ile Thr Glu Met Ala Arg Gln Phe Phe Glu Arg Thr
                115                 120                 125
Ile Asn Thr Val Gly Asn Asp Pro Thr Gly Ile Glu Gln Phe Ile Ala
                130                 135                 140
Asp Phe Asp Ala Tyr Thr Thr Ser Ile Ile Gln Glu Ala Asp Asp Arg
145                 150                 155                 160
Ala Ser Gly His Ile Arg Ser Val Glu Asp Tyr Phe Ile Leu Arg Arg
                165                 170                 175
Asp Thr Cys Gly Gly Lys Pro Ser Phe Ser Phe Gly Leu Gly Leu
                180                 185                 190
Asn Ile Pro Lys Glu Val Phe Ala His Pro Met Leu Ile Ser Met Thr
                195                 200                 205
Glu Ser Ala Thr Asp Leu Ile Ala Ile Thr Asn Asp Met His Ser Tyr
                210                 215                 220
Asn Leu Glu Gln Ser Arg Gly Leu Asp Gly His Asn Val Ile Thr Ala
225                 230                 235                 240
Ile Met His Glu Tyr Lys Ile Asn Leu Gln Gly Ala Leu Tyr Trp Leu
                245                 250                 255
Ser Gly Tyr Ala Thr Lys Thr Ile Ala Lys Phe Ile Ser Asp Arg Lys
                260                 265                 270
Asn Leu Pro Ser Trp Gly Pro Val Val Asp Arg Ala Val Glu Gln Tyr
                275                 280                 285
Phe Asp Arg Val Gly Arg Cys Val Arg Gly Tyr Asp Ala Trp Ser Tyr
                290                 295                 300
Glu Thr Lys Arg Tyr Tyr Gly Lys Asn Gly Leu Glu Ile Gln Lys Thr
305                 310                 315                 320
Arg Gln Ile Thr Leu Arg Pro Leu Asp Pro Ala Tyr Val Thr Lys Glu
                325                 330                 335
Gln Leu Gln Val Ser Met Lys Ala
                340

<210> SEQ ID NO 17
<211> LENGTH: 344
<212> TYPE: PRT
<213> ORGANISM: Artificial Sequence
<220> FEATURE:
<223> OTHER INFORMATION: Agrped1_689675_mut11

<400> SEQUENCE: 17

Met Ser Ser Gln Ile Tyr Ile Pro Asp Leu Leu Ile Thr Trp Pro Trp
  1               5                  10                  15
Gln Lys Val Arg Asn Pro Leu Leu Gln Glu Val Gln Asp Glu Ala Asn
                 20                  25                  30
Glu Trp Val Lys Ser Phe Val Leu Phe Glu Pro Glu Gln Phe Glu Lys
```

```
                35                  40                  45

Phe Lys Ala Cys Asp Phe Asn Leu Leu Gly Ala Leu Val Gly Pro Leu
    50                  55                  60

Gly Thr Lys Glu Glu Leu Arg Ile Ser Cys Asp Leu Met Asn Phe Tyr
    65                  70                  75                  80

Phe Ala Phe Asp Glu Tyr Thr Asp Leu Ala Ser Ala Asp Glu Ala Lys
                    85                  90                  95

Val Ile Ala Arg Asp Val Met Glu Ser Phe Arg His Thr Asp Lys Pro
                    100                 105                 110

Ser His Asn Lys Ile Thr Glu Met Ala Arg Gln Phe Glu Arg Thr
                    115                 120                 125

Ile Asn Thr Val Gly Asn Asp Pro Thr Gly Ile Glu Gln Phe Ile Ala
    130                 135                 140

Asp Phe Asp Ala Tyr Thr Thr Ser Ile Ile Gln Glu Ala Asp Asp Arg
    145                 150                 155                 160

Ala Ser Gly His Ile Arg Ser Val Glu Asp Tyr Phe Ile Leu Arg Arg
                    165                 170                 175

Asp Thr Cys Gly Gly Lys Pro Ser Phe Ser Phe Gly Leu Gly Leu
                    180                 185                 190

Asn Ile Pro Lys Glu Val Phe Ala His Pro Met Arg Ile Ser Met Thr
    195                 200                 205

Glu Ser Ala Thr Asp Leu Ile Ala Ile Thr Asn Asp Met His Ser Tyr
    210                 215                 220

Asn Leu Glu Gln Ser Arg Gly Leu Asp Gly His Asn Val Ile Thr Ala
    225                 230                 235                 240

Ile Met His Glu Tyr Lys Ile Asn Leu Gln Gly Ala Leu Tyr Trp Leu
                    245                 250                 255

Ser Gly Tyr Ala Thr Lys Thr Ile Ala Lys Phe Ile Ser Asp Arg Lys
                    260                 265                 270

Asn Leu Pro Ser Trp Gly Pro Val Asp Arg Ala Val Glu Gln Tyr
                    275                 280                 285

Phe Asp Arg Val Gly Arg Cys Val Arg Gly Tyr Asp Ala Trp Ser Tyr
    290                 295                 300

Glu Thr Lys Arg Tyr Tyr Gly Lys Asn Gly Leu Glu Ile Gln Lys Thr
    305                 310                 315                 320

Arg Gln Ile Thr Leu Arg Pro Leu Asp Pro Ala Tyr Val Thr Lys Glu
                    325                 330                 335

Gln Leu Gln Val Ser Met Lys Ala
                    340

<210> SEQ ID NO 18
<211> LENGTH: 331
<212> TYPE: PRT
<213> ORGANISM: Artificial Sequence
<220> FEATURE:
<223> OTHER INFORMATION: Agrped1_689675_mut12

<400> SEQUENCE: 18

Met His His His His His Ser Ser Gln Ile Tyr Ile Pro Asp Leu
1               5                   10                  15

Leu Ile Thr Trp Pro Trp Gln Lys Val Arg Asn Pro Leu Leu Gln Glu
                20                  25                  30

Val Gln Asp Glu Ala Asn Glu Trp Val Lys Ser Phe Val Leu Phe Glu
                35                  40                  45

Pro Glu Gln Phe Glu Lys Phe Lys Ala Cys Asp Phe Asn Leu Leu Gly
```

```
            50                 55                  60
Ala Leu Val Gly Pro Leu Gly Thr Lys Glu Glu Leu Arg Ile Ser Cys
 65                  70                  75                  80

Asp Leu Met Asn Phe Tyr Phe Ala Phe Asp Glu Tyr Thr Asp Leu Ala
                     85                  90                  95

Ser Ala Asp Glu Ala Lys Val Ile Ala Arg Asp Val Met Glu Ser Phe
                100                 105                 110

Arg His Thr Asp Lys Pro Ser His Asn Lys Ile Thr Glu Met Ala Arg
                115                 120                 125

Gln Phe Phe Glu Arg Thr Ile Asn Thr Val Gly Asn Asp Pro Thr Gly
                130                 135                 140

Ile Glu Gln Phe Ile Ala Asp Phe Asp Ala Tyr Thr Thr Ser Ile Ile
145                 150                 155                 160

Gln Glu Ala Asp Asp Arg Ala Ser Gly His Ile Arg Ser Val Glu Asp
                165                 170                 175

Tyr Phe Thr Leu Arg Arg Asp Thr Cys Gly Ala Lys Pro Ser Phe Ser
                180                 185                 190

Phe Phe Gly Leu Gly Leu Asn Ile Pro Asp Glu Val Phe His His Pro
                195                 200                 205

Val Val Ile Ser Met Ile Glu Gly Ala Thr Asp Leu Ile Ala Val Thr
                210                 215                 220

Asn Asp Met His Ser Tyr Asn Leu Glu His Ser Arg Gly Leu Asp Gly
225                 230                 235                 240

His Asn Val Ile Thr Ala Ile Met His Glu Tyr Gln Leu Asp Leu Gln
                245                 250                 255

Gly Ala Leu Tyr Trp Leu Ser Gly Tyr Ala Thr His Thr Ile Ala Asn
                260                 265                 270

Phe Leu Ser Asn Arg Arg Asn Leu Pro Ser Trp Gly Pro Ala Val Asp
                275                 280                 285

Lys Ala Val Glu Glu Phe Phe Asp Arg Val Gly Arg Cys Val Arg Gly
                290                 295                 300

Tyr Asp Ala Trp Ser Tyr Glu Thr Lys Arg Tyr Tyr Gly Lys Asn Gly
305                 310                 315                 320

Leu Gln Val Gln Lys Thr Arg Arg Ile Thr Leu
                325                 330

<210> SEQ ID NO 19
<211> LENGTH: 343
<212> TYPE: PRT
<213> ORGANISM: Artificial Sequence
<220> FEATURE:
<223> OTHER INFORMATION: Agrped1_689675_mut13

<400> SEQUENCE: 19

Met Ser Gln Phe Ile Ile Pro Asp Leu Leu Ser Thr Trp Pro Trp Gln
 1               5                  10                  15

Arg Val Ser Asn Pro Met Trp Arg Glu Ile Asp Glu Glu Ala Asn Ala
                20                  25                  30

Trp Val Gln Ser Phe Asp Leu Phe Glu Pro Ser Gln Phe Glu Lys Phe
                35                  40                  45

Lys Met Cys Asp Phe Asn Leu Leu Gly Ser Met Ile Gly Thr Val Glu
                50                  55                  60

Thr Lys Asp His Leu Arg Ile Ser Cys Asp Leu Met Asn Phe Tyr Phe
 65                  70                  75                  80

Ala Phe Asp Glu Tyr Thr Asp Met Ala Ser Lys Asp Glu Ala Arg Lys
```

```
                    85                  90                  95
Ile Ala Arg Asp Val Met Asp Ala Phe Arg Asn Thr Glu Lys Pro Ala
                100                 105                 110
His Asn Gln Ile Thr Glu Met Ala Arg Gln Phe Phe Lys Arg Thr Ile
            115                 120                 125
Asp Thr Val Gly Lys Asp Leu Pro Gly Val Glu Arg Phe Ile Ala Asp
        130                 135                 140
Phe Asp Ala Tyr Thr His Ser Val Ile Gln Glu Ala Asp Arg Ala
145                 150                 155                 160
Thr Gly His Ile Arg Ser Val Asn Asp Tyr Phe Ile Leu Arg Arg Asp
                165                 170                 175
Thr Cys Gly Gly Lys Pro Ser Phe Ser Phe Gly Leu Gly Leu Asn
            180                 185                 190
Ile Pro Lys Glu Val Phe Ala His Pro Met Phe Ile Ser Met Thr Glu
        195                 200                 205
Ser Ala Thr Asp Leu Ile Ala Ile Thr Asn Asp Met His Ser Tyr Asn
    210                 215                 220
Leu Glu Gln Ser Arg Gly Leu Asp Gly His Asn Val Ile Thr Ala Ile
225                 230                 235                 240
Met His Glu Tyr Lys Ile Asn Leu Gln Gly Ala Leu Tyr Trp Leu Ser
                245                 250                 255
Gly Tyr Ala Thr Lys Thr Ile Ala Lys Phe Ile Ser Arg Lys Asn
            260                 265                 270
Leu Pro Ser Trp Gly Pro Val Val Asp Arg Ala Val Glu Gln Tyr Phe
        275                 280                 285
Asp Arg Val Gly Arg Cys Val Arg Gly Tyr Asp Ala Trp Ser Tyr Glu
    290                 295                 300
Thr Lys Arg Tyr Tyr Gly Lys Asn Gly Leu Glu Ile Gln Lys Thr Arg
305                 310                 315                 320
Gln Ile Thr Leu Arg Pro Leu Asp Pro Ala Tyr Val Thr Lys Glu Gln
                325                 330                 335
Leu Gln Val Ser Met Lys Ala
            340

<210> SEQ ID NO 20
<211> LENGTH: 356
<212> TYPE: PRT
<213> ORGANISM: Artificial Sequence
<220> FEATURE:
<223> OTHER INFORMATION: AAE3_109435_mut1

<400> SEQUENCE: 20

Met His Ser Ser Thr Gln Leu Phe Thr His Ser Pro Thr Lys Met Gln
1               5                   10                  15
Ile Ile Leu Pro Asp Leu Leu Cys Ser Trp Gly Tyr Lys Gly Phe Leu
                20                  25                  30
Asn Pro His Tyr Glu Gly Ala Lys Ala Glu Ser Asn Thr Trp Ile Arg
            35                  40                  45
Pro Leu Val Val Lys Leu Phe Asp Glu Arg Gly Gln Lys Ala Phe Ala
        50                  55                  60
Lys Asp Tyr Thr Gly Leu Leu Ala Ser Met Thr Tyr Pro His His Asn
65                  70                  75                  80
Lys Glu Phe Leu Cys Val Ala Cys Asp Met Met Asn Leu Phe Phe Val
                85                  90                  95
Tyr Asp Glu Tyr Thr Asp Ile Thr Pro Pro Glu Thr Ala Gln Arg Leu
```

```
                    100                 105                 110
Ala Lys Ile Val Val Asn Ala Met Arg Asn Pro Asp Glu Ile Ala Ala
            115                 120                 125

Leu Gly Glu Asp Ser Ile Gly Thr Met Thr Lys Gln Phe Trp Arg Arg
130                 135                 140

Ala Met Thr Leu Leu Pro Pro Asn Gly Cys Asn Ser Glu Ser Cys Ile
145                 150                 155                 160

Gln His Phe Ile Asp Tyr Thr Glu Glu Tyr Leu Thr Ala Val Thr Arg
                165                 170                 175

Glu Ala Cys Asp Arg Ser Ser Gly Ser Val His Ala Val Lys Asp Tyr
            180                 185                 190

Leu Ala Met Arg Arg Ala Thr Ser Gly Ala Gly Leu Met Val Gly Leu
            195                 200                 205

Leu Glu Phe Gly Leu Asp Leu Pro Glu Glu Val Met Lys His Glu Val
            210                 215                 220

Ile Gln Glu Leu Ser Thr Gly Ala Ile Asp Met Tyr Cys Leu Leu Asn
225                 230                 235                 240

Asp Met His Ser Tyr Ala Ser Glu Leu Ser Ser Gly Gln Ala Ser His
                245                 250                 255

Asn Val Ile Thr Val Val Met His Glu Arg Asn Leu Ser Leu Gln Glu
            260                 265                 270

Ala Phe Asp Trp Leu Ala Ser Tyr Ala Ala Gly Val Val Lys Gly Phe
            275                 280                 285

Lys Thr Asn Leu Asn Arg Val Pro Ser Phe Ser Glu Leu Glu Asp His
            290                 295                 300

Ser Leu His Gly Glu Gly Met Leu Arg Asp Arg Ile Gln Arg Tyr Ile
305                 310                 315                 320

Asp Gly Leu Gly Gln Ala Val Arg Ala Glu Asp Trp Ala Phe Glu
                325                 330                 335

Thr Thr Arg Tyr His Gly Gln Asn Gly Pro Gln Ile Lys Leu Thr Arg
                340                 345                 350

Met Leu Thr Ile
        355

<210> SEQ ID NO 21
<211> LENGTH: 324
<212> TYPE: PRT
<213> ORGANISM: Artificial Sequence
<220> FEATURE:
<223> OTHER INFORMATION: Agrped1_689671_mut1

<400> SEQUENCE: 21

Met Ser Gln Phe Ile Ile Pro Asp Leu Leu Ser Thr Trp Pro Trp Gln
1               5                   10                  15

Arg Val Ser Asn Pro Met Trp Arg Glu Ile Asp Glu Glu Ala Asn Ala
            20                  25                  30

Trp Val Gln Ser Phe Asp Leu Phe Glu Pro Ser Gln Phe Glu Lys Phe
        35                  40                  45

Lys Met Cys Asp Phe Asn Leu Leu Gly Ser Met Ile Gly Thr Val Glu
    50                  55                  60

Thr Lys Asp His Leu Arg Ile Ser Cys Asp Leu Met Asn Phe Tyr Phe
65                  70                  75                  80

Ala Phe Asp Glu Tyr Thr Asp Met Ala Ser Lys Asp Glu Ala Arg Lys
                85                  90                  95

Ile Ala Arg Asp Val Met Asp Ala Phe Arg Asn Thr Glu Lys Pro Ala
```

```
                100             105             110
His Asn Gln Ile Thr Glu Met Ala Arg Gln Phe Phe Lys Arg Thr Ile
            115                 120                 125

Asp Thr Val Gly Lys Asp Leu Pro Gly Val Glu Arg Phe Ile Ala Asp
130                 135                 140

Phe Asp Ala Tyr Thr His Ser Val Ile Gln Glu Ala Asp Arg Ala
145                 150                 155                 160

Thr Gly His Ile Arg Ser Val Asn Asp Tyr Phe Thr Leu Arg Arg Asp
            165                 170                 175

Thr Cys Gly Ala Lys Pro Ser Phe Ser Phe Phe Gly Leu Gly Leu Asn
            180                 185                 190

Ile Pro Asp Glu Val Phe His His Pro Val Val Ile Ser Met Ile Glu
            195                 200                 205

Gly Ala Thr Asp Leu Ile Ala Val Thr Asn Asp Met His Ser Tyr Asn
            210                 215                 220

Leu Glu His Ser Arg Gly Leu Asp Gly His Asn Val Ile Thr Ala Ile
225                 230                 235                 240

Met His Glu Tyr Gln Leu Asp Leu Gln Gly Ala Leu Tyr Trp Leu Ser
                    245                 250                 255

Gly Tyr Ala Thr His Thr Ile Ala Asn Phe Leu Ser Asn Arg Arg Asn
                260                 265                 270

Leu Pro Ser Trp Gly Pro Ala Val Asp Lys Ala Val Glu Glu Phe Phe
            275                 280                 285

Asp Arg Val Gly Arg Cys Val Arg Gly Tyr Asp Ala Trp Ser Tyr Glu
290                 295                 300

Thr Lys Arg Tyr Tyr Gly Lys Asn Gly Leu Gln Val Gln Lys Thr Arg
305                 310                 315                 320

Arg Ile Thr Leu
```

<210> SEQ ID NO 22
<211> LENGTH: 325
<212> TYPE: PRT
<213> ORGANISM: Artificial Sequence
<220> FEATURE:
<223> OTHER INFORMATION: Galma_223690_mut1

<400> SEQUENCE: 22

```
Met Pro Ser Gln Phe Thr Ile Pro Asp Leu Leu Ile Thr Trp Pro Trp
1               5                   10                  15

Gln Glu Ile Thr Asn Pro Met Leu His Glu Val Asp Ala Glu Ala Asn
            20                  25                  30

Glu Trp Val Gln Ser Leu Asn Leu Phe Glu Pro Lys Gln Phe Glu Lys
        35                  40                  45

Phe Lys Ala Cys Asn Phe Leu Leu Gly Ser Leu Val Gly Pro Leu
    50                  55                  60

Pro Ser Arg Asp His Leu Arg Val Ser Cys Asp Leu Met Asn Phe Tyr
65                  70                  75                  80

Phe Ala Phe Asp Glu Tyr Thr Asp Met Ala Asn Lys Asp Glu Ala Met
                    85                  90                  95

Arg Ile Ala Arg Asp Val Met Gln Ala Phe Arg Asn Thr Asp Thr Pro
                100                 105                 110

Ser Asn Ser Lys Ile Thr Glu Met Ala Arg Gln Phe Phe Lys Arg Thr
            115                 120                 125

Ile Glu Val Val Gly Glu Asp Leu Pro Gly Ile Glu Arg Phe Ile Ala
130                 135                 140
```

Asp Phe Asp Ala Tyr Thr Arg Ser Val Ile Gln Glu Ala Asp Arg
145                 150                 155                 160

Val Ala Gly His Ile Arg Asn Val Glu Asp Tyr Phe Ile Leu Arg Arg
                165                 170                 175

Asp Thr Cys Gly Ala Lys Pro Ser Phe Ser Phe Tyr Gly Leu Gly Leu
            180                 185                 190

Asn Ile Pro Thr Glu Val Phe Glu His Pro Leu Leu Ile Ser Met Val
        195                 200                 205

Glu Ser Ala Thr Asp Leu Ile Ala Val Thr Asn Asp Met His Ser Tyr
    210                 215                 220

Gly Leu Glu His Ser Arg Gly Leu Asp Gly His Asn Val Ile Thr Ala
225                 230                 235                 240

Ile Met His Glu Tyr Gln Leu Asp Leu Gln Gly Ala Leu Tyr Trp Leu
                245                 250                 255

Ser Gly Tyr Ala Thr Lys Thr Ile Ser Lys Phe Leu Thr Asp Arg Lys
            260                 265                 270

Asn Leu Pro Ser Trp Gly Pro Thr Ile Asp Lys Ala Leu Glu Ile Tyr
        275                 280                 285

Leu Asp Arg Leu Gly Arg Cys Val Arg Gly Tyr Asp Ala Trp Ser Tyr
    290                 295                 300

Ser Thr Lys Arg Tyr Tyr Gly Lys Asn Gly Leu Lys Val Gln Lys Thr
305                 310                 315                 320

Arg Arg Ile Thr Leu
                325

<210> SEQ ID NO 23
<211> LENGTH: 326
<212> TYPE: PRT
<213> ORGANISM: Artificial Sequence
<220> FEATURE:
<223> OTHER INFORMATION: Hypsu_148385_mut1

<400> SEQUENCE: 23

Met Ser Ala Gln Tyr Thr Ile Pro Asp Leu Leu Ala Asn Trp Pro Trp
1               5                   10                  15

Gln Arg Val Thr Asn Ser Met Leu Asp Glu Val Arg Asp Glu Ala Asn
                20                  25                  30

Glu Trp Val Met Ser Leu Gly Leu Phe Glu Pro Ala Gln Phe Lys Lys
            35                  40                  45

Phe Lys Ala Cys Asp Phe Asn Leu Leu Ala Ser Phe Ile Gly Pro Leu
        50                  55                  60

Glu Ser Lys Glu His Leu Arg Val Ala Cys Asp Leu Met Asn Phe Tyr
65                  70                  75                  80

Phe Ala Phe Asp Glu Tyr Thr Asp Val Ala Asn Arg Glu Glu Ala Lys
                85                  90                  95

Lys Ile Ser Gln Gly Val Met His Ala Phe Lys Thr Arg Ser Ala Glu
            100                 105                 110

Pro Ser Ser Ser Lys Ile Thr Glu Met Ala Arg Gln Phe Phe Arg Arg
        115                 120                 125

Thr Val Asp Val Val Gly Glu Asp Ser Pro Ala Ile Asn Gln Phe Ile
    130                 135                 140

Thr Asp Phe Asp Thr Tyr Thr Thr Ala Val Ile Gln Glu Ala Asp Asp
145                 150                 155                 160

Arg Thr Glu Gly Thr Ile Arg Asn Val Glu Asp Tyr Phe Thr Leu Arg
                165                 170                 175

```
Arg Asp Thr Cys Gly Ala Lys Pro Ser Phe Ser Phe Ala Leu Gly
        180                 185                 190

Leu Asn Met Pro Thr Glu Val Phe Glu His Pro Leu Ile Met Ser Leu
            195                 200                 205

Val Glu Arg Ala Thr Asp Leu Ile Ala Ile Val Asn Asp Met His Ser
210                 215                 220

Tyr Gly Leu Glu Arg Ala Arg Gly Leu Asp Gly His Asn Val Val Thr
225                 230                 235                 240

Ser Ile Met Tyr Glu His Gln Leu Asp Leu Gln Gly Ala Leu His Trp
                245                 250                 255

Leu Ala Gly Tyr Ala Glu Asp Thr Ile Ala Lys Phe Leu Ser Glu Lys
            260                 265                 270

Glu Arg Leu Pro Ser Trp Gly Pro Ala Val Asp Val Ser Val Gln Glu
        275                 280                 285

Phe Val Asp Arg Leu Gly Arg Cys Val Arg Gly Tyr Asp Ala Trp Ser
    290                 295                 300

Tyr Glu Thr Asn Arg Tyr Tyr Gly Ser His Gly Leu Gln Ile Arg Gln
305                 310                 315                 320

Thr Arg Gln Ile Thr Leu
                325

<210> SEQ ID NO 24
<211> LENGTH: 620
<212> TYPE: PRT
<213> ORGANISM: Artificial Sequence
<220> FEATURE:
<223> OTHER INFORMATION: Ec.dxs_SL3

<400> SEQUENCE: 24

Met Ser Phe Asp Ile Ala Lys Tyr Pro Thr Leu Ala Leu Val Asp Ser
1               5                   10                  15

Thr Gln Glu Leu Arg Leu Leu Pro Lys Glu Ser Leu Pro Lys Leu Cys
            20                  25                  30

Asp Glu Leu Arg Arg Tyr Leu Leu Asp Ser Val Ser Arg Ser Ser Gly
        35                  40                  45

His Phe Ala Ser Gly Leu Gly Thr Val Glu Leu Thr Val Ala Leu His
    50                  55                  60

Tyr Val Tyr Asn Thr Pro Phe Asp Gln Leu Ile Trp Asp Val Gly His
65                  70                  75                  80

Gln Ala Tyr Pro His Lys Ile Leu Thr Gly Arg Arg Asp Lys Ile Gly
                85                  90                  95

Thr Ile Arg Gln Lys Gly Gly Leu Thr Pro Phe Pro Trp Arg Gly Glu
            100                 105                 110

Ser Glu Tyr Asp Val Leu Ser Val Gly His Ser Ser Thr Ser Ile Ser
        115                 120                 125

Ala Gly Ile Gly Ile Ala Val Ala Ala Glu Lys Glu Gly Lys Asn Arg
    130                 135                 140

Arg Thr Val Cys Val Ile Gly Asp Gly Ala Ile Thr Ala Gly Met Ala
145                 150                 155                 160

Phe Glu Ala Met Asn His Ala Gly Asp Ile Arg Pro Asp Met Leu Val
                165                 170                 175

Ile Leu Asn Asp Asn Glu Met Ser Ile Ser Glu Asn Val Gly Ala Leu
            180                 185                 190

Asn Asn His Leu Ala Gln Leu Leu Ser Gly Lys Leu Tyr Ser Ser Leu
        195                 200                 205
```

```
Arg Glu Gly Gly Lys Lys Val Phe Ser Gly Val Pro Pro Ile Lys Glu
            210                 215                 220
Leu Leu Lys Arg Thr Glu Glu His Ile Lys Gly Met Val Val Pro Gly
225                 230                 235                 240
Thr Leu Phe Glu Glu Leu Gly Phe Asn Tyr Ile Gly Pro Val Asp Gly
                245                 250                 255
His Asp Val Leu Gly Leu Ile Thr Thr Leu Lys Asn Met Arg Asp Leu
            260                 265                 270
Lys Gly Pro Gln Phe Leu His Ile Met Thr Lys Lys Gly Arg Gly Tyr
            275                 280                 285
Glu Pro Ala Glu Lys Asp Pro Ile Thr Phe His Ala Val Pro Lys Phe
            290                 295                 300
Asp Pro Ser Ser Gly Cys Leu Pro Lys Ser Ser Gly Gly Leu Pro Ser
305                 310                 315                 320
Tyr Ser Lys Ile Phe Gly Asp Trp Leu Cys Glu Thr Ala Ala Lys Asp
                325                 330                 335
Asn Lys Leu Met Ala Ile Thr Pro Ala Met Arg Glu Gly Ser Gly Met
            340                 345                 350
Val Glu Phe Ser Arg Lys Phe Pro Asp Arg Tyr Phe Asp Val Ala Ile
            355                 360                 365
Ala Glu Gln His Ala Val Thr Phe Ala Ala Gly Leu Ala Ile Gly Gly
370                 375                 380
Tyr Lys Pro Ile Val Ala Ile Tyr Ser Thr Phe Leu Gln Arg Ala Tyr
385                 390                 395                 400
Asp Gln Val Leu His Asp Val Ala Ile Gln Lys Leu Pro Val Leu Phe
                405                 410                 415
Ala Ile Asp Arg Ala Gly Ile Val Gly Ala Asp Gly Gln Thr His Gln
            420                 425                 430
Gly Ala Phe Asp Leu Ser Tyr Leu Arg Cys Ile Pro Glu Met Val Ile
            435                 440                 445
Met Thr Pro Ser Asp Glu Asn Glu Cys Arg Gln Met Leu Tyr Thr Gly
450                 455                 460
Tyr His Tyr Asn Asp Gly Pro Ser Ala Val Arg Tyr Pro Arg Gly Asn
465                 470                 475                 480
Ala Val Gly Val Glu Leu Thr Pro Leu Glu Lys Leu Pro Ile Gly Lys
                485                 490                 495
Gly Ile Val Lys Arg Arg Gly Glu Lys Leu Ala Ile Leu Asn Phe Gly
            500                 505                 510
Thr Leu Met Pro Glu Ala Ala Lys Val Ala Glu Ser Leu Asn Ala Thr
            515                 520                 525
Leu Val Asp Met Arg Phe Val Lys Pro Leu Asp Glu Ala Leu Ile Leu
            530                 535                 540
Glu Met Ala Ala Ser His Glu Ala Leu Val Thr Val Glu Glu Asn Ala
545                 550                 555                 560
Ile Met Gly Gly Ala Gly Ser Gly Val Asn Glu Val Leu Met Ala His
                565                 570                 575
Arg Lys Pro Val Pro Val Leu Asn Ile Gly Leu Pro Asp Phe Phe Ile
            580                 585                 590
Pro Gln Gly Thr Gln Glu Glu Met Arg Ala Glu Leu Gly Leu Asp Ala
            595                 600                 605
Ala Gly Met Glu Ala Lys Ile Lys Ala Trp Leu Ala
610                 615                 620
```

<210> SEQ ID NO 25
<211> LENGTH: 620
<212> TYPE: PRT
<213> ORGANISM: Artificial Sequence
<220> FEATURE:
<223> OTHER INFORMATION: Ec.dxs_SL5

<400> SEQUENCE: 25

```
Met Ser Phe Asp Ile Ala Lys Tyr Pro Thr Leu Ala Leu Val Asp Ser
1               5                   10                  15

Thr Gln Glu Leu Arg Leu Leu Pro Lys Glu Ser Leu Pro Lys Leu Cys
            20                  25                  30

Asp Glu Leu Arg Arg Tyr Leu Leu Asp Ser Val Ser Arg Ser Ser Gly
        35                  40                  45

His Phe Ala Ser Gly Leu Gly Thr Val Glu Leu Thr Val Ala Leu His
    50                  55                  60

Tyr Val Tyr Asn Thr Pro Phe Asp Gln Leu Ile Trp Asp Val Gly His
65                  70                  75                  80

Gln Ala Tyr Pro His Lys Ile Leu Thr Gly Arg Arg Asp Lys Ile Gly
                85                  90                  95

Thr Ile Arg Gln Lys Gly Gly Leu Phe Pro Phe Pro Trp Arg Gly Glu
            100                 105                 110

Ser Glu Tyr Asp Val Leu Ser Val Gly His Ser Ser Thr Ser Ile Ser
        115                 120                 125

Ala Gly Ile Gly Ile Ala Val Ala Ala Glu Lys Glu Gly Lys Asn Arg
    130                 135                 140

Arg Thr Val Cys Val Ile Gly Asp Gly Ala Ile Thr Ala Gly Met Ala
145                 150                 155                 160

Phe Glu Ala Met Asn His Ala Gly Asp Ile Arg Pro Asp Met Leu Val
                165                 170                 175

Ile Leu Asn Asp Asn Glu Met Ser Ile Ser Glu Asn Val Gly Ala Leu
            180                 185                 190

Asn Asn His Leu Ala Gln Leu Leu Ser Gly Lys Leu Tyr Ser Ser Leu
        195                 200                 205

Arg Asp Gly Gly Lys Lys Val Phe Ser Gly Val Pro Pro Ile Lys Glu
    210                 215                 220

Leu Leu Lys Arg Thr Glu Glu His Ile Lys Gly Met Val Val Pro Gly
225                 230                 235                 240

Thr Leu Phe Glu Glu Leu Gly Phe Asn Tyr Ile Gly Pro Val Asp Gly
                245                 250                 255

His Asp Val Leu Gly Leu Ile Thr Thr Leu Lys Asn Met Arg Asp Leu
            260                 265                 270

Lys Gly Pro Gln Phe Leu His Ile Met Thr Lys Lys Gly Arg Gly Tyr
        275                 280                 285

Glu Pro Ala Glu Lys Asp Pro Ile Thr Phe His Ala Val Pro Lys Phe
    290                 295                 300

Asp Pro Ser Ser Gly Cys Leu Pro Lys Ser Ser Gly Gly Leu Pro Ser
305                 310                 315                 320

Tyr Ser Lys Ile Phe Gly Asp Trp Leu Cys Glu Thr Ala Ala Lys Asp
                325                 330                 335

Asn Lys Leu Met Ala Ile Thr Pro Ala Met Arg Glu Gly Ser Gly Met
            340                 345                 350

Val Glu Phe Ser Arg Lys Phe Pro Asp Arg Tyr Phe Asp Val Ala Ile
        355                 360                 365
```

```
Ala Glu Gln His Ala Val Thr Phe Ala Ala Gly Leu Ala Ile Gly Gly
    370                 375                 380

Tyr Lys Pro Ile Val Ala Ile Tyr Ser Thr Phe Leu Gln Arg Ala Tyr
385                 390                 395                 400

Asp Gln Val Leu His Asp Val Ala Ile Gln Lys Leu Pro Val Thr Phe
                405                 410                 415

Ala Ile Asp Arg Ala Gly Ile Val Gly Ala Asp Gly Gln Thr His Gln
                420                 425                 430

Gly Ala Phe Asp Leu Ser Tyr Leu Arg Cys Ile Pro Glu Met Val Ile
                435                 440                 445

Met Thr Pro Ser Asp Glu Asn Glu Cys Arg Leu Met Leu Tyr Thr Gly
    450                 455                 460

Tyr His Tyr Asn Asp Gly Pro Ser Ala Val Arg Tyr Pro Arg Gly Asn
465                 470                 475                 480

Ala Val Gly Val Glu Leu Thr Pro Leu Glu Lys Leu Pro Ile Gly Lys
                485                 490                 495

Gly Ile Val Lys Arg Arg Gly Glu Lys Leu Ala Ile Leu Asn Phe Gly
                500                 505                 510

Thr Leu Met Pro Glu Ala Ala Lys Val Ala Glu Ser Leu Asn Ala Thr
    515                 520                 525

Leu Val Asp Met Arg Phe Val Lys Pro Leu Asp Glu Ala Leu Ile Leu
    530                 535                 540

Glu Met Ala Ala Ser His Glu Ala Leu Val Thr Val Glu Glu Asn Ala
545                 550                 555                 560

Ile Met Gly Gly Ala Gly Ser Gly Val Asn Glu Val Leu Met Ala His
                565                 570                 575

Arg Lys Pro Val Pro Val Leu Asn Ile Gly Leu Pro Asp Phe Phe Ile
                580                 585                 590

Pro Gln Gly Thr Gln Glu Met Arg Ala Glu Leu Gly Leu Asp Ala
                595                 600                 605

Ala Gly Met Glu Ala Lys Ile Lys Ala Trp Leu Ala
    610                 615                 620

<210> SEQ ID NO 26
<211> LENGTH: 659
<212> TYPE: PRT
<213> ORGANISM: Agrocybe aegerita

<400> SEQUENCE: 26

Met Pro Gly Ser Ala Asn Trp Thr Ala Asp Arg Phe Tyr Ile Pro Asp
1               5                   10                  15

Thr Leu Ala Asn Trp Pro Trp Pro Arg Ala Ile Asn Pro Ala Tyr Glu
                20                  25                  30

Glu Cys Lys Ala Ala Ser Ala Trp Cys Glu Lys Tyr Gly Ala Phe
                35                  40                  45

Ser Ala Arg Ala Gln Lys Ala Phe Asn Leu Cys Asp Phe Asn Leu Leu
                50                  55                  60

Ala Ser Leu Ala Tyr Ala Gly Leu Pro Ala Asp Val Asn Arg Val Gly
65              70                  75                  80

Cys Asp Leu Met Asn Leu Phe Phe Val Val Asp Glu His Thr Asp Ala
                85                  90                  95

Met Asp Ala Arg Ser Val Gln Asp Trp Val Asp Ile Val Val Asp Ala
                100                 105                 110

Leu His His Pro Arg Thr Pro Arg Pro Ala Gly Glu Pro Lys Val Gly
                115                 120                 125
```

```
Glu Ile Ala Arg Thr Phe Trp Glu Asn Gly Ile Lys Cys Met Gly Pro
        130                 135                 140

Thr Ala Gln Arg Arg Phe Val Glu Thr Phe Thr Thr Tyr Leu Gln Ser
145                 150                 155                 160

Val Val Thr Gln Ala Gln Asp Arg Asp Lys His Leu Phe Arg Asp Val
                165                 170                 175

Asp Ser Tyr Met Glu Val Arg Arg Asp Thr Ile Gly Ala Lys Pro Ser
            180                 185                 190

Phe Ala Leu Leu Glu His Asp Met Glu Leu Pro Asp Asp Val Phe Tyr
        195                 200                 205

His Pro Leu Leu Glu Lys Leu Arg Glu Trp Ala Ile Asp Met Leu Ile
210                 215                 220

Leu Gly Asn Asp Leu Cys Ser Tyr Asn Val Glu Gln Ser Arg Gly Asp
225                 230                 235                 240

Asp Gly His Asn Ile Ile Arg Leu Ala Met Leu Gln Glu Asn Thr Asn
                245                 250                 255

Val His Gly Ala Leu Arg Phe Val Ser Lys Met His Asp Asp Leu Ala
            260                 265                 270

Glu Lys Phe Leu Ser Asn Tyr Gln Gly Met Pro Ser Phe Thr Pro Gln
        275                 280                 285

Ile Asp Ala Trp Val Thr Arg Tyr Ile Asp Gly Leu Gly Asn Trp Val
290                 295                 300

Arg Ala Asn Asp Ser Trp Ser Phe Glu Ser Trp Arg Tyr Phe Lys Gly
305                 310                 315                 320

Asp Val Leu Arg Val Gln Ala Glu Arg Trp Val Glu Leu Leu Pro Pro
                325                 330                 335

Ala Pro Lys Asp Glu Leu Thr Ser Ser Ile Pro Pro Gly Ser Arg Trp
            340                 345                 350

Ile Lys Pro Ala Val Glu Pro Ser Arg Ala Arg Pro Asn Asn Val Gly
        355                 360                 365

Ile Val Ala Leu Asp Thr Tyr Thr Pro Thr Ser Glu Asp Asp Phe Gln
370                 375                 380

Thr Leu Ala Val Lys Thr Val Ser Ser Leu Leu Ser Lys Tyr Asn Ile
385                 390                 395                 400

Asn Pro Val Ser Val Gly Arg Leu Asp Ile Cys Ile Glu Arg Ala Ala
                405                 410                 415

Asp Pro Tyr Ile Ile Tyr Ala Leu Arg Asp Ala Phe Ala Ser Ala Gly
            420                 425                 430

Asn Thr Asp Val Glu Ala Ile Val Ser Ser Lys Ser Val Val Gly
        435                 440                 445

Leu Phe Asn Ala Ile Asn Trp Val Glu Ser Ser Trp Asp Gly Arg
450                 455                 460

Tyr Ala Ile Val Phe Ala Gly Asp Leu Ser Ser Gly Val Ser Ala Ala
465                 470                 475                 480

Leu Val Gly Pro Asp Ala Pro Ile Val Val Glu Pro Thr Arg Gly Thr
                485                 490                 495

Tyr Leu Gly Asp Pro Ile Ala Ser Thr Asp Glu Ala Gln Gly Ser Tyr
            500                 505                 510

Ile Asp Ser Leu Phe Gln Ser Tyr Ser His Tyr Arg Lys Lys His Pro
        515                 520                 525

Gln Phe Ser Lys Thr Ser Gly Ala Pro Asn Gly Ala His Thr Pro Thr
530                 535                 540
```

```
Thr Thr Asn Gly Ser Ile Lys Ser Asn Gly Phe Val Ser Gly Asp Thr
545                 550                 555                 560

Asn Gly His Ala Asn Gly Asn Gly His Val Gln Thr Arg Ser Ser Thr
            565                 570                 575

Pro Ser Ser Ser Ser Ser Thr Ser Ser Pro Ser Phe Asp Tyr Met
                580                 585                 590

Ile Leu His Asp Arg His Gly Lys Ile Pro Thr Gly Ala Gly Ser Ile
            595                 600                 605

Tyr Leu Gly Leu Ala Ser Leu Ile Thr Asp Ile Ala Pro Glu Thr Leu
            610                 615                 620

Ala Gly Lys Ser Ile Gly Val Phe Gly Phe Ala Asn Ser Thr Ser Thr
625                 630                 635                 640

Phe Phe Gly Ile Arg Val Ala Gly Asp Cys Ser Val Ile Cys Lys Gln
            645                 650                 655

Leu Gln Ala

<210> SEQ ID NO 27
<211> LENGTH: 353
<212> TYPE: PRT
<213> ORGANISM: Agrocybe aegerita

<400> SEQUENCE: 27

Met Ser Glu Gln Gln Tyr Thr Leu Pro Asp Leu Leu Gln Asn Trp Pro
1               5                   10                  15

Trp Asn Arg His Leu Ser Pro Tyr Tyr Glu Ala Lys Arg Glu Ser
            20                  25                  30

Ser Ala Trp Val Glu Ser Phe Lys Pro Phe Asp Gln Asp Gly Gln Arg
        35                  40                  45

Ala Phe Asp Ala Tyr Leu Leu Ala Ser Leu Thr Tyr Ser His Gly Ser
    50                  55                  60

Arg Glu Phe Val Arg Leu Gly Cys Asp Leu Met Asn Phe Tyr Phe Val
65                  70                  75                  80

Tyr Asp Glu Tyr Thr Asp Val Ser Asp Ser Ala Val Ala Asp Arg Leu
                85                  90                  95

Ala Asn Ile Val Ile Asp Ala Met Arg Asn Pro Glu Asn Ser Ser Gln
            100                 105                 110

Ser Gly Asp His Leu Leu Gly Lys Met Thr Lys His Phe Trp Thr Arg
        115                 120                 125

Ala Leu Ala Met Ala Pro Ala Gly Ser Pro Cys Phe Glu His Phe Ile
    130                 135                 140

Thr Thr Ser Glu Thr Tyr Leu Arg Ala Val Thr Gln Glu Ala Glu Asp
145                 150                 155                 160

Arg Ala Asn Lys Arg Val Arg Lys Val Asp Asp Tyr Leu Arg Leu Arg
                165                 170                 175

Arg Asp Thr Cys Gly Ala Arg Pro Thr Leu Ala Leu Ile Glu Phe Gly
            180                 185                 190

Leu Asn Leu Pro Asn Glu Val Val Arg His Pro Ser Leu Val Ala Leu
        195                 200                 205

Thr Glu Ala Ala Val Asp Leu Ile Ile Leu Val Asn Asp Met His Ser
    210                 215                 220

Tyr Val Arg Glu Leu Ser Cys Gly His Glu Asn His Asn Leu Ile Thr
225                 230                 235                 240

Ala Ile Met Leu Glu His Arg Leu Asn Gln Gln Asp Ala Phe His Trp
                245                 250                 255
```

```
Leu Gly Ser His Cys Ser Arg Val Val Asp Gln Phe Leu Ser Asp Leu
                260                 265                 270

Asp Glu Leu Pro Ser Trp Gly Glu Pro Thr Asp Ser Gly Val Arg Asp
            275                 280                 285

Tyr Ile Asn Gly Leu Gly Gln Trp Val Arg Gly Asn Asp Asp Trp Ser
        290                 295                 300

Thr Glu Ser Lys Arg Tyr Tyr Gly Glu Asp Gly Glu Thr Ile Arg Gln
305                 310                 315                 320

Glu Arg Leu Val Thr Thr Arg Ser Gly Glu Ser Asn Tyr Ile Lys Phe
                325                 330                 335

Gly Gln Val Gly Val Gln Asp Ser Val Arg Ile Gln Pro Ile Glu Ala
            340                 345                 350

Asn

<210> SEQ ID NO 28
<211> LENGTH: 346
<212> TYPE: PRT
<213> ORGANISM: Agrocybe aegerita

<400> SEQUENCE: 28

Met Cys Ala Ser Ala Thr Arg Pro Gln Pro Ser Ala Ser Asn Asn Val
1               5                   10                  15

Lys Lys Ile Ile Leu Pro Asp Leu Val Ser His Cys Thr Phe Lys Leu
            20                  25                  30

Arg His Asn Arg His Arg Lys Gln Val Thr Thr Glu Thr Lys Lys Trp
        35                  40                  45

Leu Phe Lys Asp Gly Asn Leu Gly Gln Lys Glu Arg Ala Tyr His
    50                  55                  60

Gly Leu Lys Cys Gly Leu Leu Thr Ser Met Cys Tyr Pro Asp Ala Gly
65                  70                  75                  80

Tyr Pro Gln Leu Arg Val Val Asn Asp Phe Leu Thr Tyr Leu Phe His
                85                  90                  95

Leu Asp Asn Leu Ser Asp Glu Met Asp Asn Arg Gly Thr Thr Thr Thr
            100                 105                 110

Ala Asp Glu Val Leu Asn Ser Leu Tyr His Pro His Thr Trp Arg Ser
        115                 120                 125

Ser Ala Arg Val Gly Lys Met Thr Arg Asp Phe Tyr Lys Arg Leu Val
130                 135                 140

Leu Thr Ala Ser Pro Gly Ala Gln Gln Arg Phe Ile Glu Thr Phe Asp
145                 150                 155                 160

Phe Phe Phe Gln Ser Val Thr Gln Gln Ala Leu Asp Arg Ala Ser Gly
                165                 170                 175

Val Ile Pro Asp Leu Glu Ser Tyr Ile Ser Leu Arg Arg Asp Thr Ser
            180                 185                 190

Gly Cys Lys Pro Cys Trp Ala Met Ile Glu Tyr Ala Asn Asn Leu Asp
        195                 200                 205

Ile Pro Asp Glu Val Met Asp His Pro Ile Ile Arg Ser Leu Gly Glu
    210                 215                 220

Ala Thr Asn Asp Leu Val Thr Trp Ser Asn Asp Ile Phe Ser Tyr Ser
225                 230                 235                 240

Val Glu Gln Ser Lys Gly His Thr His Asn Met Ile Pro Val Val Met
                245                 250                 255

Tyr Gln Glu Gly Leu Asp Leu Gln Ala Ala Val Asp Phe Val Gly Asp
            260                 265                 270
```

```
Met Cys Arg Gln Ser Ile Asn Arg Phe Val Glu Lys Ala Arg Leu
        275                 280                 285
Pro Ser Trp Gly Pro Lys Ile Asp Gln Asp Val Ala Ile Tyr Val Gln
290                 295                 300
Gly Leu Ala Asp Trp Ile Val Gly Ser Leu His Trp Ser Phe Glu Thr
305                 310                 315                 320
Glu Arg Tyr Phe Gly Lys Ser Gly Arg Gln Val Lys Ala Ser Arg Ile
                325                 330                 335
Val Asp Leu Leu Pro Arg Gln Arg Leu Pro
            340                 345

<210> SEQ ID NO 29
<211> LENGTH: 372
<212> TYPE: PRT
<213> ORGANISM: Agrocybe aegerita

<400> SEQUENCE: 29

Met Thr Ala Ala Pro Leu Thr Phe Thr Leu Pro Asp Leu Leu Ala Asn
1               5                   10                  15
Phe Pro Trp Lys Arg Asn Leu Ser Glu Tyr Tyr Pro Glu Cys Lys Thr
            20                  25                  30
Glu Ser Ser Ala Trp Thr Glu Ser Phe His Pro Phe Asp Asp Glu Gly
        35                  40                  45
Leu Lys Gly Phe Asn Leu Cys Asp Phe Asn Leu Leu Ala Ser Leu Ala
    50                  55                  60
Tyr Ser Pro Arg Glu Arg Glu Ile Ile Arg Leu Gly Cys Asp Leu Met
65                  70                  75                  80
Asn Ile Phe Tyr Val Phe Asp Glu Tyr Thr Asp Ile Ala Asp Gly Asp
                85                  90                  95
Gly Ala Asp Lys Ile Arg Asp Ile Met Asp Ala Phe Arg Asn Pro
            100                 105                 110
His Lys Pro Arg Pro Glu Gly Glu Leu Leu Val Gly Glu Met Ala Arg
        115                 120                 125
Asp Phe Trp Ile Arg Ala Ser Gly Tyr Val Ser Pro Asp Ala His Cys
    130                 135                 140
Leu Thr His Phe Leu Arg Asp Phe Asp Thr Tyr Thr Ala Ala Val Val
145                 150                 155                 160
Arg Glu Ala Asp Asp Arg Ala Lys Arg Val Tyr Arg Thr Phe Glu Asp
                165                 170                 175
Tyr Leu Ser Ile Arg Arg Asp Ser Ser Gly Cys Leu Pro Ser Phe Ala
            180                 185                 190
Leu Cys Glu Phe Gly Leu Asp Leu Pro Glu Glu Ala Tyr His His Pro
        195                 200                 205
Arg Met Ala Ala Leu Arg Glu Gln Ser Thr Asp Leu Ile Ala Ile Gly
    210                 215                 220
Asn Asp Ile Asp Ser Tyr Ala Met Glu Lys Ala Arg Gly Leu Glu Leu
225                 230                 235                 240
His Asn Ser Val Glu Leu Ile Ile Asn Glu His Gly Leu Asp Val Gln
                245                 250                 255
Gly Ala Ile Asn Trp Leu Glu Arg Tyr Ala Ala Gly Val His Ala Ser
            260                 265                 270
Phe Leu Asp Asn Val Ala Asn Met Pro Ser Trp Gly Glu Asp Val Asp
        275                 280                 285
Arg Arg Val Lys Met Tyr Ile Asp Gly Leu Ala Gln Trp Val Arg Gly
    290                 295                 300
```

```
Asn Asp Asp Trp Thr Phe Glu Ser Gly Arg Tyr Phe Gly Asp Lys Gly
305                 310                 315                 320

Leu Glu Val Gln Lys Thr Arg Val Met Ser Leu Leu Pro Ala Ser Lys
                325                 330                 335

Val Ser Leu Arg Ser Arg Pro Lys Ala Val Gly His Val Pro Lys Lys
                340                 345                 350

Leu Leu Arg Tyr Phe Arg Tyr Ser Thr Met Tyr Phe Phe Gly Phe His
                355                 360                 365

Val Leu Ala Lys
                370

<210> SEQ ID NO 30
<211> LENGTH: 342
<212> TYPE: PRT
<213> ORGANISM: Agrocybe aegerita

<400> SEQUENCE: 30

Met Ser Ala Leu Pro Ser Gln Phe Lys Leu Pro Asp Leu Leu Ser Thr
1               5                   10                  15

Cys Pro Leu Lys Asp Gly Thr Asn Pro Ala Tyr Lys Lys Ala Ala Ala
                20                  25                  30

Glu Ser Arg Ala Trp Ile Gly Ser Tyr Asn Met Phe Ala Asp Arg Lys
                35                  40                  45

Arg Ala Phe Phe Ile Gln Gly Gln Asn Glu Leu Leu Cys Ser His Val
                50                  55                  60

Tyr Cys Tyr Ala Gly Tyr Glu Gln Leu Arg Thr Thr Cys Asp Phe Val
65                  70                  75                  80

Asn Leu Leu Phe Val Val Asp Glu Val Ser Asp Glu Gln Ser Gly Glu
                85                  90                  95

Asp Ala Arg Ala Thr Gly Gln Val Phe Val Asn Ala Met Lys Tyr Ala
                100                 105                 110

Asp Trp His Asp Gly Ser Lys Leu Ala Lys Leu Thr Lys Asp Phe Arg
                115                 120                 125

Val Arg Phe Leu Arg Leu Ala Gly Pro Lys Asn Val Ala Arg Phe Val
130                 135                 140

Ala Leu Cys Glu Ser Tyr Thr Ala Cys Val Gly Lys Glu Ala Glu Leu
145                 150                 155                 160

Arg Glu Ser Gly Gln Val Leu Gly Val Lys Glu Phe Ile Pro Leu Arg
                165                 170                 175

Arg Gln Asn Ser Ala Val Leu Leu Cys Phe Ser Leu Val Glu Tyr Ile
                180                 185                 190

Leu Gly Ile Asp Leu Asp Asp Glu Val Tyr Arg Asp Glu Asn Phe Leu
                195                 200                 205

Asn Ala Tyr Trp Ala Ala Cys Asp His Val Cys Trp Ala Asn Asp Val
                210                 215                 220

Tyr Ser Tyr Asp Met Glu Gln Ser Lys Gly Leu Ser Asn Asn Asn Ile
225                 230                 235                 240

Val Thr Val Leu Met Glu Glu Asn His Thr Ser Leu Gln Asp Thr Ser
                245                 250                 255

Asp Tyr Ile Gly Glu Lys Cys Ala Glu Phe Val Gln Ile Tyr Leu Thr
                260                 265                 270

Ser Lys Lys Arg Leu Ser Pro Ser Leu Gly Pro Asp Ala Ala Leu Phe
                275                 280                 285

Leu Glu Ser Ile Gly Ser Trp Met Val Gly Asn Leu Ala Trp Ser Phe
```

```
            290                 295                 300
Glu Thr Ser Arg Tyr Phe Gly Ser Arg His Leu Glu Val Lys Glu Thr
305                 310                 315                 320

Gly Ile Val Ile Leu Arg Pro Arg Glu Leu Pro Glu Asp Gly Ser Ser
                325                 330                 335

Ser Asp Ser Asp Glu Glu
            340

<210> SEQ ID NO 31
<211> LENGTH: 387
<212> TYPE: PRT
<213> ORGANISM: Agrocybe aegerita

<400> SEQUENCE: 31

Met Ser Phe Phe Lys Ser Ser Gln Pro Thr Ile Tyr Ile Pro Asp Thr
1               5                   10                  15

Leu Arg Asn Trp Pro Trp Pro Arg Glu Ile Asn Pro His Tyr Glu Glu
                20                  25                  30

Cys Lys Arg Glu Ser Ala Ala Trp Val Glu Lys Phe Gly Ala Phe Ser
            35                  40                  45

Ala Lys Ala Gln Lys Ala Phe Asn Lys Cys Asp Phe Asn Leu Leu Ala
        50                  55                  60

Ser Leu Ala Trp Ser Arg Val Asn Arg Asp Gly Cys Arg Ile Gly Cys
65              70                  75                  80

Asp Leu Met Asn Leu Phe Phe Val Phe Asp Glu Trp Ser Asp Val Ser
                85                  90                  95

Asp Ala Glu Glu Thr Arg Arg Met Ala Asp Ile Ile Met Asp Ala Leu
            100                 105                 110

Tyr Asp Pro His Lys Pro Arg Pro Thr Gly Glu Trp Val Gly Gly Glu
        115                 120                 125

Val Thr Arg Gln Tyr Trp Leu Asn Ala Ile Arg Thr Ala Thr Pro Ser
130                 135                 140

Ala Gln Lys Arg Phe Ile Lys Ala Phe Lys Leu Tyr Thr Asp Ser Val
145                 150                 155                 160

Val Gln Gln Ser Ala Asp Arg Asp Lys His Leu Ile Arg Asp Ile Asp
                165                 170                 175

Ser Tyr Phe Glu Val Arg Arg Asp Thr Ile Gly Ala Lys Pro Ser Phe
            180                 185                 190

Ala Ile Asn Glu Val His Met Asn Leu Pro Asp Tyr Val Met Glu His
        195                 200                 205

Pro Val Ile Lys Asn Leu Thr Ala Tyr Cys Ile Asp Met Leu Cys Ile
210                 215                 220

Gly Asn Asp Leu Cys Ser Tyr Asn Val Glu Gln Ser Arg Gly Asp Asp
225                 230                 235                 240

Gly His Asn Leu Val Thr Ile Val Met His Gln Leu Asn Leu Asp Val
                245                 250                 255

Gln Gly Ala Phe Asp Trp Ile Gly Lys Leu His Asp Glu Leu Val Asp
            260                 265                 270

Lys Phe Leu Glu Glu Tyr Lys Asn Val Pro Thr Phe Lys Asp Lys Gln
        275                 280                 285

Val Thr Lys Glu Cys Ala Glu Tyr Ala Phe Gly Leu Gly Asn Trp Val
        290                 295                 300

Arg Gly Asn Asp Gln Trp Ser Phe Glu Ser Glu Arg Tyr Phe Gly Lys
305                 310                 315                 320
```

```
Asp Gly Met Arg Val Leu Thr Glu Arg Thr Val Val Leu Leu Pro Lys
            325                 330                 335

Lys Arg Glu Pro Pro Lys Pro Leu Asp Glu Asp Pro Ile Tyr Ser
        340                 345                 350

Ala Leu Pro Trp Trp Gly Trp Thr Ala Leu Phe Gly Phe Leu Ala Thr
            355                 360                 365

Ala Phe Thr Phe Ser Ala Arg Gln Leu Ser Thr Arg Ile Ser Ala Asn
        370                 375                 380

Leu Ile Ala
385

<210> SEQ ID NO 32
<211> LENGTH: 430
<212> TYPE: PRT
<213> ORGANISM: Agrocybe aegerita

<400> SEQUENCE: 32

Met Ala Ser Ser Leu Leu Glu Pro Ser Leu Ala Ala Ile Ala Leu Val
1               5                   10                  15

Ile Leu Leu Ala Ser Val Ser Leu Ser Arg Lys Lys Arg Pro Ala Ala
            20                  25                  30

Pro Glu Pro Gln Gly Leu Ser Val Leu Gly Asn Leu Phe Asp Ile Pro
        35                  40                  45

Lys Arg Ala Ser Ser Ile Ile Tyr Leu Ala Leu Gly Lys Pro Tyr Asn
50                  55                  60

Thr Leu Thr Lys Arg Ala Val Ser Gln Leu Gln Gly Tyr Thr Pro Gly
65                  70                  75                  80

Ser His Ile Asp Ala Thr Ser His Ser Pro Arg Val Phe Arg Leu Pro
            85                  90                  95

Asn Leu Glu Glu Thr Phe Ser Val Phe Pro Asp His Gly Leu Asn Pro
        100                 105                 110

Asn Tyr Thr Ser Ala Arg Thr Asp Ser Arg Ala Trp Ile Asn Gln Tyr
            115                 120                 125

Thr Lys Val Val Cys Gly Pro Lys Met Val Ala Phe Met Asn Asn Cys
130                 135                 140

Glu Phe Glu Leu Ser Asn Ser His Cys Tyr Pro Tyr Ala Gly Tyr Lys
145                 150                 155                 160

Gly Leu Lys Ala Thr Met Asp Leu Thr Asn Ile Leu Trp Leu Tyr Asp
            165                 170                 175

Glu Tyr Thr Asp Thr Gly Ser Gly Ala Glu Ala Val Lys Ala Ala Gly
        180                 185                 190

Ile Val Ala Arg Ala Leu Arg Glu Pro Asp Tyr Asp Asp Gly Thr Trp
            195                 200                 205

Val Cys Arg Met Met Lys Ser Phe Lys Gln Asn His Ile Asp Lys Ala
        210                 215                 220

Gly Pro Gly Val Ala Arg Arg Phe Ile Asp Asn Phe Cys Asn Tyr Val
225                 230                 235                 240

Glu Val Val Gly Arg Glu Ala Glu Leu Arg Glu Lys Asn Glu Val Leu
            245                 250                 255

Asp Ile Pro Asn Tyr Val Thr Phe Arg Arg Glu Thr Ser Ala Val Arg
        260                 265                 270

Thr Cys Phe Asp Leu Val Glu Tyr Cys Leu Asp Leu Asp Leu Pro Gln
            275                 280                 285

Tyr Val His Asp Asp Pro Val Phe Ile Ser Gly Tyr Asn Ala Gly Met
        290                 295                 300
```

```
Asp Leu Val Phe Trp Ala Asn Asp Leu Val Ser Tyr Asn Met Glu Gln
305                 310                 315                 320

Ser Lys Gly His Ser Gly Ala Asn Val Val Thr Val Ile Met Lys Ser
            325                 330                 335

Lys Gly Val Asp Leu Gln Thr Ala Val Asp Phe Leu Gly Gly Tyr Cys
        340                 345                 350

Glu Ala Leu Thr Ala Gln Leu Leu Glu Ala Lys Arg Ile Leu Gln Ala
            355                 360                 365

Arg Ser Asp Ala Ala Tyr Ser Arg Asp Val Val Arg Leu Met Asp Ala
        370                 375                 380

Phe Gly Asp Trp Val Arg Gly Asn Val Ala Trp Ser Phe Glu Thr Glu
385                 390                 395                 400

Arg Tyr Phe Gly Lys Glu Asn Lys Arg Val Lys Glu Thr Leu Leu Val
                405                 410                 415

Glu Leu Lys Glu Pro Phe Val Gly Ala Leu Ala Leu Lys Glu
            420                 425                 430

<210> SEQ ID NO 33
<211> LENGTH: 358
<212> TYPE: PRT
<213> ORGANISM: Agrocybe aegerita

<400> SEQUENCE: 33

Met Asn Ala Ser Pro Phe Leu Asn Glu Ser Ser Pro Thr Arg Pro Thr
1               5                   10                  15

Ser Phe Val Leu Pro Asp Leu Val Ser His Cys Lys Phe Pro Leu Ser
            20                  25                  30

Tyr His Pro Asn Gly Asp Glu Ile Ala Gln Glu Ser Val Asp Trp Leu
        35                  40                  45

Asp Ser Ser Cys Pro Asp Leu Thr Ala Lys Gln Arg Arg Ala Leu Arg
    50                  55                  60

Val Leu Gln Ser Gly Glu Leu Thr Ala Tyr Cys Tyr Asn Gln Ala Thr
65                  70                  75                  80

Ser Pro Glu Arg Leu Arg Val Val Ser Asp Phe Leu Thr Tyr Leu Phe
                85                  90                  95

His Leu Asp Asn Ile Ser Asp Gly Met Met Thr Arg Glu Thr Asp Val
            100                 105                 110

Leu Ala Asp Val Val Met Asn Ala Phe Trp Phe Thr Asp Lys Tyr Met
        115                 120                 125

Pro Thr Arg Gly Pro Gly Lys Glu Gln Leu Asp Glu Glu Leu Asn Pro
    130                 135                 140

Gly Lys Leu Ala Arg Asp Phe Trp Ser Arg Ala Ile Ala Asp Cys Gly
145                 150                 155                 160

Val Gly Val Gln Ala Arg Phe Lys Glu Thr Met Gly Leu Phe Phe Glu
                165                 170                 175

Ala Val Asn Ile Gln Ala Arg Met Arg Asp Glu Asp Thr Ile Pro Asp
            180                 185                 190

Leu Glu Ser Tyr Ile Asp Val Arg Arg Asp Thr Ser Gly Cys Lys Pro
        195                 200                 205

Ser Trp Val Leu Ile Glu Tyr Ala Leu Gly Ile Asp Leu Pro Asp His
    210                 215                 220

Val Val Asp His Pro Ile Met Gln Ala Leu Asn Gln Gly Thr Asn Asp
225                 230                 235                 240

Leu Val Thr Trp Ser Asn Asp Ile Phe Ser Tyr Asn Val Glu Gln Ser
```

Arg Gly Asp Thr His Asn Met Ile Val Ile Leu Met Glu Tyr His Gly
                245                 250                 255
                        260                 265                 270

His Thr Leu Gln Ser Ala Val Asp Tyr Val Gly Glu Leu Cys Ala Gln
            275                 280                 285

Thr Ile Asp Thr Phe Cys Glu Asn Lys Glu Arg Leu Pro Ser Trp Gly
        290                 295                 300

Pro Glu Ile Asp Asp Met Val Ala Arg Tyr Val Lys Gly Leu Gln Asp
305                 310                 315                 320

Trp Ile Val Gly Ser Leu His Trp Ser Phe Gln Thr Gln Arg Tyr Phe
                325                 330                 335

Gly Lys Asp Gly Leu Asp Ile Lys Lys His Arg Phe Val Lys Leu Leu
            340                 345                 350

Pro Leu Glu Ala Ala Lys
            355

<210> SEQ ID NO 34
<211> LENGTH: 389
<212> TYPE: PRT
<213> ORGANISM: Agrocybe aegerita

<400> SEQUENCE: 34

Met Val Trp Asp Phe Val Leu Ser Leu Phe His Ser Leu Leu Ala Ala
1               5                   10                  15

Phe Gln Thr Leu Thr Ser Trp Leu Thr Gly Ser Phe Leu Phe Asn Asn
            20                  25                  30

Lys Met Ala Pro Ala Pro Asn Pro Ala Pro Val Thr Phe Ile Leu Pro
        35                  40                  45

Asp Leu Glu Lys Thr Phe Asn Ser Leu Pro Asp Asp Gly Leu Asn Pro
50                  55                  60

His His Asp Val Ala Cys Ala Glu Ser Arg Gly Trp Phe Ala Lys Tyr
65                  70                  75                  80

Asn Lys Lys Val Leu Gly Ala Gln Met Gln Glu Phe Phe Arg Arg Cys
                85                  90                  95

Lys Phe Glu Leu Ile Thr Ser Tyr Thr Tyr Pro Tyr Val Asp Lys Glu
            100                 105                 110

Gly Leu Arg Ala Thr Met Asp Trp His Asn Ile Leu Trp Phe Phe Asp
        115                 120                 125

Glu Val Thr Asp Thr Glu Thr Gly Lys Asp Ala His Lys Ser Ala Ile
130                 135                 140

Ile Thr Ile Arg Thr Leu Arg Glu Pro Asp Phe Asp Asp Gly Ser Ser
145                 150                 155                 160

Leu Cys Arg Met Val Arg Asp Phe Arg Leu Ser His Leu Ser Arg Ala
                165                 170                 175

Gly Pro Glu Cys Thr Arg Arg Phe Leu Glu His Cys Asp Val Ala Phe
            180                 185                 190

His Ala Gly Ala Val Glu Ala Glu Leu Arg Glu Lys Gly Glu Val Leu
        195                 200                 205

Ser Ile Glu Gly Tyr Leu Lys Leu Arg Arg Glu Thr Ser Gly Ala Arg
210                 215                 220

Thr Cys Phe Asp Met Ala Glu Tyr Leu Met Asp Ile Asp Leu Pro Gln
225                 230                 235                 240

Asp Met Tyr Asp Asp Pro Val Phe Gln Lys Gly Tyr Ile Ala Ala Leu
                245                 250                 255

```
Asp Leu Ile Phe Leu Ala Asn Asp Leu Tyr Ser Tyr Asn Met Glu Gln
            260                 265                 270

Ala Lys Gly His Asn Gly Ala Asn Val Leu Thr Val Val Met Lys Glu
        275                 280                 285

Thr Lys Leu Asn Leu Gln Ser Ala Ala Asp Tyr Val Gly Val Leu Cys
    290                 295                 300

Glu Lys Leu Ile Lys Gln Phe Gln Glu Ala Lys Ser Thr Leu Glu Asn
305                 310                 315                 320

Arg Leu Ala Lys Glu Lys Asn Pro Ala Lys Ala Ala Leu Lys Asp
                325                 330                 335

Ala Ile Arg Ser Leu Val Gly Tyr Gly His Trp Val Arg Gly Asn Val
            340                 345                 350

Glu Trp Ser Phe Glu Thr Glu Arg Tyr Phe Gly Lys Lys Asn Lys Glu
        355                 360                 365

Ile Lys Lys Ser Arg Val Val Thr Leu Thr Pro Thr Asn Ser Val Asn
    370                 375                 380

Arg Ala Leu Lys Ala
385

<210> SEQ ID NO 35
<211> LENGTH: 1173
<212> TYPE: DNA
<213> ORGANISM: Agrocybe aegerita

<400> SEQUENCE: 35
atgcatcacc atcaccatca ccacagctcg acccagctgt tcactcactc tccgaccaaa      60
atgcagatca tcctgccgga tctgctgtgc tcctggggat ataaagggtt tctcaaccct     120
cactatgagg gcgctaaggc ggaatccaac acctggattc gcccgctcgt agtgaaactt     180
ttcgacgaac gtggccagaa agcgttcgcc aaagattaca ccggtctgct ggcgtctatg     240
acttacccgc accacaacaa gaattcctg tgtgtggctt gcgatatgat gaacctgttc     300
tttgtttatg acgagtatac cgatattacc ccgccggaaa ccgcgcagcg tctggctaaa     360
atcgttgtaa atgctatgcg caatccggat gagatcgccg ctctgggtga agacagcatc     420
ggtactatga ccaagcagtt ctggcgccgc gctatgactc tgctgccacc gaacggttgt     480
aactctgaat cttgtatcca gcacttcatt gactacaccg aagaatatct gactgcagtg     540
acgcgtgaag cttgtgatcg tagcagcggc tctgtccacg ctgtaaaaga ctatctggcg     600
atgcgtcgtg caacctctgg cgcgggtctg atggttggtt tactggaatt tggcctcgat     660
ctgccggaag aagtcatgaa acatgaagtg atccaggaac tgtctactgg cgcgatcgac     720
atgtactgtc tgctgaacga catgcatagc tacgcatctg aactgtcgtc tggtcaggcc     780
tctcacaacg ttattaccgt cgtgatgcac gaacgtaacc tgtccctgca gaagctttt     840 gattggctgg cctcttacgc ggcaggcgta gtgaagggtt caaaaccaa cctgaaccgc     900 gttcctctt ttagcgaact ggaggaccac tctctgcacg cgaaggcat gctccgtgat     960 cgcattcagc gttacatcga cggcctgggt caggcggttc gcgcggaaga tgattgggct    1020
tttgaaacta cccgctatca cggtcagaac ggcccgcaga ttaaactgac ccgtatgctg    1080
accatccgtc gcaggttaa ggacaactac gctaaacagg ctccgcgcgt cgaggctcct    1140
gaacgcccga tgttactgga agtgcgtagt taa                                1173

<210> SEQ ID NO 36
<211> LENGTH: 1050
<212> TYPE: DNA
```

<213> ORGANISM: Agrocybe pediades

<400> SEQUENCE: 36

| | | | | | |
|---|---|---|---|---|---|
| atgcatcacc | atcaccatca | ctcccaattt | attatcccgg | atctgttatc | cacttggcct | 60 |
| tggcagcgcg | tgtctaaccc | gatgtggcgt | gagattgatg | aagaagcaaa | cgcgtgggtg | 120 |
| cagtctttcg | acctgtttga | accgtcccag | ttcgagaaat | tcaagatgtg | tgatttcaac | 180 |
| ctgctgggct | cgatgattgg | taccgtggaa | accaaagatc | atctgcgcat | cagttgcgac | 240 |
| ctgatgaact | tctatttcgc | attcgacgaa | tacacggaca | tggcatccaa | agacgaagcg | 300 |
| cgtaagatcg | cccgtgacgt | gatggatgca | tttcgcaaca | ccgaaaaacc | agctcacaac | 360 |
| caaatcaccg | aaatggcccg | ccagtttttt | aaacgtacga | tcgacactgt | aggtaaagac | 420 |
| ttgccgggcg | tggaacgttt | tatcgctgac | ttcgatgctt | atacgcattc | cgtgatccag | 480 |
| gaggccgacg | accgtgctac | tggccacatc | cgcagcgtca | acgactattt | cacgttacgc | 540 |
| cgcgacactt | gcggcgcgaa | accaagcttc | agcttctttg | gcctgggtct | gaacattccg | 600 |
| gatgaggttt | tccaccatcc | tgtggttatt | tccatgatca | aggcgccac | cgatctgatt | 660 |
| gctgttacga | atgacatgca | ctcatataac | ctcgaacact | cccgtggtct | ggatggacac | 720 |
| aacgtaatca | ctgctatcat | gcacgaatac | cagctgacc | tgcagggcgc | actgtactgg | 780 |
| ctatccggtt | acgctaccca | tacgattgct | aacttcctgt | cgaaccgccg | taacctgccg | 840 |
| tcctggggcc | cggctgtcga | taaagcggta | gaagaatttt | tcgaccgtgt | tggtcgttgt | 900 |
| gttcgtggct | acgacgcttg | gagctacgaa | accaaacgct | attacgggaa | aaacggcctg | 960 |
| caggtgcaga | agacccgtcg | tatcaccctg | cgcccgcgtg | acgcgtctta | cattactaag | 1020 |
| gagcagctgc | aggtatctat | caaagcataa | | | | 1050 |

<210> SEQ ID NO 37
<211> LENGTH: 1053
<212> TYPE: DNA
<213> ORGANISM: Agrocybe pediades

<400> SEQUENCE: 37

| | | | | | |
|---|---|---|---|---|---|
| atgcatcacc | atcaccatca | ctcctctcag | atctatatcc | cggacctcct | gatcacctgg | 60 |
| ccgtggcaaa | aggtgcgcaa | cccactgctg | caagaagtgc | aggatgaggc | gaacgaatgg | 120 |
| gtgaaatctt | tcgtgctgtt | cgaaccggaa | cagtttgaga | aatttaaggc | atgtgatttc | 180 |
| aacctgctgg | gtgcactggt | tggtccgctg | ggtaccaagg | aagaactgcg | cattagctgt | 240 |
| gacctgatga | acttctactt | cgccttcgat | gagtacaccg | acctggctag | cgctgacgaa | 300 |
| gccaaagtaa | tcgcgcgcga | tgtgatggaa | agcttccgtc | acacagataa | gccaagccac | 360 |
| aacaaaatta | ctgaaatggc | ccgtcaattc | ttcgaacgta | ctatcaacac | ggttggtaac | 420 |
| gatccgactg | gcattgaaca | atttattgcg | gatttcgacg | catacaccac | ctctatcatc | 480 |
| caagaagctg | atgatcgtgc | gtctggtcac | attcgtagcg | ttgaggatta | cttcattctg | 540 |
| cgccgtgaca | cctgtggtgg | gaaaccgtcg | ttctcgttct | tcggtctggg | cctgaacatc | 600 |
| ccgaaagaag | tcttcgcaca | cccgatgttc | atctccatga | ccgaatccgc | gactgatctg | 660 |
| atcgcaatta | ccaacgatat | gcactcttat | aacctggagc | aatcccgcgg | cttggatggt | 720 |
| cacaatgtaa | ttaccgcgat | catgcacgaa | tacaaaatta | atctccaggg | tgcgctgtac | 780 |
| tggctgtcgg | gttacgctac | taaaactatt | gcgaaattta | tctctgaccg | taaaaatttg | 840 |
| ccgagctggg | gccagtggt | tgaccgcgcc | gttgaacaat | actttgaccg | tgttggtcgt | 900 |
| tgcgttcgtg | gctacgatgc | ctggtcttac | gaaaccaaac | gttattacgg | taaaaatggc | 960 |

```
ctggaaatcc agaaaactcg tcagatcacc ctgcgcccgc tggacccggc gtacgtgacc    1020
aaagaacagc tgcaggtatc catgaaggca taa                                 1053

<210> SEQ ID NO 38
<211> LENGTH: 1050
<212> TYPE: DNA
<213> ORGANISM: Galerina marginata

<400> SEQUENCE: 38
atgcatcacc atcaccatca cccgagccag ttcaccatcc ctgacctgct gatcacttgg      60
ccatggcagg aaatcaccaa cccgatgctg cacgaagtag acgctgaagc caatgaatgg     120
gttcagtcac tgaacctgtt cgaaccgaaa cagttcgaaa agttcaaagc ctgtaacttc     180
aacctgctgg gctccctggt tggaccgctg ccaagccgtg accaccttcg tgtgtcctgc     240
gacctgatga acttctactt cgctttcgat gagtacacgg acatggcaaa caaagatgaa     300
gctatgcgta tcgcccgtga cgtaatgcaa gcattccgta cactgacacg cctagcaac      360 tctaaaatca ctgaaatggc acgtcaattc ttcaaacgta ccatcgaggt tgtaggcgaa     420
gacctgccgg catcgaacg tttcatcgcc gatttcgatg catacactcg ttccgtgatt      480
caggaagcag atgatcgtgt tgcaggtcac attcgtaacg tggaggacta cttcattctg     540
cgccgtgata cgtgcggtgc taaaccgagc ttctctttct acggtctggg tctgaacatc     600
ccgaccgagg tctttgaaca cccgctgctg atttctatgg ttgaaagcgc aactgacctg     660
attgctgtca ccaatgacat gcactcttac ggtctggagc attctcgtgg cctggacggt     720
cacaatgtta tcaccgccat tatgcacgaa tatcagctgg acctacaggg tgccctgtac     780
tggctgtccg gctacgcaac taaaaccatc tccaaattcc tgactgatcg taaaaacctg     840
ccgtcctggg gcccaaccat tgacaaagct ctcgaaatct acctggaccg tttaggtcgt     900
tgcgtgcgtg gctacgatgc ttggtcctac agcactaagc gttactatgg taaaaacggt     960
ctgaaggttc aaaaaacccg ccgtatcact ttgaaaccgc gtgatgcagc ctacatcacg    1020
aaggatcagc tgcaggtgtc tatcgcttaa                                    1050

<210> SEQ ID NO 39
<211> LENGTH: 1053
<212> TYPE: DNA
<213> ORGANISM: Hypholoma sublateritium

<400> SEQUENCE: 39
atgcatcacc atcaccatca ctccgctcag tacaccatcc ctgacttact ggcgaactgg      60
ccgtggcagc gcgtgaccaa cagcatgctg gacgaggtgc gcgacgaagc aaacgagtgg     120
gtgatgtccc tgggcctgtt tgagccggct cagtttaaaa aattcaaagc atgcgacttc     180
aaccttctgg caagctttat tggtccgctg gaaagtaaag aacaccttcg tgttgcttgc     240
gatctgatga atttctattt cgctttcgat gagtacactg acgttgctaa ccgtgaagag     300
gctaaaaaaa tctctcaggg cgttatgcac gcgtttaaaa ctcgttctgc agagccgtcc     360
agctccaaaa ttacggaaat ggcgcgtcag ttctttcgtc gtaccgttga cgtcgtcggt     420
gaagattccc cggccatcaa ccagttcatt accgacttcg acacctacac cacggctgtg     480
atccaggaag cagacgatcg caccgaaggt accatccgta atgttgagga ctatttcacc     540
ctccgtcgcg acacctgcgg cgccaaacct tcttttttcgt tcttcgccct gggcctgaac     600
atgccgaccg aagtcttcga acacccctctg atcatgtctc tggtagagcg tgcaaccgac     660
```

| | |
|---|---|
| ctgatcgcga ttgtgaacga catgcactcc tacggtctgg aacgtgctcg tggcctggat | 720 |
| ggtcataacg tagtaacgtc catcatgtac gagcatcagc tggacctgca gggtgcgctg | 780 |
| cactggctgg ccggttatgc cgaagacaca atcgccaagt tcctgtcgga aaaagaacgt | 840 |
| ctcccgtcct ggggtccggc ggtagatgta tccgtgcagg aatttgttga ccgtctgggc | 900 |
| cgttgcgtgc gtggttacga cgcttggtcc tatgaaacga accgctatta cggcagccac | 960 |
| ggtctacaga ttcgtcagac tcgtcaaatc accctgccat ccaacgactc tggctacatc | 1020 |
| actcgcaagc agatgggcgt ttctatcgct taa | 1053 |

<210> SEQ ID NO 40
<211> LENGTH: 1980
<212> TYPE: DNA
<213> ORGANISM: Agrocybe aegerita

<400> SEQUENCE: 40

| | |
|---|---|
| atgcctggat cagcgaactg gactgcggac cgattttaca ttcctgacac cctggctaat | 60 |
| tggccttggc cgagagccat caatcccgcg tacgaggagt gcaaggcggc ctccgctgcc | 120 |
| tggtgcgaga aatatggcgc tttctctgct cgcgcccaga aggccttcaa cctctgcgac | 180 |
| ttcaatttat tggcctcttt ggcgtatgct ggcctccctg cagacgtcaa tcgagtagga | 240 |
| tgtgacctca tgaacctatt ttttgtcgtc gacgagcaca cagacgctat ggatgctcgg | 300 |
| tccgttcagg actgggtaga catcgtcgtg gatgccctcc atcatcctca cacgccgaga | 360 |
| cctgcgggtg aaccgaaggt cggggagata gcccgcacct tctgggaaaa tggcatcaaa | 420 |
| tgcatgggac ccaccgccca acgccgattt gttgaaacat tcaccaccta ccttcagagt | 480 |
| gtcgtgactc aagcccaaga tcgcgacaag catctcttcc gcgatgtgga cagctacatg | 540 |
| gaggttcggc gagacaccat cggagccaag ccctcgttcg ccttgcttga gcacgacatg | 600 |
| gagcttccgg acgatgtctt ctatcaccct ctcctggaga agttgaggga gtgggcgatc | 660 |
| gacatgctga tccttggaaa tgacttgtgc tcctacaatg tcgagcaatc acgaggcgac | 720 |
| gacggccaca acatcatccg actcgcaatg cttcaagaaa acaccaacgt ccacggcgct | 780 |
| ctccgctttg tctcaaagat gcacgacgac ctcgccgaga gttcctttc caactaccaa | 840 |
| ggcatgccgt ctttcactcc acaaatcgac gcatgggtca ccaggtacat cgacggcctc | 900 |
| ggtaactggg ttcgcgcaaa cgattcatgg agccttgaga gttggaggta tttcaaggga | 960 |
| gacgtgttgc gtgtccaggc agagcgttgg gtcgaattgc tccctccagc cccaaaggat | 1020 |
| gagctaacgt catcaatccc gcctgaatcc cggtggatca aacctgcggt cgagccttcg | 1080 |
| cgtgcgaggc caaataatgt cggtatcgtg gcactggata cctacacacc gacttcagag | 1140 |
| gatgatttcc agaccttggc tgtcaaaact gtgtcttcgc tcctctcgaa gtacaacatc | 1200 |
| aaccccgtct ctgtcggccg gctcgacatc tgtattgaga gggctgcaga tccttacata | 1260 |
| atttatgctc tgcgagacgc cttcgcctcc gctggcaaca cggacgtcga ggcgattgta | 1320 |
| agctcctcca gtctgtcgt cggattgttc aacgcaataa attgggtcga gtcatcgagc | 1380 |
| tgggacggcc gttacgccat cgtattcgcg ggagatctct cttcgggagt atctgcagct | 1440 |
| ttggttggcc cagacgcgcc catagtcgtg aacctactc gaggaaccta tctcggcgat | 1500 |
| cccatcgcat caacagacga ggcacagggg tcatacattg attctctctt ccaatcatac | 1560 |
| tcgcattatc gcaaaaagca cccccagttc tccaagacct ctggtgctcc aacggagcg | 1620 |
| cacactccca caacaacgaa cggcagcatt aaatccaacg gattcgtcag tggagacacc | 1680 |
| aacggccacg cgaatgggaa tggccacgtt cagacccgtt cgtccacccc ctcttcttct | 1740 |

| | | | | |
|---|---|---|---|---|
| tcttcctcca | cgtcttcccc | atctttcgac | tacatgatcc | tccacgaccg | ccatggcaag | 1800 |
| attcccaccg | gcgctgggtc | catctatctc | gggctggcct | cgcttattac | ggatatcgca | 1860 |
| ccggagacgc | tggcgggcaa | gagcatcggt | gtatttgggt | ttgcgaacag | caccagcacc | 1920 |
| ttcttcggta | ttcgcgttgc | gggtgactgc | agtgttatct | gcaagcagct | tcaggcctaa | 1980 |

<210> SEQ ID NO 41
<211> LENGTH: 1062
<212> TYPE: DNA
<213> ORGANISM: Agrocybe aegerita

<400> SEQUENCE: 41

| | | | | | | |
|---|---|---|---|---|---|---|
| atgtccgaac | agcagtacac | tcttcccgac | ctccttcaaa | attggccatg | gaaccgtcat | 60 |
| ctcagccctt | attacgaaga | ggcgaagagg | gagtcgagtg | catgggtcga | atcattcaag | 120 |
| ccatttgatc | aggatgggca | gagggccttc | gacgcttatc | tcctcgccag | cctgacctat | 180 |
| tcacatggga | gcagggaatt | tgtgcgtctc | ggatgcgatc | tcatgaactt | ctacttcgtc | 240 |
| tacgatgaat | acaccgacgt | ttccgactcc | gcggtggcgg | acaggctggc | caacattgtg | 300 |
| atcgatgcca | tgagaaaccc | cgaaaattca | tctcaaagtg | gagatcacct | cctaggggaag | 360 |
| atgactaaac | atttctggac | tcgagcgcta | gcgatggcac | cggcaggatc | accctgtttc | 420 |
| gagcatttca | tcaccacatc | ggagacatac | ctacgcgcag | taaccaaga | agcggaagac | 480 |
| agagcgaaca | agcgcgtgcg | taaggtggac | gactacctcc | gacttcgccg | ggatacgtgt | 540 |
| ggcgcacgtc | cgacgctcgc | actgatcgag | tttgggctca | atttgcctaa | tgaggtagtt | 600 |
| cgccatcctt | ctttggtagc | ccttacggaa | gcggctgtgg | atttgatcat | cctcgttaac | 660 |
| gatatgcact | cgtacgtgcg | ggaattgtct | tgtggacacg | aaaaccacaa | cctcatcact | 720 |
| gctattatgc | ttgagcatcg | tctcaatcgg | caagacgcct | tccattggct | gggatcacac | 780 |
| tgcagcaggg | ttgtggatca | atttctctct | gacttggacg | agctaccgtc | ctggggagag | 840 |
| cctaccgatt | ctggagtgag | ggattacatc | aacggcctgg | acaatgggt | tcgtggaaac | 900 |
| gacgattgga | gtaccgagag | caaaagatat | tacggagaag | atggggaaac | aatacgacag | 960 |
| gagcgcttgg | tcacaactcg | ctccggggag | tcgaattaca | tcaaattcgg | gcaagttggc | 1020 |
| gtacaagact | cggtgcgcat | ccaaccaatc | gaagccaact | ga | | 1062 |

<210> SEQ ID NO 42
<211> LENGTH: 1041
<212> TYPE: DNA
<213> ORGANISM: Agrocybe aegerita

<400> SEQUENCE: 42

| | | | | | | |
|---|---|---|---|---|---|---|
| atgtgtgcct | ccgccacgcg | cccccagcca | tcggcgtcca | caacgtgaa | gaagattatc | 60 |
| ctgcccgacc | tcgtctcaca | ttgcaccttt | aagcttcgtc | ataatcgcca | caggaaacaa | 120 |
| gttaccaccg | agacgaagaa | gtggctgttc | aaggacggca | atctcctagg | ccagaaggaa | 180 |
| agggcgtacc | acggactcaa | atgtggcctc | ctcacatcta | tgtgctaccc | ggatgcaggg | 240 |
| taccccaac | tgcgcgtcgt | caacgacttc | ctcacctatc | tcttccacct | cgataactta | 300 |
| tcagacgaga | tggacaatag | gggcacaacc | acgaccgctg | atgaggttct | aaactctctc | 360 |
| taccacccctc | acacttggcg | ttcgtcggcg | agagttggga | agatgacgcg | ggatttctat | 420 |
| aagcggctcg | ttcttacagc | gtcgcctggg | gctcagcagc | gtttcattga | gacgtttgat | 480 |
| ttcttcttcc | agagtgtaac | tcaacaagct | ttggatcgtg | cgagtggagt | aatacccgac | 540 |

```
ctcgagtctt acatctccct gcgtcgcgat acctcaggct gcaagccctg ctgggcgatg      600
atcgaatatg caaacaatct cgatatccct gatgaagtca tggatcatcc cattattcgc      660
agtctcggag aagctacgaa cgatttggtg acatggtcta acgacatctt ttcctacagt      720
gtagaacagt cgaaggggca tacacataat atgatccccg tggtcatgta ccaagaaggc      780
ttggaccttc aagctgccgt ggacttcgtc ggcgatatgt gcaggcagtc gatcaatcgc      840
tttgttgagg aaaaggcgcg tcttccttca tggggcccta agatcgacca ggacgtggcc      900
atctacgtcc aaggtctcgc cgactggatc gtcggttctc tccactggtc cttcgaaaca      960
gaacgctact ttggcaaatc aggccgccag gtgaaggcct cacggatagt tgacctcctt     1020
cccagacaac ggttaccttt a                                                1041

<210> SEQ ID NO 43
<211> LENGTH: 1119
<212> TYPE: DNA
<213> ORGANISM: Agrocybe aegerita

<400> SEQUENCE: 43
atgaccgctg caccactcac tttcactctt cctgaccttc tggcgaattt tccttggaag       60
cgcaacttaa gcgaatacta tcccgaatgc aagacagagt ccagcgcatg gactgagtcc      120
tttcacccgt cgacgacgga gggtctcaaa gggttcaatc tctgtgattt caatctgctc      180
gcttctttgg catattcgcc ccgtgagcga gagatcatca ggctcgggtg cgatctcatg      240
aacatcttct acgtcttcga cgagtacacc gacatcgcgg acggtgacgg tgccgacaaa      300
attcgagaca tcatcatgga tgctttccgt aatcctcaca agcctaggcc cgaaggagag      360
ctgctagtcg gcgaaatggc acgcgacttc tggattcggg cgtccggcta cgtgtcccccc     420 gacgcccact gcctgaccca cttcctccgt gatttcgaca cctacaccggc tgcggtcgtg      480 cgggaagccg acgaccgcgc caaacgcgtc tatcgcacct cgaagattat ctctccatc       540 cgccggggatt cctcaggctg cctgcccagc ttcgcgctct gtgagttcgg gcttgacctg      600
cccgaagagg catatccacca cccgcgaatg gctgcccttc gcgaacaaag cactgatcta      660
atcgctatcg gaaacgacat tgattcgtac gccatggaga aggcacgcgg gctggaactc      720
cataactccg ttgagctcat cataaatgag cacggccttg atgtccaagg cgctatcaac      780
tggctcgaac gttatgccgc aggggtccac gcatcgttcc tcgacaacgt cgcgaacatg      840
ccttcgtggg gcgaggacgt tgatcgacgt gtcaagatgt acattgatgg cctcgcgcaa      900
tgggtccgtg gtaatgatga ttggactttt gagagcgggc gctattttgg cgacaaaggc      960
ctggaagtcc agaagacgag agtcatgtcc ctcctgcccg ctagcaaggt ttcgttaaga     1020
agtcggccta aagccgtcgg acacgtaccc aagaaactct taagatattt ccgatactct     1080
acgatgtatt tttttggttt tcatgtacta gcgaaatga                            1119

<210> SEQ ID NO 44
<211> LENGTH: 1029
<212> TYPE: DNA
<213> ORGANISM: Agrocybe aegerita

<400> SEQUENCE: 44
atgtctgcgt tgccctctca gttcaaactg cctgacctcc tctccacctg cccgttgaag       60
gacggcacca atcccgccta caagaaagcg gccgcagagt cacgagcatg gatcggcagc      120
tacaatatgt tcgccgacag aaagcgcgct ttctttattc agggacagaa cgagctcctt      180
tgctcccatg tctactgcta tgcgggttat gaacagctcc gtactacctg cgacttcgtg      240
```

```
aatctcctgt tgttgttgga cgaggtcagc gatgaacaaa gcggtgaaga cgcacgggcg      300
acgggccaag ttttcgtgaa cgccatgaaa tacgctgatt ggcacgatgg ctcaaaactc      360
gcgaagctca ctaaagactt ccgtgtgcgc ttcctacgcc tggccggacc caaaaatgtt      420
gcccgatttg ttgccctctg cgaaagttac actgcatgcg tcggcaaaga ggccgaattg      480
cgcgaaagcg gtcaagtcct cggcgtcaaa gaatttatcc ccttacggcg gcaaaacagc      540
gcagtcttgc tctgcttctc tcttgtggag tacattctcg gcatcgacct cgacgatgag      600
gtttaccggg atgagaactt tttgaacgcc tactgggcgg cttgtgacca cgtctgctgg      660
gcgaatgacg tctactccta cgacatggag cagtccaagg ggctgagcaa caacaacatc      720
gtcaccgtac tcatggaaga aaaccacacc tcgctgcaag acacctccga ttacattgga      780
gagaagtgcg cagagtttgt gcaaatttat ttgacctcca aaaagcgtct ctcgccatcc      840
ctcggtcctg atgcagccct tttcctcgaa tcgatagggt cgtggatggt tggtaacctt      900
gcgtggagtt tcgagacttc ccgctacttc ggttctcgtc acctcgaggt gaaagagaca      960
ggaatcgtca ttcttcgccc acgagaactt ccagaagacg gcagttcttc tgactcggat     1020
gaagagtaa                                                             1029

<210> SEQ ID NO 45
<211> LENGTH: 1164
<212> TYPE: DNA
<213> ORGANISM: Agrocybe aegerita

<400> SEQUENCE: 45
atgagcttct tcaagtcttc gcagccgacg atctacattc ccgacaccct cagaaactgg       60
ccttggccca gggaaattaa ccccccattac gaggaatgca agcgagagtc agccgcctgg      120
gttgagaagt tcggggcctt cagcgctaag gcccagaaag cgttcaacaa atgcgacttc      180
aatcttttgg cctcgcttgc atggtctcga gtaaaccgcg acggctgcag gattggatgc      240
gacttgatga atttgttctt cgtcttcgat gaatggtcgg acgtttccga cgcggaagag      300
acaagacgca tggccgacat cattatggac gccctctacg atcctcataa acctcgccca      360
actggagaat gggtcggtgg cgaagttact agacagtact ggcttaacgc catccgcact      420
gctactccct ctgctcagaa gaggttcatc aaggcgttca agctctacac cgactctgtt      480
gtccagcagt ccgccgaccg cgataagcac ctcattcgcg atatcgacag ttacttcgag      540
gtcaggcgcg acactatcgg cgcgaagccg tccttcgcca tcaacgaggt gcacatgaac      600
cttccggact atgttatgga gcacccggtc atcaagaacc tcacggcata ctgcatcgac      660
atgctttgca tcggcaacga tttgtgctct tacaacgtcg aacaaagccg cggggatgat      720
gggcacaacc ttgtcactat cgtcatgcac cagctcaacc tcgacgtcca aggcgcattc      780
gattggatcg gaaagctcca cgacgagtta gtcgacaagt tcctcgaaga atacaagaat      840
gtccctacgt ttaaggacaa acaagtcacc aaggaatgcg ctgagtatgc cttcggtctc      900
ggcaattggg tccgaggaaa cgaccaatgg agcttcgaga gtgagcgcta tttcaggaaa      960
gacggcatga gggtcctgac agagcggact gtcgttctcc tgcccaagaa gcgcgaaccg     1020
cccccgaagc ccctcgatga agatccaatc tacagcgctc tgccgtggtg gggttggacg     1080
gctctctttg gattttggc cacagccttc acgttctccg cccgtcaact ctcaactcgt     1140
atttcggcga acctcattgc ttaa                                            1164

<210> SEQ ID NO 46
```

<211> LENGTH: 1170
<212> TYPE: DNA
<213> ORGANISM: Agrocybe aegerita

<400> SEQUENCE: 46

```
atggtttggg acttcgtact ctccctcttc cattcccttc tcgccgcgtt ccagaccttg      60
acatcctggc tgacgggtag tttcttgttc aacaacaaga tggccccagc tccaaatcca     120
gctcccgtta ccttcatcct tcccgacctc gaaaagacgt tcaactcgct acccgacgac     180
ggactcaacc cacatcacga cgtcgcttgc gcagagtcgc gtgaatggtt cgcaaaatac     240
aacaagaagg ttctcggtgc ccagatgcaa gagttcttca ggcgctgcaa gttcgaactc     300
atcacgtcgt acacctatcc ctacgtggac aaggaaggtc tcagagcgac tatggattgg     360
cacaatatcc tctggttctt cgacgaggtt acagacaccg aaactggcaa ggacgctcac     420
aaatccgcca tcatcactat ccgcaccctc cgcgagcccg acttcgatga cggatcatca     480
ctgtgcagaa tggtcaggga cttcgcctc agtcacctct ctcgcgccgg tcccgaatgt     540
actcgccgat tcctagagca ctgcgatgtt gcgtttcacg cgggtgcggt ggaagctgaa     600
ctccgtgaga aggcgaagt gctctcgatc gaaggatacc tcaaactccg tcgcgagacg     660
agcggagcgc gcacctgctt cgatatggcc gaatacctca tggacattga ccttccccag     720
gacatgtatg acgacccgt attccagaag ggctacatcg ctgctcttga cctcatcttc     780
ctcgctaacg atctttattc ttacaacatg aacaagcta aggggcacaa cggtgccaac     840
gttctgaccg tcgtcatgaa agagaccaag ctgaacctcc aatccgctgc tgactacgtc     900
ggtgttcttt gtgagaagct catcaagcaa ttccaagagg caaagagcac gctcgagaat     960
cgcctcgcga aggagaagaa ccccgctaag gccgctgcgc tgaaggatgc aatccgctcg    1020
ttggtcgggt acgacactg ggttcggggc aacgtcgaat ggagcttcga cagagagaga   1080
tatttcggga agaagaacaa ggagatcaag aagtctcggg ttgtgaccct gacgcctacg   1140
aacagtgtta atcgcgctct caaggcctag                                     1170
```

<210> SEQ ID NO 47
<211> LENGTH: 1077
<212> TYPE: DNA
<213> ORGANISM: Agrocybe aegerita

<400> SEQUENCE: 47

```
atgaacgcat cgcctttctt gaacgagtct tcgccaacgc ggcccacgtc cttcgtgctt      60
cctgatctcg tctcgcactg caagttcccg ctttcttatc atcccaacgg ggacgagatc     120
gcgcaggagt ctgttgattg gctcgatagt agctgcccag acctgaccgc gaaacagcgg     180
cgtgcgcttc gtgtcctgca gtcgggcgaa ctcacagcct actgctataa ccaggcgacc     240
tccccagaac gcctacgcgt cgtgtccgac tttctgacat acctctttca tttggacaac     300
atcagcgatg gaatgatgac gcgcgagacg gatgtgctcg cagacgtcgt catgaatgcg     360
ttttggttca ccgataagta tatgccgact cggggccccg aaaggaaaca gctggacgaa     420
gagcttaatc ctggcaaact ggcacgagat ttctggtcgc gggctattgc agactgtgga     480
gttggagtgc aagcccggtt caaagaaaca atgggactgt tctttgaagc cgtcaacatc     540
caggctagaa tgcgagatga agacaccata ccggacttgg agtcgtatat cgatgtccgg     600
agagacacgt cagggtgcaa accatcttgg gtgctaatcg aatatgcact cggaattgat     660
cttccggacc atgtcgttga ccatccgata atgcaagcgc taaccaagg tactaatgac     720
cttgtaacct ggtctaatga catattctct tataacgtcg aacaatcacg aggcgacacg     780
```

```
cataatatga ttgttattct tatggaatat catggtcata ccctgcagag tgctgttgat      840
tatgttggcg agttatgcgc gcaaaccatc gacacctttt gcgaaaacaa ggaacgtctt      900
ccgtcttggg gtcccgaaat cgacgatatg gttgctcgtt acgttaaggg tcttcaggac      960
tggattgttg gttctttgca ttggagtttt caaacccaac ggtatttcgg caaagacggc     1020
ttagacatca agaagcatag atttgtcaag ctcttacctt tggaagctgc aaaataa       1077
```

<210> SEQ ID NO 48
<211> LENGTH: 1341
<212> TYPE: DNA
<213> ORGANISM: Agrocybe aegerita

<400> SEQUENCE: 48

```
atgggtcgtt cttctgtggt tcgttcattt tttttgtcgg tacaagccat ggcctcttcc       60
ttgcttgagc catctttggc cgctatcgcg ctcgtcatct tgctcgcgtc tgtttccctc      120
tctcgaaaga agcgcccagc tgctccagag ccacagggc tgtcggtgct cggcaatctt      180
ttcgacatcc cgaagagagc gtcatccata atttacctcg ccttaggaaa gccgtataat      240
acgctcacca agagagctgt ctcacaactt cagggttaca ctcctgggag tcacatcgac      300
gctacttccc actctccgcg tgtcttccgt ctcccgaatc tggaagagac attctccgtc      360
ttccccgacc atggcttgaa ccccaactac acgtccgccc gtaccgactc cagagcatgg      420
atcaatcagt ataccaaggt ggtctgtggg cccaagatgg tcgccttcat gaacaactgc      480
gaatttgagc tttctaactc tcactgctac ccgtacgccg gctacaaagg actcaaggct      540
acaatggatc ttacaaatat cctctggctc tatgacgagt ataccgatac cggatccggc      600
gcggaagctg tcaaggcggc aggtattgtt gctcgcgctc tgcgagagcc agactacgat      660
gatggaactt gggtctgccg catgatgaaa tccttcaaac aaaaccacat tgataaagcg      720
ggccctggtg tcgctcgccg cttcatcgac aacttctgca actacgttga agttgtcggt      780
agagaagcag agcttcgaga aaagaacgag gtgcttgaca tccccaacta cgtcactttc      840
cgtcgtgaga caagtgccgt tcgcacttgc ttcgacttgg tggaatattg cctcgatctt      900
gaccttcccc aatacgtgca cgatgatcct gtcttcatca gtggctacaa cgcaggcatg      960
gatctcgtct tctgggctaa cgacctcgtc tcttacaaca tggagcaatc taagggacac     1020
agtggagcca acgtcgtgac cgtgatcatg aagtccaaag tgtcgatct caaacggcc      1080 gtcgatttct tgggaggata ctgcgaggca cttaccgcac agctgctcga ggcgaagcgc     1140
attcttcagg ctcgttccga tgctgcttac tccagagatg tagtccgcct tatggatgct     1200
ttcggtgatt gggtgagagg aaacgttgcg tggagctttg agacagagag gtatttcgga     1260
aaggaaaaca agagagtcaa ggagacactg cttgttgaac tcaaggagcc gttcgttggt     1320
gcactcgcct tgaaagagta a                                              1341
```

<210> SEQ ID NO 49
<211> LENGTH: 1155
<212> TYPE: DNA
<213> ORGANISM: Agrocybe aegerita

<400> SEQUENCE: 49

```
atgcactcaa gcactcaact attcactcac tcgccaacga agatgcaaat tatcctgcct       60
gacctcctct gctcttgggg gtacaaaggt ttcctgaacc cgcactatga aggcgccaag      120
gcagagtcca ataccctggat acggcccttg gtcgttaaac tctttgatga gagaggacaa      180
```

```
aaagctttcg cgaaggacta caccggcctc cttgcgagta tgacgtaccc ccatcacaac      240
aaggaatttc tttgcgtcgc atgcgacatg atgaacctct tcttcgtgta cgatgagtac      300
acagacatca ccccaccaga aactgcacaa agactcgcca agattgtcgt caacgccatg      360
aggaaccccg acgagatagc cgccctcggc gaagactcca taggaactat gacgaagcag      420
ttctggagac gggcgatgac actcctgcca cccaacggat gtaattccga gtcatgcata      480
cagcacttca tcgattacac agaagagtac ttgaccgccg tcacgcgca agcttgcgat       540 cgtagctcgg gtagcgtcca tgccgtgaaa gactaccttg caatgcgacg agcgacgagc      600
ggcgccggcc tgatggtagg gctgctcgag tttggattgg acttgcctga agaagtcatg      660
aagcacgagg taatccaaga gctctccacc ggcgccatcg acatgtactg cctactgaac      720
gatatgcatt cgtatgcgag cgagctctct tccgggcagg cgagccacaa cgtcataaca      780
gttgtaatgc atgagaggaa tctttccctt caagaagcat ttgactggtt agcttcctac      840
gcagctggcg tggtcaaggg tttcaagacg aatctgaacc gagtgccatc gttttccgag      900
ctggaggacc actctttgca cggcgaaggg atgctgagag ataggataca gagatatatc      960
gatggcctcg gccaggcggt cagggcggag gacgactggg catttgagac gacgagatac     1020
catgacagaa tgcccaca gatcaagctt acgaggatgt tgaccattcg acctcaggtc       1080
aaggacaatt acgcgaagca ggcgccgagg gtcgaggcgc ctgagaggcc tatgcttctg     1140
gaagtcagga gttga                                                      1155

<210> SEQ ID NO 50
<211> LENGTH: 1887
<212> TYPE: DNA
<213> ORGANISM: Escherichia coli

<400> SEQUENCE: 50
atgcatcatc atcaccatca cgagctcagt tttgatattg ccaaataccc gaccctggca       60
ctggtcgact ccacccagga gttacgactg ttgccgaaag agagtttacc gaaactctgc      120
gacgaactgc gccgctattt actcgacagc gtgagccgtt ccagcgggca cttcgcctcc      180
gggctgggca cggtcgaact gaccgtggcg ctgcactatg tctacaacac cccgtttgac      240
caattgattt gggatgtggg gcatcaggct tatccgcata aaattttgac cggacgccgc      300
gacaaaatcg gcaccatccg tcagaaaggc ggtctgcacc cgttcccgtg gcgcggcgaa      360
agcgaatatg acgtattaag cgtcgggcat tcatcaacct ccatcagtgc cggaattggt      420
attgcggttg ctgccgaaaa agaaggcaaa aatcgccgca ccgtctgtgt cattggcgat      480
ggcgcgatta ccgcaggcat ggcgtttgaa gcgatgaatc acgcgggcga tatccgtcct      540
gatatgctgg tgattctcaa cgacaatgaa atgtcgattt ccgaaaatgt cggcgcgctc      600
aacaaccatc tggcacagct gcttttccggt aagctttact cttcactgcg cgaaggcggg      660
aaaaagtttt tctctggcgt gccgccaatt aaagagctgc tcaaacgcac cgaagaacat      720
attaaaggca tggtagtgcc tggcacgttg tttgaagagc tgggctttaa ctacatcggc      780
ccggtggacg gtcacgatgt gctggggctt atcaccacgc taaagaacat gcgcgacctg      840
aaaggcccgc agttcctgca tatcatgacc aaaaaaggtc gtggttatga accggcagaa      900
aaagacccga tcactttcca cgccgtgcct aaatttgatc cctccagcgg ttgtttgccg      960
aaaagtagcg gcggttttgc cgagctattca aaaatctttg cgactggtt gtgcgaaacg     1020 gcagcgaaag acaacaagct gatggcgatt actccggcga tgcgtgaagg ttccggcatg     1080
gtcgagtttt cacgtaaaatt cccggatcgc tacttcgacg tggcaattgc cgagcaacac     1140
```

```
gcggtgacct tgctgcggg tctggcgatt ggtgggtaca aacccattgt cgcgatttac   1200
tccactttcc tgcaacgcgc ctatgatcag gtgctgcatg acgtggcgat tcaaaagctt   1260
ccggtcctgt tcgccatcga ccgcgcgggc attgttggtg ctgacggtca aacccatcag   1320
ggtgcttttg atctctctta cctgcgctgc ataccggaaa tggtcattat gaccccgagc   1380
gatgaaaacg aatgtcgcca gatgctctat accggctatc actataacga tggcccgtca   1440
gcggtgcgct acccgcgtgg caacgcggtc ggcgtgaaac tgacgccgct ggaaaaacta   1500
ccaattggca aaggcattgt gaagcgtcgt ggcgagaaac tggcgatcct taactttggt   1560
acgctgatgc cagaagcggc gaaagtcgcc gaatcgctga cgccacgct ggtcgatatg   1620 cgttttgtga accgcttga tgaagcgtta attctggaaa tggccgccag ccatgaagcg   1680
ctggtcaccg tagaagaaaa cgccattatg ggcggcgcag gcagcggcgt gaacgaagtg   1740
ctgatggccc atcgtaaacc agtacccgtg ctgaacattg gcctgccgga cttctttatt   1800
ccgcaaggaa ctcaggaaga aatgcgcgcc gaactcggcc tcgatgccgc tggtatggaa   1860
gccaaaatca aggcctggct ggcataa                                       1887
```

<210> SEQ ID NO 51
<211> LENGTH: 1881
<212> TYPE: DNA
<213> ORGANISM: Artificial Sequence
<220> FEATURE:
<223> OTHER INFORMATION: Ec.dxs_SL3

<400> SEQUENCE: 51

```
atgcatcatc atcaccatca cagttttgat attgccaaat acccgaccct ggcactggtc     60
gactccaccc aggagttacg actgttgccg aaagagagtt taccgaaact ctgcgacgaa    120
ctgcgccgct atttactcga cagcgtgagc cgttccagcg ggcacttcgc ctccgggctg    180
ggcacggtcg aactgaccgt ggcgctgcac tatgtctaca acaccccgtt tgaccaattg    240
atttgggatg tggggcatca ggcttatccg cataaaattt tgaccggacg ccgcgacaaa    300
atcggcacca tccgtcagaa aggcggtctg tacccattcc cgtggcgcgg cgaaagcgaa    360
tatgacgtat taagcgtcgg gcattcatca acctccatca gtgccggaat tggtattgcg    420
gttgctgccg aaaagagaag caaaaatcgc cgcaccgtct gtgtcattgg cgatggcgcg    480
attaccgcag gcatggcgtt tgaagcgatg aatcacgcgg gcgatatccg tcctgatatg    540
ctggtgattc tcaacgacaa tgaaatgtcg atttccgaaa atgtcggcgc gctcaacaac    600
catctggcac agctgctttc cggtaagctt tactcttcac tgcgcgaagg cgggaaaaaa    660
gttttctctg gcgtgccgcc aattaaagag ctgctcaaac gcaccgaaga acatattaaa    720
ggcatggtag tgcctggcac gttgtttgaa gagctgggct taactacat cggcccggtg    780 gacggtcacg atgtgctggg gcttatcacc acgctaaaga acatgcgcga cctgaaaggc    840
ccgcagttcc tgcatatcat gaccaaaaaa ggtcgtggtt atgaaccggc agaaaaagac    900
ccgatcactt tccacgccgt gcctaaattt gatccctcca gcggttgttt gccgaaaagt    960
agcggcggtt tgccgagcta ttcaaaaatc tttggcgact ggttgtgcga aacggcagcg   1020
aaagacaaca agctgatggc gattactccg gcgatgcgtg aaggttccgg catggtcgag   1080
ttttcacgta aattcccgga tcgctacttc gacgtggcaa ttgccgagca acacgcggtg   1140
acctttgctg cgggtctggc gattggtggg tacaaaccca ttgtcgcgat ttactccact   1200
ttcctgcaac gcgcctatga tcaggtgctg catgacgtgg cgattcaaaa gcttccggtc   1260
```

| | |
|---|---|
| ctgttcgcca tcgaccgcgc gggcattgtt ggtgctgacg gtcaaaccca tcagggtgct | 1320 |
| tttgatctct cttacctgcg ctgcataccg gaaatggtca ttatgacccc gagcgatgaa | 1380 |
| aacgaatgtc gccagatgct ctataccggc tatcactata cgatggccc gtcagcggtg | 1440 |
| cgctacccgc gtggcaacgc ggtcggcgtg gaactgacgc cgctggaaaa actaccaatt | 1500 |
| ggcaaaggca ttgtgaagcg tcgtggcgag aaactggcga tccttaactt tggtacgctg | 1560 |
| atgccagaag cggcgaaagt cgccgaatcg ctgaacgcca cgctggtcga tatgcgtttt | 1620 |
| gtgaaaccgc ttgatgaagc gttaattctg gaaatggccg ccagccatga agcgctggtc | 1680 |
| accgtagaag aaaacgccat tatgggcggc gcaggcagcg cgtgaacga agtgctgatg | 1740 |
| gcccatcgta aaccagtacc cgtgctgaac attggcctgc cggacttctt tattccgcaa | 1800 |
| ggaactcagg aagaaatgcg cgccgaactc ggcctcgatg ccgctggtat ggaagccaaa | 1860 |
| atcaaggcct ggctggcata a | 1881 |

<210> SEQ ID NO 52
<211> LENGTH: 1860
<212> TYPE: DNA
<213> ORGANISM: Artificial Sequence
<220> FEATURE:
<223> OTHER INFORMATION: Ec.dxs_SL5

<400> SEQUENCE: 52

| | |
|---|---|
| atgcatcatc atcaccatca cagttttgat attgccaaat acccgacccT ggcactggtc | 60 |
| gactccaccc aggagttacg actgttgccg aaagagagtt taccgaaact ctgcgacgaa | 120 |
| ctgcgccgct atttactcga cagcgtgagc cgttccagcg gcacttcgc ctccgggctg | 180 |
| ggcacggtcg aactgaccgt ggcgctgcac tatgtctaca caccccgtt tgaccaattg | 240 |
| atttgggatg tggggcatca ggcttatccg cataaaattt tgaccggacg ccgcgacaaa | 300 |
| atcggcacca tccgtcagaa aggcggtctg cacccgttcc cgtggcgcgg cgaaagcgaa | 360 |
| tatgacgtat taagcgtcgg gcattcatca acctccatca gtgccggaat tggtattgcg | 420 |
| gttgctgccg aaaaagaagg caaaaatcgc cgcaccgtct gtgtcattgg cgatggcgcg | 480 |
| attaccgcag gcatggcgtt tgaagcgatg aatcacgcgg gcgatatccg tcctgatatg | 540 |
| ctggtgattc tcaacgacaa tgaaatgtcg atttccgaaa atgtcggcgc gctcaacaac | 600 |
| catctggcac agctgctttc cggtaagctt tactcttcac tgcgcgatgg cgggaaaaaa | 660 |
| gttttctctg gcgtgccgcc aattaaagag ctgctcaaac gcaccgaaga acatattaaa | 720 |
| ggcatggtag tgcctggtac gttgtttgaa gagctgggct taactacat cggcccggtg | 780 |
| gacggtcacg atgtgctggg gcttatcacc acgctaaaga acatgcgcga cctgaaaggc | 840 |
| ccgcagttcc tgcatatcat gaccaaaaaa ggtcgtggtt atgaaccggc agaaaaagac | 900 |
| ccgatcactt tccacgccgt gcctaaattt gatccctcca gcggttgttt gccgaaaagt | 960 |
| agcggcggtt tgccgagcta ttcaaaaatc tttggcgact ggttgtgcga acggcagcg | 1020 |
| aaagacaaca agctgatggc gattactccg gcgatgcgtg aaggttccgg catggtcgag | 1080 |
| ttttcacgta aattcccgga tcgctacttc gacgtggcaa ttgccgagca acacgcggtg | 1140 |
| acctttgctg cgggtctggc gattggtggg tacaaaccca ttgtcgcgat ttactccact | 1200 |
| ttcctgcaac gcgcctatga tcaggtgctg catgacgtgg cgattcaaaa gcttccggtc | 1260 |
| accttcgcca tcgaccgcgc gggcattgtt ggtgctgacg gtcaaaccca tcagggtgct | 1320 |
| tttgatctct cttacctgcg ctgcataccg gaaatggtca ttatgacccc gagcgatgaa | 1380 |
| aacgaatgtc gcctgatgct ctataccggc tatcactata cgatggccc gtcagcggtg | 1440 |

```
cgctacccgc gtggcaacgc ggtcggcgtg gaactgacgc cgctggaaaa actaccaatt    1500
ggcaaaggca ttgtgaagcg tcgtggcgag aaactggcga tccttaactt tggtacgctg    1560
atgccagaag cggcgaaagt cgccgaatcg ctgaacgcca cgctggtcga tatgcgtttt    1620
gtgaaaccgt tgatgaagc gttaattctg gaaatggccg ccagccatga agcgctggtc    1680
accgtagaag aaaacgccat tatgggcggc gcaggcagcg cgtgaacga agtgctgatg    1740 gcccatcgta aaccgtacc cgtgctgaac attggcctgc cggacttctt tattccgcaa    1800
ggaactcagg aagaaatgcg cgccgaactc ggcctcgatg ccgctggtat ggaagccaaa    1860
```

<210> SEQ ID NO 53
<211> LENGTH: 1173
<212> TYPE: DNA
<213> ORGANISM: Agrocybe aegerita

<400> SEQUENCE: 53

```
atgcatcacc atcaccatca cccagctcg acccagctgt tcactcactc tccgaccaaa     60
atgcagatca tcctgccgga tctgctgtgc tcctggggat ataaagggtt tctcaaccct    120
cactatgagg cgctaaggc ggaatccaac acctggattc gcccgctcgt agtgaaactt    180
ttcgacgaac gtggccagaa agcgttcgcc aaagattaca ccggtctgct ggcgtctatg    240
acttacccgc accacaacaa agaattcctg tgtgtggctt gcgatatgat gaacctgttc    300
tttgtttatg acgagtatac cgatattacc ccgccggaaa ccgcgcagcg tctggctaaa    360
atcgttgtaa atgctatgcg caatccggat gagatcgccg ctctgggtga agacagcatc    420
ggtactatga ccaagcagtt ctggcgccgc gctatgactc tgctgccacc gaacggttgt    480
aactctgaat cttgtatcca gcacttcatt gactacaccg aagaatatct gactgcagtg    540
acgcgtgaag cttgtgatcg tagcagcggc tctgtccacg ctgtaaaaga ctatctggcg    600
atgcgtcgtg caacctctgg cgcgggtctg atggttggtt tactggaatt tggcctcgat    660
ctgccggaag aagtcatgaa acatgaagtg atccaggaac tgtctactgg cgcgatcgac    720
atgtactgtc tgctgaacga catgcatagc tacgcatctg aactgtcgtc tggtcaggcc    780
tctcacaacg ttattaccgt cgtgatgcac gaacgtaacc tgtcccctgca agaagctttt    840 gattggctgg cctcttacgc ggcaggcgta gtgaagggtt tcaaaaccaa cctgaaccgc    900
gttccttctt ttagcgaact ggaggaccac tctctgcacg cgaaggcat gctccgtgat    960 cgcattcagc gttacatcga cggcctgggt caggcggttc gcgcggaaga tgattgggct   1020
tttgaaacta cccgctatca cggtcagaac ggcccgcaga ttaaactgac ccgtatgctg   1080
accatccgtc cgcaggttaa ggacaactac gctaaacagg ctccgcgcgt cgaggctcct   1140
gaacgcccga tgttactgga agtgcgtagt taa                                1173
```

<210> SEQ ID NO 54
<211> LENGTH: 1050
<212> TYPE: DNA
<213> ORGANISM: Agrocybe pediades

<400> SEQUENCE: 54

```
atgcatcacc atcaccatca ctcccaattt attatcccgg atctgttatc cacttggcct     60
tggcagcgcg tgtctaaccc gatgtggcgt gagattgatg aagaagcaaa cgcgtgggtg    120
cagtctttcg aacctgtttga accgtcccag ttcgagaaat tcaagatgtg tgatttcaac    180
ctgctgggct cgatgattgg taccgtgaa accaaagatc atctgcgcat cagttgcgac    240
```

```
ctgatgaact tctatttcgc attcgacgaa tacacggaca tggcatccaa agacgaagcg    300
cgtaagatcg cccgtgacgt gatggatgca tttcgcaaca ccgaaaaacc agctcacaac    360
caaatcaccg aaatggcccg ccagttttt  aaacgtacga tcgacactgt aggtaaagac    420
ttgccgggcg tggaacgttt tatcgctgac ttcgatgctt atacgcattc cgtgatccag    480
gaggccgacg accgtgctac tggccacatc cgcagcgtca acgactattt cacgttacgc    540
cgcgacactt cgcggcgcgaa accaagcttc agcttctttg gcctgggtct gaacattccg    600
gatgaggttt tccaccatcc tgtggttatt tccatgatcg aaggcgccac cgatctgatt    660
gctgttacga atgacatgca ctcatataac ctcgaacact cccgtggtct ggatggacac    720
aacgtaatca ctgctatcat gcacgaatac cagctggacc tgcagggcgc actgtactgg    780
ctatccggtt acgctaccca tacgattgct aacttcctgt cgaaccgccg taacctgccg    840
tcctggggcc cggctgtcga taaagcggta gaagaatttt tcgaccgtgt tggtcgttgt    900
gttcgtggct acgacgcttg gagctacgaa accaaacgct attacgggaa aaacggcctg    960
caggtgcaga gacccgtcg  tatcaccctg cgcccgcgtg acgcgtctta cattactaag   1020
gagcagctgc aggtatctat caaagcataa                                     1050
```

<210> SEQ ID NO 55
<211> LENGTH: 1053
<212> TYPE: DNA
<213> ORGANISM: Agrocybe pediades

<400> SEQUENCE: 55

```
atgcatcacc atcaccatca ctcctctcag atctatatcc cggacctcct gatcacctgg     60
ccgtggcaaa aggtgcgcaa cccactgctg caagaagtgc aggatgaggc gaacgaatgg    120
gtgaaatctt tcgtgctgtt cgaaccgaaa cagtttgaga aatttaaggc atgtgatttc    180
aacctgctgg gtgcactggt tggtccgctg gtaccaagg  aagaactgcg cattagctgt    240
gacctgatga acttctactt cgccttcgat gagtacaccg acctggctag cgctgacgaa    300
gccaaagtaa tcgcgcgcga tgtgatggaa agcttccgtc acacagataa gccaagccac    360
aacaaaatta ctgaaatggc ccgtcaattc ttcgaacgta ctatcaacac ggttggtaac    420
gatccgactg gcattgaaca atttattgcg gatttcgacg catacaccac ctctatcatc    480
caagaagctg atgatcgtgc gtctggtcac attcgtagcg ttgaggatta cttcattctg    540
cgccgtgaca cctgtggtgg gaaaccgtcg ttctcgttct tcggtctggg cctgaacatc    600
ccgaaagaag tcttcgcaca cccgatgttc atctccatga ccgaatccgc gactgatctg    660
atcgcaatta ccaacgatat gcactcttat aacctggagc aatcccgcgg cttggatggt    720
cacaatgtaa ttaccgcgat catgcacgaa tacaaaatta atctccaggg tgcgctgtac    780
tggctgtcgg gttacgctac taaaactatt gcgaaattta tctctgaccg taaaaatttg    840
ccgagctggg gcccagtggt tgaccgcgcc gttgaacaat actttgaccg tgttggtcgt    900
tgcgttcgtg gctacgatgc ctggtcttac gaaaccaaac gttattacgg taaaaatggc    960
ctggaaatcc agaaaactcg tcagatcacc ctgcgcccgc tggacccggc gtacgtgacc   1020
aaagaacagc tgcaggtatc catgaaggca taa                                 1053
```

<210> SEQ ID NO 56
<211> LENGTH: 1050
<212> TYPE: DNA
<213> ORGANISM: Galerina marginata

<400> SEQUENCE: 56

```
atgcatcacc atcaccatca cccgagccag ttcaccatcc ctgacctgct gatcacttgg    60
ccatggcagg aaatcaccaa cccgatgctg cacgaagtag acgctgaagc caatgaatgg   120
gttcagtcac tgaacctgtt cgaaccgaaa cagttcgaaa agttcaaagc ctgtaacttc   180
aacctgctgg gctccctggt tggaccgctg ccaagccgtg accaccttcg tgtgtcctgc   240
gacctgatga acttctactt cgctttcgat gagtacacgg acatggcaaa caaagatgaa   300
gctatgcgta tcgcccgtga cgtaatgcaa gcattccgta acactgacac gcctagcaac   360
tctaaaatca ctgaaatggc acgtcaattc ttcaaacgta ccatcgaggt tgtaggcgaa   420
gacctgccgg gcatcgaacg tttcatcgcc gatttcgatg catacactcg ttccgtgatt   480
caggaagcag atgatcgtgt tgcaggtcac attcgtaacg tggaggacta cttcattctg   540
cgccgtgata cgtgcggtgc taaaccgagc ttctctttct acggtctggg tctgaacatc   600
ccgaccgagg tctttgaaca cccgctgctg atttctatgg ttgaaagcgc aactgacctg   660
attgctgtca ccaatgacat gcactcttac ggtctggagc attctcgtgg cctggacggt   720
cacaatgtta tcaccgccat tatgcacgaa tatcagctgg acctacaggg tgccctgtac   780
tggctgtccg gctacgcaac taaaaccatc tccaaattcc tgactgatcg taaaaacctg   840
ccgtcctggg gcccaaccat tgacaaagct ctcgaaatct acctggaccg tttaggtcgt   900
tgcgtgcgtg gctacgatgc ttggtcctac agcactaagc gttactatgg taaaaacggt   960
ctgaaggttc aaaaaacccg ccgtatcact ttgaaaccgc gtgatgcagc ctacatcacg  1020
aaggatcagc tgcaggtgtc tatcgcttaa                                    1050

<210> SEQ ID NO 57
<211> LENGTH: 1053
<212> TYPE: DNA
<213> ORGANISM: Hypholoma sublateritium

<400> SEQUENCE: 57
atgcatcacc atcaccatca ctccgctcag tacaccatcc ctgacttact ggcgaactgg    60
ccgtggcagc gcgtgaccaa cagcatgctg gacgaggtgc gcgacgaagc aaacgagtgg   120
gtgatgtccc tgggcctgtt tgagccggct cagtttaaaa aattcaaagc atgcgacttc   180
aaccttctgg caagctttat tggtccgctg gaaagtaaag aacaccttcg tgttgcttgc   240
gatctgatga atttctattt cgctttcgat gagtacactg acgttgctaa ccgtgaagag   300
gctaaaaaaa tctctcaggg cgttatgcac gcgtttaaaa ctcgttctgc agagccgtcc   360
agctccaaaa ttacggaaat ggcgcgtcag ttctttcgtc gtaccgttga cgtcgtcggt   420
gaagattccc cggccatcaa ccagttcatt accgacttcg acacctacac cacggctgtg   480
atccaggaag cagacgatcg caccgaaggt accatccgta atgttgagga ctatttcacc   540
ctccgtcgcg acacctgcgg cgccaaacct tcttttttcgt tcttcgccct gggcctgaac   600
atgccgaccg aagtcttcga cacccctctg atcatgtctc tggtagagcg tgcaaccgac   660
ctgatcgcga ttgtgaacga catgcactcc tacggtctgg aacgtgctcg tggcctggat   720
ggtcataacg tagtaacgtc catcatgtac gagcatcagc tggacctgca gggtgcgctg   780
cactggctgg ccggttatgc cgaagacaca atcgccaagt tcctgtcgga aaaagaacgt   840
ctcccgtcct ggggtccggc ggtagatgta tccgtgcagg aatttgttga ccgtctgggc   900
cgttgcgtgc gtggttacga cgcttggtcc tatgaaacga accgctatta cggcagccac   960
ggtctacaga ttcgtcagac tcgtcaaatc accctgccat ccaacgactc tggctacatc  1020
```

```
actcgcaagc agatgggcgt ttctatcgct taa                                 1053
```

<210> SEQ ID NO 58
<211> LENGTH: 1029
<212> TYPE: DNA
<213> ORGANISM: Artificial Sequence
<220> FEATURE:
<223> OTHER INFORMATION: Agrped1_689675_mut1

<400> SEQUENCE: 58

```
atgcatcacc atcaccatca ctcctctcag atctatatcc cggacctcct gatcacctgg    60
ccgtggcaaa aggtgcgcaa cccactgctg caagaagtgc aggatgaggc gaacgaatgg   120
gtgaaatctt tcgtgctgtt cgaaccggaa cagtttgaga aatttaaggc atgtgatttc   180
aacctgctgg gtgcactggt tggtccgctg ggtaccaagg aagaactgcg cattagctgt   240
gacctgatga acttctactt cgccttcgat gagtacaccg acctggctag cgctgacgaa   300
gccaaagtaa tcgcgcgcga tgtgatggaa agcttccgtc acacagataa gccaagccac   360
aacaaaatta ctgaaatggc ccgtcaattc ttcgaacgta ctatcaacac ggttggtaac   420
gatccgactg gcattgaaca atttattgcg gatttcgacg catacaccac ctctatcatc   480
caagaagctg atgatcgtgc gtctggtcac attcgtagcg ttgaggatta cttcattctg   540
cgccgtgaca cctgtggtgg gaaaccgtcg ttctcgttct tcggtctggg cctgaacatc   600
ccgaaagaag tcttcgcaca cccgatgttc atctccatga ccgaatccgc gactgatctg   660
atcgcaatta ccaacgatat gcactcttat aacctggagc aatcccgcgg cttggatggt   720
cacaatgtaa ttaccgcgat catgcacgaa tacaaaatta atctccaggg tgcgctgtac   780
tggctgtcgg gttacgctac taaaactatt gcgaaattta tctctgaccg taaaaatttg   840
ccgagctggg gccagtggt tgaccgcgcc gttgaacaat actttgaccg tgttggtcgt   900
tgcgttcgtg gctacgatgc ctggtcttac gaaaccaaac gttattacgg taaaaatggc   960
ctggaaatcc agaaaactcg tcagatcacc ctgcgcccgc tggacccggc gtacgtgacc  1020
aaagaataa                                                          1029
```

<210> SEQ ID NO 59
<211> LENGTH: 996
<212> TYPE: DNA
<213> ORGANISM: Artificial Sequence
<220> FEATURE:
<223> OTHER INFORMATION: Agrped1_689675_mut2

<400> SEQUENCE: 59

```
atgcatcacc atcaccatca ctcctctcag atctatatcc cggacctcct gatcacctgg    60
ccgtggcaaa aggtgcgcaa cccactgctg caagaagtgc aggatgaggc gaacgaatgg   120
gtgaaatctt tcgtgctgtt cgaaccggaa cagtttgaga aatttaaggc atgtgatttc   180
aacctgctgg gtgcactggt tggtccgctg ggtaccaagg aagaactgcg cattagctgt   240
gacctgatga acttctactt cgccttcgat gagtacaccg acctggctag cgctgacgaa   300
gccaaagtaa tcgcgcgcga tgtgatggaa agcttccgtc acacagataa gccaagccac   360
aacaaaatta ctgaaatggc ccgtcaattc ttcgaacgta ctatcaacac ggttggtaac   420
gatccgactg gcattgaaca atttattgcg gatttcgacg catacaccac ctctatcatc   480
caagaagctg atgatcgtgc gtctggtcac attcgtagcg ttgaggatta cttcattctg   540
cgccgtgaca cctgtggtgg gaaaccgtcg ttctcgttct tcggtctggg cctgaacatc   600
ccgaaagaag tcttcgcaca cccgatgttc atctccatga ccgaatccgc gactgatctg   660
```

| | |
|---|---:|
| atcgcaatta ccaacgatat gcactcttat aacctggagc aatcccgcgg cttggatggt | 720 |
| cacaatgtaa ttaccgcgat catgcacgaa tacaaaatta atctccaggg tgcgctgtac | 780 |
| tggctgtcgg gttacgctac taaaactatt gcgaaattta tctctgaccg taaaaatttg | 840 |
| ccgagctggg gcccagtggt tgaccgcgcc gttgaacaat actttgaccg tgttggtcgt | 900 |
| tgcgttcgtg gctacgatgc ctggtcttac gaaaccaaac gttattacgg taaaaatggc | 960 |
| ctggaaatcc agaaaactcg tcagatcacc ctgtaa | 996 |

<210> SEQ ID NO 60
<211> LENGTH: 930
<212> TYPE: DNA
<213> ORGANISM: Artificial Sequence
<220> FEATURE:
<223> OTHER INFORMATION: Agrped1_689675_mut3

<400> SEQUENCE: 60

| | |
|---|---:|
| atgcatcacc atcaccatca ctcctctcag atctatatcc cggacctcct gatcacctgg | 60 |
| ccgtggcaaa aggtgcgcaa cccactgctg caagaagtgc aggatgaggc gaacgaatgg | 120 |
| gtgaaatctt tcgtgctgtt cgaaccggaa cagtttgaga aatttaaggc atgtgatttc | 180 |
| aacctgctgg gtgcactggt tggtccgctg gtaccaagg aagaactgcg cattagctgt | 240 |
| gacctgatga acttctactt cgccttcgat gagtacaccg acctggctag cgctgacgaa | 300 |
| gccaaagtaa tcgcgcgcga tgtgatggaa agcttccgtc acacagataa gccaagccac | 360 |
| aacaaaatta ctgaaatggc ccgtcaattc ttcgaacgta ctatcaacac ggttggtaac | 420 |
| gatccgactg gcattgaaca atttattgcg gatttcgacg catacaccac ctctatcatc | 480 |
| caagaagctg atgatcgtgc gtctggtcac attcgtagcg ttgaggatta cttcattctg | 540 |
| cgccgtgaca cctgtggtgg gaaaccgtcg ttctcgttct tcggtctggg cctgaacatc | 600 |
| ccgaaagaag tcttcgcaca cccgatgttc atctccatga ccgaatccgc gactgatctg | 660 |
| atcgcaatta ccaacgatat gcactcttat aacctggagc aatcccgcgg cttggatggt | 720 |
| cacaatgtaa ttaccgcgat catgcacgaa tacaaaatta atctccaggg tgcgctgtac | 780 |
| tggctgtcgg gttacgctac taaaactatt gcgaaattta tctctgaccg taaaaatttg | 840 |
| ccgagctggg gcccagtggt tgaccgcgcc gttgaacaat actttgaccg tgttggtcgt | 900 |
| tgcgttcgtg gctacgatgc ctggtcttaa | 930 |

<210> SEQ ID NO 61
<211> LENGTH: 993
<212> TYPE: DNA
<213> ORGANISM: Artificial Sequence
<220> FEATURE:
<223> OTHER INFORMATION: Agrped1_689675_mut4

<400> SEQUENCE: 61

| | |
|---|---:|
| atgcatcacc atcaccatca ctggccgtgg caaaaggtgc gcaacccact gctgcaagaa | 60 |
| gtgcaggatg aggcgaacga atgggtgaaa tctttcgtgc tgttcgaacc ggaacagttt | 120 |
| gagaaattta aggcatgtga tttcaacctg ctgggtgcac tggttggtcc gctgggtacc | 180 |
| aaggaagaac tgcgcattag ctgtgacctg atgaacttct acttcgcctt cgatgagtac | 240 |
| accgacctgg ctagcgctga cgaagccaaa gtaatcgcgc gcgatgtgat ggaaagcttc | 300 |
| cgtcacacag ataagccaag ccacaacaaa attactgaaa tggcccgtca attcttcgaa | 360 |
| cgtactatca acacggttgg taacgatccg actggcattg aacaatttat tgcggatttc | 420 |

| | |
|---|---|
| gacgcataca ccacctctat catccaagaa gctgatgatc gtgcgtctgg tcacattcgt | 480 |
| agcgttgagg attacttcat tctgcgccgt gacacctgtg gtgggaaacc gtcgttctcg | 540 |
| ttcttcggtc tgggcctgaa catcccgaaa gaagtcttcg cacaccgat gttcatctcc | 600 |
| atgaccgaat ccgcgactga tctgatcgca attaccaacg atatgcactc ttataacctg | 660 |
| gagcaatccc gcggcttgga tggtcacaat gtaattaccg cgatcatgca cgaatacaaa | 720 |
| attaatctcc agggtgcgct gtactggctg tcgggttacg ctactaaaac tattgcgaaa | 780 |
| tttatctctg accgtaaaaa tttgccgagc tggggcccag tggttgaccg cgccgttgaa | 840 |
| caatactttg accgtgttgg tcgttgcgtt cgtggctacg atgcctggtc ttacgaaacc | 900 |
| aaacgttatt acgtaaaaa tggcctggaa atccagaaaa ctcgtcagat caccctgcgc | 960 |
| ccgctggacc cggcgtacgt gaccaaagaa taa | 993 |

<210> SEQ ID NO 62
<211> LENGTH: 946
<212> TYPE: DNA
<213> ORGANISM: Artificial Sequence
<220> FEATURE:
<223> OTHER INFORMATION: Agrped1_689675_mut5

<400> SEQUENCE: 62

| | |
|---|---|
| atgcatcacc atcaccatca cgaggcgaac gaatgggtga atctttcgt gctgttcgaa | 60 |
| ccggaacagt ttgagaaatt taaggcatgt gatttcaacc tgctgggtgc actggttggt | 120 |
| ccgctgggta ccaaggaaga actgcgcatt agctgtgacc tgatgaactt ctacttcgcc | 180 |
| ttcgatgagt acaccgacct ggctagcgct gacgaagcca agtaatcgc gcgcgatgtg | 240 |
| atggaaagct tccgtcacac agataagcca agccacaaca aaattactga atggcccgt | 300 |
| caattcttcg aacgtactat caacacggtt ggtaacgatc cgactggcat tgaacaattt | 360 |
| attgcggatt tcgacgcata caccacctct atcatccaag aagctgatga tcgtgcgtct | 420 |
| ggtcacattc gtagcgttga ggattacttc attctgcgcc gtgacacctg tggtgggaaa | 480 |
| ccgtcgttct cgttcttcgg tctgggcctg aacatcccga agaagtctt cgcacacccg | 540 |
| atgttcatct ccatgaccga atccgcgact gatctgatcg caattaccaa cgatatgcac | 600 |
| tcttataacc tggagcaatc ccgcggcttg gatggtcaca atgtaattac cgcgatcatg | 660 |
| cacgaataca aaattaatct ccagggtgcg ctgtactggc tgtcgggtta cgctactaaa | 720 |
| actattgcga aatttatctc tgaccgtaaa aatttgccga gctggggccc agtggttgac | 780 |
| cgcgccgttg aacaatactt tgaccgtgtt ggtcgttgcg ttcgtggcta cgatgcctgg | 840 |
| tcttacgaaa ccaaacgtta ttacggtaaa aatggcctgg aaatccagaa aactcgtcag | 900 |
| atcaccctgc gcccgctgga cccggcgtac gtgaccaaag aataaa | 946 |

<210> SEQ ID NO 63
<211> LENGTH: 1053
<212> TYPE: DNA
<213> ORGANISM: Artificial Sequence
<220> FEATURE:
<223> OTHER INFORMATION: Agrped1_689675_mut6

<400> SEQUENCE: 63

| | |
|---|---|
| atgcatcacc atcaccatca ctcctctcag atctatatcc cggacctcct gatcacctgg | 60 |
| ccgtggcaaa aggtgcgcaa cccactgctg caagaagtgc aggatgaggc gaacgaatgg | 120 |
| gtgaaatctt tcgtgctgtt cgaaccggaa cagtttgaga aatttaaggc atgtgatttc | 180 |
| aacctgctgg gtgcactggt tggtccgctg gtaccaagg aagaactgcg cattagctgt | 240 |

```
gacctgatga acttctactt cgccttcgat gagtacaccg acctggctag cgctgacgaa    300
gccaaagtaa tcgcgcgcga tgtgatggaa agcttccgtc acacagataa gccaagccac    360
aacaaaatta ctgaaatggc ccgtcaattc ttcgaacgta ctatcaacac ggttggtaac    420
gatccgactg gcattgaaca atttattgcg gatttcgacg catacaccac ctctatcatc    480
caagaagctg atgatcgtgc gtctggtcac attcgtagcg ttgaggatta cttcattctg    540
cgccgtgaca cctgtggtgg gaaaccgtcg ttctcgttct tcggtctggg cctgaacatc    600
ccgaaagaag tcttcgcaca cccgatgggc atctccatga ccgaatccgc gactgatctg    660
atcgcaatta ccaacgatat gcactcttat aacctggagc aatcccgcgg cttggatggt    720
cacaatgtaa ttaccgcgat catgcacgaa tacaaaatta atctccaggg tgcgctgtac    780
tggctgtcgg gttacgctac taaaactatt gcgaaattta tctctgaccg taaaaatttg    840
ccgagctggg gcccagtggt tgaccgcgcc gttgaacaat actttgaccg tgttggtcgt    900
tgcgttcgtg gctacgatgc ctggtcttac gaaaccaaac gttattacgg taaaaatggc    960
ctggaaatcc agaaaactcg tcagatcacc ctgcgcccgc tggacccggc gtacgtgacc   1020
aaagaacagc tgcaggtatc catgaaggca taa                                1053
```

<210> SEQ ID NO 64
<211> LENGTH: 1053
<212> TYPE: DNA
<213> ORGANISM: Artificial Sequence
<220> FEATURE:
<223> OTHER INFORMATION: Agrped1_689675_mut7

<400> SEQUENCE: 64

```
atgcatcacc atcaccatca ctcctctcag atctatatcc cggacctcct gatcacctgg     60
ccgtggcaaa aggtgcgcaa cccactgctg caagaagtgc aggatgaggc gaacgaatgg    120
gtgaaatctt tcgtgctgtt cgaaccggaa cagtttgaga aatttaaggc atgtgatttc    180
aacctgctgg gtgcactggt tggtccgctg ggtaccaagg aagaactgcg cattagctgt    240
gacctgatga acttctactt cgccttcgat gagtacaccg acctggctag cgctgacgaa    300
gccaaagtaa tcgcgcgcga tgtgatggaa agcttccgtc acacagataa gccaagccac    360
aacaaaatta ctgaaatggc ccgtcaattc ttcgaacgta ctatcaacac ggttggtaac    420
gatccgactg gcattgaaca atttattgcg gatttcgacg catacaccac ctctatcatc    480
caagaagctg atgatcgtgc gtctggtcac attcgtagcg ttgaggatta cttcattctg    540
cgccgtgaca cctgtggtgg gaaaccgtcg ttctcgttct tcggtctggg cctgaacatc    600
ccgaaagaag tcttcgcaca cccgatggtc atctccatga ccgaatccgc gactgatctg    660
atcgcaatta ccaacgatat gcactcttat aacctggagc aatcccgcgg cttggatggt    720
cacaatgtaa ttaccgcgat catgcacgaa tacaaaatta atctccaggg tgcgctgtac    780
tggctgtcgg gttacgctac taaaactatt gcgaaattta tctctgaccg taaaaatttg    840
ccgagctggg gcccagtggt tgaccgcgcc gttgaacaat actttgaccg tgttggtcgt    900
tgcgttcgtg gctacgatgc ctggtcttac gaaaccaaac gttattacgg taaaaatggc    960
ctggaaatcc agaaaactcg tcagatcacc ctgcgcccgc tggacccggc gtacgtgacc   1020
aaagaacagc tgcaggtatc catgaaggca taa                                1053
```

<210> SEQ ID NO 65
<211> LENGTH: 1053
<212> TYPE: DNA

<213> ORGANISM: Artificial Sequence
<220> FEATURE:
<223> OTHER INFORMATION: Agrped1_689675_mut8

<400> SEQUENCE: 65

| | | | | | |
|---|---|---|---|---|---|
| atgcatcacc | atcaccatca | ctcctctcag | atctatatcc | cggacctcct | gatcacctgg | 60 |
| ccgtggcaaa | aggtgcgcaa | cccactgctg | caagaagtgc | aggatgaggc | gaacgaatgg | 120 |
| gtgaaatctt | tcgtgctgtt | cgaaccggaa | cagtttgaga | aatttaaggc | atgtgatttc | 180 |
| aacctgctgg | gtgcactggt | tggtccgctg | ggtaccaagg | aagaactgcg | cattagctgt | 240 |
| gacctgatga | acttctactt | cgccttcgat | gagtacaccg | acctggctag | cgctgacgaa | 300 |
| gccaaagtaa | tcgcgcgcga | tgtgatggaa | agcttccgtc | acacagataa | gccaagccac | 360 |
| aacaaaatta | ctgaaatggc | ccgtcaattc | ttcgaacgta | ctatcaacac | ggttggtaac | 420 |
| gatccgactg | gcattgaaca | atttattgcg | gatttcgacg | catacaccac | ctctatcatc | 480 |
| caagaagctg | atgatcgtgc | gtctggtcac | attcgtagcg | ttgaggatta | cttcattctg | 540 |
| cgccgtgaca | cctgtggtgg | gaaaccgtcg | ttctcgttct | tcggtctggg | cctgaacatc | 600 |
| ccgaaagaag | tcttcgcaca | cccgatgatc | atctccatga | ccgaatccgc | gactgatctg | 660 |
| atcgcaatta | ccaacgatat | gcactcttat | aacctggagc | aatcccgcgg | cttggatggt | 720 |
| cacaatgtaa | ttaccgcgat | catgcacgaa | tacaaaatta | atctccaggg | tgcgctgtac | 780 |
| tggctgtcgg | gttacgctac | taaaactatt | gcgaaattta | tctctgaccg | taaaaatttg | 840 |
| ccgagctggg | gcccagtggt | tgaccgcgcc | gttgaacaat | actttgaccg | tgttggtcgt | 900 |
| tgcgttcgtg | gctacgatgc | ctggtcttac | gaaaccaaac | gttattacgg | taaaaatggc | 960 |
| ctggaaatcc | agaaaactcg | tcagatcacc | ctgcgcccgc | tggacccggc | gtacgtgacc | 1020 |
| aaagaacagc | tgcaggtatc | catgaaggca | taa | | | 1053 |

<210> SEQ ID NO 66
<211> LENGTH: 1053
<212> TYPE: DNA
<213> ORGANISM: Artificial Sequence
<220> FEATURE:
<223> OTHER INFORMATION: Agrped1_689675_mut9

<400> SEQUENCE: 66

| | | | | | |
|---|---|---|---|---|---|
| atgcatcacc | atcaccatca | ctcctctcag | atctatatcc | cggacctcct | gatcacctgg | 60 |
| ccgtggcaaa | aggtgcgcaa | cccactgctg | caagaagtgc | aggatgaggc | gaacgaatgg | 120 |
| gtgaaatctt | tcgtgctgtt | cgaaccggaa | cagtttgaga | aatttaaggc | atgtgatttc | 180 |
| aacctgctgg | gtgcactggt | tggtccgctg | ggtaccaagg | aagaactgcg | cattagctgt | 240 |
| gacctgatga | acttctactt | cgccttcgat | gagtacaccg | acctggctag | cgctgacgaa | 300 |
| gccaaagtaa | tcgcgcgcga | tgtgatggaa | agcttccgtc | acacagataa | gccaagccac | 360 |
| aacaaaatta | ctgaaatggc | ccgtcaattc | ttcgaacgta | ctatcaacac | ggttggtaac | 420 |
| gatccgactg | gcattgaaca | atttattgcg | gatttcgacg | catacaccac | ctctatcatc | 480 |
| caagaagctg | atgatcgtgc | gtctggtcac | attcgtagcg | ttgaggatta | cttcattctg | 540 |
| cgccgtgaca | cctgtggtgg | gaaaccgtcg | ttctcgttct | tcggtctggg | cctgaacatc | 600 |
| ccgaaagaag | tcttcgcaca | cccgatggac | atctccatga | ccgaatccgc | gactgatctg | 660 |
| atcgcaatta | ccaacgatat | gcactcttat | aacctggagc | aatcccgcgg | cttggatggt | 720 |
| cacaatgtaa | ttaccgcgat | catgcacgaa | tacaaaatta | atctccaggg | tgcgctgtac | 780 |
| tggctgtcgg | gttacgctac | taaaactatt | gcgaaattta | tctctgaccg | taaaaatttg | 840 |

```
ccgagctggg gcccagtggt tgaccgcgcc gttgaacaat actttgaccg tgttggtcgt    900
tgcgttcgtg gctacgatgc ctggtcttac gaaaccaaac gttattacgg taaaaatggc    960
ctggaaatcc agaaaactcg tcagatcacc ctgcgcccgc tggacccggc gtacgtgacc   1020
aaagaacagc tgcaggtatc catgaaggca taa                                1053
```

<210> SEQ ID NO 67
<211> LENGTH: 1053
<212> TYPE: DNA
<213> ORGANISM: Artificial Sequence
<220> FEATURE:
<223> OTHER INFORMATION: Agrped1_689675_mut10

<400> SEQUENCE: 67

```
atgcatcacc atcaccatca ctcctctcag atctatatcc cggacctcct gatcacctgg     60
ccgtggcaaa aggtgcgcaa cccactgctg caagaagtgc aggatgaggc gaacgaatgg    120
gtgaaatctt tcgtgctgtt cgaaccggaa cagtttgaga aatttaaggc atgtgatttc    180
aacctgctgg gtgcactggt tggtccgctg gtaccaagg aagaactgcg cattagctgt     240
gacctgatga acttctactt cgccttcgat gagtacaccg acctggctag cgctgacgaa    300
gccaaagtaa tcgcgcgcga tgtgatggaa agcttccgtc acacagataa gccaagccac    360
aacaaaatta ctgaaatggc ccgtcaattc ttcgaacgta ctatcaacac ggttggtaac    420
gatccgactg gcattgaaca atttattgcg gatttcgacg catacaccac ctctatcatc    480
caagaagctg atgatcgtgc gtctggtcac attcgtagcg ttgaggatta cttcattctg    540
cgccgtgaca cctgtggtgg gaaaccgtcg ttctcgttct tcggtctggg cctgaacatc    600
ccgaaagaag tcttcgcaca cccgatgctc atctccatga ccgaatccgc gactgatctg    660
atcgcaatta ccaacgatat gcactcttat aacctggagc aatcccgcgg cttggatggt    720
cacaatgtaa ttaccgcgat catgcacgaa tacaaaatta atctccaggg tgcgctgtac    780
tggctgtcgg gttacgctac taaaactatt gcgaaattta tctctgaccg taaaaatttg    840
ccgagctggg gcccagtggt tgaccgcgcc gttgaacaat actttgaccg tgttggtcgt    900
tgcgttcgtg gctacgatgc ctggtcttac gaaaccaaac gttattacgg taaaaatggc    960
ctggaaatcc agaaaactcg tcagatcacc ctgcgcccgc tggacccggc gtacgtgacc   1020
aaagaacagc tgcaggtatc catgaaggca taa                                1053
```

<210> SEQ ID NO 68
<211> LENGTH: 1053
<212> TYPE: DNA
<213> ORGANISM: Artificial Sequence
<220> FEATURE:
<223> OTHER INFORMATION: Agrped1_689675_mut11

<400> SEQUENCE: 68

```
atgcatcacc atcaccatca ctcctctcag atctatatcc cggacctcct gatcacctgg     60
ccgtggcaaa aggtgcgcaa cccactgctg caagaagtgc aggatgaggc gaacgaatgg    120
gtgaaatctt tcgtgctgtt cgaaccggaa cagtttgaga aatttaaggc atgtgatttc    180
aacctgctgg gtgcactggt tggtccgctg gtaccaagg aagaactgcg cattagctgt     240
gacctgatga acttctactt cgccttcgat gagtacaccg acctggctag cgctgacgaa    300
gccaaagtaa tcgcgcgcga tgtgatggaa agcttccgtc acacagataa gccaagccac    360
aacaaaatta ctgaaatggc ccgtcaattc ttcgaacgta ctatcaacac ggttggtaac    420
```

| | |
|---|---|
| gatccgactg gcattgaaca atttattgcg gatttcgacg catacaccac ctctatcatc | 480 |
| caagaagctg atgatcgtgc gtctggtcac attcgtagcg ttgaggatta cttcattctg | 540 |
| cgccgtgaca cctgtggtgg gaaaccgtcg ttctcgttct tcggtctggg cctgaacatc | 600 |
| ccgaaagaag tcttcgcaca cccgatgcgt atctccatga ccgaatccgc gactgatctg | 660 |
| atcgcaatta ccaacgatat gcactcttat aacctggagc aatcccgcgg cttggatggt | 720 |
| cacaatgtaa ttaccgcgat catgcacgaa tacaaaatta atctccaggg tgcgctgtac | 780 |
| tggctgtcgg gttacgctac taaaactatt gcgaaattta tctctgaccg taaaaatttg | 840 |
| ccgagctggg gcccagtggt tgaccgcgcc gttgaacaat actttgaccg tgttggtcgt | 900 |
| tgcgttcgtg gctacgatgc ctggtcttac gaaaccaaac gttattacgg taaaaatggc | 960 |
| ctggaaatcc agaaaactcg tcagatcacc ctgcgcccgc tggacccggc gtacgtgacc | 1020 |
| aaagaacagc tgcaggtatc catgaaggca taa | 1053 |

<210> SEQ ID NO 69
<211> LENGTH: 996
<212> TYPE: DNA
<213> ORGANISM: Artificial Sequence
<220> FEATURE:
<223> OTHER INFORMATION: Agrped1_689675_mut12

<400> SEQUENCE: 69

| | |
|---|---|
| atgcatcacc atcaccatca ctcctctcag atctatatcc cggacctcct gatcacctgg | 60 |
| ccgtggcaaa aggtgcgcaa cccactgctg caagaagtgc aggatgaggc gaacgaatgg | 120 |
| gtgaaatctt tcgtgctgtt cgaaccggaa cagtttgaga aatttaaggc atgtgatttc | 180 |
| aacctgctgg gtgcactggt tggtccgctg gtaccaagg aagaactgcg cattagctgt | 240 |
| gacctgatga acttctactt cgccttcgat gagtacaccg acctggctag cgctgacgaa | 300 |
| gccaaagtaa tcgcgcgcga tgtgatggaa agcttccgtc acacagataa gccaagccac | 360 |
| aacaaaatta ctgaaatggc ccgtcaattc ttcgaacgta ctatcaacac ggttggtaac | 420 |
| gatccgactg gcattgaaca atttattgcg gatttcgacg catacaccac ctctatcatc | 480 |
| caagaagctg atgatcgtgc gtctggtcac attcgtagcg ttgaggatta tttcacgtta | 540 |
| cgccgcgaca cttgcggcgc gaaaccaagc ttcagcttct ttggcctggg tctgaacatt | 600 |
| ccggatgagt ttttccacca tcctgtggtt atttccatga tcgaaggcgc caccgatctg | 660 |
| attgctgtta cgaatgacat gcactcatat aacctcgaac actcccgtgg tctggatgga | 720 |
| cacaacgtaa tcactgctat catgcacgaa taccagctgg acctgcaggg cgcactgtac | 780 |
| tggctatccg gttacgctac ccatacgatt gctaacttcc tgtcgaaccg ccgtaacctg | 840 |
| ccgtcctggg gccggctgt cgataaagcg gtagaagaat ttttcgaccg tgttggtcgt | 900 |
| tgtgttcgtg gctacgacgc ttggagctac gaaaccaaac gctattacgg gaaaaacggc | 960 |
| ctgcaggtgc agaagacccg tcgtatcacc ctgtaa | 996 |

<210> SEQ ID NO 70
<211> LENGTH: 1050
<212> TYPE: DNA
<213> ORGANISM: Artificial Sequence
<220> FEATURE:
<223> OTHER INFORMATION: Agrped1_689675_mut13

<400> SEQUENCE: 70

| | |
|---|---|
| atgcatcacc atcaccatca ctcccaattt attatcccgg atctgttatc cacttggcct | 60 |
| tggcagcgcg tgtctaaccc gatgtggcgt gagattgatg aagaagcaaa cgcgtgggtg | 120 |

```
cagtctttcg acctgtttga accgtcccag ttcgagaaat tcaagatgtg tgatttcaac    180
ctgctgggct cgatgattgg taccgtggaa accaaagatc atctgcgcat cagttgcgac    240
ctgatgaact tctatttcgc attcgacgaa tacacggaca tggcatccaa agacgaagcg    300
cgtaagatcg cccgtgacgt gatggatgca tttcgcaaca ccgaaaaacc agctcacaac    360
caaatcaccg aaatggcccg ccagtttttt aaacgtacga tcgacactgt aggtaaagac    420
ttgccgggcg tggaacgttt tatcgctgac ttcgatgctt atacgcattc cgtgatccag    480
gaggccgacg accgtgctac tggccacatc cgcagcgtca acgactactt cattctgcgc    540
cgtgacacct gtggtgggaa accgtcgttc tcgttcttcg gtctgggcct gaacatcccg    600
aaagaagtct tcgcacaccc gatgttcatc tccatgaccg aatccgcgac tgatctgatc    660
gcaattacca acgatatgca ctcttataac ctggagcaat cccgcggctt ggatggtcac    720
aatgtaatta ccgcgatcat gcacgaatac aaaattaatc tccagggtgc gctgtactgg    780
ctgtcgggtt acgctactaa aactattgcg aaatttatct ctgaccgtaa aaatttgccg    840
agctggggcc cagtggttga ccgcgccgtt gaacaatact ttgaccgtgt tggtcgttgc    900
gttcgtggct acgatgcctg gtcttacgaa accaaacgtt attacggtaa aaatggcctg    960
gaaatccaga aaactcgtca gatcaccctg cgcccgctgg acccggcgta cgtgaccaaa   1020
gaacagctgc aggtatccat gaaggcataa                                    1050
```

<210> SEQ ID NO 71
<211> LENGTH: 1089
<212> TYPE: DNA
<213> ORGANISM: Artificial Sequence
<220> FEATURE:
<223> OTHER INFORMATION: AAE3_109435_mut1

<400> SEQUENCE: 71

```
atgcatcacc atcaccatca ccacagctcg acccagctgt tcactcactc tccgaccaaa     60
atgcagatca tcctgccgga tctgctgtgc tcctggggat ataaagggtt tctcaaccct    120
cactatgagg cgctaaggc ggaatccaac acctggattc gcccgctcgt agtgaaactt    180
ttcgacgaac gtggccagaa agcgttcgcc aaagattaca ccggtctgct ggcgtctatg    240
acttacccgc accacaacaa agaattcctg tgtgtggctt gcgatatgat gaacctgttc    300
tttgtttatg acgagtatac cgatattacc ccgccggaaa ccgcgcagcg tctggctaaa    360
atcgttgtaa atgctatgcg caatccggat gagatcgccg ctctgggtga agacagcatc    420
ggtactatga ccaagcagtt ctggcgccgc gctatgactc tgctgccacc gaacggttgt    480
aactctgaat cttgtatcca gcacttcatt gactacaccg aagaatatct gactgcagtg    540
acgcgtgaag cttgtgatcg tagcagcggc tctgtccacg ctgtaaaaga ctatctggcg    600
atgcgtcgtg caacctctgg cgcgggtctg atggttggtt tactggaatt tggcctcgat    660
ctgccggaag aagtcatgaa acatgaagtg atccaggaac tgtctactgg cgcgatcgac    720
atgtactgtc tgctgaacga catgcatagc tacgcatctg aactgtcgtc tggtcaggcc    780
tctcacaacg ttattaccgt cgtgatgcac gaacgtaacc tgtccctgca agaagctttt    840
gattggctgg cctcttacgc ggcaggcgta gtgaagggtt caaaaccaa cctgaaccgc    900 gttccttctt ttagcgaact ggaggaccac tctctgcacg gcgaaggcat gctccgtgat    960
cgcattcagc gttacatcga cggcctgggt caggcggttc gcgcggaaga tgattgggct   1020
tttgaaacta cccgctatca cggtcagaac ggcccgcaga ttaaactgac ccgtatgctg   1080
``` accatctaa 1089

<210> SEQ ID NO 72
<211> LENGTH: 993
<212> TYPE: DNA
<213> ORGANISM: Artificial Sequence
<220> FEATURE:
<223> OTHER INFORMATION: Agrped1_689671_mut1

<400> SEQUENCE: 72

| | | | | | |
|---|---|---|---|---|---|
| atgcatcacc | atcaccatca | ctcccaattt | attatcccgg | atctgttatc | cacttggcct | 60 |
| tggcagcgcg | tgtctaaccc | gatgtggcgt | gagattgatg | aagaagcaaa | cgcgtgggtg | 120 |
| cagtctttcg | acctgtttga | accgtcccag | ttcgagaaat | tcaagatgtg | tgatttcaac | 180 |
| ctgctgggct | cgatgattgg | taccgtggaa | accaaagatc | atctgcgcat | cagttgcgac | 240 |
| ctgatgaact | tctatttcgc | attcgacgaa | tacacggaca | tggcatccaa | agacgaagcg | 300 |
| cgtaagatcg | cccgtgacgt | gatggatgca | tttcgcaaca | ccgaaaaacc | agctcacaac | 360 |
| caaatcaccg | aaatggcccg | ccagtttttt | aaacgtacga | tcgacactgt | aggtaaagac | 420 |
| ttgccgggcg | tggaacgttt | tatcgctgac | ttcgatgctt | atacgcattc | cgtgatccag | 480 |
| gaggccgacg | accgtgctac | tggccacatc | cgcagcgtca | acgactattt | cacgttacgc | 540 |
| cgcgacactt | gcggcgcgaa | accaagcttc | agcttctttg | gcctgggtct | gaacattccg | 600 |
| gatgaggttt | tccaccatcc | tgtggttatt | tccatgatcg | aaggcgccac | cgatctgatt | 660 |
| gctgttacga | atgacatgca | ctcatataac | ctcgaacact | cccgtggtct | ggatggacac | 720 |
| aacgtaatca | ctgctatcat | gcacgaatac | cagctggacc | tgcagggcgc | actgtactgg | 780 |
| ctatccggtt | acgctaccca | tacgattgct | aacttcctgt | cgaaccgccg | taacctgccg | 840 |
| tcctggggcc | cggctgtcga | taaagcggta | gaagaatttt | tcgaccgtgt | tggtcgttgt | 900 |
| gttcgtggct | acgacgcttg | gagctacgaa | accaaacgct | attacgggaa | aaacggcctg | 960 |
| caggtgcaga | agacccgtcg | tatcaccctg | taa | | | 993 |

<210> SEQ ID NO 73
<211> LENGTH: 996
<212> TYPE: DNA
<213> ORGANISM: Artificial Sequence
<220> FEATURE:
<223> OTHER INFORMATION: Galma_223690_mut1

<400> SEQUENCE: 73

| | | | | | |
|---|---|---|---|---|---|
| atgcatcacc | atcaccatca | cccgagccag | ttcaccatcc | ctgacctgct | gatcacttgg | 60 |
| ccatggcagg | aaatcaccaa | cccgatgctg | cacgaagtag | acgctgaagc | caatgaatgg | 120 |
| gttcagtcac | tgaacctgtt | cgaaccgaaa | cagttcgaaa | agttcaaagc | ctgtaacttc | 180 |
| aacctgctgg | gctccctggt | tggaccgctg | ccaagccgtg | accaccttcg | tgtgtcctgc | 240 |
| gacctgatga | acttctactt | cgcttttcgat | gagtacacgg | acatggcaaa | caaagatgaa | 300 |
| gctatgcgta | tcgcccgtga | cgtaatgcaa | gcattccgta | acactgacac | gcctagcaac | 360 |
| tctaaaatca | ctgaaatggc | acgtcaattc | ttcaaacgta | ccatcgaggt | tgtaggcgaa | 420 |
| gacctgccgg | gcatcgaacg | tttcatcgcc | gatttcgatg | catacactcg | ttccgtgatt | 480 |
| caggaagcag | atgatcgtgt | tgcaggtcac | attcgtaacg | tggaggacta | cttcattctg | 540 |
| cgccgtgata | cgtgcggtgc | taaaccgagc | ttctctttct | acggtctggg | tctgaacatc | 600 |
| ccgaccgagg | tctttgaaca | cccgctgctg | atttctatgg | ttgaaagcgc | aactgacctg | 660 |
| attgctgtca | ccaatgacat | gcactcttac | ggtctggagc | attctcgtgg | cctggacggt | 720 |

```
cacaatgtta tcaccgccat tatgcacgaa tatcagctgg acctacaggg tgccctgtac    780
tggctgtccg gctacgcaac taaaaccatc tccaaattcc tgactgatcg taaaaacctg    840
ccgtcctggg gcccaaccat tgacaaagct ctcgaaatct acctggaccg tttaggtcgt    900
tgcgtgcgtg gctacgatgc ttggtcctac agcactaagc gttactatgg taaaaacggt    960
ctgaaggttc aaaaaacccg ccgtatcact ttgtaa                              996
```

<210> SEQ ID NO 74
<211> LENGTH: 999
<212> TYPE: DNA
<213> ORGANISM: Artificial Sequence
<220> FEATURE:
<223> OTHER INFORMATION: Hypsu_148385_mut1

<400> SEQUENCE: 74

```
atgcatcacc atcaccatca ctccgctcag tacaccatcc ctgacttact ggcgaactgg     60
ccgtggcagc gcgtgaccaa cagcatgctg gacgaggtgc gcgacgaagc aaacgagtgg    120
gtgatgtccc tgggcctgtt tgagccggct cagtttaaaa aattcaaagc atgcgacttc    180
aaccttctgg caagctttat tggtccgctg aaagtaaag aacaccttcg tgttgcttgc     240
gatctgatga atttctattt cgctttcgat gagtacactg acgttgctaa ccgtgaagag    300
gctaaaaaaa tctctcaggg cgttatgcac gcgtttaaaa ctcgttctgc agagccgtcc    360
agctccaaaa ttacggaaat ggcgcgtcag ttctttcgtc gtaccgttga cgtcgtcggt    420
gaagattccc cggccatcaa ccagttcatt accgacttcg acacctacac cacggctgtg    480
atccaggaag cagacgatcg caccgaaggt accatccgta atgttgagga ctatttcacc    540
ctccgtcgcg acacctgcgg cgccaaacct tcttttcgt tcttcgccct gggcctgaac     600
atgccgaccg aagtcttcga caccctctg atcatgtctc tggtagagcg tgcaaccgac    660
ctgatcgcga ttgtgaacga catgcactcc tacggtctgg aacgtgctcg tggcctggat    720
ggtcataacg tagtaacgtc catcatgtac gagcatcagc tggacctgca gggtgcgctg    780
cactggctgg ccggttatgc cgaagacaca atcgccaagt tcctgtcgga aaaagaacgt    840
ctcccgtcct ggggtccggc ggtagatgta tccgtgcagg aatttgttga ccgtctgggc    900
cgttgcgtgc gtggttacga cgcttggtcc tatgaaacga accgctatta cggcagccac    960
ggtctacaga ttcgtcagac tcgtcaaatc accctgtaa                          999
```

<210> SEQ ID NO 75
<211> LENGTH: 555
<212> TYPE: PRT
<213> ORGANISM: Solanum lycopersicum

<400> SEQUENCE: 75

```
Met Ala Pro Ala Ala Ala Leu Met Ser Lys Cys Gln Glu Glu Glu Glu
1               5                   10                  15

Ile Val Arg Pro Val Ala Asp Phe Ser Pro Ser Leu Trp Gly Asp Arg
            20                  25                  30

Phe His Ser Phe Ser Leu Asp Asn Gln Val Ala Glu Lys Tyr Val Glu
        35                  40                  45

Glu Ile Glu Thr Leu Lys Glu Gln Thr Arg Ser Met Leu Met Ser Gly
    50                  55                  60

Lys Thr Leu Ala Glu Lys Leu Asn Leu Ile Asp Ile Val Glu Arg Leu
65                  70                  75                  80

Gly Ile Ala Tyr His Phe Glu Lys Gln Ile Asp Asp Met Leu Asn His
```

```
            85                  90                  95
Ile Phe Asn Ile Asp Pro Asn Phe Glu Ala His Glu Tyr Asn Asp Leu
            100                 105                 110
Cys Thr Leu Ser Leu Gln Phe Arg Ile Leu Arg Gln His Gly Tyr Tyr
            115                 120                 125
Ile Ser Pro Lys Ile Phe Ser Arg Phe Gln Asp Ala Asn Gly Lys Phe
            130                 135                 140
Lys Glu Ser Leu Cys Asp Asp Ile Arg Gly Ile Leu Asn Leu Tyr Glu
145                 150                 155                 160
Ala Ser His Val Arg Thr His Gly Asp Thr Leu Glu Glu Ala Leu
                165                 170                 175
Ala Phe Ser Thr Ala His Leu Glu Ser Ala Ala Pro His Leu Lys Ser
                180                 185                 190
Pro Leu Ser Lys Gln Val Thr His Ala Leu Glu Gln Ser Leu His Lys
            195                 200                 205
Ser Ile Pro Arg Val Glu Thr Arg Tyr Phe Ile Ser Ile Tyr Glu Glu
    210                 215                 220
Glu Glu Leu Lys Asn Asp Val Phe Leu Arg Phe Ala Lys Leu Asp Phe
225                 230                 235                 240
Asn Leu Leu Gln Met Leu His Lys Gln Glu Leu Ser Glu Val Ser Arg
                245                 250                 255
Trp Trp Lys Asp Leu Asp Phe Val Thr Thr Leu Pro Tyr Ala Arg Asp
                260                 265                 270
Arg Ala Val Glu Cys Tyr Phe Trp Thr Met Gly Val Tyr Ala Glu Pro
                275                 280                 285
Gln Tyr Ser Gln Ala Arg Val Met Leu Ala Lys Thr Ile Ala Met Ile
            290                 295                 300
Ser Ile Val Asp Asp Thr Phe Asp Ala Tyr Gly Ile Val Lys Glu Leu
305                 310                 315                 320
Glu Val Tyr Thr Asp Ala Ile Gln Arg Trp Asp Val Ser Gln Ile Asp
                325                 330                 335
Arg Leu Pro Glu Tyr Met Lys Ile Ser Tyr Lys Ala Leu Leu Asp Leu
                340                 345                 350
Tyr Asn Asp Tyr Glu Thr Glu Leu Ser Asn Asp Gly Arg Ser Asp Val
            355                 360                 365
Val Gln Tyr Ala Lys Glu Arg Met Lys Glu Ile Val Arg Asn Tyr Phe
            370                 375                 380
Val Glu Ala Lys Trp Phe Ile Glu Gly Tyr Met Pro Pro Val Ser Glu
385                 390                 395                 400
Tyr Leu Ser Asn Ala Leu Ala Thr Ser Thr Tyr Tyr Leu Leu Thr Thr
                405                 410                 415
Thr Ser Tyr Leu Gly Met Lys Ser Ala Thr Lys Lys Asp Phe Glu Trp
            420                 425                 430
Leu Ala Lys Asn Pro Lys Ile Leu Glu Ala Asn Val Thr Leu Cys Arg
            435                 440                 445
Val Ile Asp Asp Ile Ala Thr Tyr Glu Val Glu Lys Gly Arg Gly Gln
    450                 455                 460
Ile Ala Thr Gly Ile Glu Cys Tyr Met Arg Asp Tyr Gly Val Ser Thr
465                 470                 475                 480
Gln Val Ala Met Asp Lys Phe Gln Glu Met Ala Glu Thr Ala Trp Lys
                485                 490                 495
Asp Val Asn Glu Gly Ile Leu Arg Pro Thr Pro Val Ser Ala Lys Ile
            500                 505                 510
```

```
Leu Thr Arg Ile Leu Asn Leu Ala Arg Ile Ile Asp Val Thr Tyr Lys
            515                 520                 525

His Asn Gln Asp Gly Tyr Thr His Pro Glu Lys Val Leu Lys Pro His
    530                 535                 540

Ile Ile Ala Leu Leu Val Asp Ser Ile Glu Ile
545                 550                 555

<210> SEQ ID NO 76
<211> LENGTH: 567
<212> TYPE: PRT
<213> ORGANISM: Melaleuca quinquenervia

<400> SEQUENCE: 76

Met Ser Gln Val Ser Ala Ile Pro Thr Thr Ser Pro Asn Lys Gly Thr
1               5                   10                  15

Gly Asp Val Ile Glu Arg Arg Ser Ala Gly Tyr His Pro Ser Val Trp
            20                  25                  30

Gly Asp Tyr Phe Leu Lys Tyr Asp Ser Pro Ser Asn Ser Val Lys Phe
        35                  40                  45

Glu Phe Leu Gly Arg Val Glu Glu Gln Ile Glu Glu Leu Lys Gly Glu
50                  55                  60

Val Arg Lys Met Leu Ala Gly Ala Val Asp Lys Pro Trp Gln Met Leu
65                  70                  75                  80

His Leu Ile Asp Gln Ile Arg Leu Gly Ile Glu Tyr His Phe Glu
                85                  90                  95

Arg Glu Leu Asp Glu His Leu Glu Arg Ile His Lys Ser Phe Ser Gln
            100                 105                 110

Leu Thr His Gly Tyr Phe Lys Gly Asp Asp Leu Arg Met Ile Ser Leu
        115                 120                 125

Leu Phe Arg Leu Leu Arg Gln Gln Gly Tyr Asn Ile Ser Ser Glu Val
130                 135                 140

Phe Asn Lys Phe Lys Asp Ser Glu Gly Asn Phe Gly Glu Ser Leu Ala
145                 150                 155                 160

Thr Asp Leu Arg Gly Leu Leu Ser Leu Tyr Glu Ala Cys His Leu Arg
                165                 170                 175

Cys His Gly Asp Ile Ile Leu Asp Glu Ala Leu Pro Phe Ala Ile Ser
            180                 185                 190

His Leu Glu Ser Ile Asp Glu Ser Lys Ala Gly Ala Asn Leu Ala Lys
        195                 200                 205

Gln Val Asn His Ala Leu Lys Gln Pro Leu Arg Arg Gly Leu Pro Arg
210                 215                 220

Leu Glu Ala Arg Arg Tyr Ile Pro Leu Tyr Glu Glu Glu Pro Ser His
225                 230                 235                 240

Asp Lys Val Leu Leu Ala Leu Ala Lys Leu Asp Phe Asn Leu Leu Gln
                245                 250                 255

Glu Gln His Gln Lys Glu Leu Gly Asn Val Ser Arg Trp Trp Lys Asp
            260                 265                 270

Ile Asp Val Pro Arg Lys Phe Pro Phe Ala Arg Asp Arg Ile Ala Glu
        275                 280                 285

Leu Phe Phe Trp Ala Cys Gly Val Tyr Phe Glu Pro Glu Phe Ser Val
290                 295                 300

Ala Arg Val Ile Gln Ala Lys Ala Phe Ala Met Thr Ser Ile Leu Asp
305                 310                 315                 320

Asp Ile Tyr Asp Val Tyr Gly Thr Leu Glu Glu Leu Val Leu Leu Thr
```

```
                325                 330                 335
Glu Ala Ile Glu Lys Trp Asp Val Asp Ala Met Asp Gly Leu Pro Glu
            340                 345                 350

Tyr Met Gln Ala Phe Tyr Lys Glu Leu Leu His Phe Tyr Glu Glu Val
        355                 360                 365

Gly Asn Glu Val Ala Ala Lys Gly Arg Ser Tyr Arg Leu Val Tyr Ala
    370                 375                 380

Lys Glu Val Met Lys Lys Leu Ala Arg Ala Tyr Tyr Gln Glu Ala Lys
385                 390                 395                 400

Trp Phe His Thr Asn Tyr Thr Pro Thr Leu Glu Glu Tyr Met Pro Leu
                405                 410                 415

Gln Leu Ile Thr Thr Gly Tyr Gly Met Met Ala Thr Thr Ser Leu Val
            420                 425                 430

Gly Met Asp Asp Val Val Pro Lys His Val Phe Glu Trp Ser Ile Gly
        435                 440                 445

Asp Cys Lys Ile Val Lys Ala Ala Gln Thr Ile Cys Arg Leu Met Asp
    450                 455                 460

Asp Ile Ser Ser His Glu Phe Glu Gln Lys Arg Gly His Leu Val Ser
465                 470                 475                 480

Ser Val Glu Leu Leu Met Lys Glu Arg Ser Leu Ser Glu Arg Glu Ala
                485                 490                 495

Gly Glu Glu Leu Gln Lys Gly Val Ile Asp Ala Trp Lys Asp Thr Asn
            500                 505                 510

Glu Glu Phe Leu Arg Pro Thr Ala Val Pro Met Lys Ile Leu Thr Arg
        515                 520                 525

Val Leu Asn Leu Ser Arg Ala Met Asp Val Leu Tyr Ser Asp Gly Asp
    530                 535                 540

Asn Tyr Thr His Ser Gly Thr Lys Leu Lys Asp Phe Val Thr Ser Leu
545                 550                 555                 560

Phe Val Ser Pro Leu Pro Val
                565

<210> SEQ ID NO 77
<211> LENGTH: 354
<212> TYPE: PRT
<213> ORGANISM: Galerina marginata

<400> SEQUENCE: 77

Met Ser Glu Gln Gln Tyr Arg Leu Pro Asp Leu Leu Cys Asp Trp Pro
1               5                   10                  15

Trp Thr Arg Tyr Ser Ser Pro His Tyr Pro Lys Ala Lys Lys Glu Ser
            20                  25                  30

Ser Asp Trp Val Asn Ser Phe His Pro Phe Ser Ala Arg Gly Gln Lys
        35                  40                  45

Gly Phe Glu Ala Cys Asp Leu Asn Leu Leu Ala Ser Leu Thr Tyr Ser
    50                  55                  60

Arg Arg Asn Glu Glu Phe Val Arg Ala Gly Cys Asp Leu Met Asn Phe
65                  70                  75                  80

Tyr Phe Val Tyr Asp Glu Tyr Thr Asp Val Ser Asp Pro Val Ser Ala
                85                  90                  95

Ala Asn Leu Ala Asn Ile Val Ile Asp Ala Met Lys Asn Pro Asp Ala
            100                 105                 110

Phe Pro Ser Asn Gly Ser His Leu Leu Gly Glu Met Thr Arg Gln Phe
        115                 120                 125
```

Trp Arg Arg Ala Ser Thr Leu Ala Lys Pro Gly Ser Pro Cys Phe Glu
130                 135                 140

His Phe Ile Ala Thr Ser Glu Thr Tyr Leu His Ala Val Thr Gln Glu
145                 150                 155                 160

Ala Glu Asp Arg Ala Ser Glu Arg Ile Arg Ser Val Asp Asp Tyr Leu
                165                 170                 175

Asp Leu Arg Arg Asp Thr Cys Gly Ala Arg Pro Thr Leu Ala Phe Ile
                180                 185                 190

Glu Phe Gly Leu Glu Leu Pro Ala Glu Val Thr Ser His Pro Val Ile
            195                 200                 205

Val Ser Leu Thr Glu Ala Ala Val Asp Leu Ile Ile Leu Val Asn Asp
210                 215                 220

Met His Ser Tyr Thr Arg Glu Ile Ser Cys Gly Leu Ala Asn His Asn
225                 230                 235                 240

Ile Ile Thr Ala Ile Met His Glu Tyr Asn Leu Asp Leu Gln Ser Ala
                245                 250                 255

Phe Asp Cys Leu Asp Ala Tyr Ala Asn Glu Val Val Thr Arg Phe Leu
                260                 265                 270

Ser Asp Leu Asp Arg Val Pro Cys Trp Gly Asp Asp Val Asp Glu Arg
            275                 280                 285

Val Trp Met Tyr Val Asp Gly Leu Gly Gln Trp Val Arg Gly Asn Asp
290                 295                 300

Asp Trp Ser Cys Glu Gly Lys Arg Tyr Tyr Gly Asp Asp Gly Leu Arg
305                 310                 315                 320

Ile Met Glu Thr Arg Leu Val Ser Leu Lys Leu Pro Lys Val Arg Arg
                325                 330                 335

Arg Met Ala Arg Lys Trp Gly Trp Tyr Gly Lys Val Arg Gln Lys Phe
                340                 345                 350

Ser Ala

<210> SEQ ID NO 78
<211> LENGTH: 372
<212> TYPE: PRT
<213> ORGANISM: Hypoxylon sp

<400> SEQUENCE: 78

Met Arg Pro Ile Thr Cys Ser Phe Asp Pro Val Gly Ile Ser Phe Gln
1               5                   10                  15

Thr Glu Ser Lys Gln Glu Asn Phe Glu Phe Leu Arg Glu Ala Ile Ser
                20                  25                  30

Arg Ser Val Pro Gly Leu Glu Asn Cys Asn Val Phe Asp Pro Arg Ser
            35                  40                  45

Leu Gly Val Pro Trp Pro Thr Ser Phe Pro Ala Ala Gln Ser Lys
        50                  55                  60

Tyr Trp Lys Asp Ala Glu Glu Ala Ala Glu Leu Met Asp Gln Ile
65                  70                  75                  80

Val Ala Ala Ala Pro Gly Glu Gln Gly Ser Leu Pro Ala Glu Leu Ala
                85                  90                  95

Val Ser Asp Lys Lys Ala Ala Lys Arg Arg Glu Leu Leu Asp Thr Ser
            100                 105                 110

Val Ser Ala Pro Met Asn Met Phe Pro Ala Ala Asn Ala Pro Arg Ala
        115                 120                 125

Arg Ile Met Ala Lys Ala Asn Leu Leu Ile Phe Met His Asp Asp Val
    130                 135                 140

```
Cys Glu Tyr Gln Ser Val Gln Ser Thr Ile Ile Asp Ser Ala Leu Ala
145                 150                 155                 160

Asp Thr Ser Thr Pro Asn Gly Lys Gly Ala Asp Ile Leu Trp Gln Asn
                165                 170                 175

Arg Ile Phe Lys Glu Phe Ser Glu Thr Asn Arg Glu Asp Pro Val
            180                 185                 190

Val Gly Pro Gln Phe Leu Gln Gly Ile Leu Asn Trp Val Glu His Thr
        195                 200                 205

Arg Lys Ala Leu Pro Ala Ser Met Thr Phe Arg Ser Phe Asn Glu Tyr
    210                 215                 220

Ile Asp Tyr Arg Ile Gly Asp Phe Ala Val Asp Phe Cys Asp Ala Ala
225                 230                 235                 240

Ile Leu Leu Thr Cys Glu Ile Phe Leu Thr Pro Ala Asp Met Glu Pro
                245                 250                 255

Leu Arg Lys Leu His Arg Leu Tyr Met Thr His Phe Ser Leu Thr Asn
            260                 265                 270

Asp Leu Tyr Ser Phe Asn Lys Glu Val Val Ala Glu Gln Glu Thr Gly
        275                 280                 285

Ser Ala Val Ile Asn Ala Val Arg Val Leu Glu Gln Leu Val Asp Thr
290                 295                 300

Ser Thr Arg Ser Ala Lys Val Leu Leu Arg Ala Phe Leu Trp Asp Leu
305                 310                 315                 320

Glu Leu Gln Ile His Asp Glu Leu Thr Arg Leu Lys Gly Thr Asp Leu
                325                 330                 335

Thr Pro Ser Gln Trp Arg Phe Ala Arg Gly Met Val Glu Val Cys Ala
            340                 345                 350

Gly Asn Ile Phe Tyr Ser Ala Thr Cys Leu Arg Tyr Ala Lys Pro Gly
        355                 360                 365

Leu Arg Gly Ile
370

<210> SEQ ID NO 79
<211> LENGTH: 412
<212> TYPE: PRT
<213> ORGANISM: Hypoxylon sp

<400> SEQUENCE: 79

Met Lys Ser Ser Lys Met Met Arg Thr Thr Leu Leu Arg Leu Ala Arg
1               5                   10                  15

Arg Ala Arg Ser Arg Leu Leu Ser Ile Leu Ser Pro His Ser Val Pro
            20                  25                  30

Ala Ala Gln Glu Val Gln Arg Thr Ser Glu Lys Pro Ser Ala Gln Gln
        35                  40                  45

Gly Leu Cys Gly Glu Ala Leu Val Leu Ala Ser Gln Leu Asp Gly Lys
    50                  55                  60

Thr Phe His Val Pro Asp Leu Trp Lys Val Phe Ser Asp Trp Pro Leu
65                  70                  75                  80

Ala Ala Asn Pro His Ala Gln Arg Leu Asp Ala Leu Val Asp Ser Leu
                85                  90                  95

Leu Glu Arg Ile Ile Thr Asn Glu Lys Lys Leu Lys Ala Leu Lys Gln
            100                 105                 110

Ala Asn Phe Gly Arg Leu Ile Ser Leu Trp Tyr Pro Asp Ala Glu Trp
        115                 120                 125

Ser Glu Leu Glu Ile Ala Ala Ala Tyr Ser Val Trp Ile Phe Val Trp
    130                 135                 140
```

Asp Asp Glu Val Asp Ala Asn Asp Thr Asp Val Ser Asn Asp Glu Glu
145                 150                 155                 160

Leu Ser Arg Ala Tyr Tyr Gln Lys Ser Leu Arg Thr Ile His Asn Leu
                165                 170                 175

Leu Gly Leu Asp Pro Val Glu Asp Gly Gln Glu Pro Val Phe Glu Asp
            180                 185                 190

Asp Gln Ser Leu His Pro Asn Met Ala Leu Phe Ala Asp Val Gly Arg
        195                 200                 205

Gly Met Arg Ala Thr Thr Asp Lys Ile Gln Arg Glu Arg Phe Tyr Arg
    210                 215                 220

Glu Leu Glu Asn Phe Met Val Gln Val Gly Val Glu His Val His Arg
225                 230                 235                 240

Met Arg Gly Ser Ile Pro Ser Val Glu Lys Tyr Ile Glu Ile Arg Ser
                245                 250                 255

Gly Ser Val Gly Cys Ala Pro Gln Ile Ala Ile Thr Asp Ala Met Leu
            260                 265                 270

Arg Ile Arg Leu Pro Glu Ser Ile Met Glu Cys Ala Ala Met Lys Ala
        275                 280                 285

Leu Trp Arg Glu Thr Val Val Ile Cys Phe Ile Leu Asn Asp Val Tyr
    290                 295                 300

Ser Val Gln Lys Glu Ile Ala Gln Asp Ser Leu Leu Asn Leu Val Pro
305                 310                 315                 320

Val Met Tyr Lys Asn Leu Asp Pro Glu Lys Gln Ser Leu Asp Thr Val
                325                 330                 335

Thr Arg Asp Ile Glu Val Leu Leu Gln Asp Thr Val Arg Lys Phe Glu
            340                 345                 350

Glu Ala Ala Lys Ser Leu Ser Glu Met Thr Ser Asn Asp Ala Gln Val
        355                 360                 365

Ser Lys Asp Val Gln Ala Phe Ile Lys Trp Cys Arg Tyr Phe Ile Thr
    370                 375                 380

Gly Val Gln Gln Trp Ser Leu Glu Ser Arg Arg Tyr Gly Met Ala Lys
385                 390                 395                 400

Cys Val Asn Glu Asp Gly Ser Leu Ser Ile Val Leu
                405                 410

<210> SEQ ID NO 80
<211> LENGTH: 376
<212> TYPE: PRT
<213> ORGANISM: Hypoxylon sp

<400> SEQUENCE: 80

Met Ala Ala Thr Ile Gln Gly Asn Glu Arg Ser Gly Leu Asn Pro Gln
1               5                   10                  15

Leu Leu Pro Phe Ser Val Asn Thr Arg Glu Gln Leu Leu Thr Asp Thr
                20                  25                  30

Arg Gly Ser Arg Val Met Ile Pro Asp Leu Gln Ser Met Ile Ser His
            35                  40                  45

Trp Pro Gln Arg Thr Asn Thr Asp Val Glu Arg Leu Asp Glu Tyr Val
        50                  55                  60

Glu Lys Ala Leu Thr Cys Phe Ser Ser Leu Ser Asn Asn Glu Ala Arg
65                  70                  75                  80

Val Arg Arg Leu Lys Ala Thr Asn Val Ala Phe Ile Ala Ala Thr Trp
                85                  90                  95

Trp Pro Tyr Ala Ser Tyr Lys Ala Leu Glu Val Leu Thr Ser Leu Leu

```
                100                 105                 110
Leu Trp Leu Phe Ala Trp Asp Asp Glu Thr Asp Ser Pro Glu Phe Ser
        115                 120                 125

Ala Val Ile Asn Asp Trp Asp Lys Ala Ser Thr Phe Arg Gln Arg Thr
    130                 135                 140

Thr Asn Tyr Leu Gln Gln Ser Leu Leu Lys Asn Ser Lys Ser Asn Leu
145                 150                 155                 160

Ala Asn Met Ser Thr Asp Pro Ile Asn Ala Leu Phe Gly Pro Val Ala
                165                 170                 175

Glu Ala Ile Ser Glu Ser Cys Asp Asp Arg Gln Val Gly Thr Phe Leu
            180                 185                 190

Asp Glu Leu Leu Phe Tyr Val Lys Met Cys Gly Glu Glu Gln Lys Leu
        195                 200                 205

Gln Val Ala His Arg Leu Pro Thr Val Glu Glu Tyr Val Arg Leu Arg
    210                 215                 220

Leu Gly Ser Gly Ala Val Arg Val Cys Phe Ala Thr Ile Glu Tyr Ala
225                 230                 235                 240

Tyr Gly Ile Thr Leu Ser Gln Lys Ile Met Asp Asp Glu Ala Met Gln
                245                 250                 255

Arg Ile Trp His Glu Ala Asn Ile Ile His Thr Thr Asn Asp Ile
            260                 265                 270

Leu Ser Val Lys Lys Glu Val Ala Gln Ser Gln Val Asp Ser Leu Val
        275                 280                 285

Pro Leu Leu Ala Leu Glu Leu Gly Ser Met Gln Ala Ala Met Asn His
    290                 295                 300

Ala Val Asp Ile Val Arg Ser Ser Ile Gln Arg Phe Asp Thr Ala Ala
305                 310                 315                 320

Ile Glu Ile Leu Glu Arg Tyr Ala Thr Thr Pro Lys Val Gln Glu Asp
                325                 330                 335

Ile Arg Lys Ser Ile Asp Ala Cys Arg Tyr Ala Cys Thr Ser Asn Leu
            340                 345                 350

Asn Trp Ser Leu Val Ser Gly Arg Tyr Lys Leu Asn Cys Gln Ser Met
        355                 360                 365

Glu Gly Gly Leu Tyr Ile Thr Leu
    370                 375

<210> SEQ ID NO 81
<211> LENGTH: 367
<212> TYPE: PRT
<213> ORGANISM: Omphalotus olearius

<400> SEQUENCE: 81

Met Ala Ile Glu Asn Thr Ile Ala Ser Ala Pro Ala Ser Thr Pro Ala
1               5                   10                  15

Lys Gln Leu Asp Thr Pro Asp His Phe Ile Leu Pro Asp Leu Val Ser
            20                  25                  30

His Cys Thr Phe Pro Leu Val Tyr His Ser Asn Gly Asp Ala Val Ala
        35                  40                  45

Ala Gln Ser Val Lys Trp Leu Asp Thr Asn Cys Pro Asp Leu Asn Asp
    50                  55                  60

Lys Arg Arg Lys Ala Leu Tyr Gly Leu Gln Ala Gly Glu Leu Thr Ala
65                  70                  75                  80

Tyr Cys Tyr Asn Thr Ala Pro Asp Gln Arg Leu Arg Val Val Ser Asp
                85                  90                  95
```

```
Phe Met Asn Tyr Leu Phe His Leu Asp Asn Ile Ser Asp Gly Met Met
                100                 105                 110

Thr Lys Asp Thr Asp Ala Leu Ser Asp Ala Val Met Asn Ala Leu Trp
            115                 120                 125

Phe Thr Glu Trp Tyr Arg Pro Thr Lys Lys Ser Asp Tyr Val Gln Pro
        130                 135                 140

Asp Glu Glu Leu Asn Ala Gly Lys Leu Ala Arg Asp Phe Trp His Arg
145                 150                 155                 160

Cys Ile Gln Asp Ala Gly Pro Gly Cys Gln Ala Arg Phe Lys Glu Thr
                165                 170                 175

Leu Glu Leu Phe Phe Glu Ala Val Asn Ile Gln Ala Lys Ala Arg Asp
            180                 185                 190

Ala Gly Val Ile Pro Asp Leu Glu Ser Tyr Ile Asp Val Arg Arg Asp
        195                 200                 205

Thr Ser Gly Cys Lys Pro Cys Trp Ala Leu Ile Glu Tyr Gly Leu Gly
210                 215                 220

Ile Asp Leu Pro Asp Tyr Val Ala Glu Asp Pro Ile Ile Lys Ser Leu
225                 230                 235                 240

Asn Gln Ser Thr Asn Asp Leu Val Thr Trp Ser Asn Asp Ile Phe Ser
                245                 250                 255

Tyr Asn Val Glu Gln Ser Arg Gly Asp Thr His Asn Met Ile Val Ile
            260                 265                 270

Leu Met Leu Tyr His Gly His Asn Leu Gln Ser Ala Ile Asp Tyr Val
        275                 280                 285

Gly Asp Leu Cys Arg Gln Thr Ile Asp Asp Phe Lys Glu Asn Arg Lys
290                 295                 300

Lys Ile Pro Ser Trp Gly Pro Glu Val Asp Asp Ile Val Lys Gln Tyr
305                 310                 315                 320

Val Gln Gly Leu Gln Asp Trp Ile Val Gly Ser Leu His Trp Ser Phe
                325                 330                 335

Met Thr Thr Arg Tyr Phe Gly Lys Gln Gly Gln Glu Val Lys Lys Asn
            340                 345                 350

Arg Tyr Val Lys Leu Leu Pro Val Gly Glu Glu Ala Asn Lys Trp
        355                 360                 365

<210> SEQ ID NO 82
<211> LENGTH: 425
<212> TYPE: PRT
<213> ORGANISM: Coprinopsis cinerea

<400> SEQUENCE: 82

Met Ser Thr Pro Ser Ser Ser Leu Thr Thr Asp Glu Ser Pro Ala Ser
1               5                   10                  15

Phe Ile Leu Pro Asp Leu Val Ser His Cys Pro Phe Pro Leu Arg Tyr
            20                  25                  30

His Pro Lys Gly Asp Glu Val Ala Lys Gln Thr Val His Trp Leu Asp
        35                  40                  45

Ser Asn Cys Pro Asp Leu Thr Ala Lys Glu Arg Lys Ala Met Tyr Gly
    50                  55                  60

Leu Gln Ala Gly Glu Leu Thr Gly Tyr Cys Tyr Pro Tyr Thr Thr Pro
65                  70                  75                  80

Glu Arg Leu Arg Val Val Ala Asp Phe Leu Asn Tyr Leu Phe His Leu
                85                  90                  95

Asp Asn Ile Ser Asp Gly Met Met Thr Arg Glu Thr Ala Val Leu Ala
            100                 105                 110
```

```
Asp Val Val Met Asn Ala Leu Trp Phe Pro Glu Asp Tyr Arg Pro Thr
            115                 120                 125

Lys Gly Gln Ala Ala Glu Leu Asn Pro Gly Lys Leu Ala Arg Asp
        130                 135                 140

Phe Trp Ser Arg Cys Ile Pro Asp Cys Gly Pro Gly Thr Gln Ala Arg
145                 150                 155                 160

Phe Lys Glu Thr Phe Gly Ser Phe Phe Glu Ala Val Asn Ile Gln Ala
                165                 170                 175

Arg Ala Arg Asp Glu Gly Val Ile Pro Asp Leu Glu Ser Tyr Ile Asp
                180                 185                 190

Val Arg Arg Asp Thr Ser Gly Cys Lys Pro Cys Trp Val Leu Ile Glu
                195                 200                 205

Tyr Ala Leu Gly Ile Asp Leu Pro Asp Phe Val Val Glu His Pro Val
                210                 215                 220

Ile Ala Ala Leu Asn Gln Gly Thr Asn Asp Leu Val Thr Trp Ser Asn
225                 230                 235                 240

Asp Ile Phe Ser Tyr Asn Val Glu Gln Ser Lys Gly Asp Thr His Asn
                245                 250                 255

Met Ile Ile Ile Leu Met Glu His His Gly His Thr Leu Gln Ser Ala
                260                 265                 270

Val Asp Tyr Val Gly Ser Leu Cys Gln Gln Thr Ile Asn Thr Phe Cys
                275                 280                 285

Glu Asn Lys Gln Gln Leu Pro Ser Trp Gly Pro Glu Ile Asp Asp Met
                290                 295                 300

Val Ala Lys Tyr Val Gln Gly Leu Glu Asp Trp Ile Val Gly Ser Leu
305                 310                 315                 320

His Trp Ser Phe Gln Thr Arg Arg Tyr Phe Gly Asp Glu Gly Gln Glu
                325                 330                 335

Ile Lys Gln His Arg Leu Val Lys Leu Leu Thr Val Ala Pro Pro Pro
                340                 345                 350

Pro Pro Pro Pro Thr Pro Pro Gln Ser Ser Asp Ala Asp Thr
                355                 360                 365

Lys Lys Gln Lys Val Lys Ala Gln Asp Gly Lys Gly Pro Val Ser Asp
        370                 375                 380

Glu Glu Val Trp Ala Leu Val Arg Ala Glu Gln Ser Lys Gly Ser Ile
385                 390                 395                 400

Leu Glu Ser Leu Phe Gly Phe Leu Thr Thr Ser Leu Ser Arg Ile Phe
                405                 410                 415

Phe Gly Tyr Phe Phe Ala Tyr Ser His
                420                 425

<210> SEQ ID NO 83
<211> LENGTH: 345
<212> TYPE: PRT
<213> ORGANISM: Coprinopsis cinerea

<400> SEQUENCE: 83

Met Ser Ser Leu Asp Ala Thr Ile His Pro Val Leu Asn Phe Glu Asp
1               5                   10                  15

Lys Lys Ile Val Leu Pro Asp Leu Val Ser His Cys Asn Phe Lys Leu
                20                  25                  30

Arg Val Ser Arg His Arg Lys Arg Ile Thr Gly Glu Thr Lys Arg Trp
            35                  40                  45

Leu Phe Lys Gly Asp Asn Leu Val Gly Pro Ala Arg Asn Lys Tyr His
```

```
            50                  55                  60
Gly Leu Lys Ala Gly Leu Leu Thr Ala Met Thr Tyr Pro Asp Ala Ala
 65                  70                  75                  80

Tyr Pro Gln Leu Arg Leu Cys Asn Asp Phe Leu Thr Tyr Leu Phe His
                 85                  90                  95

Ile Asp Asn Leu Ser Asp Met Asp Asn Arg Gly Thr Trp Ser Thr
            100                 105                 110

Ala Asn Glu Val Leu Asn Ser Leu Tyr His Pro Tyr Thr Tyr His Gly
            115                 120                 125

Gln Ala Arg Val Gly Arg Met Thr Arg Asp Tyr Trp Arg Arg Met Ile
        130                 135                 140

Leu Thr Ala Ser Pro Gly Ser Gln Gln Arg Phe Ile Glu Thr Phe Asp
145                 150                 155                 160

Phe Phe Phe Gln Ser Val Thr Gln Ala Ile Asp Arg Leu Thr Gly
                165                 170                 175

Glu Ile Pro Asp Leu Glu Ser Tyr Ile Ala Leu Arg Arg Asp Thr Ser
            180                 185                 190

Gly Cys Lys Pro Cys Trp Ala Leu Ile Glu Tyr Ala Asn Asn Leu Asp
        195                 200                 205

Leu Pro Asp Glu Val Met Asp His Pro Val Val Arg Ser Leu Gly Glu
210                 215                 220

Ala Ala Asn Asp Leu Val Thr Trp Ser Asn Asp Ile Phe Ser Phe Asn
225                 230                 235                 240

Val Glu Gln Ser Lys Gly Asp Thr His Asn Met Ile Pro Val Val Met
                245                 250                 255

His Gln Glu Gly Leu Asp Leu Gln Ser Ala Val Asp Phe Val Gly Glu
            260                 265                 270

Met Cys Lys Ser Ala Ile Asp Arg Phe Ile Glu Asp Gln Asn Tyr Leu
        275                 280                 285

Pro Ser Trp Gly Pro Lys Ile Asp Arg Asp Leu Ala Val Tyr Ile Asn
290                 295                 300

Gly Leu Ala Asp Trp Ile Val Gly Ser Leu His Trp Ser Phe Glu Thr
305                 310                 315                 320

Glu Arg Tyr Phe Gly Lys Asn Gly Arg Gln Val Lys Ser Ser Arg Val
                325                 330                 335

Ile Asp Leu Leu Pro Arg Arg Ser Gln
            340                 345

<210> SEQ ID NO 84
<211> LENGTH: 332
<212> TYPE: PRT
<213> ORGANISM: Omphalotus olearius

<400> SEQUENCE: 84

Met Lys Tyr Thr Ser Phe Ala Leu Pro Asp Leu Ala Ser Ser Cys Asp
 1               5                  10                  15

Tyr Asn Leu Arg Phe Asn Lys Tyr His Arg Ser Val Ser Pro Glu Thr
                20                  25                  30

Lys Lys Trp Phe Phe Arg Leu Ser Pro Ala Ser Gln Ala Asp Leu Thr
            35                  40                  45

Thr Tyr Asp Ala Gln Arg Phe Thr Leu Leu Ala Ala Val Cys Tyr Pro
        50                  55                  60

Asp Ala Gly Tyr Pro Gln Leu Arg Val Cys Ser Asp Phe Leu Ala Tyr
 65                  70                  75                  80
```

```
Leu Phe Tyr Leu Asp Asn Leu Thr Asp Asp Met Asp Asp Lys Ser Thr
                85                  90                  95
Arg Ser Val Ala Asp Leu Val Leu Asn Ser Leu Asn Glu Pro Glu Thr
            100                 105                 110
Phe Gln Thr Gln Tyr Arg Ile Gly Lys Met Thr Ser Asp Tyr Phe Lys
        115                 120                 125
Arg Ile Ile Gln Thr Ser Asn Asp Gly Thr Lys Lys Arg Phe Ile Asp
    130                 135                 140
Thr Met Asp Ser Phe Phe Lys Ser Val Asp Asp Gln Ala Arg Asp Arg
145                 150                 155                 160
Leu Ala Gly His Ile Pro Asp Leu Glu Ser Tyr Ile Ala Leu Arg Arg
                165                 170                 175
Glu Thr Ser Gly Cys Lys Thr Cys Phe Ser Leu Ile Glu Tyr Ala Asn
            180                 185                 190
Asn Leu His Ile Pro Asp Glu Val Ile Ser His Pro His Ile Glu Gln
        195                 200                 205
Met Glu Thr Ala Ala Asn Asp Val Val Ser Phe Ala Asn Asp Ile Tyr
    210                 215                 220
Ser Phe Asn Ile Glu Gln Ser Lys Gly Asp Thr His Asn Met Ile Pro
225                 230                 235                 240
Val Leu Met His Ala Asn Pro Asp Met Asp Phe Leu Glu Ala Val Ser
                245                 250                 255
Phe Val Arg Asp Leu Thr Ile Lys Ala Met Asp Arg Phe Asn Glu Leu
            260                 265                 270
Arg Ala Thr Leu Pro Ser Trp Gly Leu Asp Ile Asp Lys Asp Met Lys
        275                 280                 285
Val Tyr Val Asn Gly Leu Glu Asn Trp Met Val Gly Ile Leu Phe Trp
    290                 295                 300
Ser Phe Glu Thr Glu Arg Tyr Phe Gly Lys Ser Val Arg Ser Val Lys
305                 310                 315                 320
Ala Thr Lys Thr Val Asn Leu Leu Pro Ser Arg Ala
                325                 330

<210> SEQ ID NO 85
<211> LENGTH: 333
<212> TYPE: PRT
<213> ORGANISM: Omphalotus olearius

<400> SEQUENCE: 85

Met Ala Ser Thr Ala Pro Ser Lys Phe Ile Leu Pro Asp Leu Val Ser
1               5                   10                  15
His Cys Ser Phe Asp Leu His His Asn Arg His Arg Lys Gln Ile Thr
            20                  25                  30
Thr Glu Thr Lys Lys Trp Leu Phe Lys Gly Asp Asn Leu Thr Gly Arg
        35                  40                  45
Lys Arg Asp Gln Tyr His Gly Leu Lys Cys Gly Leu Leu Ser Ala Met
    50                  55                  60
Cys Tyr Pro Asn Ala Ala Tyr Pro Gln Leu Arg Val Cys Asn Asp Phe
65                  70                  75                  80
Leu Thr Tyr Leu Phe His Leu Asp Asn Leu Ser Asp Asp Met Asp Asn
                85                  90                  95
Arg Gly Thr Thr Thr Thr Ala Asp Val Val Leu Asn Ser Leu Tyr His
            100                 105                 110
Pro Gly Tyr Phe Gln Ser Ala Arg Val Gly Lys Met Thr Arg Asp Tyr
        115                 120                 125
```

```
Trp Lys Arg Leu Ile Ser Thr Ala Ser Pro Gly Thr Gln Gln Arg Phe
            130                 135                 140

Ile Glu Thr Phe Asp Phe Phe Gln Ser Val Thr Glu Gln Ala His
145                 150                 155                 160

Asp Arg Gln Ala Gly Val Ile Pro Asp Leu Glu Ser Tyr Ile Ala Leu
                165                 170                 175

Arg Arg Asp Thr Ser Gly Cys Lys Thr Ser Phe Val Leu Ile Glu Tyr
                180                 185                 190

Ala Asn Asn Leu Asp Ile Pro Asp Gly Val Met Asp His Pro Leu Ile
            195                 200                 205

Arg Ser Leu Gly Glu Ala Ala Asn Asp Leu Val Thr Trp Ser Asn Asp
            210                 215                 220

Ile Phe Ser Tyr Asn Val Glu Gln Ala Lys Gly Asp Thr His Asn Met
225                 230                 235                 240

Ile Pro Val Ile Met Asn Glu His Gly Leu Asp Leu Gln Ser Ala Val
                245                 250                 255

Asp Tyr Val Gly Arg Leu Cys Gln Gln Ser Ile Asp Arg Phe Ile Ser
                260                 265                 270

Asp Arg Ala Gln Leu Pro Ser Trp Gly Pro Glu Ile Asp Arg Gln Val
            275                 280                 285

Ala Ile Tyr Val Asp Gly Leu Thr Asp Trp Ile Val Gly Ser Leu His
            290                 295                 300

Trp Ser Phe Glu Ser Glu Arg Tyr Phe Gly Lys Ser Gly Arg Gln Ile
305                 310                 315                 320

Lys Lys Ser Arg Val Ile Asn Leu Leu Pro Arg Arg Ala
                325                 330

<210> SEQ ID NO 86
<211> LENGTH: 348
<212> TYPE: PRT
<213> ORGANISM: Coprinopsis cinerea

<400> SEQUENCE: 86

Met Pro Ser Pro Ala Gly Ala Leu Pro Lys Ser Phe Ile Leu Pro Asp
1               5                   10                  15

Leu Val Asn Asp Cys Pro Phe Pro Leu Arg Val Asn Pro Leu Cys Asp
                20                  25                  30

Glu Val Gly Arg Leu Ser Glu Gln Trp Phe Leu Arg His Ala Asn Tyr
            35                  40                  45

Ser Pro Pro Arg Ala Val Ala Phe Met Ala Leu Lys Ala Gly Glu Leu
        50                  55                  60

Thr Ala Ala Cys Tyr Pro Asp Ala Asp Ala Phe His Leu Arg Val Ser
65                  70                  75                  80

Asp Asp Phe Met Asn Phe Leu Phe Asn Ala Asp Asp Trp Leu Asp Asp
                85                  90                  95

Phe Asp Ile Glu Asp Thr Tyr Gly Leu Ala Asn Cys Thr Val Arg Ala
            100                 105                 110

Leu Arg Asp Pro Val Asn Phe Ile Thr Asp Lys Arg Ala Gly Leu Met
        115                 120                 125

Thr Lys Ser Tyr Phe Ser Arg Phe Leu Lys Thr Ala Gly Pro Arg Cys
    130                 135                 140

Thr Glu Arg Phe Ile Gln Thr Leu Ala Leu Tyr Phe Glu Ser Val Val
145                 150                 155                 160

Thr Gln Lys Gln Ala Arg Asn Asn Gly Thr Leu Pro Asp Leu Glu Ser
```

```
            165                 170                 175
Tyr Ile Thr Ile Arg Arg Asn Asn Ser Gly Cys Lys Pro Cys Tyr Ala
        180                 185                 190

Leu Ile Glu Phe Cys Ala Gly Ile Asp Leu Pro Asp Glu Val Ile Asn
        195                 200                 205

His Pro Ile Ile Gln Ser Leu Glu Asp Ala Ser Asn Asp Leu Ile Ala
        210                 215                 220

Trp Ser Asn Asp Ile Phe Ser Phe Asn Arg Glu Gln Ser Arg His Asp
225                 230                 235                 240

Ser Phe Asn Met Val Ser Ile Val Met His Gln Lys Gly Phe Ala Leu
                245                 250                 255

Gln Glu Ala Val Asn Phe Val Gly Glu Leu Cys Lys Lys Ala Met Glu
                260                 265                 270

Arg Phe Gln Ala Asp Lys Arg Asn Leu Pro Ser Trp Gly Pro Glu Ile
                275                 280                 285

Asp Gly Glu Val Ala Met Tyr Val Asp Gly Leu Gln Asn Trp Ile Val
                290                 295                 300

Gly Ser Leu Asn Trp Ser Ile Asp Gly Thr Glu Arg Tyr Phe Gly Lys
305                 310                 315                 320

Asp Gly Pro Gly Ile Lys Lys His Arg Lys Val Lys Leu Phe Pro Lys
                325                 330                 335

Arg Pro Leu Lys Thr Pro Ala Val Arg Val Leu Ala
                340                 345

<210> SEQ ID NO 87
<211> LENGTH: 345
<212> TYPE: PRT
<213> ORGANISM: Coprinopsis cinerea

<400> SEQUENCE: 87

Met Arg Pro Thr Ala Arg Gln Phe Thr Leu Pro Asp Leu Phe Ser Ile
1               5                   10                  15

Cys Pro Leu Gln Asp Ala Thr Asn Pro Trp Tyr Lys Gln Ala Ala Ala
                20                  25                  30

Glu Ser Arg Ala Trp Ile Asn Ser Tyr Asn Ile Phe Thr Asp Arg Lys
            35                  40                  45

Arg Ala Phe Phe Ile Gln Gly Ser Asn Glu Leu Leu Cys Ser His Val
        50                  55                  60

Tyr Ala Tyr Ala Gly Tyr Glu Gln Phe Arg Thr Cys Cys Asp Phe Val
65                  70                  75                  80

Asn Leu Leu Phe Val Val Asp Glu Ile Ser Asp Asp Gln Asn Gly Gln
                85                  90                  95

Asp Ala Arg Ala Thr Gly Arg Ile Phe Val Asn Ala Met Arg Asp Ala
                100                 105                 110

His Trp Asp Asp Gly Ser Ile Leu Ala Lys Ile Thr His Glu Phe Arg
            115                 120                 125

Glu Arg Phe Val Arg Leu Ala Gly Pro Lys Thr Val Arg Arg Phe Ala
        130                 135                 140

Asp Leu Cys Glu Ser Tyr Thr Asp Cys Val Ala Arg Glu Ala Glu Leu
145                 150                 155                 160

Arg Glu Arg Asn Gln Val Leu Gly Leu Asn Asp Phe Ile Ala Leu Arg
                165                 170                 175

Arg Gln Asn Ser Ala Val Leu Leu Cys Tyr Ser Leu Val Glu Tyr Ile
                180                 185                 190
```

```
Leu Gly Ile Asp Leu Asp Asp Glu Val Tyr Glu Asp Thr Phe Ala
            195                 200                 205
Lys Ala Tyr Trp Ala Ala Cys Asp Phe Val Cys Trp Ala Asn Asp Val
210                 215                 220
Tyr Ser Tyr Asp Met Glu Gln Ala Lys Gly His Thr Gly Asn Asn Val
225                 230                 235                 240
Val Thr Val Leu Met Lys Glu Lys Asp Leu Ser Leu Gln Glu Ala Ser
            245                 250                 255
Asp Tyr Ile Gly Arg Glu Cys Glu Lys Gln Met Arg Asp Tyr Leu Glu
            260                 265                 270
Ala Lys Ser Gln Leu Leu Gln Ser Thr Asp Leu Pro Gln Glu Ala Val
            275                 280                 285
Arg Tyr Ile Glu Ala Leu Gly Tyr Trp Met Val Gly Asn Leu Val Trp
            290                 295                 300
Ser Phe Glu Ser Gln Arg Tyr Phe Gly Ala Gln His Glu Arg Val Lys
305                 310                 315                 320
Ala Thr His Val Val His Leu Arg Pro Ser Ser Val Leu Glu Ala Ser
            325                 330                 335
Cys Asp Ser Asp Ser Asp Ser Asp Cys
            340                 345

<210> SEQ ID NO 88
<211> LENGTH: 346
<212> TYPE: PRT
<213> ORGANISM: Stereum hirsutum

<400> SEQUENCE: 88

Met Ala Thr Ser Asn Pro Pro Ser Thr Pro His His Glu Ser Leu Ile
1               5                   10                  15
Leu Pro Asp Leu Leu Ser Leu Ser Thr Pro Phe Asn Gly Ser Thr Asn
            20                  25                  30
Pro His Trp Ala Met Ala Ala Pro Glu Ser Ser Ala Trp Val Ser Ser
            35                  40                  45
Tyr Asn Leu Phe Ser Asp Arg Lys Arg Thr Asp Phe Ile Thr Gly Ser
50                  55                  60
Asn Glu Leu Leu Val Ser His Thr Tyr Pro His Ala Asp Tyr Asp Ala
65                  70                  75                  80
Phe Arg Thr Cys Cys Asp Phe Val Asn Leu Leu Phe Val Ile Asp Glu
            85                  90                  95
Ile Ser Asp Asp Gln Ser Gly Lys Ala Ala Arg Arg Thr Gly Glu Val
            100                 105                 110
Tyr Leu Asn Ala Met Arg Asp Pro Glu Trp Thr Asp Gly Ser Asp Leu
            115                 120                 125
Ala Lys Met Thr Gln Gln Phe Arg Ala Arg Phe Leu Arg Ser Val Gly
130                 135                 140
Pro Gln Ser Phe Arg Arg Phe Leu Arg His Ser Glu Asp Tyr Ile Asp
145                 150                 155                 160
Cys Val Ala Lys Glu Ala Glu Tyr Arg Glu Arg Gly Gln Val Leu Asp
            165                 170                 175
Met Asp Ser Phe Lys Ser Leu Arg Glu Asn Ser Ala Ile Arg Leu
            180                 185                 190
Cys Phe Gly Leu Phe Glu Phe Thr Leu Gly Ile Asp Leu Pro Asp Ser
            195                 200                 205
Val Phe Glu Asp Glu Thr Phe Met Lys Met Tyr Trp Ala Ser Ala Asp
210                 215                 220
```

```
Met Val Cys Trp Ala Asn Asp Val Tyr Ser Tyr Asn Val Glu Gln Ala
225                 230                 235                 240

Lys Gly His Ser Gly Asn Asn Ile Val Thr Val Leu Met Ala Ala Arg
            245                 250                 255

Asp Ile Asp Met Gln Ala Ala Ser Asp Tyr Val Gly Tyr Tyr Ala
                260                 265                 270

Glu Leu Met Glu Glu Tyr Met Thr Ala Lys Ala Glu Leu Ala Ser Lys
            275                 280                 285

Ser Phe Gly Ser Arg Asp Leu Asp Glu Asp Val Trp Lys Tyr Val Asn
            290                 295                 300

Ala Met Glu Asn Trp Pro Ile Gly Asn Leu Glu Trp Ser Phe Lys Thr
305                 310                 315                 320

Asn Arg Tyr Phe Gly Thr Leu His Asp Glu Val Lys Arg Thr Arg Leu
                325                 330                 335

Val Val Ile Lys Pro Arg Lys Val Val Val
            340                 345

<210> SEQ ID NO 89
<211> LENGTH: 344
<212> TYPE: PRT
<213> ORGANISM: Omphalotus olearius

<400> SEQUENCE: 89

Met Ser Ser Ala Pro Thr Arg Phe Leu Leu Pro Asp Leu Leu Ser Ala
1               5                   10                  15

Cys Pro Leu Lys Gly Ser Val Asn Pro Tyr Tyr Lys Glu Ala Gly Ala
            20                  25                  30

Glu Ser Ser Ala Trp Ile Asn Ser Tyr Asp Ile Phe Thr Asp Arg Lys
        35                  40                  45

Arg Ala Phe Phe Val Gln Gly Cys Asn Glu Leu Leu Val Ala His Thr
    50                  55                  60

Tyr Pro Tyr Ala Gly Tyr Glu Glu Phe Arg Thr Cys Cys Asp Phe Ile
65                  70                  75                  80

Asn Val Leu Phe Val Leu Asp Glu Val Ser Asp Glu Gln Ser Gly Ser
                85                  90                  95

Asp Ala Arg Phe Thr Gly Glu Val Phe Leu Asn Ala Leu Arg Asn Pro
            100                 105                 110

Glu Asn Asp Asp Thr Ser Lys Leu Ser Lys Ile Ser Lys Glu Phe Arg
        115                 120                 125

Ala Arg Tyr Phe Lys Arg Ala Gly Pro Arg Thr Ala Glu Arg Phe Leu
    130                 135                 140

Gln His Cys Gln Asp Tyr Ile Asp Cys Val Thr Arg Glu Ala Glu Leu
145                 150                 155                 160

Arg Glu Arg Gly Glu Val Leu Asp Leu Pro Ser Phe Thr Ala Leu Arg
                165                 170                 175

Arg Glu Asn Ser Ala Ile Arg Val Cys Phe Cys Leu Phe Glu Tyr Ala
            180                 185                 190

Leu Gly Phe Asp Leu Pro Gln Glu Val Phe Asp Pro Thr Phe Met
        195                 200                 205

Glu Met Tyr Trp Ala Ala Ala Asp Leu Val Cys Trp Ala Asn Asp Val
    210                 215                 220

Tyr Ser Tyr Asn Lys Glu Gln Ala Gln Gly His Gly Gly Asn Asn Ile
225                 230                 235                 240

Val Thr Val Leu Met Lys Ala Lys Asp Leu Asp Leu Gln Ala Ala Cys
```

-continued

```
                245                 250                 255
Asp Tyr Ile Gly Val Tyr Cys Glu Glu Leu Met Gly Arg Tyr Leu Ser
            260                 265                 270

Ala Lys Ala Arg Leu Pro Ser Trp Gly Pro Glu Val Asp Ala Ala Val
            275                 280                 285

Ala Gln Tyr Val Glu Ala Ser Gly His Trp Val Arg Gly Asn Leu Asp
            290                 295                 300

Trp Ser Phe Glu Thr Gln Arg Tyr Phe Gly Ala Gln His Ala Glu Ile
305                 310                 315                 320

Lys Glu Thr Arg Leu Val Thr Leu Thr Pro Ala Ile Pro Glu Asp Phe
                325                 330                 335

Ser Asp Thr Gly Ser Glu Ser Glu
            340
```

<210> SEQ ID NO 90
<211> LENGTH: 345
<212> TYPE: PRT
<213> ORGANISM: Omphalotus olearius

<400> SEQUENCE: 90

```
Met Ser Pro Asp Pro Thr Arg Ile Val Leu Pro Asp Phe Leu Ala Ala
1               5                   10                  15

Cys Pro Phe Glu Ser Ser Thr Lys Asn Pro His Leu Lys Ala Ala Gly
            20                  25                  30

Ala Glu Ser Ser Ala Trp Val Asn Ser His Val Val Phe Asn Asp Arg
        35                  40                  45

Lys Arg Ala Ala Phe Met Gln Asp Ile Tyr Glu Leu Leu Val Ala Tyr
50                  55                  60

Ala Phe Pro Trp Ala Asp Tyr Glu Asp Phe Arg Thr Met Cys Asp Phe
65                  70                  75                  80

Ile Asn Leu Leu Phe Val Leu Asp Glu Leu Ser Asp Asp Gln Asn Gly
                85                  90                  95

Lys Asp Ala Gly Tyr Thr Gly Lys Leu Phe Met Asp Ala Met Arg Asn
            100                 105                 110

Ile Asp Asn Gly Asp Thr Ser Glu Leu Thr Glu Leu Cys Arg Glu Phe
        115                 120                 125

Lys Ala Arg Tyr Ser Lys Arg Val Ser Pro Gln Val Asn Glu Arg Phe
130                 135                 140

Leu Gln His Leu Gln Ser Tyr Thr Asp Cys Val Ala Gln Glu Ala Asp
145                 150                 155                 160

Leu Arg Glu Arg Gly Glu Ile Leu Asp Leu Glu Ser Tyr Val Ala Leu
                165                 170                 175

Arg Arg Glu Asn Ser Ala Ile Arg Pro Cys Phe Asp Leu Val Glu Tyr
            180                 185                 190

Ile Ile Asp Phe Asp Ile Pro Gln Glu Val Ile Asp His Pro Val Phe
        195                 200                 205

Ser Glu Met Tyr Trp Ala Ser Val Asp Leu Val Cys Trp Ser Asn Asp
210                 215                 220

Val Tyr Ser Tyr Asn Val Glu Gln Ala Lys Gly His Gly Gly Ser Asn
225                 230                 235                 240

Val Val Thr Val Leu Met Lys Glu Lys Asn Leu Asp Leu Gln Ala Ala
                245                 250                 255

Cys Asp Tyr Val Gly Val Tyr Tyr Glu Glu Leu Met Asp Arg Tyr Leu
            260                 265                 270
```

```
Ser Ala Lys Ala Arg Leu Pro Ser Trp Gly Pro Glu Ile Asp Ala Ala
        275                 280                 285

Val Gly Lys Tyr Ile Leu Ala Glu Ala Gln Phe Val Arg Gly Asn Leu
        290                 295                 300

Asp Trp Ser Phe Asp Ser Pro Arg Tyr Phe Gly Pro Gln His Asp Gln
305                 310                 315                 320

Val Lys Lys Thr Gly Ile Val Thr Leu Thr Pro Ala Pro Lys Lys Phe
                325                 330                 335

Gly Ser Asp Ser Gly Ser Glu Ser Glu
                340                 345

<210> SEQ ID NO 91
<211> LENGTH: 345
<212> TYPE: PRT
<213> ORGANISM: Omphalotus olearius

<400> SEQUENCE: 91

Met Ser Pro Ala Pro Ser Arg Ile Val Leu Pro Asp Phe Phe Ala Ser
1               5                   10                  15

Cys Pro Phe Glu Ser Ser Thr Ile Asn Pro His Phe Lys Ala Ala Gly
            20                  25                  30

Ala Glu Ser Ser Ala Trp Val Asn Ser His Val Val Phe Asn Asp Arg
        35                  40                  45

Lys Arg Ala Ala Leu Met Gln Asn Ser Tyr Glu Leu Leu Val Ala Tyr
50                  55                  60

Ala Phe Pro Trp Ala Ser Tyr Glu Asp Phe Arg Thr Leu Cys Asp Phe
65                  70                  75                  80

Ile Asn Leu Leu Phe Val Phe Asp Glu Val Ser Asp Asp Gln Asn Gly
                85                  90                  95

Lys Asp Ala Gly Tyr Thr Ser Lys Ile Phe Met Asp Ala Met Arg Asn
            100                 105                 110

Ile Asp Asn Gly Asp His Ser Glu Leu Thr Glu Leu Cys Lys Glu Phe
        115                 120                 125

Lys Ala Arg Phe Ser Arg Arg Leu Ser Pro Gln Val Asn Glu Arg Phe
130                 135                 140

Leu Gln His Leu Gln Ser Tyr Thr Asp Cys Val Ala Gln Glu Ala Asp
145                 150                 155                 160

Leu Arg Glu Arg Gly Glu Ile Leu Asp Leu Glu Ser Tyr Val Ile Leu
                165                 170                 175

Arg Arg Glu Asn Ser Ala Val Arg Pro Cys Phe Asp Leu Val Glu Tyr
            180                 185                 190

Ile Met Asp Phe Asp Ile Pro Gln Glu Val Leu Asp His Pro Val Phe
        195                 200                 205

Ser Glu Met Tyr Trp Ala Ser Val Asp Leu Val Cys Trp Ser Asn Asp
            210                 215                 220

Val Tyr Ser Tyr Asn Val Glu Gln Ala Lys Gly His Arg Gly Ser Asn
225                 230                 235                 240

Val Val Thr Val Leu Met Asn Glu Lys Asn Leu Asp Leu Gln Ala Ala
                245                 250                 255

Cys Asp Tyr Val Gly Val Tyr Tyr Gln Glu Leu Met Asp Arg Tyr Leu
            260                 265                 270

Ser Ala Lys Ala Arg Leu Pro Ser Trp Gly Pro Glu Ile Asp Ala Ala
        275                 280                 285

Val Gly Lys Tyr Val Leu Ala Glu Ala Gln Phe Val Arg Gly Asn Leu
        290                 295                 300
```

```
Asp Trp Ser Phe Asp Thr Pro Arg Tyr Phe Gly Pro Gln Arg Asp Gln
305                 310                 315                 320

Ile Lys Lys Ser Arg Ile Val Thr Leu Thr Pro Ala Pro Lys Lys Phe
                325                 330                 335

Gly Ser Asp Ser Gly Ser Glu Ser Glu
            340                 345

<210> SEQ ID NO 92
<211> LENGTH: 355
<212> TYPE: PRT
<213> ORGANISM: Agrocybe aegerita

<400> SEQUENCE: 92

Met Gln Ile Ile Leu Pro Asp Ile Leu Gln Thr Trp Ala Tyr Ala Arg
1               5                   10                  15

Leu Leu Asn Pro His Tyr Asp Gly Ala Lys Leu Glu Ser Ser Leu Trp
                20                  25                  30

Ile His Pro Leu Val Ala Lys Leu Phe Asp Gln Lys Gly Gln Lys Ala
            35                  40                  45

Phe Gln Asn Asp Tyr Thr Ser Leu Leu Ala Ser Leu Met Tyr Ser His
        50                  55                  60

Gln Gly Lys Val Pro Ser Arg Arg Cys Asp Met Met Asn Leu Phe Phe
65                  70                  75                  80

Val Tyr Asp Glu Tyr Thr Asp Val Val Ser Pro Glu Ile Ala His Arg
                85                  90                  95

Leu Ser Lys Ile Val Val Asp Ala Met Lys Asn Ser Asp Glu Met Ser
            100                 105                 110

Pro Cys Gly Glu His Pro Ile Gly Asp Lys Ala Lys Glu Phe Trp Arg
        115                 120                 125

Leu Ala Thr Thr Leu Leu Pro Ala Thr Gly Ser Asn Ser Asp Val Cys
130                 135                 140

Lys Ser Arg Phe Ile Asn Leu Thr Glu Glu Tyr Leu Asn Ala Val Thr
145                 150                 155                 160

Val Glu Ala Arg Asp Arg Asn Glu Gly Thr Ile His Ser Val Lys Glu
                165                 170                 175

Tyr Leu Thr Met Arg Arg Ala Thr Ser Gly Ala Gly Leu Met Leu Ala
            180                 185                 190

Leu Ile Glu Phe Glu Leu Asp Leu Pro Lys Ala Val Leu Glu His Lys
        195                 200                 205

Phe Val Gln Ala Leu Glu Glu Ile Tyr Thr Arg Thr Arg Val Ser Ser
210                 215                 220

Gly Gln Ala Asn His Asn Leu Ile Thr Val Val Met His Glu Asn Pro
225                 230                 235                 240

Gly Leu Ser Leu Gln Gly Ala Phe Asp Trp Leu Gly Ser Tyr Ala Ala
                245                 250                 255

Gly Val Val Glu Cys Phe Gln Thr Asn Val Arg Asn Leu Pro Ser Phe
            260                 265                 270

Cys Asp Val Glu Gly Pro Ala Cys Glu Ser Val Asp Gly Thr Leu Gln
        275                 280                 285

Glu Arg Val Asp Lys Tyr Ile Ser Gly Leu Gly Gln Ala Val Arg Ala
        290                 295                 300

Glu Asp Asp Trp Ala Phe Glu Thr Thr Arg Tyr Tyr Gly Glu Asp Gly
305                 310                 315                 320

Pro Lys Val Arg Glu Thr Arg Val Leu Val Ile Arg Pro Val Lys Arg
```

325                 330                 335
Ile Thr Arg Arg His Leu Leu Gln Ser Leu Glu Ile Lys Tyr Ser Met
                340                 345                 350
Val Arg Gly
        355

<210> SEQ ID NO 93
<211> LENGTH: 307
<212> TYPE: PRT
<213> ORGANISM: Agrocybe aegerita

<400> SEQUENCE: 93

Met Ser Leu Asn Phe Phe Leu Arg Arg Tyr Thr Val Phe Pro Trp Ser
1               5                   10                  15

Arg Lys Leu Gly Gln Tyr Tyr His Asp Ala Lys Arg Glu Ser Ser Ala
            20                  25                  30

Trp Thr Glu Ser Phe His Pro Phe Asp Glu Asp Leu Ser Lys Ala Ala
        35                  40                  45

Leu Thr Phe Cys Ile Thr Ala Leu Leu Ala Ser Leu Ala Tyr Phe Leu
    50                  55                  60

Arg Gln Lys Glu Ile Val Arg Leu Gly Cys Asp Leu Met Asn Ile Phe
65                  70                  75                  80

Tyr Val Phe Asp Glu Cys Ala Asp Ile Ala Asp Lys Glu Gly Ala Ser
                85                  90                  95

Gln Ile Arg Asp Val Val Met Asp Asp Leu His Arg Pro Glu Lys Thr
            100                 105                 110

Cys Pro Gly Gly Glu Ile Leu Pro Gly Glu Met Val Lys Tyr Val Leu
        115                 120                 125

Leu Leu Cys Pro Glu Ile Pro Glu Thr Tyr Tyr Asn Thr Lys Ser Phe
    130                 135                 140

Gly Phe Ala Pro Gln Ser Ser Pro Gln Pro His Ile Val Cys Ala
145                 150                 155                 160

Thr Leu Ser Arg Ile Ser Met Pro Thr Gln Gln Trp Phe Asn Val
                165                 170                 175

Lys Arg Thr Ile Gly Pro Asn Val Phe Leu Ala Arg Ser Ala Thr Val
            180                 185                 190

Leu Pro Tyr Ala Glu Thr His Thr Phe Tyr His Pro Arg Met Ile Ala
        195                 200                 205

Leu Arg Glu Gln Ala Pro Phe Leu Asp Ile Asn Ser Tyr Pro Met Lys
    210                 215                 220

Val Arg Gly Leu Val Gln Gly Ser Ile Asn Trp Leu Glu Gly Tyr Ala
225                 230                 235                 240

Ala Gly Val Gln Ala Ala Phe Leu Asp Asn Ile Ala Asn Leu Pro Ser
                245                 250                 255

Cys Ala Lys Glu Val Glu Ser Arg Val Asn Ile Tyr Val Asn Glu Leu
            260                 265                 270

Ala Gln Trp Ala Arg Gly Asn Asp Asp Trp Thr Phe Glu Ser Gly Arg
        275                 280                 285

Tyr Phe Gly Asp Arg Gly Pro Glu Asn Gln Ser Asp Ile Pro Thr Ser
    290                 295                 300

Ser Asn Arg
305

<210> SEQ ID NO 94
<211> LENGTH: 345

<212> TYPE: PRT
<213> ORGANISM: Agrocybe aegerita

<400> SEQUENCE: 94

Met Pro Gly Ser Ala Asn Trp Thr Ala Asp Arg Phe Tyr Ile Pro Asp
1               5                   10                  15

Thr Leu Ala Asn Trp Pro Trp Pro Arg Ala Ile Asn Pro Ala Tyr Glu
            20                  25                  30

Glu Cys Lys Ala Ala Ser Ala Ala Trp Cys Glu Lys Tyr Gly Ala Phe
        35                  40                  45

Ser Ala Arg Ala Gln Lys Ala Phe Asn Leu Cys Asp Phe Asn Leu Leu
    50                  55                  60

Ala Ser Leu Ala Tyr Ala Gly Leu Pro Ala Asp Val Asn Arg Val Gly
65                  70                  75                  80

Cys Asp Leu Met Asn Leu Phe Phe Val Val Asp Glu His Thr Asp Ala
                85                  90                  95

Met Asp Ala Arg Ser Val Gln Asp Trp Val Asp Ile Val Val Asp Ala
            100                 105                 110

Leu His His Pro His Thr Pro Arg Pro Ala Gly Glu Pro Lys Val Gly
        115                 120                 125

Glu Ile Ala Arg Thr Phe Trp Glu Asn Gly Ile Lys Cys Met Gly Pro
    130                 135                 140

Thr Ala Gln Arg Arg Phe Val Glu Thr Phe Thr Thr Tyr Leu Gln Ser
145                 150                 155                 160

Val Val Thr Gln Ala Gln Asp Arg Asp Lys His Leu Phe Arg Asp Val
                165                 170                 175

Asp Ser Tyr Met Glu Val Arg Arg Asp Thr Ile Gly Ala Lys Pro Ser
            180                 185                 190

Phe Ala Leu Leu Glu His Asp Met Glu Leu Pro Asp Asp Val Phe Tyr
        195                 200                 205

His Pro Leu Leu Glu Lys Leu Arg Glu Trp Ala Ile Asp Met Leu Ile
    210                 215                 220

Leu Gly Asn Asp Leu Cys Ser Tyr Asn Val Glu Gln Ser Arg Gly Asp
225                 230                 235                 240

Asp Gly His Asn Ile Ile Arg Leu Ala Met Leu Gln Glu Asn Thr Asn
                245                 250                 255

Val His Gly Ala Leu Arg Phe Val Ser Lys Met His Asp Leu Ala
            260                 265                 270

Glu Lys Phe Leu Ser Asn Tyr Gln Gly Met Pro Ser Phe Thr Pro Gln
        275                 280                 285

Ile Asp Ala Trp Val Thr Arg Tyr Ile Asp Gly Leu Gly Asn Trp Val
    290                 295                 300

Arg Ala Asn Asp Ser Trp Ser Phe Glu Ser Trp Arg Tyr Phe Lys Gly
305                 310                 315                 320

Asp Val Leu Arg Val Gln Ala Glu Arg Trp Val Glu Leu Leu Pro Pro
                325                 330                 335

Ala Pro Lys Asp Glu Leu Thr Pro Ala
            340                 345

<210> SEQ ID NO 95
<211> LENGTH: 357
<212> TYPE: PRT
<213> ORGANISM: Omphalotus olearius

<400> SEQUENCE: 95

```
Met Ile Ala Lys Asn Ser Glu Ile Asp Arg Phe Tyr Ile Pro Asp Thr
1               5                   10                  15

Leu Ala Asn Trp Pro Trp Pro Arg His Leu Asn Pro Ala Tyr Pro Glu
                20                  25                  30

Ala Lys Lys Ala Ser Ala Ala Trp Leu Arg Ser Phe Asn Ala Phe Asn
            35                  40                  45

Glu Arg Ser Gln Lys Ala Phe Asp Leu Cys Asp Phe Asn Leu Leu Ala
        50                  55                  60

Ser Leu Ala Phe Pro Leu Ala Asp Leu Tyr Cys Leu Arg Ser Gly Cys
65                  70                  75                  80

Asp Leu Met Asn Cys Phe Phe Ile Phe Asp Glu Tyr Ser Asp Val Ala
                85                  90                  95

Asp Pro Gln Thr Val Arg Gln Gln Ala Asp Ile Ile Met Asp Ala Ile
                100                 105                 110

Arg Asn Pro His Val Pro Arg Pro Gly Glu Phe Ile Gly Gly Glu
                115                 120                 125

Ala His Arg Gln Phe Trp Glu Arg Ala Met Gln Gly Ala Thr Pro Thr
            130                 135                 140

Ala Gln Arg Arg Phe Ile Asp Thr Tyr Gln Gln Tyr Thr Asp Ala Val
145                 150                 155                 160

Val Gln Gln Ala Thr Asp Arg Ala Asp Asn His Ile Arg Asp Val Glu
                165                 170                 175

Gly Tyr Phe Thr Val Arg Arg Asp Thr Ile Gly Ala Lys Pro Ser Phe
                180                 185                 190

Thr Leu Leu Glu Phe Thr Met Asp Ile Pro Asp Glu Val Met Gly His
            195                 200                 205

Pro Val Ile Lys Asp Leu Ser Leu Trp Cys Ile Asp Met Leu Ile Ile
            210                 215                 220

Gly Asn Asp Leu Cys Ser Tyr Asn Val Glu Gln Ala His Gly Asp Asp
225                 230                 235                 240

Leu His Asn Leu Val Thr Ile Val Met Asn Gln Tyr Asn Leu Asp Leu
                245                 250                 255

Pro Gly Ala Met Glu Trp Ile Gly Lys Phe His Asp Asp Ile Ala Asp
            260                 265                 270

Lys Phe Leu Asp Thr Phe Ala Lys Leu Pro Ser Trp Gly Pro Glu Ile
        275                 280                 285

Asp Pro Gln Ile Arg Arg Tyr Val Asp Gly Leu Gly Asn Trp Val Arg
        290                 295                 300

Gly Asn Asp Ser Trp Ser Phe Glu Ser Trp Arg Tyr Phe Arg Gly Lys
305                 310                 315                 320

Gly Pro Glu Ile Glu Lys Thr Arg Trp Val Asp Leu Met Pro Thr Glu
                325                 330                 335

Glu Ala Thr Ile Thr Pro Lys Tyr Glu Ser Asp Ser Asn Ala Ala Gln
                340                 345                 350

Pro Ala Gln Ser Thr
            355

<210> SEQ ID NO 96
<211> LENGTH: 351
<212> TYPE: PRT
<213> ORGANISM: Stereum hirsutum

<400> SEQUENCE: 96

Met Thr Val Val Asp Ser Pro Gln Arg Phe Tyr Ile Pro Asn Cys Leu
1               5                   10                  15
```

Glu Tyr Trp Pro Trp Pro Arg His Ile Asn Pro His Tyr Gln Glu Val
            20                  25                  30

Lys Lys Ala Ser Ala Ala Trp Ala Glu Ser Phe Gly Ala Phe Asn Pro
            35                  40                  45

Lys Ala Gln His Ala Tyr Asn Ala Cys Asp Phe Asn Leu Leu Ala Ser
 50                  55                  60

Leu Ala Tyr Pro Leu Glu Ser Glu Arg Leu Arg Thr Gly Cys Asp
 65                  70                  75                  80

Leu Met Asn Met Phe Phe Val Phe Asp Glu Tyr Ser Asp Val Ser Ser
                 85                  90                  95

Pro Lys Asp Val Ile Gln Gln Ala Ile Ile Met Asp Ala Leu Arg
                100                 105                 110

Asn Pro Tyr Ala Pro Arg Pro Asp Asp Glu Trp Val Gly Gly Glu Val
            115                 120                 125

Thr Arg Gln Phe Trp Lys Arg Ala Ile Lys Thr Ala Thr Ala Gly Ala
    130                 135                 140

Gln Arg Arg Phe Ile Asp Ala Phe Glu Ser Tyr Thr Gln Ser Val Val
145                 150                 155                 160

Gln Gln Ala Lys Asp Arg His His Gly Phe Ile Arg Asp Val Asp Ser
                165                 170                 175

Tyr Leu Glu Met Arg Arg Glu Thr Ile Gly Ala Lys Pro Ser Phe Val
                180                 185                 190

Val Leu Gln Met Asp Met Thr Leu Pro Asp Glu Val Leu Ala His Pro
                195                 200                 205

Val Ile Gln Gln Leu Ser Ala Leu Ser Thr Asp Met Ile Cys Leu Gly
            210                 215                 220

Asn Asp Ile Cys Ser Tyr Asn Val Glu Gln Ala Arg Gly Asp Asp Leu
225                 230                 235                 240

His Asn Ile Ile Thr Ile Ala Met Asn Gln Phe Asp Ile Asp Ile Ala
                245                 250                 255

Gly Ala Met Asp Trp Val Val Lys Tyr His Ala Lys Leu Glu Arg Lys
                260                 265                 270

Phe Leu Tyr Leu Tyr Asn Asn Gly Leu Pro Ser Trp Gly Lys Glu Leu
            275                 280                 285

Asp Pro Gln Val Glu Arg Tyr Val Cys Gly Leu Gly Asn Trp Val Arg
    290                 295                 300

Ala Ser Asp Gln Trp Gly Phe Glu Ser Glu Arg Tyr Phe Gly Lys Lys
305                 310                 315                 320

Gly Lys Glu Ile Phe Lys Arg Arg Trp Val Asn Leu Met Gln Pro Glu
                325                 330                 335

Arg Ala Gln Asp Ile Gly Pro Thr Leu Val Asp Gly Thr Arg Leu
            340                 345                 350

<210> SEQ ID NO 97
<211> LENGTH: 345
<212> TYPE: PRT
<213> ORGANISM: Omphalotus olearius

<400> SEQUENCE: 97

Met Pro Glu Thr Phe Tyr Leu Pro Asp Cys Leu Ala Asn Trp Lys Trp
1               5                   10                  15

Lys Arg Ala Leu Asn Pro Asn Tyr Pro Glu Val Lys Ala Ala Ser Ser
            20                  25                  30

Glu Trp Leu Arg Ser Phe Lys Ala Phe Pro Pro Lys Ala Gln Glu Ala

```
            35                  40                  45
Tyr Asp Arg Cys Asp Phe Asn Leu Leu Ala Ser Leu Ala Tyr Pro Leu
 50                  55                  60

Ala Asp Lys Asp Gly Leu Arg Thr Gly Cys Asp Leu Met Asn Met Phe
 65                  70                  75                  80

Phe Val Phe Asp Glu Tyr Ser Asp Val Ala His Glu Ser Glu Val Gln
                     85                  90                  95

Val Gln Ala Asp Ile Ile Met Asp Ala Leu Arg Asn Pro His Lys Pro
            100                 105                 110

Arg Pro Val Gly Glu Trp Val Gly Gly Glu Val Thr Arg Gln Phe Trp
            115                 120                 125

Glu Leu Ala Ile Lys Thr Ala Ser Pro Gln Ser Gln Lys Arg Phe Ile
            130                 135                 140

Glu Thr Phe Asp Thr Tyr Thr Lys Ser Val Val Gln Gln Ala Ala Asp
145                 150                 155                 160

Arg Thr Gln His Tyr Val Arg Thr Val Asp Glu Tyr Leu Glu Val Arg
                    165                 170                 175

Arg Asp Thr Ile Gly Ala Lys Pro Ser Phe Ala Ile Leu Glu Leu Thr
            180                 185                 190

Met Asp Ile Pro Asp Glu Val Ile His His Pro Thr Ile Glu Arg Leu
            195                 200                 205

Ala Ile Leu Ala Ile Asp Met Ile Leu Leu Gly Asn Asp Thr Ala Ser
210                 215                 220

Tyr Asn Tyr Glu Gln Ala Arg Gly Asp Asp Asn His Asn Met Val Thr
225                 230                 235                 240

Ile Val Met His Gln Tyr Lys Thr Asp Ile Gln Gly Ala Leu Ser Trp
                    245                 250                 255

Ile Glu Lys Tyr His Lys Glu Leu Glu Glu Phe Met Gln Leu Tyr
            260                 265                 270

Asn Ser Leu Pro Lys Trp Gly Gly Gln Ile Asp Val Asp Ile Ala Arg
            275                 280                 285

Tyr Val Asp Gly Leu Gly Asn Trp Val Arg Ala Ser Asp Gln Trp Gly
            290                 295                 300

Phe Glu Ser Glu Arg Tyr Phe Gly Thr Lys Ala Pro Glu Ile Gln Lys
305                 310                 315                 320

Thr Arg Trp Val Thr Leu Met Pro Lys Lys Arg Ala Glu Gly Val Gly
                    325                 330                 335

Pro Glu Ile Val Asp Ile Ser Glu Leu
            340                 345

<210> SEQ ID NO 98
<211> LENGTH: 346
<212> TYPE: PRT
<213> ORGANISM: Armillaria gallica

<400> SEQUENCE: 98

Met Ser Gln Arg Ile Phe Leu Pro Asp Thr Leu Ala Asn Trp Gln Trp
 1               5                  10                  15

Pro Arg His Leu Trp Pro His Tyr Ala Glu Val Lys Lys Ala Ser Ala
            20                  25                  30

Ala Trp Ala Lys Ser Phe Arg Ala Phe Gln Thr Lys Ala Gln Glu Ala
            35                  40                  45

Phe Asp Arg Cys Asp Phe Asn Leu Leu Ala Ser Phe Ala Tyr Pro Leu
 50                  55                  60
```

```
Ala Asp Glu Ala Arg Leu Arg Ser Gly Cys Asp Leu Met Asn Leu Phe
 65                  70                  75                  80

Phe Val Ile Asp Glu Tyr Ser Asp Val Ser Thr Glu Glu Val Arg
             85                  90                  95

Ala Gln Lys Asp Ile Val Met Asp Ala Ile Arg Asn Thr Glu Lys Pro
             100                 105                 110

Arg Pro Ala Gly Glu Trp Ile Gly Gly Glu Val Ser Arg Gln Phe Trp
             115                 120                 125

Asp Leu Ala Lys Lys Thr Ala Ser Thr Gln Ala Gln Lys Arg Phe Ile
130                 135                 140

Asp Thr Phe Asp Glu Tyr Leu Glu Ser Val Val Gln Gln Ala Ala Asp
145                 150                 155                 160

Arg Asn Asn Ser His Val Arg Gly Ile Glu Ser Tyr Leu Glu Val Arg
             165                 170                 175

Arg Asn Thr Ile Gly Ala Lys Pro Ser Phe Ala Leu Leu Glu Phe Asp
             180                 185                 190

Met Gln Leu Pro Asp Glu Ser His Gln Ser Ser Gly Tyr Gln Arg Asn
             195                 200                 205

Leu Arg Lys Ser Cys Ile Asp Met Leu Cys Leu Gly Asn Asp Val Val
             210                 215                 220

Ser Tyr Asn Leu Glu Gln Ala Arg Asp Asp Gly His Asn Ile Val
225                 230                 235                 240

Thr Ile Ala Met Asn Glu Leu Arg Thr Asp Val Ala Gly Ala Met Ile
             245                 250                 255

Trp Val Asp Glu Tyr His Lys Gln Leu Glu Ser Arg Phe Met Glu Asn
             260                 265                 270

Phe Lys Lys Val Pro Arg Trp Gly Gly Pro Ile Asp Leu Gln Val Ala
             275                 280                 285

Arg Tyr Cys Asp Gly Leu Gly Asn Trp Val Arg Ala Asn Asp Gln Trp
             290                 295                 300

Ser Phe Glu Ser Glu Arg Tyr Phe Gly Lys Lys Gly Pro Glu Ile Ile
305                 310                 315                 320

Gln Arg Arg Trp Ile Thr Leu Met Pro Lys Met Val Ser Glu Glu Leu
             325                 330                 335

Gly Pro Gln Ile Val Asp Gly Phe His Leu
             340                 345

<210> SEQ ID NO 99
<211> LENGTH: 369
<212> TYPE: PRT
<213> ORGANISM: Stereum hirsutum

<400> SEQUENCE: 99

Met Ala Val Ala Thr Ser Val Ala Thr Pro Val Pro Thr Pro Ala Tyr
 1               5                  10                  15

Ser Ala Gly Arg Ala Pro Ala Lys Glu Lys Lys Ile Tyr Leu Pro Asp
             20                  25                  30

Thr Leu Ala Glu Trp Pro Trp Pro Arg Ala Ile Asn Pro His Tyr Ala
             35                  40                  45

Glu Ala Lys Glu Glu Ser Gln Ala Trp Ala Ala Ser Phe Asn Ala Phe
 50                  55                  60

Ser Pro Lys Ala Gln His Ala Phe Asn Arg Cys Asp Phe Asn Leu Leu
 65                  70                  75                  80

Ala Ser Leu Ala Tyr Pro Leu Ala Thr Lys His Gly Cys Arg Ser Gly
             85                  90                  95
```

-continued

```
Cys Asp Leu Met Asn Leu Phe Phe Val Ile Asp Glu Tyr Ser Asp Ile
                100                 105                 110
Ala Pro Val Glu Glu Val Arg Gln Gln Lys Asp Ile Val Met Asp Ala
            115                 120                 125
Leu Arg Asn Pro His Lys Pro Arg Pro Glu Gly Glu Trp Val Gly Gly
    130                 135                 140
Glu Val Ala Arg Gln Phe Trp Ala Leu Thr Ile Thr Asn Ala Ser Ala
145                 150                 155                 160
Gln Ser Gln Lys His Phe Ile Glu Thr Phe Asp Glu Tyr Leu Asp Ser
                165                 170                 175
Val Val Gln Gln Ala Glu Asp Arg Ser Glu Ser Arg Ile Arg Asp Ile
            180                 185                 190
Gln Ser Tyr Ile Asp Val Arg Arg Asn Thr Ile Gly Ala Lys Pro Ser
    195                 200                 205
Phe Ala Leu Leu Glu Leu Asp Met Asp Leu Pro Asp Glu Val Leu Ala
210                 215                 220
His Pro Thr Ile Gln Ser Leu Ser Leu Ala Thr Ile Asp Met Leu Cys
225                 230                 235                 240
Leu Gly Asn Asp Ile Val Ser Tyr Asn Leu Glu Gln Ala Arg Gly Asp
                245                 250                 255
Ala Ser His Asn Ile Ile Thr Ile Val Met Asn Glu Leu Asn Leu Asp
            260                 265                 270
Val Asn Gly Ala Met Arg Trp Val Gly Asp Phe His Lys Gln Leu Glu
    275                 280                 285
Lys Gln Phe Phe Glu Ala Phe Asn Asn Leu Pro Lys Trp Gly Asn Ala
290                 295                 300
Glu Leu Asp Ala Gln Ile Ala Val Tyr Cys Asp Gly Leu Gly Asn Trp
305                 310                 315                 320
Val Arg Ala Asn Asp Gln Trp Ser Phe Glu Ser Glu Arg Tyr Phe Gly
                325                 330                 335
Ala Arg Gly Leu Glu Ile Met Glu Thr Lys Thr Leu Ala Met Met Pro
            340                 345                 350
Ile Gln Arg Thr Glu Ala Leu Gly Pro Gln Leu Val Ala Asp Ser Ile
    355                 360                 365
Leu

<210> SEQ ID NO 100
<211> LENGTH: 350
<212> TYPE: PRT
<213> ORGANISM: Stereum hirsutum

<400> SEQUENCE: 100

Met Val Arg Ser Pro Val Ser Asp Lys Phe Cys Ile Pro Asp Thr Leu
1               5                   10                  15
Ala Ser Trp Pro Tyr Pro Arg Ile Leu Asn Pro His Tyr Ala Glu Glu
                20                  25                  30
Lys Ala Ala Ser Ala Ala Trp Thr Lys Gly Phe Gly Ala Phe Gly Pro
            35                  40                  45
Lys Ala Gln Asp Ala Phe Asp Arg Cys Asp Phe Asn Leu Leu Ala Cys
    50                  55                  60
Leu Ala Tyr Pro Ile Ala Thr Pro Glu Arg Cys Arg Ser Gly Cys Asp
65                  70                  75                  80
Leu Met Asn Leu Phe Phe Val Ile Asp Glu His Ser Asp Thr His Gly
                85                  90                  95
```

```
Glu Glu Thr Val Arg Lys Met Lys Asp Val Met Asp Ala Ile Arg
            100                 105                 110

Asn Pro His Lys Pro Arg Pro Asn Asp Glu Trp Ile Gly Gly Glu Ile
            115                 120                 125

Ala Arg Gln Phe Trp Glu Arg Ala Met Cys Tyr Ala Ser Glu Ile Ser
            130                 135                 140

Gln Arg Arg Phe Ile Asp Thr Phe Asp Glu Tyr Leu Glu Ser Val Val
145                 150                 155                 160

Asp Gln Ala Ala Asp Arg Asp Ser Ala Arg Ile Arg Asp Ile Glu Ser
                165                 170                 175

Tyr Ile Asn Ile Arg Arg Asn Thr Ile Gly Ala Lys Pro Ser Phe Val
                180                 185                 190

Ile Met Glu Gln Gly Met Asp Ile Pro Asp Asn Val Phe Glu Asn Glu
                195                 200                 205

Val Phe Gln Arg Leu Arg Met Ala Thr Ile Asp Met Leu Cys Leu Gly
            210                 215                 220

Asn Asp Ile Val Ser Tyr Asn Ile Glu Gln Ala Arg Gly Asp Asp Ser
225                 230                 235                 240

His Asn Ile Val Arg Ile Val Met Asn Glu Leu Asp Thr Asp Val Pro
                245                 250                 255

Arg Ala Met Asp Trp Val Ala Gln Arg His Thr Gln Leu Glu Arg Glu
            260                 265                 270

Phe Phe Thr Ala Leu Ser Glu Leu Pro Thr Trp Gly Glu Pro Ile Asp
            275                 280                 285

Gly Trp Val Lys Glu Tyr Val Tyr Gly Leu Gly Asn Trp Val Arg Ala
            290                 295                 300

Asn Asp Gln Trp Ser Phe Glu Ser Gln Arg Tyr Phe Gly Thr Lys Gly
305                 310                 315                 320

Met Glu Ile Met Lys Ser Arg Trp Leu Ser Val Leu Pro Lys Val Arg
                325                 330                 335

Pro Ala Glu Val Gly Pro Gln Leu Val Asp Gln Ser Leu Leu
            340                 345                 350

<210> SEQ ID NO 101
<211> LENGTH: 330
<212> TYPE: PRT
<213> ORGANISM: Coprinopsis cinerea

<400> SEQUENCE: 101

Met Val Gly Ser Tyr Thr Gly Lys Val Ile His Val Pro Ala Leu Leu
1               5                   10                  15

Glu Ser Trp Pro Trp Pro Ala Ala Ile Asn Pro Leu Tyr Glu Gln Val
            20                  25                  30

Gln Glu Glu Ser Thr Ser Trp Phe Arg Lys Phe Asp Leu Tyr Arg Asp
            35                  40                  45

Arg Lys Lys Gln Ala Ile His Asp His Leu Asp Thr Ala Lys Phe Gly
        50                  55                  60

Ala Ser Val Cys Pro Lys Ala Asp Tyr Ala Leu Leu Arg Leu Ala Thr
65                  70                  75                  80

Asp Tyr Leu His Leu Gly Phe Trp Ile Asp Tyr Phe Phe Asp Thr Ser
                85                  90                  95

Pro Ser Asp Val Ile Arg Gln Leu Thr Glu Ser Ile Ala His Leu Leu
            100                 105                 110

Glu Ser Gly Asp Pro Arg Leu Asp Ser Ser Ser Pro Gln Ser His Ile
```

```
            115                 120                 125
Ala Cys Met Glu Ile Leu Arg Asp Phe Arg Lys Arg Ile Glu Thr Phe
130                 135                 140

Asn Pro Ser Gln Glu Asp Leu Arg Arg Phe Val Lys Glu Tyr Arg Gly
145                 150                 155                 160

Phe Leu Glu Ala Glu Leu Thr Gln Ala Ile Asp His Glu Asn Lys Val
                165                 170                 175

Ile Arg Asp Ile Glu Ser Tyr Leu Ser Ile Arg Arg Ser Thr Ile Ala
            180                 185                 190

Ile Arg Pro Gly Ile Ala Leu Leu Gly Leu Ala Leu Gly Ile Pro Gln
            195                 200                 205

Glu Ile Leu Asp Asp Pro Tyr Thr Asp Thr Leu Thr Asn Ala Cys Leu
210                 215                 220

Asp Met Val Ile Ile Gln Asn Asp Ala Tyr Ser Trp Asn Val Glu Gln
225                 230                 235                 240

Val Arg Lys Ala Asp Gly His Asn Ile Ile Thr Val Leu Met Lys Gln
                245                 250                 255

Arg Asp Ile Asp Val Gln Glu Ala Tyr Glu His Ala Ala Gln Leu His
            260                 265                 270

Arg Glu Thr Gln Glu His Phe Leu Glu Leu His Ala Lys Arg Pro Asp
            275                 280                 285

Trp Gly Asn Glu Gly Ser Ile Gln Ala Phe Phe Asp Gly Leu Gly Glu
            290                 295                 300

Phe Val Arg Gly Val Asp Glu Trp Ser Ser Met Cys Leu Gly Glu His
305                 310                 315                 320

Ala Leu Ser Val Gly Ala Gly Phe Leu Lys
                325                 330

<210> SEQ ID NO 102
<211> LENGTH: 372
<212> TYPE: PRT
<213> ORGANISM: Stereum hirsutum

<400> SEQUENCE: 102

Met Glu Ser Val Arg Glu His Ile Pro Arg Leu Gln His Phe Leu Gly
1               5                   10                  15

Glu Ile Gly Tyr Arg His Thr Thr Pro Pro Ala Pro Thr Leu Asp Phe
            20                  25                  30

Leu His Ala His His His Trp Ile His Val Leu Gly Pro Met Thr
            35                  40                  45

Ser Trp Thr Val Ala Lys Leu Asn Ala Leu Glu Asp Ser Ser Thr
50                  55                  60

Ile Phe Glu Arg Ala Tyr Pro Leu Ser Asp Ala Glu Met Lys Phe Val
65                  70                  75                  80

Leu Ala Lys Leu Thr Ala Ile Ala Ile Phe Leu Asp Asp Ser Leu Glu
                85                  90                  95

Asp Glu Glu Thr Tyr Asp Asp Ile Gly Asn Phe Ala His Arg Val Tyr
            100                 105                 110

Leu Gly Glu Ala Gln Pro Thr Gly Val Leu Thr Leu Tyr His Gln Gly
            115                 120                 125

Ile Gln Glu Leu Ser Lys Met His Glu Gly Asp Ala Val Phe Arg Gly
130                 135                 140

Leu Ala Val Ala Pro Trp Ile Thr Phe Ile Asp Ala Cys Met Leu Glu
145                 150                 155                 160
```

```
Lys Arg Leu Leu Thr Phe Asp Ser Lys Leu Arg Val Ser Pro Arg Asp
                165                 170                 175

Leu Gly Tyr Gln Arg Leu Arg Asn Ser Thr Asp Phe Thr Ser Leu Arg
            180                 185                 190

Ala Pro Lys Ala Thr Pro Ser Glu Val Glu Val Ser Phe Pro Ile Phe
        195                 200                 205

Leu Arg His Lys Ser Gly Ile Gly Glu Ala Tyr Ala Ala Ile Phe
    210                 215                 220

Lys Ser Ser Arg Tyr Gln Glu Leu Pro Leu Ser Arg Phe Val Lys Ser
225                 230                 235                 240

Met Pro Asp Met Ile Tyr Tyr Ile Glu Leu Val Asn Asp Leu Met Ser
                245                 250                 255

Phe Tyr Lys Glu Gln Leu Ala Gly Glu Thr Ala Asn Leu Ile His Leu
                260                 265                 270

Gln His Gln Ser Trp Lys Gly Gly Gln Gly Thr Gly Pro Tyr Gly Ser
            275                 280                 285

Trp Thr Leu Leu Asp Thr Phe Ser Arg Leu Cys Asp Glu Thr Arg Asp
290                 295                 300

Ala Ala Phe Arg Val Asp Glu Leu Leu Arg Leu Asp Glu Cys Glu Lys
305                 310                 315                 320

Ile Ala Asn Gly Glu Leu Arg Gly Glu Val Gly Leu Ser Pro Met
                325                 330                 335

Asp Val Thr Met Ala Ala Gln Trp Arg Glu Phe Arg Asp Gly Tyr Val
                340                 345                 350

Ser Trp His Leu Glu Cys Gln Arg Tyr Lys Leu Asp Phe Ile Lys Leu
            355                 360                 365

Ser Thr Phe Glu
    370

<210> SEQ ID NO 103
<211> LENGTH: 325
<212> TYPE: PRT
<213> ORGANISM: Coprinopsis cinerea

<400> SEQUENCE: 103

Met Pro Ala Ala Leu Pro Tyr Asn Val Ser Arg Asp Asn Lys Trp Asp
1               5                   10                  15

Ile Lys Lys Ile Ile Gln Asp Phe Phe Lys Arg Cys Asp Val Pro Tyr
            20                  25                  30

Gln Val Ile Pro Tyr Asp Thr Glu Leu Trp Asn Ala Cys Leu Lys Arg
        35                  40                  45

Ala Lys Glu Lys Gly Tyr Pro Val Glu Pro Asp Ser Pro Met Ser Leu
    50                  55                  60

Tyr Arg Ser Phe Lys Val Gly Val Val Ile Thr Arg Thr Ser Tyr Gly
65                  70                  75                  80

His Ile Gln Asp Tyr Glu Ile Leu Ile Trp Val Ala Thr Phe Thr Ala
                85                  90                  95

Phe Val Thr Tyr Ala Asp Asp Ala Phe Gln Glu Asp Ile Gln His Leu
            100                 105                 110

His Ser Phe Ala Arg Thr Phe Leu Gln Asn Glu Lys His Glu His Pro
        115                 120                 125

Val Leu Glu Ala Phe Ala Gln Phe Leu Arg Glu Ser Ser Ile Arg Phe
    130                 135                 140

Ser His Phe Val Ala Asn Thr Val Val Ser Ser Ala Leu Arg Phe Met
145                 150                 155                 160
```

Met Ser Ile Ala Leu Glu Phe Glu Gly Gln Asn Val Ser Val Ser Thr
            165                 170                 175

Glu Ala Arg Glu Tyr Pro Gly Tyr Ile Arg Ile Leu Ser Gly Leu Ser
            180                 185                 190

Asp Ile Tyr Ala Leu Phe Ala Phe Pro Met Asp Leu Pro Arg Ser Thr
            195                 200                 205

Tyr Ile Gln Ala Phe Pro Glu Gln Ile Asp Tyr Ile Asn Gly Thr Asn
        210                 215                 220

Asp Leu Leu Ser Phe Tyr Lys Glu Glu Leu Asp Cys Glu Thr Val Asn
225                 230                 235                 240

Phe Ile Ser Ala Ala Ala Thr Ser Gln Gln Val Ser Lys Leu Glu Val
            245                 250                 255

Leu Arg Asn Ala Ala Glu Lys Ala Ala Tyr Ser Tyr Asp Val Val
            260                 265                 270

Asn Val Leu Lys Pro Tyr Pro Glu Ala Leu Ala Ala Trp Lys Ser Phe
            275                 280                 285

Ala Arg Gly Phe Cys Tyr Phe His Thr Ser Ser Pro Arg Tyr Arg Leu
            290                 295                 300

Gly Glu Met Phe His Asp Phe Glu His Asp Leu Val Cys Lys Cys Ala
305                 310                 315                 320

Ser Cys Thr Glu Ile
            325

<210> SEQ ID NO 104
<211> LENGTH: 328
<212> TYPE: PRT
<213> ORGANISM: Omphalotus olearius

<400> SEQUENCE: 104

Met Thr Leu Pro Thr Glu Gln Val Glu Leu Ser Val Cys Pro Val Glu
1               5                   10                  15

Ser Ser Thr His Thr Thr Arg Asp Ile Met Arg Asn Phe Leu Ser Gln
            20                  25                  30

Cys Gln Ile Pro Leu Gln Arg Gly Val Pro Leu Asp Pro Thr Phe His
            35                  40                  45

Gln Glu Cys Ala Asn Val Leu Ile Glu Asp Tyr Leu Lys Pro Ser Ala
        50                  55                  60

Ala Val Thr Leu Glu Asn Leu Pro Ser Leu Met Ser Phe Asn Pro
65                  70                  75                  80

Phe Leu Thr Leu Gly Val Arg Met Ala Ser Thr Gly Tyr Ala His Leu
            85                  90                  95

Thr His Thr Pro Thr Arg Val Tyr Val Ala Leu Phe Thr Ala Leu Leu
            100                 105                 110

Val Cys Leu Asp Asp Ile Phe Pro Glu Asn Val Glu Leu Met Cys Gly
            115                 120                 125

Phe Asn Glu Arg Phe Ile Lys Asn Glu Thr Gln Gly Glu Pro Ile Leu
        130                 135                 140

Asp Ala Val Ala Gly Leu Leu Arg Ser Thr Ser Lys Tyr Phe Ser Met
145                 150                 155                 160

Leu Ser Ser Asn Leu Ile Val Thr Ser Ala Leu Asn Tyr Val Thr Ser
            165                 170                 175

Leu Ser Leu Asp Gln Gly Leu His Ser Ile Lys Leu Ala Glu His Ser
            180                 185                 190

Arg Asn Phe Ala Arg Leu Cys Arg Asn Met Ser Gly Ile Pro Glu Ala

```
            195                 200                 205
Phe Ala Ala Phe Val Phe Pro Pro Glu Val Pro Phe Thr Ala Tyr Ile
210                 215                 220
Gln Cys Phe Pro Asp Leu Tyr Thr Tyr Ala Asn Tyr Val Asn Asp Val
225                 230                 235                 240
Leu Ser Phe Tyr Lys Glu Asp Ile Ala Gly Thr Glu Asn Leu Val
                    245                 250                 255
Ser Ile Leu Ala Gln Thr Gln Pro Asn Ser Ser Arg Tyr Gln Val Leu
            260                 265                 270
Gln Gln Leu Ala Asp Glu Ala Ala Ala Asn Ala Asn Ile Arg Asp
            275                 280                 285
Ile Leu Ser Asp Gln Lys Ser Ile Leu Asp Ala Tyr Asp Ala Phe Arg
290                 295                 300
Val Gly Phe Val Gln Phe His Ile Asp Ser Pro Arg Tyr Arg Leu Ala
305                 310                 315                 320
Glu Leu Phe Pro Cys Ile Asp Gly
                    325
```

<210> SEQ ID NO 105
<211> LENGTH: 350
<212> TYPE: PRT
<213> ORGANISM: Omphalotus olearius

<400> SEQUENCE: 105

```
Met Ser Gln Ile Leu His Leu Trp Ser Lys Phe Ser Thr Ser Leu
1               5                   10                  15
Pro Ser Thr Val Thr Ile Gly Ser Asp Pro Gln Thr Leu Gln Leu Val
                20                  25                  30
His Ser Pro Ala Pro Asn Val Asn Ala Asn Ala Leu Glu Ile Tyr Lys
            35                  40                  45
Ile Val Asp Asn Phe Leu Ser Arg Cys Gly Ile Arg Leu Glu Ser Thr
50                  55                  60
Pro Leu Asp Val Glu Phe Tyr Asn Glu Cys Lys Lys Thr Leu Leu Ser
65                  70                  75                  80
His Tyr Ile Gly Ile His Asp Ser Asp Lys Val Ser Glu Ser Trp Phe
                85                  90                  95
Lys Arg Tyr Leu Ser Val Gly Val Ile Ile Thr Thr Asn Ala Tyr Gly
                100                 105                 110
His Leu Asp Asn Lys Leu Thr Lys Ile Tyr Ile Ala Leu Tyr Thr Ala
            115                 120                 125
Leu Ala Thr Cys Phe Asp Asp Val Phe Glu Lys Asn Val Asp His Met
130                 135                 140
Ser Gly Phe Asn Glu Arg Phe Met Lys Ala Leu Pro Gln Gly Asp Val
145                 150                 155                 160
Phe Leu Asp Ala Phe Ala Lys Val Leu Leu Asp Ala Pro Lys Tyr Phe
                165                 170                 175
Gly Arg Leu Ala Ser Asn Ile Ile Val Thr Ser Thr Leu Asp Phe Ile
                180                 185                 190
Thr Ser Met Ser Val Asp Val Leu Thr Lys Gly Met Lys Phe Asn Gln
            195                 200                 205
Asn Leu His Lys Phe Ala Met Ala Cys Arg Asn Met Ser Gly Ile Ala
            210                 215                 220
Tyr Thr Tyr Ala Pro Phe Ile Phe Pro Lys Glu Val Pro Phe Ala Ile
225                 230                 235                 240
```

Tyr Ala Gln Cys Leu Pro Asp Met Arg Ile Tyr Ile Asn His Val Asn
                245                 250                 255

Asp Val Leu Ser Phe Tyr Lys Glu Asp Lys Ala Gly Glu Thr Glu Asn
            260                 265                 270

Leu Ala Ser Ile Leu Gly Gln Val His Pro Ser Met Thr Lys Tyr Gln
        275                 280                 285

Ile Val Gln Gly Leu Ala Asp Ala Ala Glu Ala Asp Leu Arg Val
    290                 295                 300

Arg Thr Val Leu Ser Gln Tyr Gln Pro Ala Leu Asp Ala Tyr Asn Cys
305                 310                 315                 320

Phe Arg Gln Gly Tyr Val Ser Phe His Ala Ser Ser Gly Arg Tyr Arg
                325                 330                 335

Leu Asp Glu Leu Phe Ser Phe Val Glu Pro Glu Pro Ile Val
            340                 345                 350

<210> SEQ ID NO 106
<211> LENGTH: 347
<212> TYPE: PRT
<213> ORGANISM: Omphalotus olearius

<400> SEQUENCE: 106

Met Ser Gln Ile Leu His Leu Leu Trp Ser Lys Phe Ser Thr Ser Leu
1               5                   10                  15

Pro Ser Thr Val Thr Ile Gly Ser Asp Pro Gln Thr Leu Gln Leu Val
            20                  25                  30

His Ser Pro Ala Pro Asn Val Asn Ala Asn Ala Leu Glu Ile Arg Arg
        35                  40                  45

Ile Val Asn Asn Phe Leu Thr Arg Cys Ser Ile Arg Leu Glu Gly Thr
    50                  55                  60

Pro Leu Asp Val Asp Phe Tyr Asn Glu Cys Lys Lys Thr Leu Leu Ser
65                  70                  75                  80

His Tyr Ile Gly Ile His Asp Ser Asp Lys Val Ser Glu Ser Trp Phe
                85                  90                  95

Arg Arg Tyr Leu Ser Val Gly Val Ile Ile Thr Thr Asn Ala Tyr Gly
            100                 105                 110

His Ile Asp Asp Lys Pro Thr Arg Val Tyr Ile Cys Leu Tyr Thr Ala
        115                 120                 125

Leu Leu Thr Ser Phe Asp Asp Val Phe Glu Ala Asn Val Glu Gln Phe
    130                 135                 140

Gly Gly Phe Asn Glu Arg Phe Met Lys Gly Glu Pro Gln Glu Asp Leu
145                 150                 155                 160

Phe Leu Asp Ala Leu Ala Arg Ile Leu Leu Asp Ala Pro Arg Tyr Tyr
                165                 170                 175

Gly Arg Leu Ala Thr Asn Ile Ile Val Thr Ala Thr Leu Asp Phe Phe
            180                 185                 190

Thr Gly Leu Phe Leu Glu Leu Gln Ala Arg Asp Met Thr Phe Asn Glu
        195                 200                 205

Asp Leu His Asn Phe Ala Val Phe Cys Arg Asn Leu Thr Gly Ile Ala
    210                 215                 220

His Ala Tyr Ala Val Phe Met Phe Pro Arg Asp Val Pro Phe Thr Val
225                 230                 235                 240

Tyr Val Arg Ser Leu Pro Glu Leu Lys Thr Asp Ile Asn Tyr Val Asn
                245                 250                 255

Asp Ile Met Ser Phe Tyr Lys Glu Asp Arg Ala Glu Glu Thr Asp Asn
            260                 265                 270

```
Leu Ala Ser Ile Leu Arg Gln Val His Pro Ser Met Thr Lys His Gln
            275                 280                 285

Val Leu Gln Lys Ile Val Asp Asp Ala Val Glu Ala Asp Val Arg Ala
    290                 295                 300

Arg Lys Ile Leu Ala Asp Tyr Gln Pro Ala Leu Asp Ala Tyr Glu His
305                 310                 315                 320

Phe Arg Lys Gly Tyr Ala Met Phe His Val Ser Ser Gly Arg Tyr Arg
                325                 330                 335

Leu Asp Glu Leu Phe Ser Tyr Ile Arg Phe Glu
                340                 345

<210> SEQ ID NO 107
<211> LENGTH: 17
<212> TYPE: PRT
<213> ORGANISM: Hypoxylon sp

<400> SEQUENCE: 107

Met Ala Lys Ala Asn Leu Leu Ile Phe Met His Asp Asp Val Cys Glu
1               5                   10                  15

Tyr

<210> SEQ ID NO 108
<211> LENGTH: 21
<212> TYPE: PRT
<213> ORGANISM: Hypoxylon sp

<400> SEQUENCE: 108

Phe Ser Leu Thr Asn Asp Leu Tyr Ser Phe Asn Lys Glu Val Val Ala
1               5                   10                  15

Glu Gln Glu Thr Gly
            20

<210> SEQ ID NO 109
<211> LENGTH: 16
<212> TYPE: PRT
<213> ORGANISM: Hypoxylon sp

<400> SEQUENCE: 109

Val Trp Asp Asp Glu Val Asp Ala Asn Asp Thr Asp Val Ser Asn Asp
1               5                   10                  15

<210> SEQ ID NO 110
<211> LENGTH: 21
<212> TYPE: PRT
<213> ORGANISM: Hypoxylon sp

<400> SEQUENCE: 110

Cys Phe Ile Leu Asn Asp Val Tyr Ser Val Gln Lys Glu Ile Ala Gln
1               5                   10                  15

Asp Ser Leu Leu Asn
            20

<210> SEQ ID NO 111
<211> LENGTH: 17
<212> TYPE: PRT
<213> ORGANISM: Hypoxylon sp

<400> SEQUENCE: 111

Ala Trp Asp Asp Glu Thr Asp Ser Pro Glu Phe Ser Ala Val Ile Asn
1               5                   10                  15
```

Asp

<210> SEQ ID NO 112
<211> LENGTH: 21
<212> TYPE: PRT
<213> ORGANISM: Hypoxylon sp

<400> SEQUENCE: 112

Ile His Thr Thr Asn Asp Ile Leu Ser Val Lys Lys Glu Val Ala Gln
1               5                   10                  15

Ser Gln Val Asp Ser
            20

<210> SEQ ID NO 113
<211> LENGTH: 10
<212> TYPE: PRT
<213> ORGANISM: Omphalotus olearius

<400> SEQUENCE: 113

His Leu Asp Asn Ile Ser Asp Gly Met Met
1               5                   10

<210> SEQ ID NO 114
<211> LENGTH: 21
<212> TYPE: PRT
<213> ORGANISM: Omphalotus olearius

<400> SEQUENCE: 114

Val Thr Trp Ser Asn Asp Ile Phe Ser Tyr Asn Val Glu Gln Ser Arg
1               5                   10                  15

Gly Asp Thr His Asn
            20

<210> SEQ ID NO 115
<211> LENGTH: 10
<212> TYPE: PRT
<213> ORGANISM: Agrocybe aegerita

<400> SEQUENCE: 115

His Leu Asp Asn Ile Ser Asp Gly Met Met
1               5                   10

<210> SEQ ID NO 116
<211> LENGTH: 21
<212> TYPE: PRT
<213> ORGANISM: Agrocybe aegerita

<400> SEQUENCE: 116

Val Thr Trp Ser Asn Asp Ile Phe Ser Tyr Asn Val Glu Gln Ser Arg
1               5                   10                  15

Gly Asp Thr His Asn
            20

<210> SEQ ID NO 117
<211> LENGTH: 10
<212> TYPE: PRT
<213> ORGANISM: Coprinopsis cinerea

<400> SEQUENCE: 117

His Leu Asp Asn Ile Ser Asp Gly Met Met
1               5                   10

<210> SEQ ID NO 118

```
<211> LENGTH: 21
<212> TYPE: PRT
<213> ORGANISM: Coprinopsis cinerea

<400> SEQUENCE: 118

Val Thr Trp Ser Asn Asp Ile Phe Ser Tyr Asn Val Glu Gln Ser Lys
1               5                   10                  15

Gly Asp Thr His Asn
            20

<210> SEQ ID NO 119
<211> LENGTH: 10
<212> TYPE: PRT
<213> ORGANISM: Agrocybe aegerita

<400> SEQUENCE: 119

His Leu Asp Asn Leu Ser Asp Glu Met Asp
1               5                   10

<210> SEQ ID NO 120
<211> LENGTH: 21
<212> TYPE: PRT
<213> ORGANISM: Agrocybe aegerita

<400> SEQUENCE: 120

Val Thr Trp Ser Asn Asp Ile Phe Ser Tyr Ser Val Glu Gln Ser Lys
1               5                   10                  15

Gly His Thr His Asn
            20

<210> SEQ ID NO 121
<211> LENGTH: 10
<212> TYPE: PRT
<213> ORGANISM: Coprinopsis cinerea

<400> SEQUENCE: 121

His Ile Asp Asn Leu Ser Asp Asp Met Asp
1               5                   10

<210> SEQ ID NO 122
<211> LENGTH: 21
<212> TYPE: PRT
<213> ORGANISM: Coprinopsis cinerea

<400> SEQUENCE: 122

Val Thr Trp Ser Asn Asp Ile Phe Ser Phe Asn Val Glu Gln Ser Lys
1               5                   10                  15

Gly Asp Thr His Asn
            20

<210> SEQ ID NO 123
<211> LENGTH: 10
<212> TYPE: PRT
<213> ORGANISM: Omphalotus olearius

<400> SEQUENCE: 123

Tyr Leu Asp Asn Leu Thr Asp Asp Met Asp
1               5                   10

<210> SEQ ID NO 124
<211> LENGTH: 21
<212> TYPE: PRT
<213> ORGANISM: Omphalotus olearius
```

```
<400> SEQUENCE: 124

Val Ser Phe Ala Asn Asp Ile Tyr Ser Phe Asn Ile Glu Gln Ser Lys
1               5                   10                  15

Gly Asp Thr His Asn
            20

<210> SEQ ID NO 125
<211> LENGTH: 10
<212> TYPE: PRT
<213> ORGANISM: Omphalotus olearius

<400> SEQUENCE: 125

His Leu Asp Asn Leu Ser Asp Asp Met Asp
1               5                   10

<210> SEQ ID NO 126
<211> LENGTH: 21
<212> TYPE: PRT
<213> ORGANISM: Omphalotus olearius

<400> SEQUENCE: 126

Val Thr Trp Ser Asn Asp Ile Phe Ser Tyr Asn Val Glu Gln Ala Lys
1               5                   10                  15

Gly Asp Thr His Asn
            20

<210> SEQ ID NO 127
<211> LENGTH: 10
<212> TYPE: PRT
<213> ORGANISM: Coprinopsis cinerea

<400> SEQUENCE: 127

Asn Ala Asp Asp Trp Leu Asp Asp Phe Asp
1               5                   10

<210> SEQ ID NO 128
<211> LENGTH: 21
<212> TYPE: PRT
<213> ORGANISM: Coprinopsis cinerea

<400> SEQUENCE: 128

Ile Ala Trp Ser Asn Asp Ile Phe Ser Phe Asn Arg Glu Gln Ser Arg
1               5                   10                  15

His Asp Ser Phe Asn
            20

<210> SEQ ID NO 129
<211> LENGTH: 10
<212> TYPE: PRT
<213> ORGANISM: Agrocybe aegerita

<400> SEQUENCE: 129

Phe Phe Asp Glu Val Thr Asp Thr Glu Thr
1               5                   10

<210> SEQ ID NO 130
<211> LENGTH: 21
<212> TYPE: PRT
<213> ORGANISM: Agrocybe aegerita

<400> SEQUENCE: 130

Ile Phe Leu Ala Asn Asp Leu Tyr Ser Tyr Asn Met Glu Gln Ala Lys
1               5                   10                  15
```

-continued

Gly His Asn Gly Ala
            20

<210> SEQ ID NO 131
<211> LENGTH: 10
<212> TYPE: PRT
<213> ORGANISM: Agrocybe aegerita

<400> SEQUENCE: 131

Leu Tyr Asp Glu Tyr Thr Asp Thr Gly Ser
1               5                   10

<210> SEQ ID NO 132
<211> LENGTH: 21
<212> TYPE: PRT
<213> ORGANISM: Agrocybe aegerita

<400> SEQUENCE: 132

Val Phe Trp Ala Asn Asp Leu Val Ser Tyr Asn Met Glu Gln Ser Lys
1               5                   10                  15

Gly His Ser Gly Ala
            20

<210> SEQ ID NO 133
<211> LENGTH: 10
<212> TYPE: PRT
<213> ORGANISM: Agrocybe aegerita

<400> SEQUENCE: 133

Val Val Asp Glu Val Ser Asp Glu Gln Ser
1               5                   10

<210> SEQ ID NO 134
<211> LENGTH: 21
<212> TYPE: PRT
<213> ORGANISM: Agrocybe aegerita

<400> SEQUENCE: 134

Val Cys Trp Ala Asn Asp Val Tyr Ser Tyr Asp Met Glu Gln Ser Lys
1               5                   10                  15

Gly Leu Ser Asn Asn
            20

<210> SEQ ID NO 135
<211> LENGTH: 10
<212> TYPE: PRT
<213> ORGANISM: Coprinopsis cinerea

<400> SEQUENCE: 135

Val Val Asp Glu Ile Ser Asp Asp Gln Asn
1               5                   10

<210> SEQ ID NO 136
<211> LENGTH: 21
<212> TYPE: PRT
<213> ORGANISM: Coprinopsis cinerea

<400> SEQUENCE: 136

Val Cys Trp Ala Asn Asp Val Tyr Ser Tyr Asp Met Glu Gln Ala Lys
1               5                   10                  15

Gly His Thr Gly Asn
            20

<210> SEQ ID NO 137
<211> LENGTH: 10
<212> TYPE: PRT
<213> ORGANISM: Stereum hirsutum

<400> SEQUENCE: 137

Val Ile Asp Glu Ile Ser Asp Asp Gln Ser
1               5                   10

<210> SEQ ID NO 138
<211> LENGTH: 21
<212> TYPE: PRT
<213> ORGANISM: Stereum hirsutum

<400> SEQUENCE: 138

Val Cys Trp Ala Asn Asp Val Tyr Ser Tyr Asn Val Glu Gln Ala Lys
1               5                   10                  15

Gly His Ser Gly Asn
            20

<210> SEQ ID NO 139
<211> LENGTH: 10
<212> TYPE: PRT
<213> ORGANISM: Omphalotus olearius

<400> SEQUENCE: 139

Val Leu Asp Glu Val Ser Asp Glu Gln Ser
1               5                   10

<210> SEQ ID NO 140
<211> LENGTH: 21
<212> TYPE: PRT
<213> ORGANISM: Omphalotus olearius

<400> SEQUENCE: 140

Val Cys Trp Ala Asn Asp Val Tyr Ser Tyr Asn Lys Glu Gln Ala Gln
1               5                   10                  15

Gly His Gly Gly Asn
            20

<210> SEQ ID NO 141
<211> LENGTH: 10
<212> TYPE: PRT
<213> ORGANISM: Omphalotus olearius

<400> SEQUENCE: 141

Val Leu Asp Glu Leu Ser Asp Asp Gln Asn
1               5                   10

<210> SEQ ID NO 142
<211> LENGTH: 21
<212> TYPE: PRT
<213> ORGANISM: Omphalotus olearius

<400> SEQUENCE: 142

Val Cys Trp Ser Asn Asp Val Tyr Ser Tyr Asn Val Glu Gln Ala Lys
1               5                   10                  15

Gly His Gly Gly Ser
            20

<210> SEQ ID NO 143
<211> LENGTH: 10
<212> TYPE: PRT

-continued

<213> ORGANISM: Omphalotus olearius

<400> SEQUENCE: 143

Val Phe Asp Glu Val Ser Asp Asp Gln Asn
1               5                   10

<210> SEQ ID NO 144
<211> LENGTH: 21
<212> TYPE: PRT
<213> ORGANISM: Omphalotus olearius

<400> SEQUENCE: 144

Val Cys Trp Ser Asn Asp Val Tyr Ser Tyr Asn Val Glu Gln Ala Lys
1               5                   10                  15

Gly His Arg Gly Ser
            20

<210> SEQ ID NO 145
<211> LENGTH: 10
<212> TYPE: PRT
<213> ORGANISM: Agrocybe aegerita

<400> SEQUENCE: 145

Val Tyr Asp Glu Tyr Thr Asp Val Ser Asp
1               5                   10

<210> SEQ ID NO 146
<211> LENGTH: 21
<212> TYPE: PRT
<213> ORGANISM: Agrocybe aegerita

<400> SEQUENCE: 146

Ile Ile Leu Val Asn Asp Met His Ser Tyr Val Arg Glu Leu Ser Cys
1               5                   10                  15

Gly His Glu Asn His
            20

<210> SEQ ID NO 147
<211> LENGTH: 10
<212> TYPE: PRT
<213> ORGANISM: Agrocybe aegerita

<400> SEQUENCE: 147

Val Tyr Asp Glu Tyr Thr Asp Val Val Ser
1               5                   10

<210> SEQ ID NO 148
<211> LENGTH: 10
<212> TYPE: PRT
<213> ORGANISM: Agrocybe aegerita

<400> SEQUENCE: 148

Thr Arg Val Ser Ser Gly Gln Ala Asn His
1               5                   10

<210> SEQ ID NO 149
<211> LENGTH: 10
<212> TYPE: PRT
<213> ORGANISM: Agrocybe aegerita

<400> SEQUENCE: 149

Val Phe Asp Glu Tyr Thr Asp Ile Ala Asp
1               5                   10

```
<210> SEQ ID NO 150
<211> LENGTH: 21
<212> TYPE: PRT
<213> ORGANISM: Agrocybe aegerita

<400> SEQUENCE: 150

Ile Ala Ile Gly Asn Asp Ile Asp Ser Tyr Ala Met Glu Lys Ala Arg
1               5                   10                  15

Gly Leu Glu Leu His
            20

<210> SEQ ID NO 151
<211> LENGTH: 10
<212> TYPE: PRT
<213> ORGANISM: Agrocybe aegerita

<400> SEQUENCE: 151

Val Phe Asp Glu Cys Ala Asp Ile Ala Asp
1               5                   10

<210> SEQ ID NO 152
<211> LENGTH: 12
<212> TYPE: PRT
<213> ORGANISM: Agrocybe aegerita

<400> SEQUENCE: 152

Asp Ile Asn Ser Tyr Pro Met Lys Val Arg Gly Leu
1               5                   10

<210> SEQ ID NO 153
<211> LENGTH: 10
<212> TYPE: PRT
<213> ORGANISM: Agrocybe aegerita

<400> SEQUENCE: 153

Val Phe Asp Glu Trp Ser Asp Val Ser Asp
1               5                   10

<210> SEQ ID NO 154
<211> LENGTH: 21
<212> TYPE: PRT
<213> ORGANISM: Agrocybe aegerita

<400> SEQUENCE: 154

Leu Cys Ile Gly Asn Asp Leu Cys Ser Tyr Asn Val Glu Gln Ser Arg
1               5                   10                  15

Gly Asp Asp Gly His
            20

<210> SEQ ID NO 155
<211> LENGTH: 10
<212> TYPE: PRT
<213> ORGANISM: Agrocybe aegerita

<400> SEQUENCE: 155

Val Val Asp Glu His Thr Asp Ala Met Asp
1               5                   10

<210> SEQ ID NO 156
<211> LENGTH: 21
<212> TYPE: PRT
<213> ORGANISM: Agrocybe aegerita

<400> SEQUENCE: 156
```

```
Leu Ile Leu Gly Asn Asp Leu Cys Ser Tyr Asn Val Glu Gln Ser Arg
1               5                   10                  15

Gly Asp Asp Gly His
            20

<210> SEQ ID NO 157
<211> LENGTH: 10
<212> TYPE: PRT
<213> ORGANISM: Omphalotus olearius

<400> SEQUENCE: 157

Ile Phe Asp Glu Tyr Ser Asp Val Ala Asp
1               5                   10

<210> SEQ ID NO 158
<211> LENGTH: 21
<212> TYPE: PRT
<213> ORGANISM: Omphalotus olearius

<400> SEQUENCE: 158

Leu Ile Ile Gly Asn Asp Leu Cys Ser Tyr Asn Val Glu Gln Ala His
1               5                   10                  15

Gly Asp Asp Leu His
            20

<210> SEQ ID NO 159
<211> LENGTH: 10
<212> TYPE: PRT
<213> ORGANISM: Stereum hirsutum

<400> SEQUENCE: 159

Val Phe Asp Glu Tyr Ser Asp Val Ser Ser
1               5                   10

<210> SEQ ID NO 160
<211> LENGTH: 21
<212> TYPE: PRT
<213> ORGANISM: Stereum hirsutum

<400> SEQUENCE: 160

Ile Cys Leu Gly Asn Asp Ile Cys Ser Tyr Asn Val Glu Gln Ala Arg
1               5                   10                  15

Gly Asp Asp Leu His
            20

<210> SEQ ID NO 161
<211> LENGTH: 10
<212> TYPE: PRT
<213> ORGANISM: Omphalotus olearius

<400> SEQUENCE: 161

Val Phe Asp Glu Tyr Ser Asp Val Ala His
1               5                   10

<210> SEQ ID NO 162
<211> LENGTH: 21
<212> TYPE: PRT
<213> ORGANISM: Omphalotus olearius

<400> SEQUENCE: 162

Ile Leu Leu Gly Asn Asp Thr Ala Ser Tyr Asn Tyr Glu Gln Ala Arg
1               5                   10                  15
```

Gly Asp Asp Asn His
            20

<210> SEQ ID NO 163
<211> LENGTH: 10
<212> TYPE: PRT
<213> ORGANISM: Armillaria gallica

<400> SEQUENCE: 163

Val Ile Asp Glu Tyr Ser Asp Val Ser Thr
1               5                   10

<210> SEQ ID NO 164
<211> LENGTH: 21
<212> TYPE: PRT
<213> ORGANISM: Armillaria gallica

<400> SEQUENCE: 164

Leu Cys Leu Gly Asn Asp Val Val Ser Tyr Asn Leu Glu Gln Ala Arg
1               5                   10                  15

Asp Asp Asp Gly His
            20

<210> SEQ ID NO 165
<211> LENGTH: 10
<212> TYPE: PRT
<213> ORGANISM: Stereum hirsutum

<400> SEQUENCE: 165

Val Ile Asp Glu Tyr Ser Asp Ile Ala Pro
1               5                   10

<210> SEQ ID NO 166
<211> LENGTH: 21
<212> TYPE: PRT
<213> ORGANISM: Stereum hirsutum

<400> SEQUENCE: 166

Leu Cys Leu Gly Asn Asp Ile Val Ser Tyr Asn Leu Glu Gln Ala Arg
1               5                   10                  15

Gly Asp Ala Ser His
            20

<210> SEQ ID NO 167
<211> LENGTH: 10
<212> TYPE: PRT
<213> ORGANISM: Stereum hirsutum

<400> SEQUENCE: 167

Val Ile Asp Glu His Ser Asp Thr His Gly
1               5                   10

<210> SEQ ID NO 168
<211> LENGTH: 21
<212> TYPE: PRT
<213> ORGANISM: Stereum hirsutum

<400> SEQUENCE: 168

Leu Cys Leu Gly Asn Asp Ile Val Ser Tyr Asn Ile Glu Gln Ala Arg
1               5                   10                  15

Gly Asp Asp Ser His
            20

-continued

```
<210> SEQ ID NO 169
<211> LENGTH: 10
<212> TYPE: PRT
<213> ORGANISM: Coprinopsis cinerea

<400> SEQUENCE: 169

Trp Ile Asp Tyr Phe Phe Asp Thr Ser Pro
1               5                   10

<210> SEQ ID NO 170
<211> LENGTH: 21
<212> TYPE: PRT
<213> ORGANISM: Coprinopsis cinerea

<400> SEQUENCE: 170

Val Ile Ile Gln Asn Asp Ala Tyr Ser Trp Asn Val Glu Gln Val Arg
1               5                   10                  15

Lys Ala Asp Gly His
            20

<210> SEQ ID NO 171
<211> LENGTH: 10
<212> TYPE: PRT
<213> ORGANISM: Stereum hirsutum

<400> SEQUENCE: 171

Leu Asp Asp Ser Leu Glu Asp Glu Glu Thr
1               5                   10

<210> SEQ ID NO 172
<211> LENGTH: 21
<212> TYPE: PRT
<213> ORGANISM: Stereum hirsutum

<400> SEQUENCE: 172

Ile Glu Leu Val Asn Asp Leu Met Ser Phe Tyr Lys Glu Gln Leu Ala
1               5                   10                  15

Gly Glu Thr Ala Asn
            20

<210> SEQ ID NO 173
<211> LENGTH: 10
<212> TYPE: PRT
<213> ORGANISM: Coprinopsis cinerea

<400> SEQUENCE: 173

Ala Phe Val Thr Tyr Ala Asp Asp Ala Phe
1               5                   10

<210> SEQ ID NO 174
<211> LENGTH: 21
<212> TYPE: PRT
<213> ORGANISM: Coprinopsis cinerea

<400> SEQUENCE: 174

Ile Asn Gly Thr Asn Asp Leu Leu Ser Phe Tyr Lys Glu Glu Leu Asp
1               5                   10                  15

Cys Glu Thr Val Asn
            20

<210> SEQ ID NO 175
<211> LENGTH: 10
<212> TYPE: PRT
<213> ORGANISM: Omphalotus olearius
```

<400> SEQUENCE: 175

Ala Leu Leu Val Cys Leu Asp Asp Ile Phe
1               5                   10

<210> SEQ ID NO 176
<211> LENGTH: 21
<212> TYPE: PRT
<213> ORGANISM: Omphalotus olearius

<400> SEQUENCE: 176

Ala Asn Tyr Val Asn Asp Val Leu Ser Phe Tyr Lys Glu Asp Ile Ala
1               5                   10                  15

Gly Glu Thr Glu Asn
            20

<210> SEQ ID NO 177
<211> LENGTH: 10
<212> TYPE: PRT
<213> ORGANISM: Omphalotus olearius

<400> SEQUENCE: 177

Ala Leu Ala Thr Cys Phe Asp Asp Val Phe
1               5                   10

<210> SEQ ID NO 178
<211> LENGTH: 21
<212> TYPE: PRT
<213> ORGANISM: Omphalotus olearius

<400> SEQUENCE: 178

Ile Asn His Val Asn Asp Val Leu Ser Phe Tyr Lys Glu Asp Lys Ala
1               5                   10                  15

Gly Glu Thr Glu Asn
            20

<210> SEQ ID NO 179
<211> LENGTH: 10
<212> TYPE: PRT
<213> ORGANISM: Omphalotus olearius

<400> SEQUENCE: 179

Ala Leu Leu Thr Ser Phe Asp Asp Val Phe
1               5                   10

<210> SEQ ID NO 180
<211> LENGTH: 21
<212> TYPE: PRT
<213> ORGANISM: Omphalotus olearius

<400> SEQUENCE: 180

Ile Asn Tyr Val Asn Asp Ile Met Ser Phe Tyr Lys Glu Asp Arg Ala
1               5                   10                  15

Glu Glu Thr Asp Asn
            20

METHODS FOR TERPENOID PRODUCTION

CROSS-REFERENCE TO RELATED APPLICATIONS

This application claims the benefit of priority of Singapore application No. 10201807514P, filed 31 Aug. 2018, the contents of it being hereby incorporated by reference in its entirety for all purposes.

FIELD OF THE INVENTION

The invention is in the field of biotechnology. In particular, the invention relates to methods for the discovery of fungal terpene synthases and the use of fungal terpene synthases for the production of terpenoids.

INCORPORATION BY REFERENCE OF MATERIAL SUBMITTED ELECTRONICALLY

The Sequence Listing, which is a part of the present disclosure, is submitted concurrently with the specification as a text file. The name of the text file containing the Sequence Listing is "56461_Seqlisting.txt", which was created on Feb. 26, 2021 and is 296,381 bytes in size. The subject matter of the Sequence Listing is incorporated herein in its entirety by reference.

BACKGROUND OF THE INVENTION

Terpenoids constitute one of the most structurally diverse classes of natural products with wide applications as pharmaceuticals (such as Taxol and artemisinin), as food coloring (such as carotenoids), flavors and fragrances (such as nootkatone and sclareol) and biofuels (such as farnesene). The terpenoid diversity is attributed primarily to terpene synthases (TPSs), which convert acyclic prenyl diphosphate precursors into a multitude of cyclic and acyclic terpene scaffolds. Specifically, the terpene skeletal diversity arises from two main features of TPSs: a large number of TPSs with vastly different functions and the ability of many TPSs to catalyze multiple terpene products from a single substrate. Almost half of the characterized monoterpene and sesquiterpene synthases produce significant amounts of additional products, apart from their main products.

Structurally, all sesquiterpene synthases (STSs) from plants, fungi and bacteria have a conserved metal binding motif (unlike plant STSs are DDXXD, fungal STSs are DE(N)XXD) and NSE triad. However, outside of the motif, there is limited sequence similarity between plant and microbial TPSs. Many plant TPSs have been discovered and studied over the past few decades, however, the study of fungal terpene synthases was lagging behind. Currently, only a handful of fungal TPS have been cloned and functionally characterized (less than 50, Table 1).

Fungi have enormous diversity (~5 million species) and outnumber plants by at least 10 times. Each fungus has an average of 10-20 putative TPS homologs in Basidiomycota, indicating that fungal terpenoids and TPS genes represent rich but largely untapped natural resources. In addition to the discovery of novel TPS genes and terpenoids, it is also valuable to identify other potentially more efficient TPSs than existing TPSs with the same functions or products. This is due to the various applications of terpenoids and huge commercial interests in terpenoids. In some cases, the production of terpenoids was limited by insufficient activity of terpene synthases. Identification of TPS enzymes with novel products, superior activity and selectivity would greatly benefit the industrial biotechnology society for terpenoid production.

SUMMARY

In one aspect, there is provided a bacterial strain comprising one or more vectors encoding
a) one or more enzymes to produce one or more terpene precursors; and
b) a fungal terpene synthase (FTPS).

In another aspect, there is provided a genetically modified 1-deoxyxylulose-5-phosphate synthase (DXS) enzyme, wherein the genetic modification is a mutation at one or more amino acid positions.

In another aspect, there is provided a genetically modified fungal terpene synthase (FTPS), wherein the genetic modification is a mutation at one or more amino acid positions.

In another aspect, there is provided a method of producing a terpenoid comprising a) culturing the bacterial strain as described herein in an expression medium, and b) isolating the terpenoid from said expression medium.

In another aspect, there is provided a method of producing a terpenoid comprising a) culturing a bacterial strain comprising a vector encoding the genetically modified FTPS as described herein in an expression medium and b) isolating the terpenoid from said expression medium.

In another aspect, there is provided a fungal terpene synthase (FTPS) encoded by a polynucleotide comprising a nucleic acid sequence selected from the group consisting of SEQ ID NO: 35, SEQ ID NO: 36, SEQ ID NO: 37, SEQ ID NO: 38 and SEQ ID NO:39.

In another aspect, there is provided an isolated nucleic acid molecule comprising a nucleic acid sequence selected from the group consisting of SEQ ID NO: 35, SEQ ID NO: 36, SEQ ID NO: 37, SEQ ID NO: 38 and SEQ ID NO:39.

DEFINITIONS

As used herein, the term "terpene" refers to a class of organic compounds produced by plants, bacteria, fungi and insects. The building blocks of terpenes have a five-carbon isoprene unit.

As used herein, the term "terpenoid" refers to a large and diverse class of organic compounds derived from terpenes and include terpenes. The building blocks of terpenes have a five-carbon isoprene unit and contain additional functional groups, typically oxygen-containing functional groups. Terpenes are a subset of terpenoids.

As used herein, the term "terpene precursor" refers to a substrate that is converted to a terpene or terpenoid by a terpene synthase. The substrate may be converted to a terpene or a terpenoid.

As used herein, the term "terpene synthase" (TPS) refers to an enzyme that converts terpene precursors to terpenes and/or terpenoids. The term "fungal terpene synthase" (FTPS) refers to a terpene synthase that is isolated from a fungus.

As used herein, the term "UP" in the context of a fungal terpene synthase (FTPS) refers to a domain of the FTPS. The UP domain is situated upstream of the DW domain.

As used herein, the term "DW" in the context of a FTPS refers to a domain of the FTPS. The DW domain is situated downstream of the UP domain.

BRIEF DESCRIPTION OF THE DRAWINGS

The invention will be better understood with reference to the detailed description when considered in conjunction with the non-limiting examples and the accompanying drawings, in which:

FIG. 5 shows the mass spectra of terpene compounds analyzed in this study.

FIG. 15 shows the similarity analysis of AAE3_12839 (SEQ ID NO: 34) and TPS31 (SEQ ID NO: 75) from *Solanum lycopersicum* (Tomato). The fungal viridiflorene synthase (AAE3_12839) shares little identity and similarity with plant viridiflorene synthase.

FIG. 16 shows the similarity analysis of AAE3_13291 (SEQ ID NO: 32) and MqTPS1 (SEQ ID NO: 76) from *Melaleuca quinquenervia*. The fungal viridiflorol synthase (AAE3_12839) shares little identity and similarity with plant viridiflorol synthase.

FIG. 22 shows the Sequencing alignment of validated LNSs and the LS. Sequencing alignment indicated similar positions of these TPSs are 107/34=31%. Based on the alignment, a key amino acid F204 was identified that could impact the activity of the LS (Agrped1_689675).

FIG. 25 shows the metal binding motif of the characterized TPSs in this study and in literature.

FIG. 26 shows crystal structures of homologue models for Agrped1_689675 and Agrped1_689675, where the substrate-binding pockets are highlighted. The model was generated using the Swiss Model homology-modeling server and alignment mode with 5nx6 and 5nx5 as templates. Protein models were visualized and aligned with their template structure using PyMol.

DETAILED DESCRIPTION OF THE PRESENT INVENTION

Figure 1:
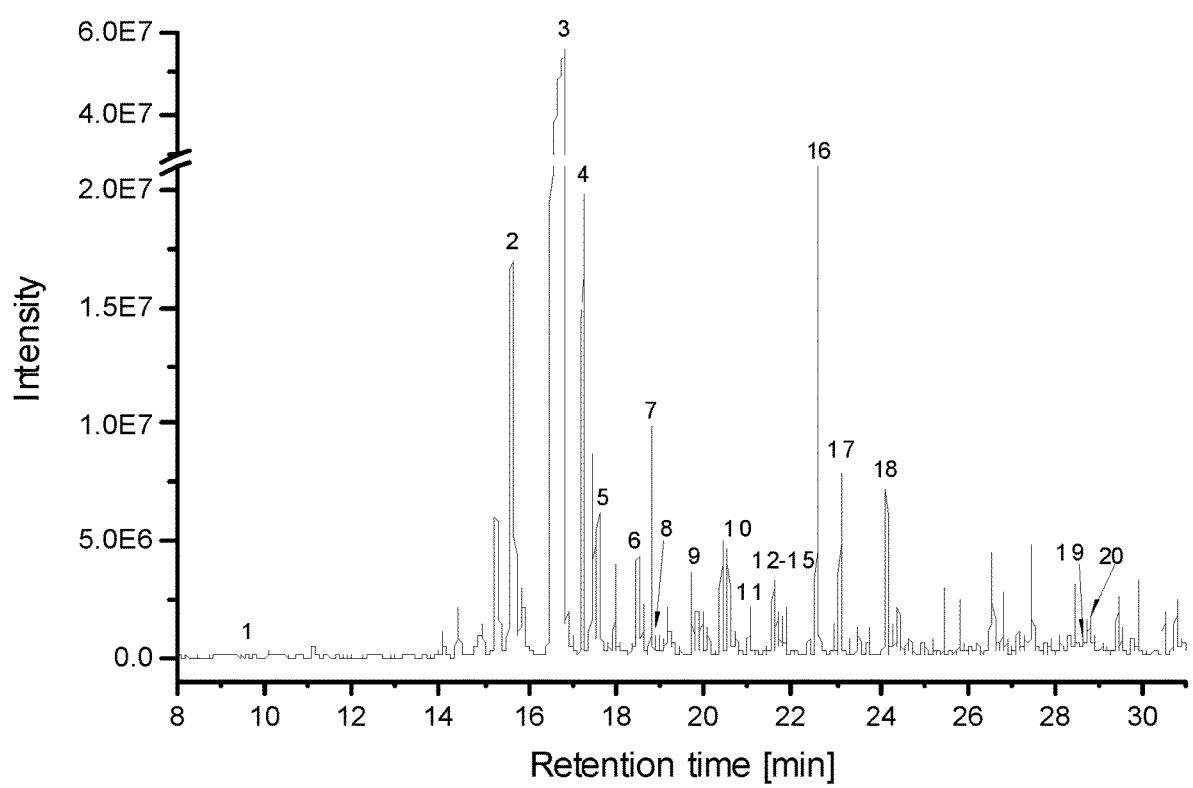
FIG. 1 shows the volatile terpenoids produced by *A. aegerita*. Volatile metabolites from *A. aegerita* culture were sampled by solid phase microextraction (SPME) and analyzed by GC-MS. The structure and mass spectra of identified terpene compounds are shown in FIGS. 4 and 5, respectively.
Figure 1:
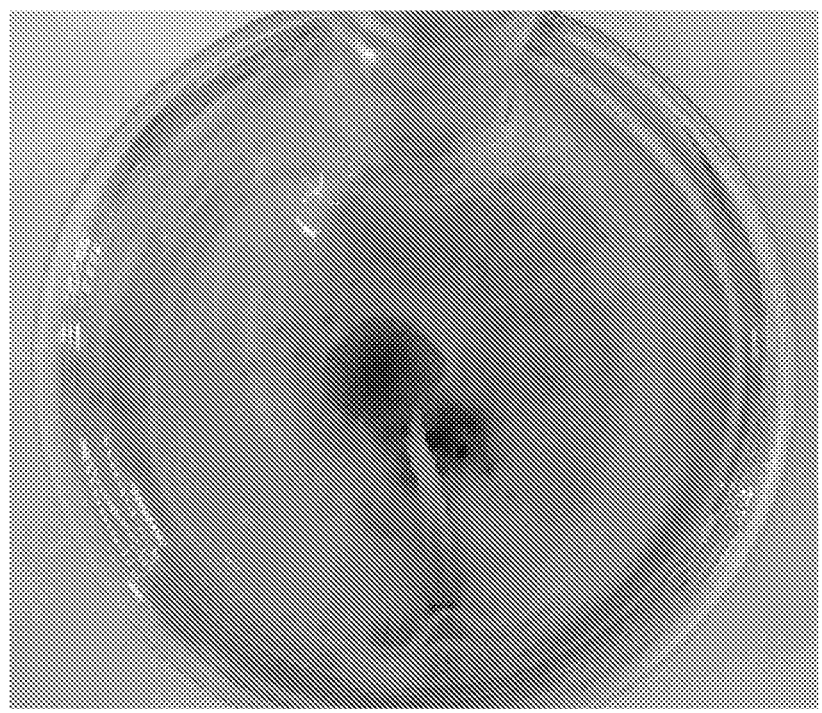

In a first aspect, the present invention refers to a bacterial strain comprising one or more vectors encoding a) one or more enzymes to produce one or more terpene precursors, and b) a fungal terpene synthase (FTPS).

It will be appreciated by a person skilled in the art that the one or more vectors comprise polynucleotide sequences that encode the one or more enzymes to produce one or more terpene precursors and FTPS.

The polynucleotides encoding the one or more enzymes to produce one or more terpene precursors and the FTPS may be located on separate vectors, on a single vector or combinations thereof. In one embodiment, the polynucleotides encoding the one or more enzymes to produce one or more terpene precursors are in a single vector and the polynucleotide encoding the FTPS is in a separate vector.

In one embodiment, the one or more vectors comprise one or more nucleotide sequences encoding the one or more enzymes and the FTPS, operably linked to a promoter.

In some embodiments, the promoter is a constitutive promoter or an inducible promoter. In a preferred embodiment, the promoter is an inducible promoter. Examples of inducible promoters include but are not limited to T7 RNA polymerase promoter, araBAD promoter, a lac promoter, a trp promoter and a Tac promoter (ptac) or the variants of these promoters.

In a preferred embodiment, the inducible promoter is T7 RNA polymerase promoter.

In one embodiment, the one or more enzymes to produce the one or more terpene precursors are part of the 1-deoxy-D-xylulose 5-phosphate (DXP) pathway. It will be appreciated by a person of skill in the art that the DXP pathway is also referred to as the non-mevalonate pathway, the mevalonate-independent pathway or the 2-C-methyl-D-erythritol 4-phosphate/1-deoxy-D-xylulose 5-phosphate (MEP/DOXP) pathway. The DXP pathway converts pyruvate and glyceraldehyde-3-phosphate to terpene precursors and the enzymes in this pathway include DOXP synthase (DXS), DXP reductoisomerase (DXR), 2-C-methyl-D-erythritol 4-phosphate cytidylyltransferase (IspD), 4-diphosphocytidyl-2-C-methyl-D-erythritol kinase (IspE), 2-C-methyl-D-erythritol 2,4-cyclodiphosphate synthase (IspF), HMB-PP synthase (ispG), HMB-PP reductase (IspH) and isopentenyl diphosphate isomerase (IDI).

In a preferred embodiment, the enzyme is 1-deoxyxylulose-5-phosphate synthase (DXS), isopentenyl diphosphate isomerase (IDI) or both.

In one embodiment, the DXS comprises the amino acid sequence set forth in SEQ ID NO: 6.

In some embodiments, the DXS may be genetically modified. The genetic modification may be a mutation at one or more amino acid positions of the amino acid sequence encoding the DXS. In some examples, the mutation is an amino acid substitution, insertion, deletion or combinations thereof.

In some embodiments, the genetically modified DXS has a higher solubility than an unmodified or wild-type DXS.

In some embodiments, the mutation is selected from the group consisting of H105T, E210D, Q459L, L415T and a combination thereof of SEQ ID NO: 6.

In a preferred embodiment, the mutation is H105T.

In another preferred embodiment, the mutation is E210D, Q459L and L415T.

In one embodiment, the genetically modified DXS comprises the amino acid sequence set forth in SEQ ID NO: 24 or 25.

In one embodiment, the DXS comprises an amino acid sequence having at least 50%, at least 60%, at least 70%, at least 80%, at least 90%, at least 95%, at least 96%, at least 97%, at least 98%, at least 99% or 100% identity to an amino acid sequence set forth in SEQ ID NO: 6, SEQ ID NO: 24 or 25.

In one embodiment, the one or more enzymes to produce the one or more terpene precursors is expressed at an elevated level compared to a wild type enzyme. The one or more enzymes may be genetically modified.

In some embodiments, the terpene precursors described herein is farnesyl pyrophosphate (FPP), geranyl pyrophosphate (GPP), geranylgeranyl pyrophosphate (GGPP), or combinations thereof.

In a preferred embodiment, the terpene precursors are FPP and/or GPP.

The bacterial strain described herein comprises one more vectors encoding a fungal terpene synthase (FTPS). In a preferred embodiment, the FTPS is a monoterpene synthase or a sesquiterpene synthase. In a further preferred embodiment, the FTPS is a linalool synthase, a nerolidol synthase or a linalool and nerolidol synthase (LNS).

In some embodiments, the FTPS is isolated from *Agrocybe aegerita, Agrocybe pediades, Galerina marginata, Hypholoma sublateritium, Dendrothele bispora, Moniliophthora roreri, Piloderma croceum, Sphaerobolus stellatus, Coprinopsis cinerea, Omphalotus olearius, Fomitopsis pinicola, Stereum hirsutum, Fusarium graminearum, Fusarium fujikuroi, Fusarium sporotrichioides, Aspergillus terreus, Penicillium roqueforti, Hypoxylon sp., Armillaria gallica, Botrytis cinerea, Daldinia eschscholzii* or combinations thereof.

In one embodiment, the FTPS is isolated from *Agrocybe aegerita, Agrocybe pediades, Galerina marginata, Hypholoma sublateritium, Hebeloma cylindrosporum* or combinations thereof.

In a preferred embodiment, the FTPS is isolated from *Agrocybe aegerita* or *Agrocybe pediades*.

In some embodiments, the FTPS comprises an amino acid sequence selected from the group consisting of SEQ ID NO: 1, SEQ ID NO: 2, SEQ ID NO: 3, SEQ ID NO: 4, SEQ ID NO: 5, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33 and SEQ ID NO: 34.

In some embodiments, the FTPS comprises a nucleic acid sequence selected from the group consisting of SEQ ID NO: 35, SEQ ID NO: 36, SEQ ID NO: 37, SEQ ID NO: 38, SEQ ID NO: 39.

In one example, the bacterial strain described herein contains an FTPS that is expressed at a higher level than a wild-type FTPS.

In some embodiments, the FTPS may be genetically modified. The genetic modification may be an amino acid substitution, insertion, deletion, C-terminal truncation, N-terminal truncation or combinations thereof. The mutation may be one or more mutations in the UP domain of the FTPS, one or more mutations in the DW domain of the FTPS, or both. The UP and DW domains would be understood by the skilled person to vary based on the fungal strain. In one example, the UP domain of the FTPS isolated from Agrped1_689675 (SEQ ID NO: 3) is characterized by amino acid positions 1-170. In another embodiment, the UP domain of the FTPS isolated from Agrped1_689671 (SEQ ID NO: 2) is characterized by amino acid positions 1-169. In yet another embodiment, the DW domain for the FTPS isolated from Agrped1_689675 (SEQ ID NO: 3) is characterized by amino acid positions 171-325. In yet another embodiment, the DW domain of the FTPS isolated from Agrped1_689671 (SEQ ID NO: 2) is characterized by amino acid positions 170-324.

In a preferred embodiment, the mutation is F204D, F204G, F204R, F204I, F204L, F204V or combinations thereof of SEQ ID NO: 3.

In some embodiments, the genetically modified FTPS comprises an amino acid sequence selected from the group consisting of SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO: 16 SEQ ID NO:17, SEQ ID NO: 18, SEQ ID NO: 19, SEQ ID NO: 20, SEQ ID NO: 21, SEQ ID NO: 22 and SEQ ID NO: 23.

In some embodiments, the FTPS comprises an amino acid sequence having at least 80%, at least 90%, at least 95%, at least 96%, at least 97%, at least 98%, at least 99% or 100% identity to amino acid sequences set forth in SEQ ID NO: 1, SEQ ID NO: 2, SEQ ID NO:3, SEQ ID NO:4, SEQ ID NO:5, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO: 16, SEQ ID NO:17, SEQ ID NO: 18, SEQ ID NO: 19, SEQ ID NO: 20, SEQ ID NO: 21, SEQ ID NO: 22, SEQ ID NO: 23, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33 and SEQ ID NO: 34.

In some embodiments, the bacterial strain is modified or genetically modified.

In one embodiment, the bacterial strain described herein is *Escherichia coli*.

In one aspect, the present invention refers to a genetically modified 1-deoxyxylulose-5-phosphate synthase (DXS) enzyme, wherein the genetic modification is a mutation at one or more amino acid positions. In one embodiment, the mutation described herein is an amino acid substitution or insertion or deletion. In yet another embodiment, the mutation is selected from the group consisting of H105T, E210D, Q459L, L415T and a combination thereof of SEQ ID NO: 6.

In a preferred embodiment, the mutation is E210D, Q459L and L415T.

In another preferred embodiment, the mutation is H105T.

In another aspect, the present invention refers to a genetically modified DXS enzyme comprising an amino acid sequence as set forth in SEQ ID NO: 24 or SEQ ID NO: 25.

In yet another aspect, the present invention refers to a genetically modified DXS enzyme comprising an amino acid sequence having at least 50%, at least 60%, at least 70%, at least 80%, at least 90%, at least 95%, at least 96%, at least 97%, at least 98%, at least 99% or 100% identity to an amino acid sequence set forth in SEQ ID NO: 24 or SEQ ID NO: 25.

In one aspect, the present invention refers to a genetically modified fungal terpene synthase (FTPS), wherein the genetic modification is a mutation at one or more amino acid positions.

The genetically modified FTPS is modified relative to a wild type or unmodified FTPS. In one embodiment, the unmodified FTPS is isolated from *Agrocybe aegerita, Agrocybe pediades, Galerina marginata, Hypholoma sublateritium, Hebeloma cylindrosporum* or combinations thereof.

In a preferred embodiment, the unmodified FTPS is isolated from *Agrocybe aegerita* or *Agrocybe pediades*.

In some embodiments, the mutation described herein is an amino acid substitution, insertion, deletion, C-terminal truncation, N-terminal truncation or combinations thereof. The mutation may be one or more mutations in the UP domain of the FTPS, one or more mutations in the DW domain of the FTPS, or both. The UP and DW domains would be understood by the skilled person to vary based on the fungal strain. In one example, the UP domain of the FTPS isolated from Agrped1_689675 (SEQ ID NO: 3) is characterized by amino acid positions 1-170. In another embodiment, the UP domain of the FTPS isolated from Agrped1_689671 (SEQ ID NO: 2) is characterized by amino acid positions 1-169. In yet another embodiment, the DW domain for the FTPS isolated from Agrped1_689675 (SEQ ID NO: 3) is characterized by amino acid positions 171-325. In yet another embodiment, the DW domain of the FTPS isolated from Agrped1_689671 (SEQ ID NO: 2) is characterized by amino acid positions 170-324.

In a preferred embodiment, the mutation is selected from the group consisting of F204D, F204G, F204R, F204I, F204L and F204V of SEQ ID NO: 3.

In some embodiments, the genetically modified FTPS described herein is a linalool synthase, nerolidol synthase or both.

In one embodiment, the present invention refers to a genetically modified FTPS comprising an amino acid sequence having at least 50%, at least 60%, at least 70%, at least 80%, at least 90%, at least 95%, at least 96%, at least 97%, at least 98%, at least 99% or 100% identity to an amino acid sequence selected from the group consisting of: SEQ ID NO: 7, SEQ ID NO: 8, SEQ ID NO: 9, SEQ ID NO: 10, SEQ ID NO: 11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22 and SEQ ID NO:23.

In one aspect, the present invention refers to a method of producing a terpenoid comprising a) culturing the bacterial strain as described herein in an expression medium and b) isolating the terpenoid from said expression medium.

Culturing the bacterial strain in the expression medium will allow the expression of the one or more enzymes to produce one or more terpene precursors and expression of the FTPS.

In another aspect, the present invention refers to a method of producing a terpenoid comprising a) culturing a bacterial strain comprising a vector encoding the genetically modified FTPS as described herein in an expression medium and b) isolating the terpenoid from said expression medium.

The expression medium may be any culture medium that supports growth of the bacterial strain. The expression medium may comprise inducers capable of inducing the inducible promoter in the one or more vectors. The expression medium may also be an auto-inducing medium. In one example, the auto-inducing medium is ZYM5052. In other examples, the auto-inducing medium is lysogeny broth (LB), Terrific Broth (TB) or 2xPY.

The expression medium may be further supplemented with spherical C18 resin or Ni-nitrilotriacetic acid resin.

In one embodiment, the method described herein further comprises the step of isolating the FTPS from the bacterial cell and mixing the isolated FTPS with one or more terpene precursors to produce the terpenoid. The isolated FTPS may be mixed with the one or more terpene precursors in the same cell culture vessel or in a different vessel from the original culture. The FTPS may be isolated using a variety of methods. In some embodiment, the FTPS is isolated the bacterial cell by Ni-nitrilotriacetic acid resin, column based methods or both.

In another embodiment, the isolated FTPS described herein is further purified prior to mixing with one or more terpene precursors.

In yet another embodiment, the isolated FTPS is further mixed with one or more additional enzymes prior to mixing with one or more terpene precursors.

In one embodiment, the one or more additional enzymes described herein is Acetyl-CoA acetyltransferase, Hydroxymethylglutaryl-CoA synthase (HMGS), Hydroxymethylglutaryl-CoA synthase reductase (HMGR), IDI, melonate kinase (MK), Phosphomevalonate kinase (PMK) or mevalonate diphosphate decarboxylase (MVD1). In some embodiments, the Acetyl-CoA acetyltransferase is PhaA or atoB. [SF: any others?]

In one embodiment, terpenes or terpenoids may be produced using the FTPS of the present invention as follows: 1. Using crude cell lysate, the bacterial cells expressing only FTPS are harvested and lysed by freeze/thaw method and/or sonication method. The lysed cell supernatant containing soluble FTPS is mixed with substrates (GPP or FPP), 2.5 mM $MgCl_2$ and 50 mM Tris/HCl buffer (pH 6.5-8.5) to produce terpenoids at 30-37° C. In another example, the FTPS will be purified from the bacterial cells by Ni-nitrilotriacetic acid resin and/or column-based method. The purified FTPS is mixed with substrates (GPP or FPP), 2.5 mM $MgCl_2$ and 50 mM Tris/HCl buffer (pH 6.5-8.5) to produce terpenoids at 30-37° C. In addition, the FTPS may be coupled into a multienzyme reaction, for example at pH 7.5 and at 30° C., by mixing the FTPS with other enzymes such as IDI, MK, PMK or mevalonate pyrophosphate decarboxylase (PMD) to convert mevalonate into terpenoids.

In one embodiment, the product of the method described herein is a monoterpenoid, sesquiterpenoid or a mixture of both. In some embodiments, the monoterpenoid is selected from the group consisting of β-myrcene, linalool, geranyl acetate and combinations thereof.

In some embodiments, the sesquiterpenoid is selected from the group consisting of Δ6-protoilludene, α-muurolene, γ-muurolene, β-cadinene, β-copaene, δ-cadinene, δ-cadinene, epizonarene, α-cubebene, cubebol, epicubenol, nerolidol, viridiflorol, viridiflorene, α-cadinol, α-epi-cadinol, β-selinene, α-selinene, T-muurolol, β-elemene, β-gurjunene, germacrene A, germacrene D and combinations thereof.

In a preferred embodiment, the product is Δ6-protoilludene, linalool, geranyl acetate or combinations thereof.

The present invention also discloses the use of the FTPS described herein to produce one or more terpenoids.

In some embodiments, the one or more terpenoids is selected from the group consisting of β-myrcene, linalool, geranyl acetate, Δ6-protoilludene, α-muurolene, γ-muurolene, β-cadinene, β-copaene, δ-cadinene, γ-cadinene, epizonarene, α-cubebene, cubebol, epicubenol, nerolidol, viridiflorol, viridiflorene, α-cadinol, α-epi-cadinol, β-selinene, α-selinene, T-muurolol, β-elemene, β-gurjunene, germacrene A, germacrene D, trans-β-ocimene, β-cubebene, α-isocomene, longifolene, cadina-3,5-diene, caryophyllene, α-humulene, cubenene, calamenene, cubenol, δ-cadinol, cadina-1(6), 4-diene and combinations thereof.

In another embodiment, the one or more terpenoids described herein is produced in vitro or in vivo. In some embodiments, the one or more terpenoids is produced in vivo in a bacterial cell, a yeast cell, a plant cell, an animal cell or a fungal cell. In one example, the bacterial cell is an *E.coli* cell. In another example, the yeast cell is a *Saccharomyces cerevisiae* or a *Yarrowia lipolitica* cell.

In another embodiment, the one or more terpenoids described herein is produced in vitro.

In some embodiments, the FTPS described herein is isolated from a bacterial cell, a yeast cell, a plant cell, an animal cell or a fungal cell, and mixed with one or more terpene precursors to produce the one or more terpenoids.

In another embodiment, the isolated FTPS is further mixed with one or more additional enzymes prior to mixing with one or more terpene precursors. In one example, the one or more additional enzymes is IDI, MK, PMK or PMD.

The present invention also discloses a vector comprising a polynucleotide sequence encoding a 1-deoxyxylulose-5-phosphate synthase (DXS) enzyme comprising an amino acid sequence set forth in SEQ ID NO: 6, or a genetically modified 1-deoxyxylulose-5-phosphate synthase (DXS) enzyme as described herein.

In another example, the present invention refers to a vector comprising a polynucleotide sequence encoding a fungal terpene synthase (FTPS) comprising an amino acid sequence selected from the group consisting of SEQ ID NO: 1, SEQ ID NO: 2, SEQ ID NO:3, SEQ ID NO:4 and SEQ ID NO:5, or a genetically modified fungal terpene synthase (FTPS) as described herein.

The polynucleotide sequences generated from amino acid sequences may be optimized for improved expression in a host cell or an expression vector. The DNA sequences may be generated from amino acid sequences to have optimised Codon Adaptation Index (>0.6) and GC percentage (40-60%). Codon usage frequency table may be based on a strain of bacterial cell, for example, on *Escherichia coli* K-12 MG1655 strain. In most cases, a guided random method based on a Monte Carlo algorithm may be used. However, manual adjustments may be introduced to remove certain regions with complex secondary structures or repeated sequences. It will generally be understood that various codon optimization methods may be employed to improve expression of a protein or polypeptide in a host cell or expression vector.

In one aspect, the present invention refers to an FTPS encoded by a polynucleotide comprising a nucleic acid sequence selected from the group consisting of SEQ ID NO: 35, SEQ ID NO: 36, SEQ ID NO: 37, SEQ ID NO: 38 and SEQ ID NO: 39.

In another aspect, the present invention refers to an isolated nucleic acid molecule comprising a nucleic acid sequence selected from the group consisting of SEQ ID NO: 35, SEQ ID NO: 36, SEQ ID NO: 37, SEQ ID NO: 38 and SEQ ID NO:39.

In some embodiments, the nucleic acid sequence has at least 50%, at least 60%, at least 70%, at least 80%, at least 90%, at least 95%, at least 96%, at least 97%, at least 98% or, at least 99% or 100% identity to the nucleic acid sequence selected from the group consisting of SEQ ID NO: 35, SEQ ID NO: 36, SEQ ID NO: 37, SEQ ID NO: 38 and SEQ ID NO: 39.

The bacterial strain as disclosed herein may be used to characterize a FTPS. In another embodiment, the FTPS may be characterized by a product produced by the FTPS, the activity of the FTPS, or both.

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

EXPERIMENTAL SECTION

Non-limiting examples of the invention and comparative examples will be further described in greater detail by reference to specific Examples, which should not be construed as in any way limiting the scope of the invention.

The fungal TPSs that have been cloned and functionally characterized are shown in Table 1.

TABLE 1

Published functionally characterized fungal terpene synthases.

| | Accession or JGI Protein ID | Abbreviation | Organisms | Main product | Minor products | Reference |
|---|---|---|---|---|---|---|
| 1 | EAU89322 | Cop1 | Coprinopsis cinerea | germacrene A | | (Agger et al., 2009) |
| 2 | EAU85264 | Cop2 | Coprinopsis cinerea | germacrene A | | (Agger et al., 2009) |
| 3 | EAU88892 | Cop3 | Coprinopsis cinerea | α-muurolene | β-elemene, γ-muurolene, germacrene D and δ-cadinene | (Agger et al., 2009) |
| 4 | EAU85540 | Cop4 | Coprinopsis cinerea | δ-cadinene | β-cubebene, sativene, β-copaene, cubebol | (Agger et al., 2009) |
| 5 | EAU89298 | Cop6 | Coprinopsis cinerea | α-cuprenene | | (Agger et al., 2009) |
| 6 | / | Omp1 | Omphalotus olearius | α-muurolene | | (Wawrzyn et al., 2012) |
| 7 | / | Omp3 | Omphalotus olearius | α-muurolene | β-elemene and selina-4,7-diene | (Wawrzyn et al., 2012) |
| 8 | / | Omp4 | Omphalotus olearius | δ-cadinene | 16 different sesquiterpenes | (Wawrzyn et al., 2012) |

TABLE 1-continued

Published functionally characterized fungal terpene synthases.

| | Accession or JGI Protein ID | Abbreviation | Organisms | Main product | Minor products | Reference |
|---|---|---|---|---|---|---|
| 9 | / | Omp5 | Omphalotus olearius | γ-cadinene | epi-zonarene | (Wawrzyn et al., 2012) |
| 10 | / | Omp6 | Omphalotus olearius | Δ6-protoilludene | | (Wawrzyn et al., 2012) |
| 11 | / | Omp7 | Omphalotus olearius | Δ6-protoilludene | | (Wawrzyn et al., 2012) |
| 12 | / | Omp9 | Omphalotus olearius | α-barbatene | β-barbatene | (Wawrzyn et al., 2012) |
| 13 | / | Omp10 | Omphalotus olearius | trans-dauca-4(11),8-diene | daucene | (Wawrzyn et al., 2012) |
| 14 | / | Fompil_84944 | Fomitopsis pinicola | α-cuprenene | | (Wawrzyn et al., 2012) |
| 15 | / | Stehi_64702 | Stereum hirsutum | Δ6-protoilludene | | (Quin et al., 2013) |
| 16 | / | Stehi_73029 | Stereum hirsutum | Δ6-protoilludene | | (Quin et al., 2013) |
| 17 | / | Stehi_25180 | Stereum hirsutum | Δ6-protoilludene | | (Quin et al., 2013) |
| 18 | / | Stehi_128 017 | Stereum hirsutum | δ-cadinene | β-copaene, sativene, γ-muurolene, α-muurolene etc | (Quin et al., 2013) |
| 19 | / | Stehi_159379 | Stereum hirsutum | β-barbatene | α-barbatene and β-barbatene | (Quin et al., 2013) |
| 20 | ACY69978 | CLM1 FgLS | Fusarium graminearum | longiborneol | | (McCormick et al., 2010) |
| 21 | CCP20071.1 | Ffsc6 | Fusarium fujikuroi | (−)-α-acorenol | | (Brock et al., 2013) |
| 22 | CCP20072.1 | Ffsc4 | Fusarium fujikuroi | koraiol | | (Brock et al., 2013) |
| 23 | AAD13657 | FsTDS | Fusarium sporotrichioides | trichodiene | | (Rynkiewicz et al., 2001) |
| 24 | AAF13264 | AtARS | Aspergillus terreus | aristolochene | | (Cane and Kang, 2000) |
| 25 | AAA33694 | PrARS | Penicillium roqueforti | aristolochene | | (Hohn and Plattner, 1989) |
| 26 | KJ433269 | Hyp1 | Hypoxylon sp. | trans-nerolidol | | (Shaw et al., 2015) |
| 27 | KJ433270 | Hyp2 | Hypoxylon sp. | δ-cadinene | 21 other peaks | (Shaw et al., 2015) |
| 28 | KJ433271 | Hyp3 | Hypoxylon sp. | 1,8-cineole (C10) | D-limonene (C10) | (Shaw et al., 2015) |
| 29 | KJ433272 | Hyp4 | Hypoxylon sp. | D-limonene (C10) | 12 other peaks | (Shaw et al., 2015) |
| 30 | KJ433273 | Hyp5 | Hypoxylon sp. | β-ocimene (C10) | sabinene (C10), α-bulnesene and unknown peaks | (Shaw et al., 2015) |
| 31 | / | Pro1 | Armillaria gallica | Δ-protoilludene | | (Engels et al., 2011) |
| 32 | CCT65043 | STC3 | Fusarium fujikuroi | (+)-eremophilene | | (Burkhardt et al., 2016) |
| 33 | CCT75704 | STC5 | Fusarium fujikuroi | (−)-guaia-6,10(14)-diene | | (Burkhardt et al., 2016) |
| 34 | AAQ16575 | BcBOT2 or BcPSPS | Botrytis cinerea | presilphiperfolan-8β-ol | | (Moraga et al., 2016) |
| 35 | JGI ID: 17536 | EC12-PGS | Daldinia eschscholzii EC12 | Guaiene | Pinene (C10) | (Wu et al., 2016) |
| 36 | JGI ID: 315006 | EC12-GS | Daldinia eschscholzii EC12 | Gurnunene | | (Wu et al., 2016) |
| 37 | JGI ID: 24646 | EC12-SS | Daldinia eschscholzii EC12 | Selinene | | (Wu et al., 2016) |
| 38 | JGI ID: 70183 | EC12-ILS | Daldinia eschscholzii EC12 | IsoLedene | | (Wu et al., 2016) |
| 39 | JGI ID: 6706 | CI4A-CS | Hypoxylon sp. CI4A | Caryophyllene | | (Wu et al., 2016) |
| 40 | JGI ID: 322581 | CI4A-CPS | Hypoxylon sp. CI4A | Chamigrene | Pinene (C10) | (Wu et al., 2016) |

TABLE 1-continued

Published functionally characterized fungal terpene synthases.

| | Accession or JGI Protein ID | Abbreviation | Organisms | Main product | Minor products | Reference |
|---|---|---|---|---|---|---|
| 41 | JGI ID: 397991 | CO27-CS | Hypoxylon sp. CO27 | Caryophyllene | | (Wu et al., 2016) |
| 42 | JGI ID: 392541 | CO27-CPS | Hypoxylon sp. CO27 | Chamigrene | Pinene (C10) | (Wu et al., 2016) |
| 43 | JGI ID: 373976 | EC38-CS | Hypoxylon sp. EC38 | Caryophyllene | | (Wu et al., 2016) |
| 44 | JGI ID: 328361 | EC38-CPS | Hypoxylon sp. EC38 | Chamigrene | Pinene (C10) | (Wu et al., 2016) |

Cultivation of *Agrocybe aegerita* and Analysis of its Fruiting Bodies

*Agrocybe aegerita* wildtype-strain AAE-3 was grown at 24° C. in the dark in modified crystallizing dishes (FIG. 1; lower dish: 70 mm in diameter, upper dish: 80 mm in diameter; glass pipe attached to the upper dish: outer diameter 16 mm, inner diameter 14 mm) with 16 mL 1.5% MEA (containing 15 g malt extract and 15 g agar per liter) and sealed with Parafilm. The ten days after the inoculation, the mycelium covered the complete agar surface. The Parafilm was removed and the samples were transferred to a climate chamber (24° C., 95% rH, 12/12 h day/night rhythm) and cultured on glass plates for further 16 days. Volatile organic compounds were collected by solid phase microextraction (SPME) using a divinylbenzene-carboxen-polydimethylsiloxane (50/30 µm DVB/CAR/PDMS) fiber. Beginning with day 10 after inoculation, volatiles were absorbed directly in the crystallizing dishes for 14 h (7/7 h day/night). This extraction was carried out every second day. For GC-MS analysis an Agilent Technologies 7890A gas chromatograph (Agilent Technologies, Waldbronn, Germany) equipped with a VF WAXms column (Agilent Technologies; 30 m×0.25 mm, 0.25 µm) and connected to an Agilent 5975C MSD Triple Axis mass spectrometer (MS) was used. Helium was used as gas carrier, with a flow rate of 1.2 ml×min$^{-1}$. Mass spectra were acquired in the mass range of 33 300 m/z. Ionisation was performed by electron impact at 70 eV with an ion source temperature set at 230° C. The SPME fiber was inserted into the injector of the gas chromatograph for thermal desorption in splitless mode for 1 min, with the injector temperature held at 250° C. The GC oven temperature was programmed to ramp from 40° C. (held for 3 min) to 240° C. (held for 7 min) at 5° C.×min$^{-1}$. Volatile compounds were identified by comparing mass spectra with data from the NIST14 database and matching determined retention indices with published ones. Furthermore, Cubeb oil and a humulene were used as standards.

Gas Chromatography-Mass Spectrometry Analysis of Terpenoids

Volatile compounds in the headspace were sampled at room temperature for 15 min by SPME with a DVB/CAR/PDMS (50/30 µm divinylbenzene/carboxen/polydimethylsiloxane) fiber (length 1 cm; Supelco, Steinheim, Germany). Compounds were desorbed in the split/splitless inlet (250° C. or 150° C.; SPME liner, 0.75 mm i.d.; Supelco) of an Agilent 7980B gas chromatography equipped with an Agilent 7200 accurate-mass quadrupole time-of-flight (GC/MS-TOF; Agilent Technologies, Singapore) for 1 min. In addition, for liquid culture analysis, dodecane (20% v/v) was used to extract the terpenoid produced in *E. coli* cultures. The obtained dodecane was diluted at 1:100 in hexane for GC-MS analysis. The GC/MS-TOF was equipped either with a VF-WAXms column (Agilent Technologies; 30 m×0.25 mm i.d., 0.25 µm film thickness) or a DB-5 ms column (Agilent Technologies; 30 m×0.25 mm i.d., 0.25 µm film thickness), and the system was operated on the following conditions: (1) VF-WAXms, compounds were detected in split mode at split ratio of 10:1, the GC oven temperature was programmed to ramp from 80° C. (held for 2 min) to 240° C. (held for 5 min) at 10° C.×min$^{-1}$; (2) DB-5 ms, compounds were detected in split mode at split ratio of 10:1, the GC oven temperature was programmed to ramp from 50° C. (held for 2 min) to 160° C. at 10° C.×min$^{-1}$, to 230° C. at 8° C.×min$^{-1}$ and finally to 320° C. (held for 3 min). Mass spectra were acquired in the mass range of 33 300 m/z at the acquisition rate of 2 spectra/s. Ionization was performed by electron impact at 70 eV with an ion source temperature set at 230° C.

Structural Identification of Terpenoids

Mass spectra obtained by electron ionization mode were used for initial compound identification by comparing them with the spectra of terpenoids in the National Institute of Standards and Technology (NIST) database and published terpene spectra. Furthermore, Kovats retention indices of compounds produced were identified by calibrating with GC-MS with a C8-C30 alkane mix and were compared to the published retention indices in literature or in the NIST database. Major terpene products were verified, whenever possible, by comparison of retention time and mass spectra with authentic standards or essential oils with known terpene compositions. Niaouli essential oil [viridiflorene 6 (10.1% w/w), viridiflorol 7 (18.1% w/w)], Cedrela woods oil [α-muurolene 5 (1% w/w), δ-cadinene 4 (11.7% w/w)], Cubeb oil [germacrene D (1% w/w), γ-muurolene 2 (4.2% w/w), β-cubebene (4.4% w/w), cubebol (15.2% w/w)], Amyris wood oil [β-elemene (germacrene A) (0.1% w/w), δ-cadinenol, 0.2%]. In addition, the structure of Δ6-protoiludene was further confirmed by nuclear magnetic resonance spectroscopy.

Functional Annotation for Terpene Synthases and its Gene Clusters in the *Agrocybe aegerita* Genome All the predicted amino acid sequences of protein-coding genes present in the genome of the dikaryotic strain *A. aegerita* AAE-3 have been searched for homologues to already characterized sesquiterpene synthases of *Coprinopsis cinerea, Omphalotus olearius* and *Stereum hirsutum* by blastp using Geneious® (version 9.1.8, Biomatters Ltd., Auckland, New Zealand). The predicted TPSs genes were then manually annotated. In addition, antiSMASH analysis was performed using the BiosynML plugin for Geneious® to predict terpene gene clusters in the *A. aegerita* genome.

Cloning and Expression of Terpene Synthase Genes in *E. coli*

Candidate fungal TPS genes were synthesized by Integrated DNA technologies and codon-optimized for expression in *E. coli*. The genes were cloned into pET11a vector for expression under the control of the T7 promoter. The resulting plasmid was transformed into BL 21 strains carrying the plasmid p15A-cam-T7-dxs-idi which was redesigned from the plasmid pACM-T7-dxs-T7-idi-T7-ADS-ispA. Furthermore, the dxs in the plasmid was mutated to SL3 or SL5 (FIG. 2) to improve the solubility and activity. Single colony of the transformed *E. coli* cells was inoculated into 4 ml ZYM5052 auto-inducing medium (1% tryptone, 0.5% yeast extract, 25 mM Na2HPO4, 25 mM KH2PO4, 50 mM NH4Cl, 5 mM Na2SO4, 2 mM MgSO4, 0.5% glycerol, 0.05% glucose, 0.2% α-lactose) (Studier, 2005) with ampicillin (100 mg/L) and chloramphenicol (33 mg/L). After 14 h of cultivation at 28° C. and 250 rpm on a shaking incubator, the culture fluid was transferred into a 20 mL headspace screw top vials (Merck) and the headspace was sampled at 50° C. for 15 min by SPME.

Homology Searches and Phylogenetic Tree Construction

The 11 *A. aegerita* TPSs were used to search other fungal TPSs in Basidiomycota and Ascomycota genomes sequenced and published by the Joint Genome Institute under the Fungal Genomics Program (http://genome.jgi-psf.org/programs/fungi/index.jsf) and in the UniProt database by Basic Local Alignment Search Tool program (http://www.uniprot.org/blast/). In addition, the previously published 392 basidiomycota TPSs were incorporated. The combined TPS candidates were manually inspected for duplicate sequences, erroneous protein predictions, such as incomplete sequences that deviated from the expected protein length (200-800 aa, except for two putative TPSs, Disac1_349444 and EXIGL_831178) or lacking the conserved metal-binding DxxxD and NSE/DTE triad, or with predicted additional domains (such as geranylgeranyl pyrophosphate synthase functions). Upon identification of putative TPS amino acid sequences, their alignments were performed using Clustal Omega and phylogenetic analyses were conducted with the Neighbor-Joining method using Clustal Omega or MEGA version 7.0.26.

Analysis of TPS Homologues by Sequence Similarity Networks

The curated fungal TPSs were analyzed by Enzyme Function Initiative-Enzyme Similarity Tool (EFI-EST) web tool (http://efi.igb.illinois.edu/efi-est/) to generate sequence similarity networks (SSNs). The resulting SSNs were visualized using the open source software Cytoscape (http://www.cytoscape.org/). Inspection of the resulting SSNs is essential to obtain isofunctional clusters. Based on the SSNs generated by EFI-EST and sequentially varying a series of database-independent alignment score, a group of putative isofunctional groups (PIGs) were obtained. The data of PIGs and traditional phylogenetic trees were compared to select the putative isofunctional TPSs. Here, the three novel TPSs (viridiflorol synthase AAE3_13291, viridiflorene synthase AAE3_12839, and linalool/nerolidol synthase AAE3_9435) were chosen to probe other putative isofunctional TPSs which were further validated by experiments.

Δ6-Protoilludene Extraction and NMR Validation of its Structure

The AAE3_10454 recombinant *E. coli* strain was cultured in 200 mL of ZYM5052 auto-inducing medium, supplemented with 100 mg of the spherical C18 resin (VersaFlash spherical C18 bonded flash silica 45-75 um, Sigma-Aldrich). After 24 h of cultivation at 28° C. and 150 rpm, the cell culture was manually filtered by a C18 cartridge and was subsequently washed twice by deionized water. After filtration, the cells and liquid media were removed from the C18 cartridge. The terpene compound bound to the C18 resin was eluted by 10 mL of hexane. The eluted terpene solution was evaporated at 4° C. and subsequently analyzed on a Bruker DRX-400 NMR spectrometer with Cryoprobe, using 5-mm BBI (1H, G-COSY, multiplicity-edited G-HSQC, and G-HMBC spectra) or BBO (13C spectra) probe heads equipped with z-gradients. Spectra were calibrated to residual protonated solvent signals CHCl3 δH 7.24 and CDCl3 δC 77.23). The terpene compound was verified as Δ6-protoilludene by comparing the NMR spectral data with those reported in the literature.

Example 1

Engineering an *E. coli* Strain for TPS Characterization.

Figure 2A:
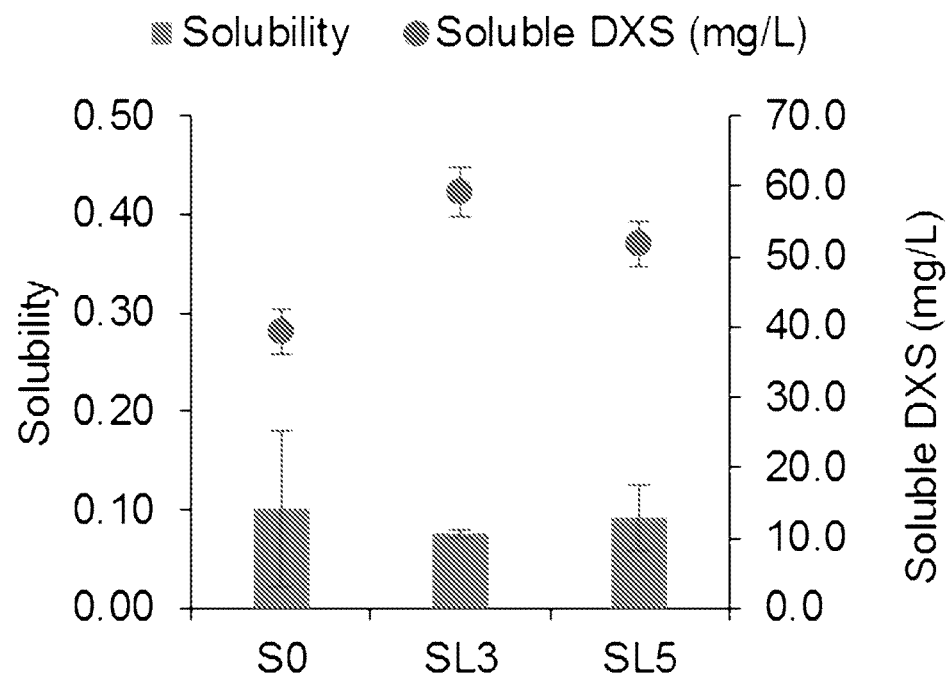
FIG. 2 shows experimental results for the improvement of the solubility and activity of DXS enzyme. In all measurements, S0 is the wide type DXS from *Escherichia coli*. (A) shows the solubility and soluble DXS at 5 h after induction. (B) shows the in vitro enzymatic activity measurements of DXS and its mutants. (C) shows the specific lycopene yield when different DXS mutants were used. (D) shows the annotations for DXS mutants.
Figure 2B:
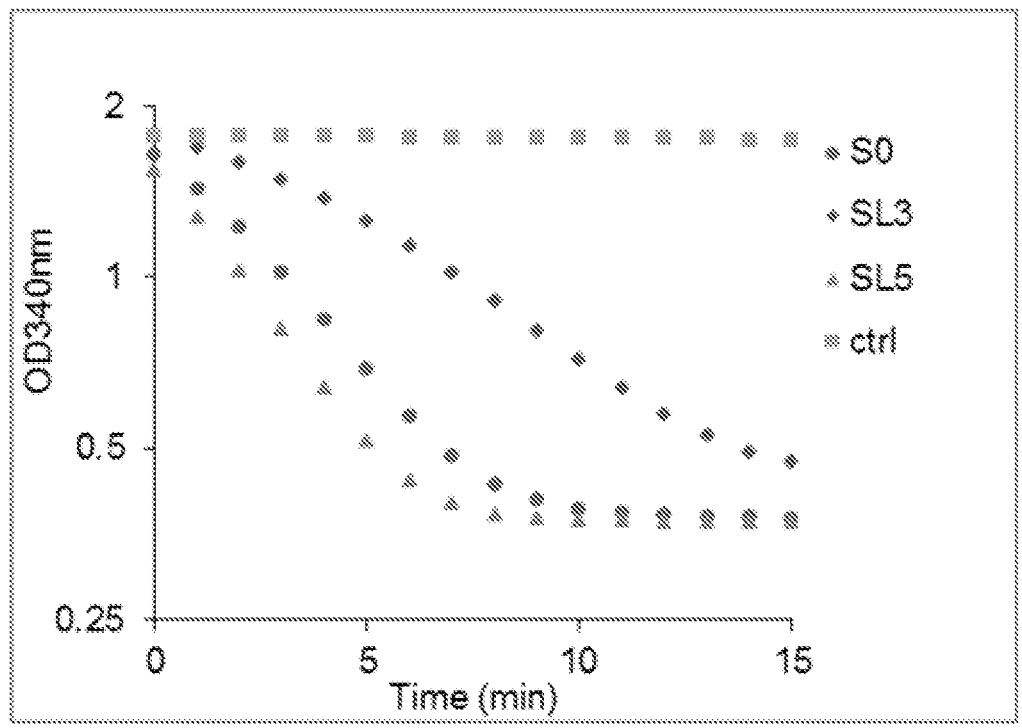
Figures 2C, 2D:
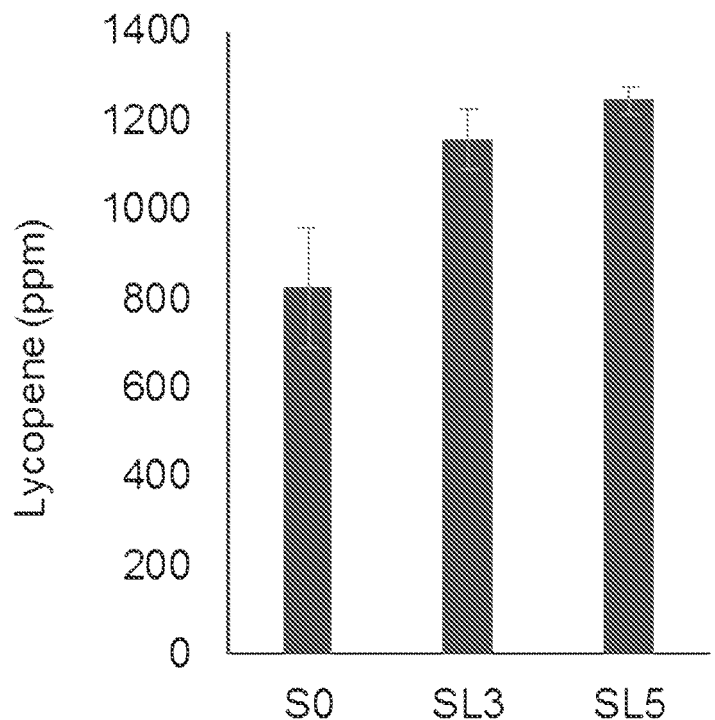
Figure 3:
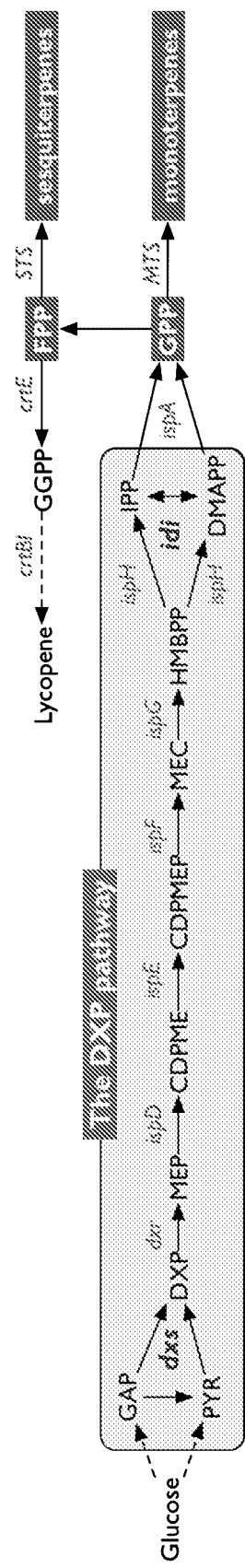
FIG. 3 shows a schematic of an engineered *Escherichia coli* strain for screening of terpene synthases. Metabolites in the pathway are: GAP, glyceraldehyde-3-phosphate; DXP, 1-deoxy-D-xylulose-5-phosphate; MEP, methylerythritol phosphate; CDP-ME, 4-diphosphocytidyl-2-C-methyl-D-erythritol; CDPMEP, 4-diphosphocytidyl-2-C-methyl-D-erythritol-2-phosphate; MEC, 2-C-methyl-D-erythritol-2,4-diphosphate; HMBPP, 1-hydroxy-2-methyl-2-(E)-butenyl-4-diphosphate; IPP, isopentenyl pyrophosphate; DMAPP, dimethylallyl pyrophosphate; GPP, geranyl pyrophosphate; FPP, farnesyl pyrophosphate and GGPP, geranylgeranyl pyrophosphate. Enzymes are: dxs, DXP synthase; dxr, DXP reductase; ispD, CDPME synthase; ispE, CDPME kinase; ispF, CDPMEP synthase; ispG, MBPP synthase; ispH, HMBPP reductase; idi, IPP isomerase; STS, sesquiterpene synthase and MTS, monoterpene synthase.
Figure 27:
FIG. 27 shows the crystal structure of DXS (PDB ID: 2o1s), where the substrates and mutated amino acids are highlighted.

The wild-type *E. coli* BL21 produces little amount of terpene precursors (GPP and FPP), therefore, it is not suitable as a TPS characterization platform. To improve the detection sensitivity and accuracy, DXS and IDI were overexpressed to improve the intracellular precursors (FIG. 3). Distinct from existing methods, two DXS mutants (SL3 and SL5) were identified based on random mutagenesis and screening. As shown in FIG. 2, SL3 and SL5 had higher solubility over wild-type DXS, and therefore a higher activity than wild-type DXS. More importantly, SL5 has higher specific activity than wild-type DXS (FIG. 2B). As a result, the lycopene yield in the strain overexpressing SL3 or SL5 was higher than that of wild-type DXS. Here, lycopene was used as an indicator to prove that GPP and FPP in the strains (SL3 and SL5) are higher. With the DXS mutants, the detection sensitivity of the cell platform is further improved. Hence, the *E. coli* strain (SL3 or SL5) was used as the platform for characterization of TPSs. FIG. 27 shows a crystal structure of DXS where beneficial mutations have been highlighted. The mutants are related to the improved solubility of DXS by enzyme engineering approach. The ligand pyrophosphate was shown in salmon color and magnesium was in firebrick color.

Example 2

Analysis of Terpenes Produced in *A. aegerita*

Figure 4:
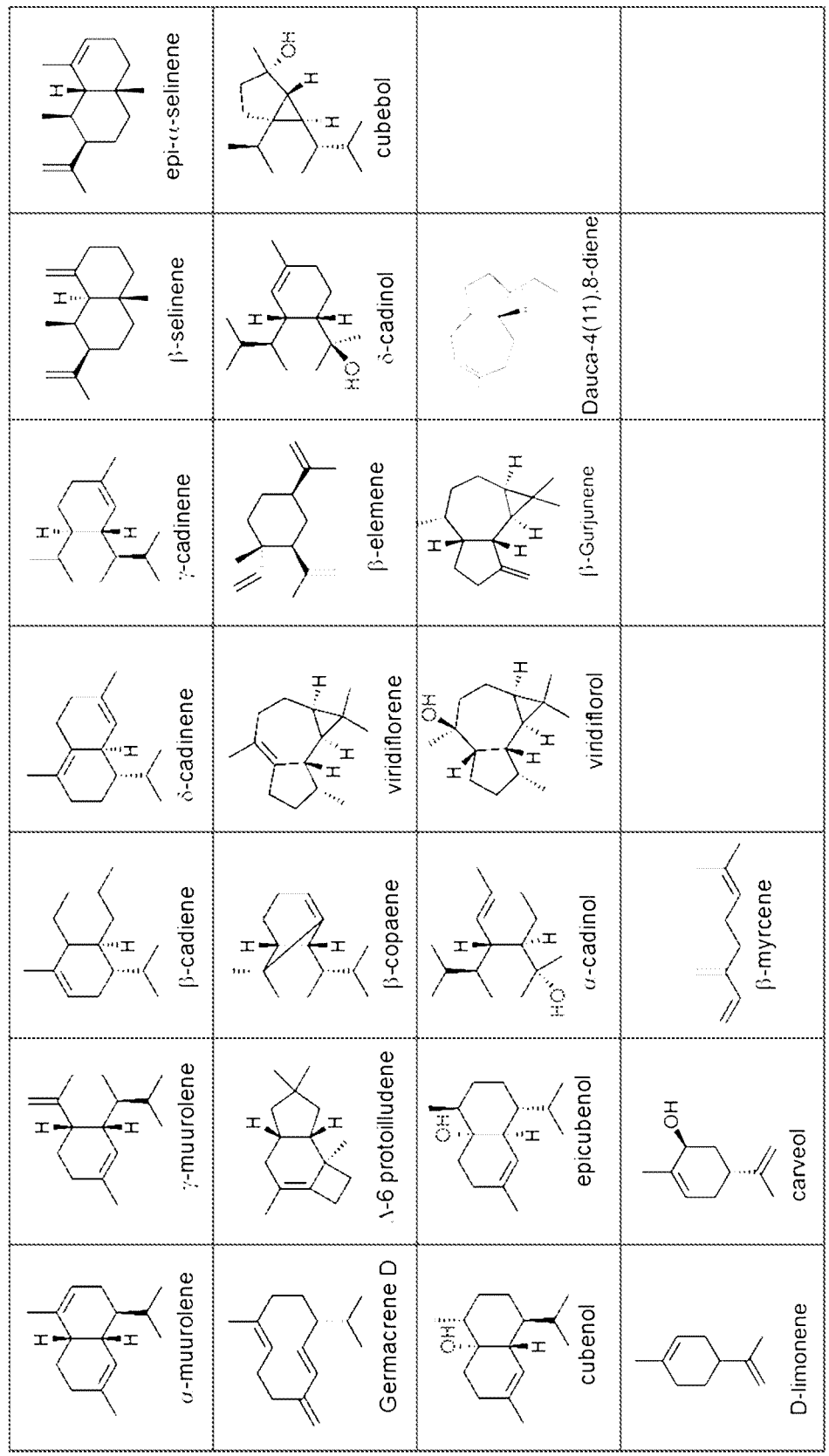
FIG. 4 shows the terpene compounds identified in this study.

To obtain an estimate of terpenes produced in *A. aegerita*, volatile compounds produced by its liquid cultures were analyzed. The illudin precursor, Δ(6)-protoilludene 1, was a dominant metabolite produced by *A. aegerita* (FIG. 1). In addition, small amount of α-ioscomene[#], α-, β-cubebene, β-copaene, γ-muurolene 2, δ-cadinene 4, β-selinene[#]9, cubenene, epicubenol 10 and cubenol (FIGS. 4 and 5 for chemical structure and mass spectra of all the terpene identified in the study, respectively) were observed after 26 days of culture. The results proved that the mushroom, *A. aegerita* produces structurally diverse terpenes.

Example 3

The Sesquiterpenome of *A. aegerita*

Figure 6:
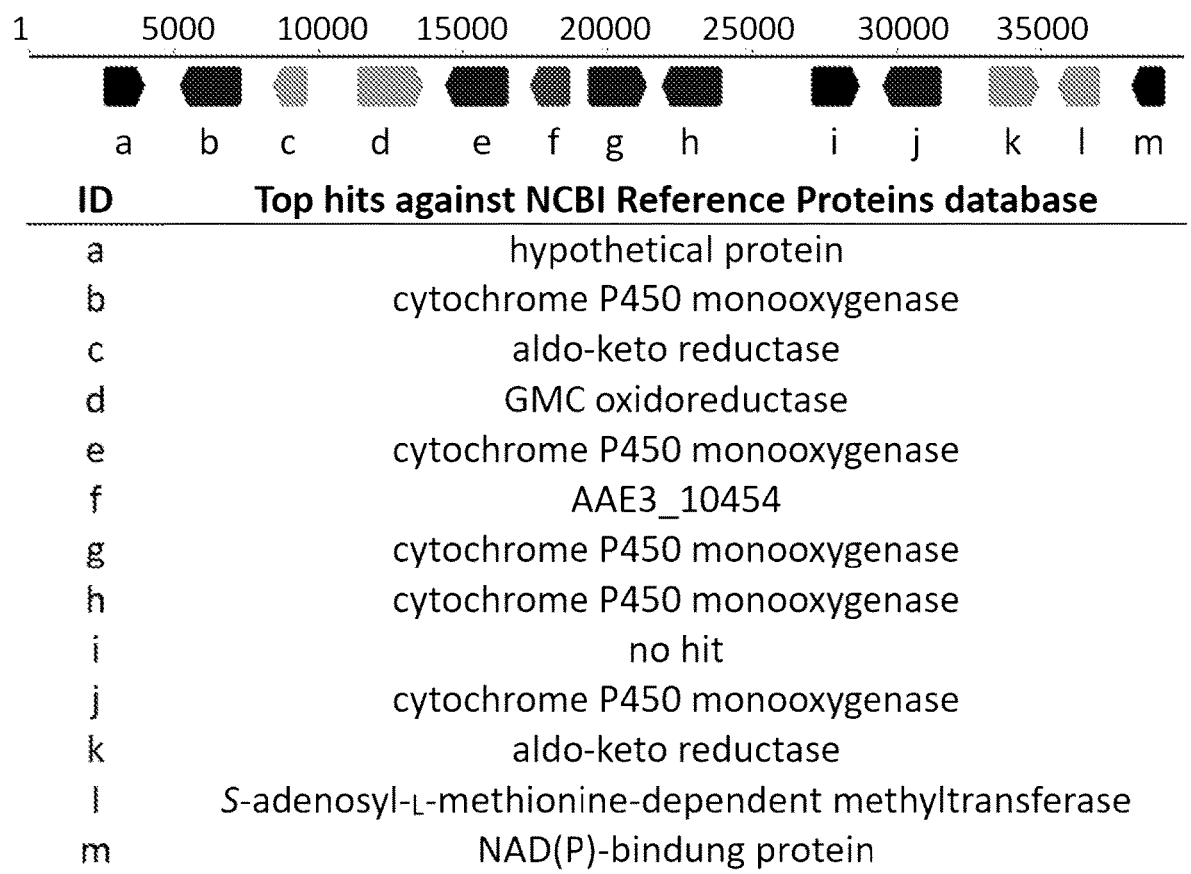
FIG. 6 shows the predicted biosynthetic gene clusters in *A. aegerita*. Four putative TPSs (AAE3_09008, AAE3_06743, AAE3_04444 and AAE3_05024) compile to an own cluster. Four of the STS genes (AAE3_10454, AAE3_12839, AAE3_04120 and AAE3_13291) are part of clusters consists amongst other of two to five P450 monooxygenases.
Figure 6:
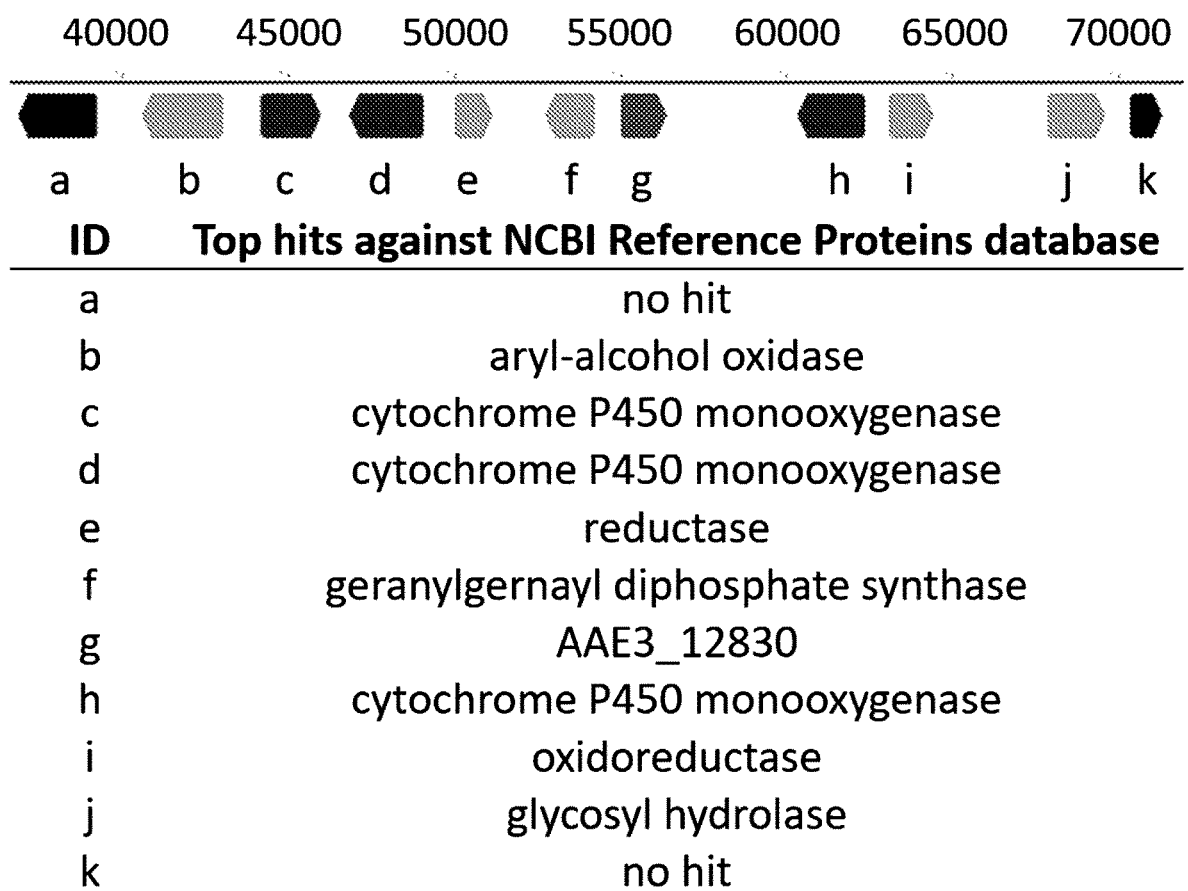
Figure 6:
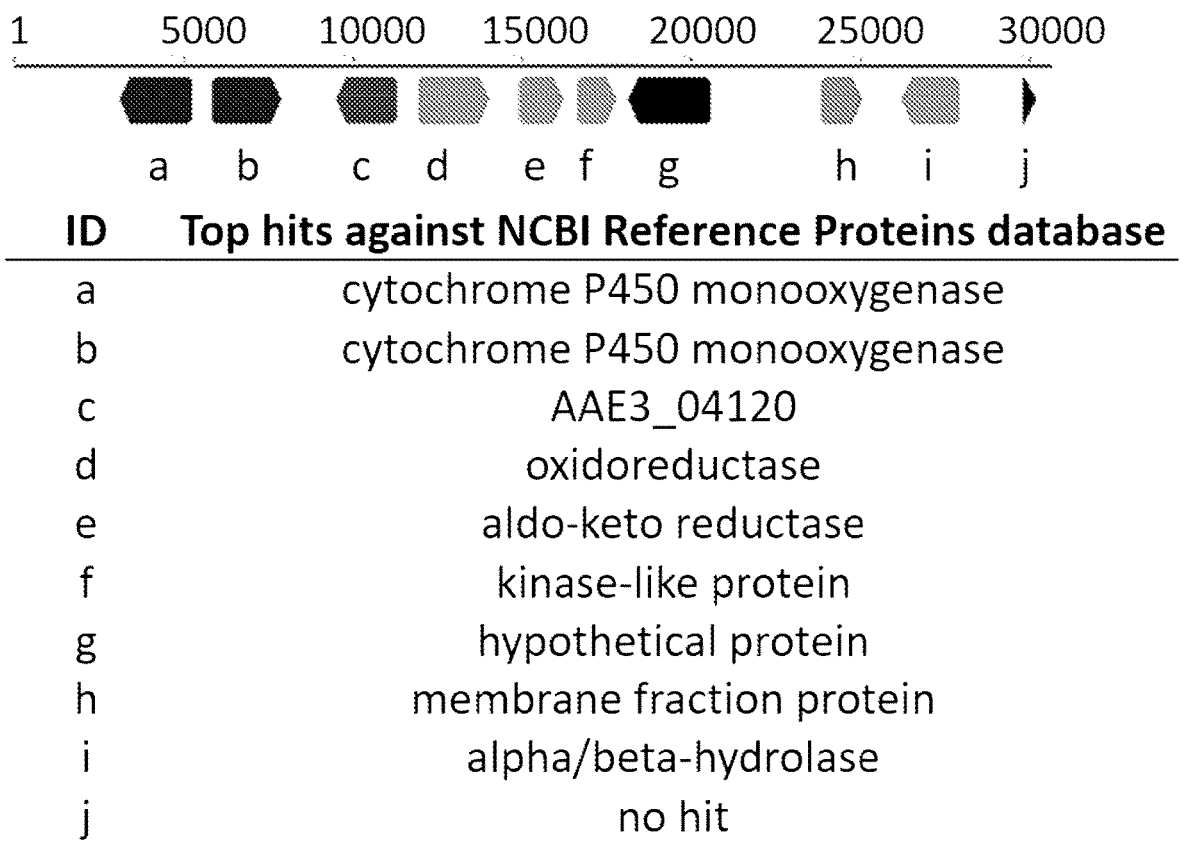
Figure 6:
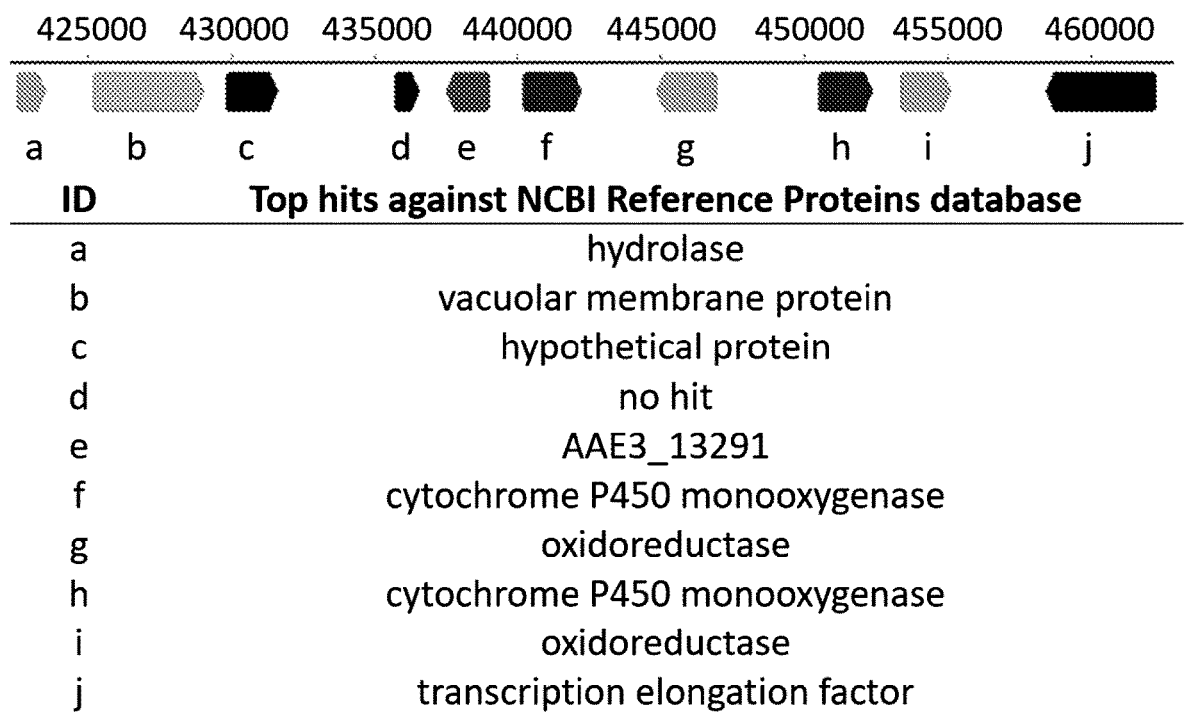

During fructification of *A. aegerita* 20 putative terpenoids were detected by means of GC/MS analysis, of which the tentatively identified Δ6-protoilludene[#] was the most prominent compound (FIG. 1). Other major compounds were α-cubebene, α-isocomene, β-cubebene and δ-cadinene (Compound structures in FIG. 4, the mass spectra in FIG. 5). The blastp search for putative STSs present in the genome of *A. aegerita* revealed 11 genes (Table 2 and FIG. 6). Seven of the TPSs cluster with already known basidiomycete TPSs into at least three different groups. Four putative TPSs (AAE3_09008, AAE3_06743, AAE3_04444 and AAE3_05024) compile to an own cluster (FIG. 6). Four of the STS genes (AAE3_10454, AAE3_12839, AAE3_04120 and AAE3_13291) are part of clusters consists amongst other of two to five P450 monooxygenases.

TABLE 2

Details on *Agrocybe aegerita* STSs genes.

| Protein ID | scaffold | gene start | gene stop | gene length | number of introns | protein length |
|---|---|---|---|---|---|---|
| 04120 | 2 | 9,526 | 11,372 | 1,847 | 6 | 659 |
| 04120 short | 2 | 10,043 | 11,372 | 1,330 | 5 | 346 |
| 04444 | 2 | 1,033,830 | 1,035,120 | 1,291 | 4 | 353 |
| 09164 | 4 | 405,253 | 406,500 | 1,248 | 4 | 342 |
| 13190 | 8 | 106,456 | 107,896 | 1,441 | 6 | 358 |
| 13291 | 8 | 437,487 | 439,057 | 1,571 | 5 | 430 |
| 05024 | 21 | 111,488 | 112,812 | 1,325 | 4 | 355 |
| 06595 | 28 | 328,403 | 329,611 | 1,209 | 3 | 346 |
| 06743 | 29 | 231,813 | 233,188 | 1,376 | 4 | 372 |
| 09008 | 39 | 347,841 | 349,082 | 1,242 | 6 | 308 |
| 10454 | 49 | 17,315 | 18,741 | 1,427 | 5 | 387 |
| 12839 | 70 | 55,035 | 56,437 | 1,403 | 4 | 389 |

Example 4

Characterization of 11 Predicted Sesquiterpene Synthases

All 11 predicted STSs were codon optimized and cloned into the pET vector, which was transformed into an engineered *E.coli* BL21 strain overproducing farnesyl pyrophosphate (FPP), the sesquiterpene precursor. Compounds tentatively identified on basis of their retention index (RI) and mass spectra in comparison to those in the literature and databases as described in the methods are marked with a hashmark (#).

Figure 7:
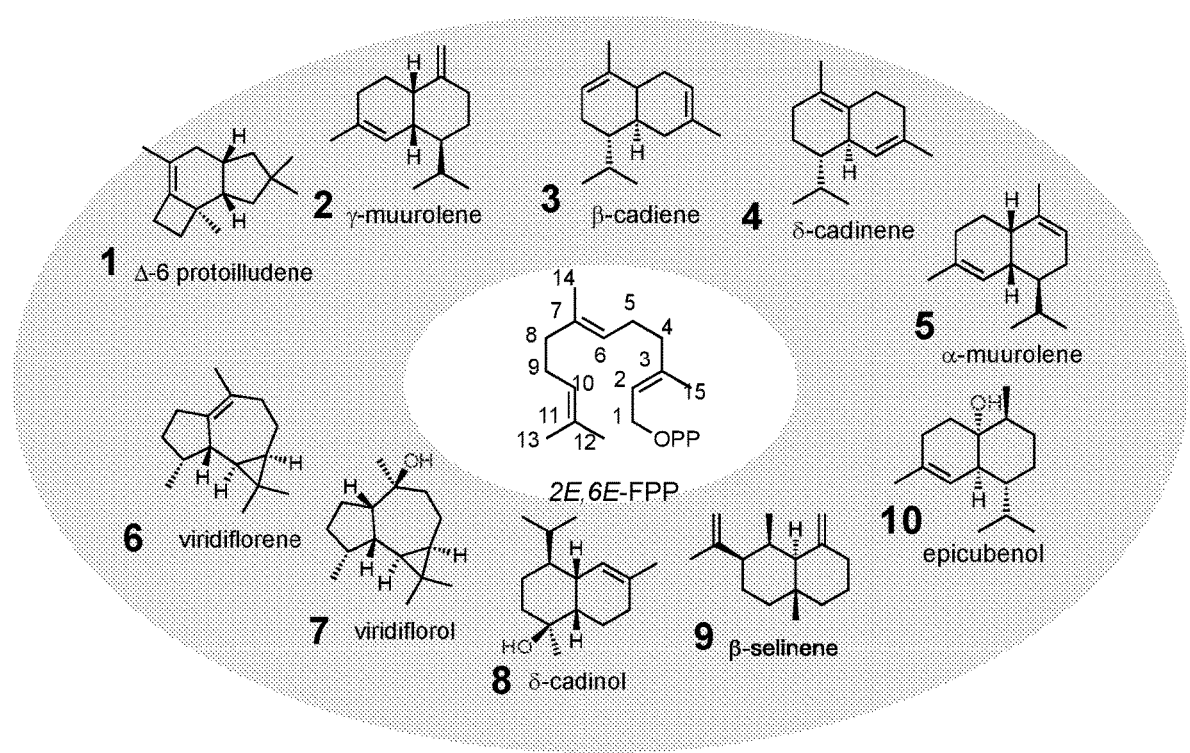
FIG. 7 shows the terpenes produced by *E. coli* expressing TPS genes from *A. aegerita*. The metabolites were analysed by GC-MS with DB5 column. The metabolite profiles analysed by GC-MS with VF-WAXms column were shown in FIG. 8. Major compound peaks are labelled by numbers corresponding to structure shown below. See FIG. 5 for mass spectra and Table 3 for summary of terpene compounds analysed by both DB5 and VF-WAXms column.
Figure 7:
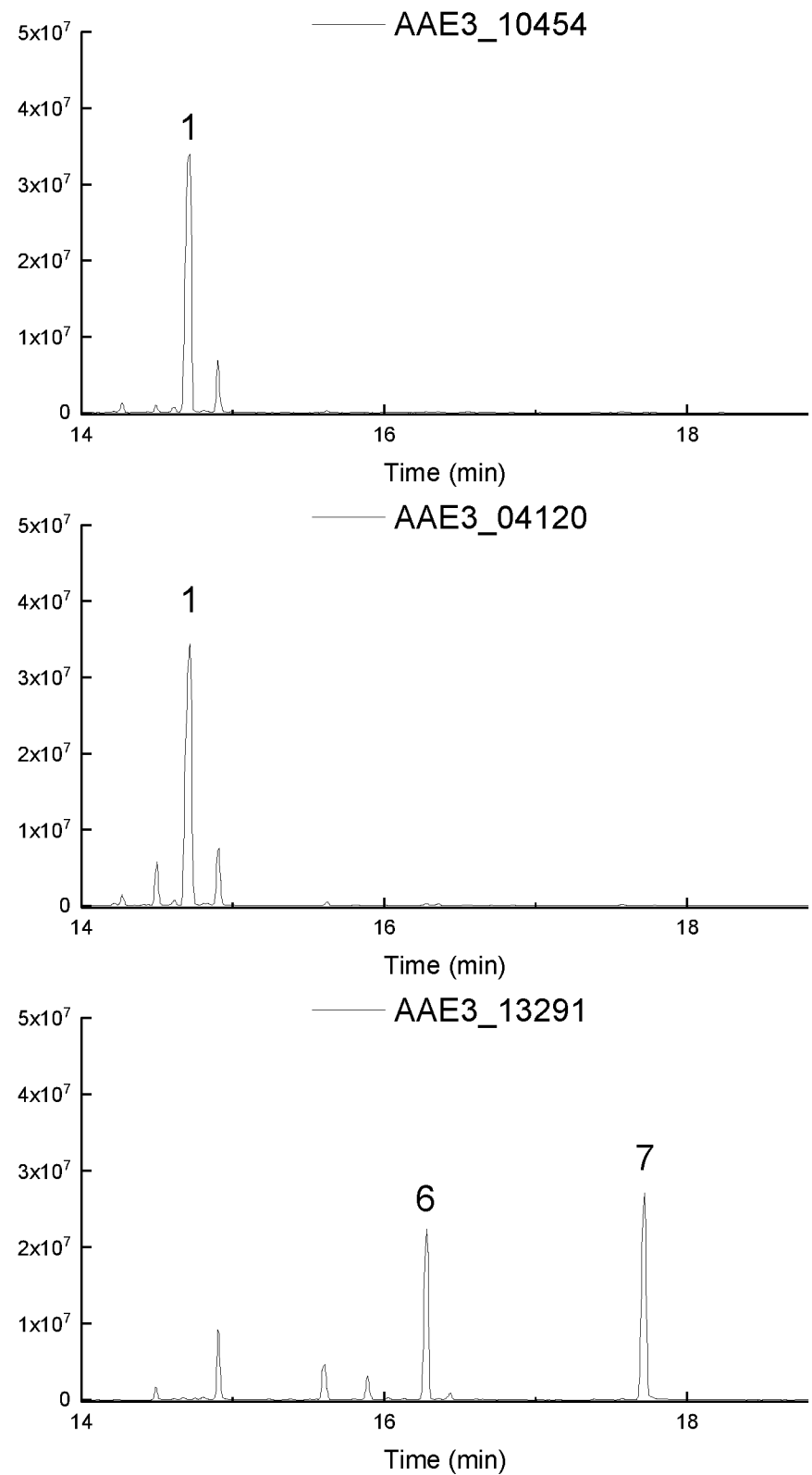
Figure 7:
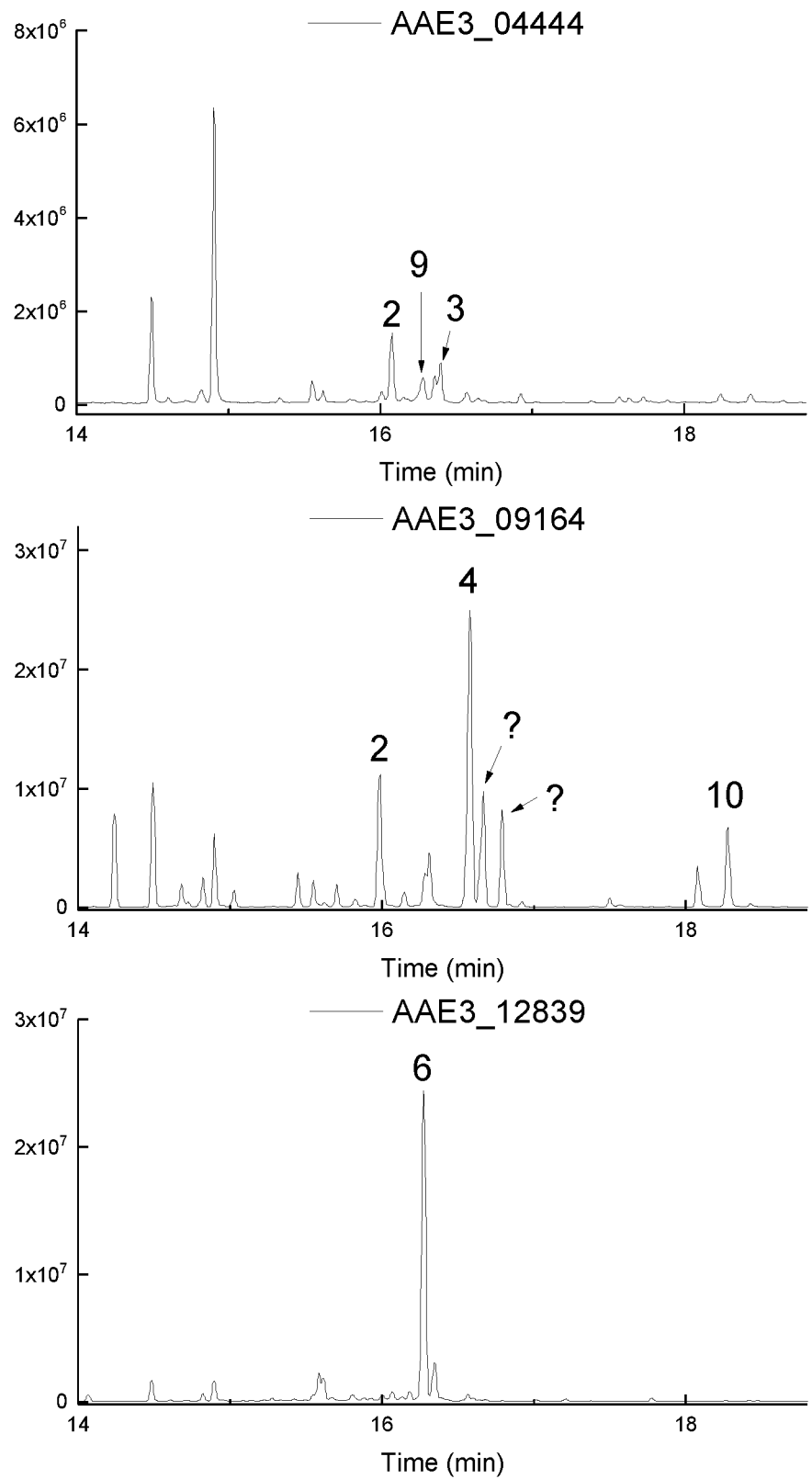
Figure 7:
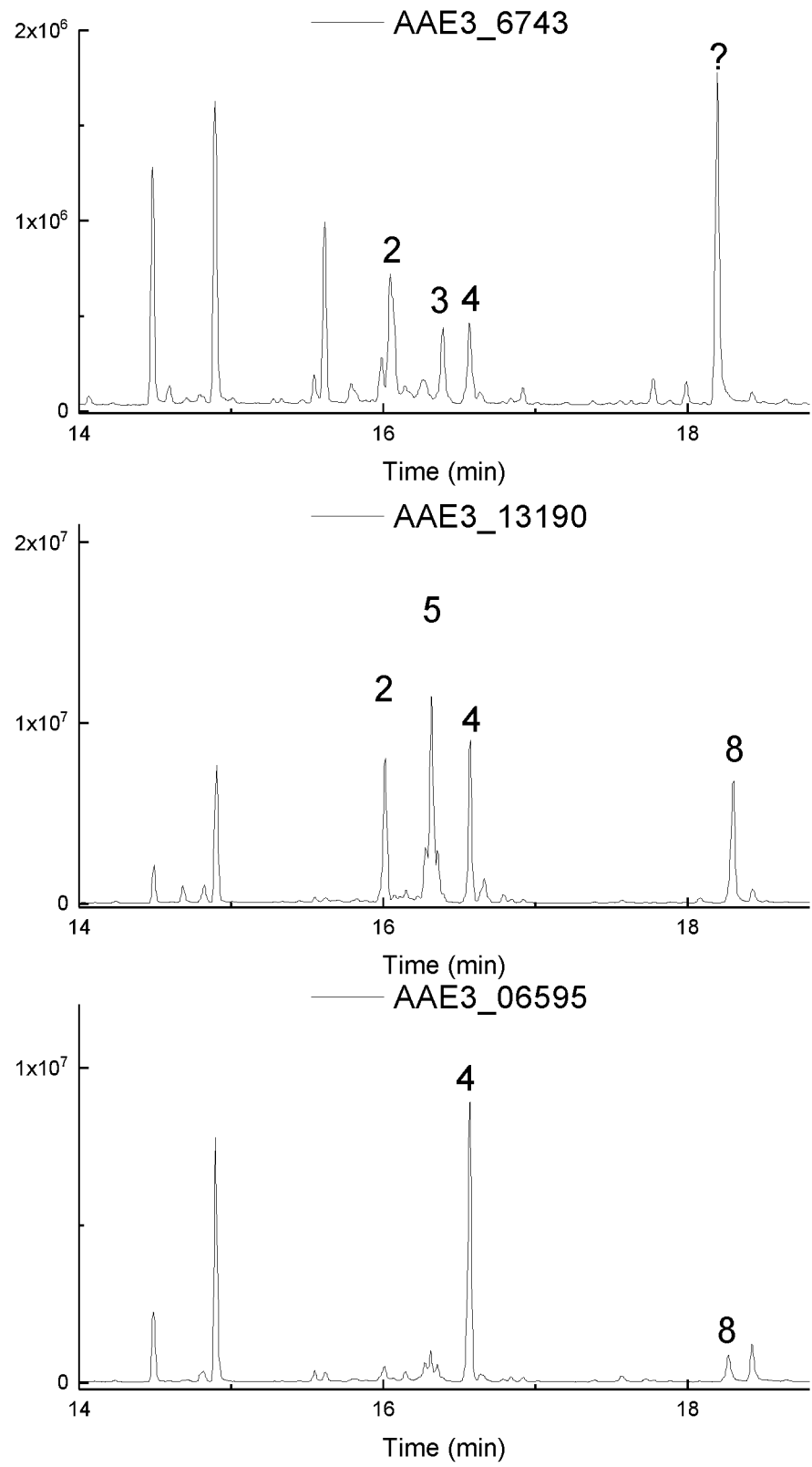
Figure 8:
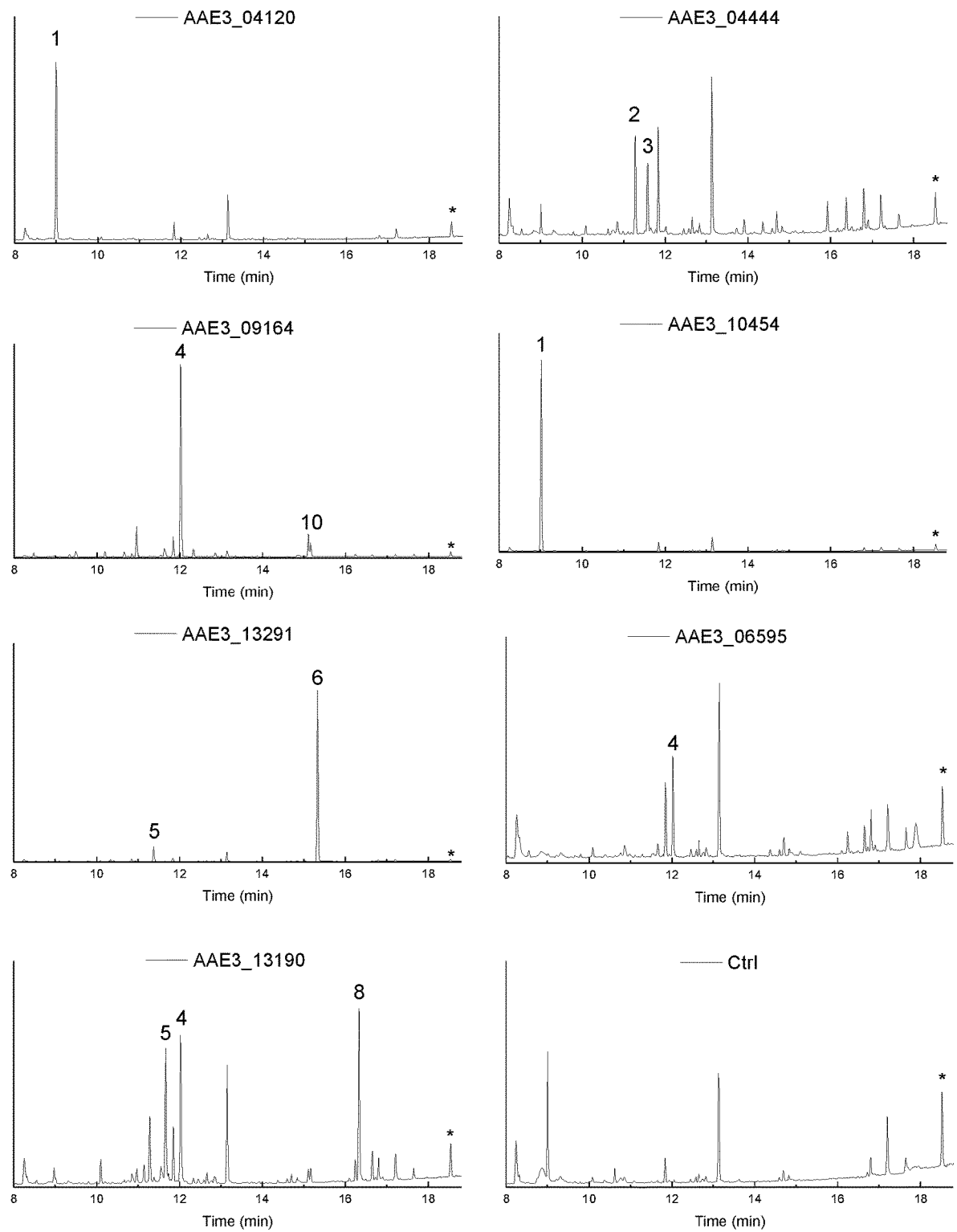
FIG. 8 shows the GC-MS profiles of terpenes produced by *E. coli* expressing TPS genes from *A. aegerita*. The metabolites were analyzed by VF-WAXms column. 'Ctrl' is the GC-MS profile of volatile metabolites produced by *E. coli* strain with empty vector. Indole (*) endogenously produced by *E. coli* serves as an internal reference to compare the relative amount of the terpene production.
Figure 9:
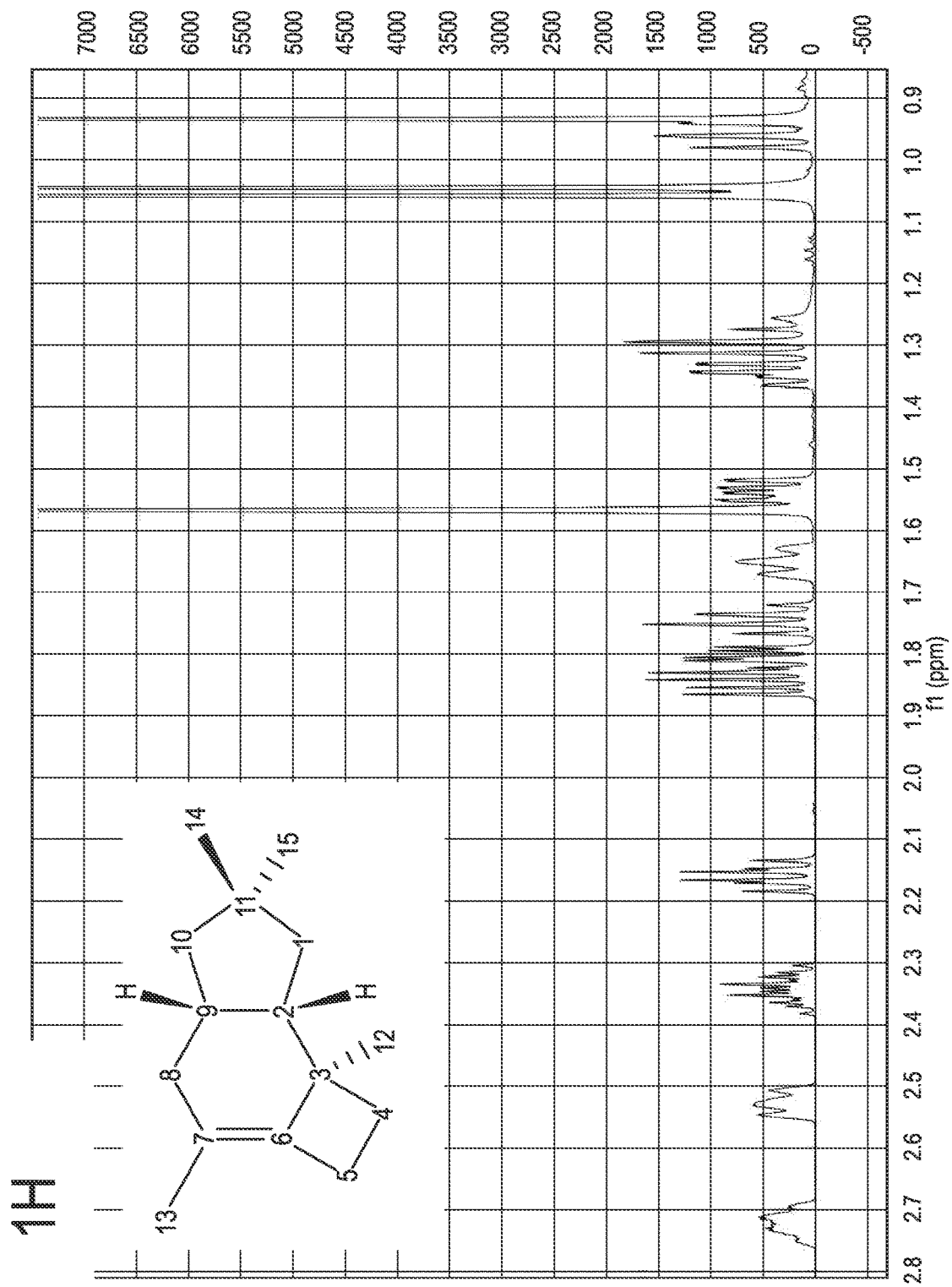
FIG. 9 shows the nuclear magnetic resonance (NMR) spectroscopy analysis of the product of AAE3_10454.
Figure 9:
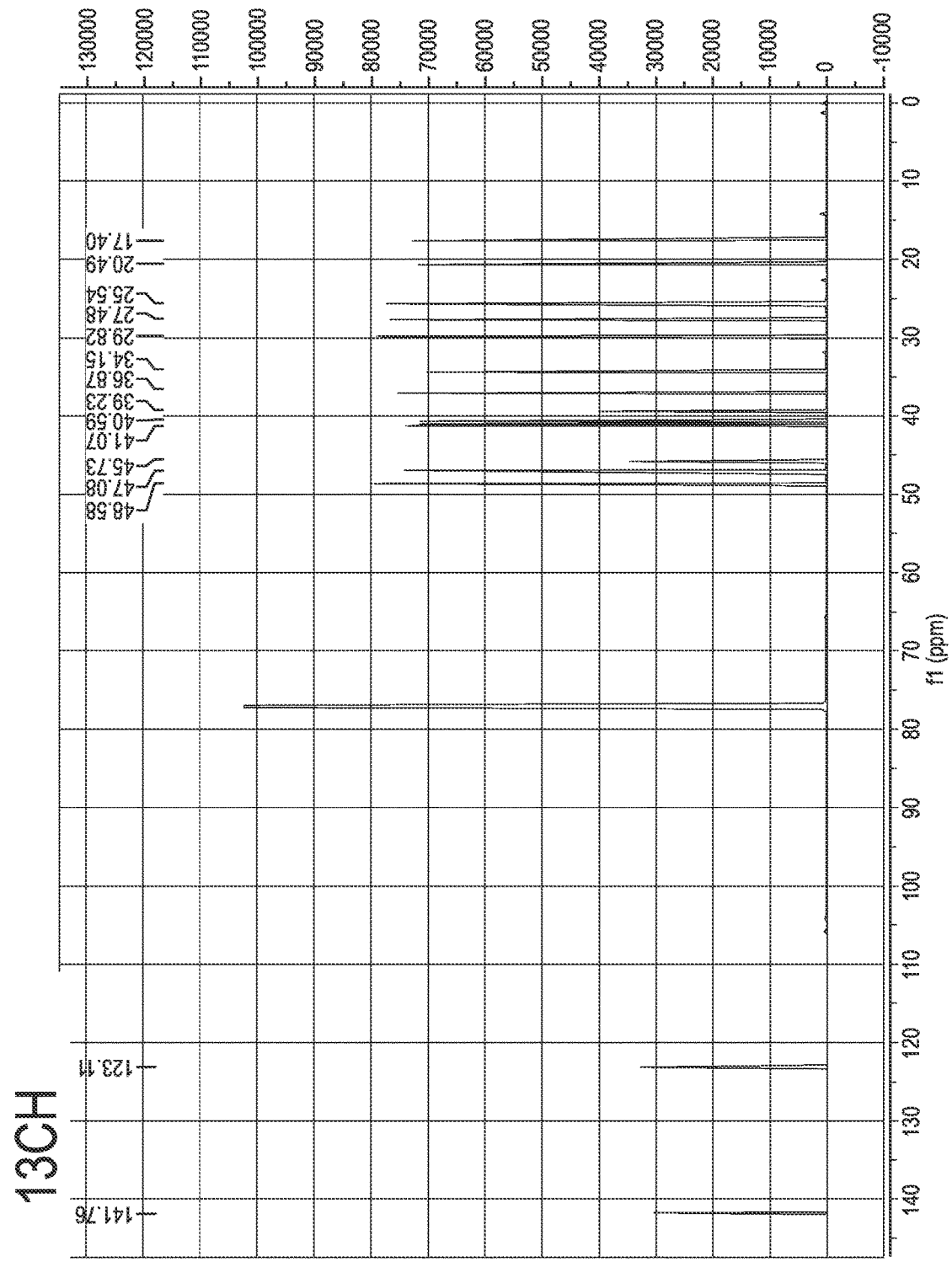
Figure 9:
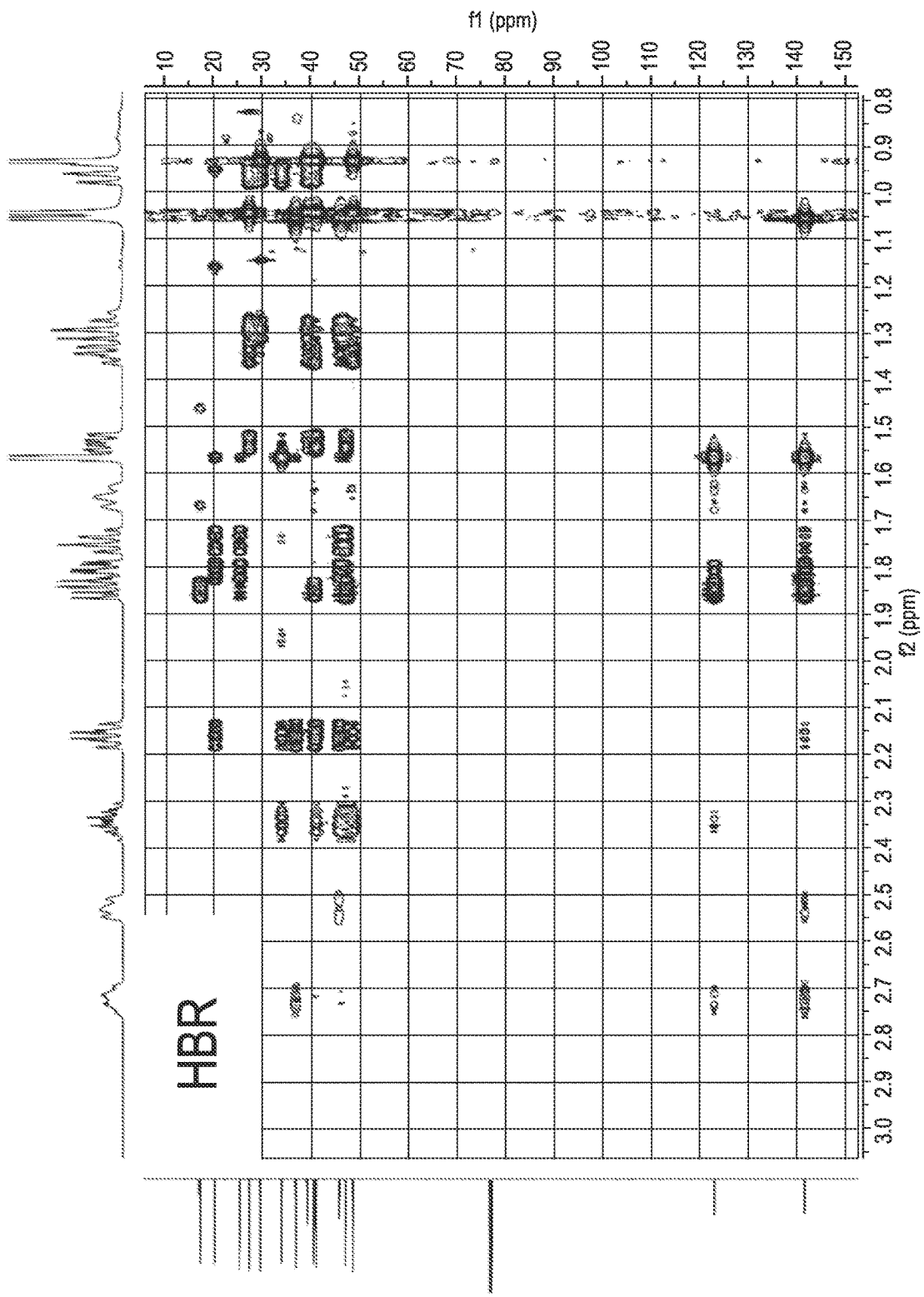
Figure 9:
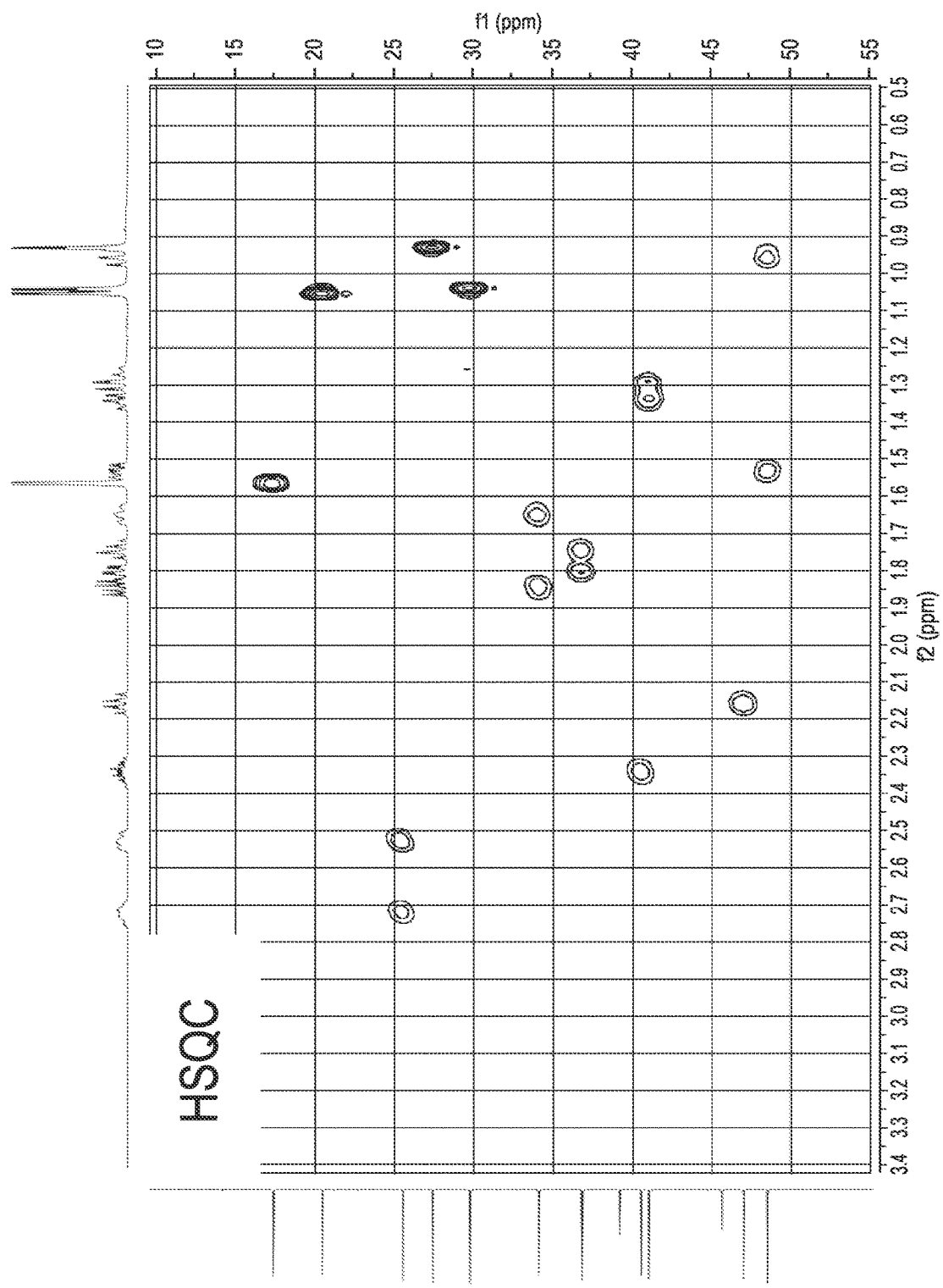

All STSs (TPSs) except AAE3_09008 and AAE3_05024 gave rise to one or more sesquiterpenes in liquid cultures of the corresponding *E. coli* clone (FIG. 7 (DB-5 ms column), FIG. 8 (VFWAXms column) and Table 3). AAE3_04120 and AAE3_10454 produced the same sesquiterpene as the only product. NIST database search and a comparison with mass spectra of fungal sesquiterpenes from previous reports (FIG. 5 and Table 3) revealed this compound could be Δ6-protoilludene 1. And its structure was further validated by the NMR analysis which had the identical spectrum with previous report (FIG. 9). Δ6-protoilludene is the precursor for illudins that have shown anti-tumor and antimicrobial effects. Till now, six Δ6-protoilludene synthases from three fungal species have been reported, Omp6 and Omp7 from *Omphalotus olearius*, Pro1 from *Armillaria gallica* and Stehi1_25180, Stehi1_64702 and Stehi1_73029 from *Stereum hirsutum*. Interestingly, AAE3_04120 and AAE3_10454 form a closely related subgroup with the six reported synthases in the phylogenetic clustering (FIG. 1), indicating that the 6-protoilludene synthases are highly related among different fungal species.

TABLE 3

Terpene products of the TPSs in this study.

| SPME data Gene | Products | DB5 (Non-polar) | | | VFWAXms (Polar) | | |
|---|---|---|---|---|---|---|---|
| | | Area % | RI | Literature RI | Area % | RI | Literature RI |
| AAE3_04120 | Δ6-protoilludene | 100% | 1391 | 1393 | 100% | 1513 | / |
| AAE3_04444 | β-elemene | /8% | 1400 | 1391 ± 2 (521) | / | / | 1591 ± 9 (259) |
| | γ-muurolene | 33% | 1487 | 1477 ± 3 (392) | 30% | 1706 | 1692 ± 12 (165) |
| | β-selinene | 18% | 1509 | 1486 ± 3 (349) | / | / | 1717 ± 13 (167) |
| | α-selinene | 14% | 1515 | 1517 | / | / | 1656 ± 0 (2) |
| | β-cadinene | 21% | 1518 | 1518 ± 10 (30) | 22% | 1733 | 1720 ± N/A (1) |
| | δ-cadinene | /6% | 1529 | 1524 ± 2 (751) | /4% | 1772 | 1758 ± 13 (374) |
| | α-epi-Cadinol | / | / | / | /9% | 2213 | 2169 ± 16 (145) |
| AAE3_06595 | γ-muurolene | /5% | 1489 | 1477 ± 3 (392) | / | / | 1692 ± 12 (165) |
| | β-selinene | /5% | 1508 | 1486 ± 3 (349) | / | / | 1717 ± 13 (167) |
| | α-muurolene | /7% | 1511 | 1499 ± 3 (427) | /8% | 1739 | 1726 ± 13 (198) |
| | α-Selinene | /5% | 1514 | 1517 | / | / | 1656 ± 0 (2) |
| | δ-cadinene | 60% | 1529 | 1524 ± 2 (751) | 57% | 1772 | 1758 ± 13 (374) |
| | T-muurolol | /8% | 1659 | / | 13% | 2198 | 2186 ± 16 (140) |
| | α-cadinol | 10% | 1671 | / | 18% | 2243 | 2226 ± 9 (182) |
| AAE3_6743 | γ-muurolene | 27% | 1488 | 1477 ± 3 (392) | 14% | 1706 | 1692 ± 12 (165) |
| | β-cadinene | 13% | 1516 | 1518 ± 10 (30) | 13% | 1733 | 1720 ± N/A (1) |
| | δ-cadinene | 13% | 1527 | 1524 ± 2 (751) | 6% | 1772 | 1758 ± 13 (374) |
| | Unknown sesquiterpene alcohol | 44% | 1650 | / | 52% | 2176 | |
| AAE3_9164 | β-myrcene* | 10% | 989 | 991 ± 2 (841) | /7% | 1172 | 1161 ± 7 (569) |
| | β-copaene | / | / | / | /2% | 1610 | 1586 ± 12 (15) |
| | α-cubebene | /8% | 1358 | 1351 ± 2 (338) | /1% | 1469 | 1463 ± 6 (186) |
| | γ-muurolene | 15% | 1487 | 1477 ± 3 (392) | /8% | 1677 | 1692 ± 12 (165) |
| | δ-cadinene | 37% | 1531 | 1524 ± 2 (751) | 59% | 1772 | 1758 ± 13 (374) |
| | epizonarene | 13% | 1538 | 1501 ± 4 (28) | /8% | 1677 | 1677 ± 1 (15) |
| | Unknown sesquiterpene | /9% | 1548 | / | /4% | 1736 | 1786 ± 13 (65) |
| | epicubenol | /8% | 1660 | 1627 ± 2 (144) | /7% | 2076 | 2067 ± 21 (67) |
| | cubebol | / | / | / | /7% | 1951 | 1957 |

TABLE 3-continued

Terpene products of the TPSs in this study.

| SPME data Gene | Products | DB5 (Non-polar) Area % | RI | Literature RI | VFWAXms (Polar) Area % | RI | Literature RI |
|---|---|---|---|---|---|---|---|
| AAE3_10454 | Δ6-protoilludene | 100% | 1392 | 0 | 100% | 1513 | / |
| AAE3_12839 | δ-elemene | /2% | 1345 | 1338 ± 2 (221) | / | / | 1470 ± 9 (86) |
|  | (+)-aromadendrene | /7% | 1457 | 1440 ± 1 (5) | / | / | 1635 ± 2 (3) |
|  | viridiflorene | 82% | 1508 | 1493 ± 4 (114) | 81% | 1712 | 1697 ± 7 (76) |
|  | Unknown sesquiterpene | /9% | 1514 | / | / | / | / |
| AAE3_13190 | γ-muurolene | 22% | 1489 | 1477 ± 3 (392) | /9% | 1706 | 1692 ± 12 (165) |
|  | (−)-germacrene D | / | / | / | /4% | 1730 | 1710 ± 14 (325) |
|  | α-muurolene | 32% | 1512 | 1499 ± 3 (427) | 20% | 1740 | 1726 ± 13 (198) |
|  | δ-cadinene | 24% | 1529 | 1524 ± 2 (751) | 24% | 1772 | 1758 ± 13 (374) |
|  | Cubenol | / | / | / | /4% | 2076 | 2080 ± 4 (65) |
|  | δ-cadinol/δ-cedrol | 21% | 1662 | 1645 | 24% | 2209 | 2187 ± 10 |
| AAE3_13291 | viridiflorene | 42% | 1509 | 1493 ± 4 (114) | /9% | 1714 | 1697 ± 7 (76) |
|  | viridiflorol* | 58% | 1617 | 1591 ± 2 (198) | 91% | 2099 | 2095 ± 10 (108) |
| Denbil_816208 | vindiflorene | 31% | 1509 | 1493 ± 4 (114) | /8% | 1714 | 1697 ± 7 (76) |
|  | viridiflorol* | 57% | 1617 | 1591 ± 2 (198) | 92% | 2099 | 2095 ± 10 (108) |
| Sphst_47084 | viridiflorene | 32% | 1509 | 1493 ± 4 (114) | /8% | 1714 | 1697 ± 7 (76) |
|  | viridiflorol* | 58% | 1617 | 1591 ± 2 (198) | 92% | 2099 | 2095 ± 10 (108) |
| Pilcr_825684 | β-elemene | /7% | 1401 | 1391 ± 2 (521) | / | / | 1591 ± 9 (259) |
|  | Unknown sesquiterpene | 12% | 1490 | / | / | / | / |
|  | Viridiflorene | /6% | 1509 | 1493 ± 4 (114) | /8% | 1714 | 1697 ± 7 (76) |
|  | epi-α-Selinene | /8% | 1514 | 1485 ± N/A (1) | 12% | 1726 | 1725 |
|  | γ-cadinene | 45% | 1529 | 151 ± 2 (485) | 30% | 1774 | 1765± 11 (199) |
|  | Unknown sesquiterpene | 15% | 1538 | / | / | / | / |
| Galma_104215 | β-gurjunene | 83% | 1441 | 1432 ± 3 (234) | 81% | 1673 | 1669 ± 17 (14) |
|  | Unknown sesquiterpene | 10% | 1439 | / | 12% | 1634 | / |

The *E. coli* strains expressing AAE3_0444 (SEQ ID NO: 27) and AAE3_6743 (SEQ ID NO: 29) produced several sesquiterpene compounds (FIG. 7, FIG. 8 and Table 3). γ-Muurolene 2 and β-cadinene[#]3 are the main products of AAE3_0444, together accounting for >50% of the total sesquiterpenes detected. In addition, small amounts of β-selinene[#]9, α-selinene[#]13, β-elemene (germacrene A) 11 and δ-cadinene 4 (verified by Cubeb essential oil, FIGS. 10 and S7) were detected in the headspace of AAE3_0444 culture. AAE3_6743 produced an unknown sesquiterpenol as the main product, together with small amounts of γ-muurolene 2 (27%), β-cadinene[#]3 (13%) and δ-cadinene 4 (13%).

Figure 10:
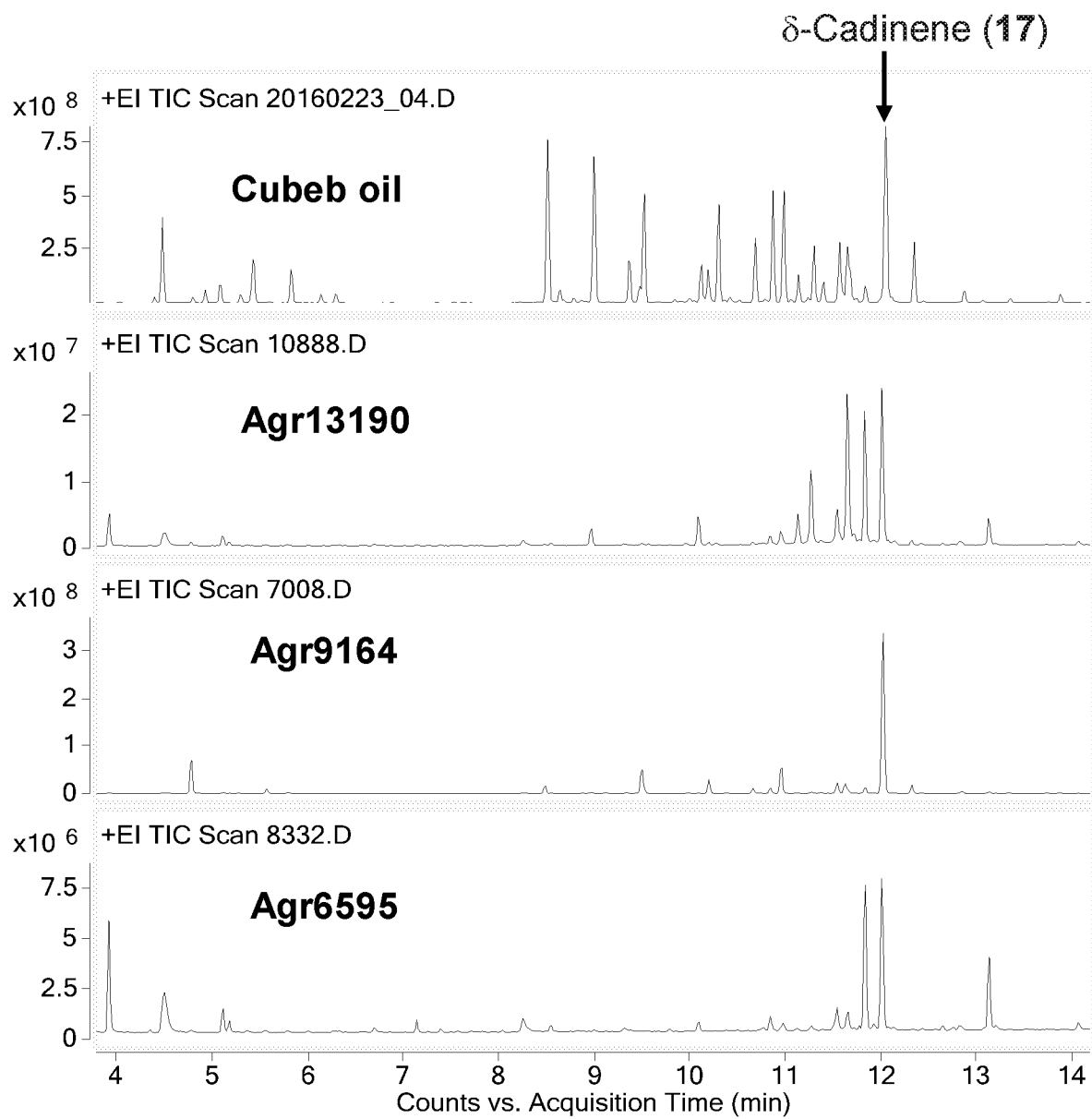
FIG. 10 shows the use of essential oils as chemical standards to identify terpene compounds identified. VF-WAXms column was used in this study.
Figure 11:
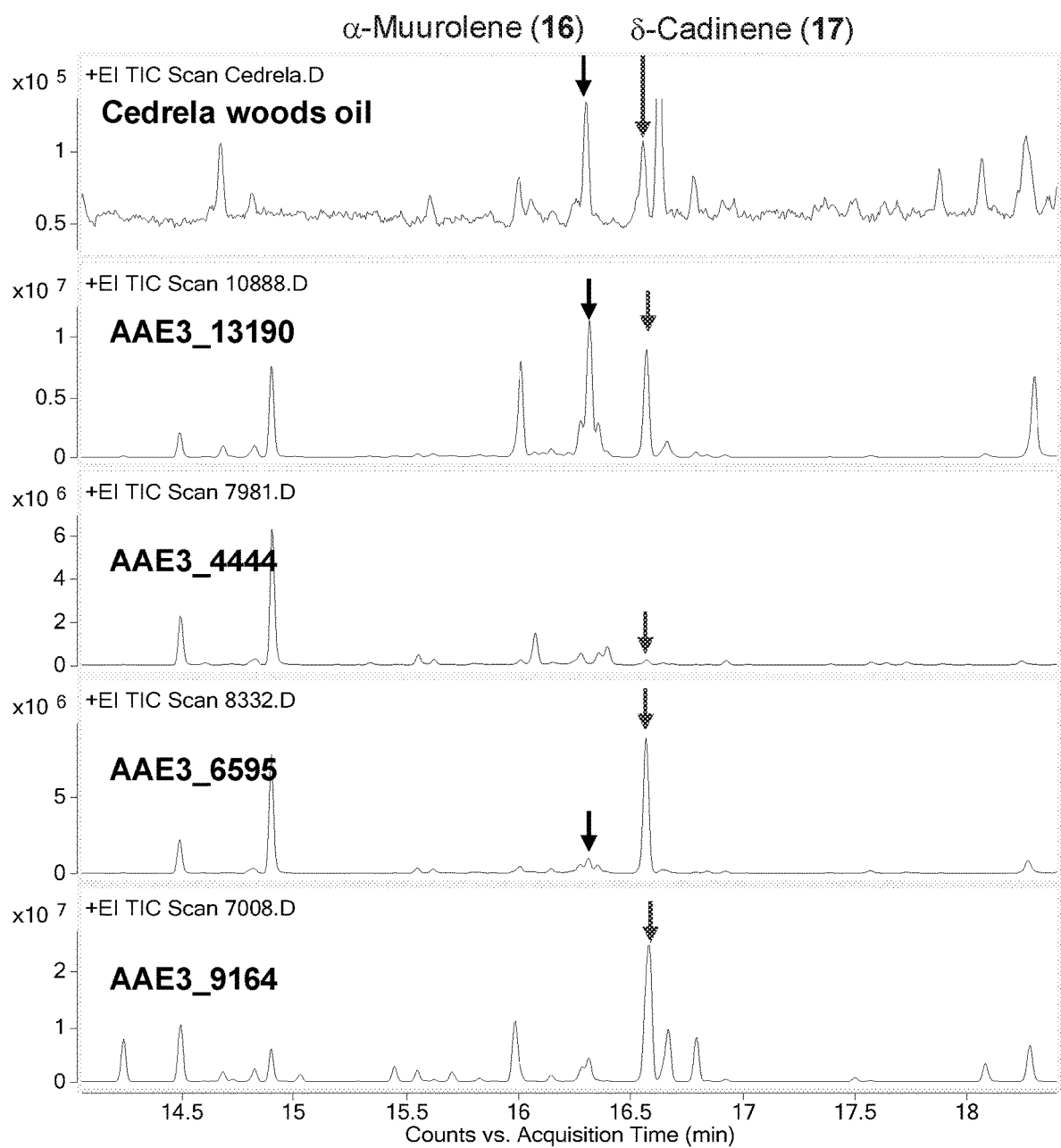
FIG. 11 shows the use of essential oils as chemical standards to identify terpene compounds identified. DB-5 ms column was used in this study.
Figure 12:
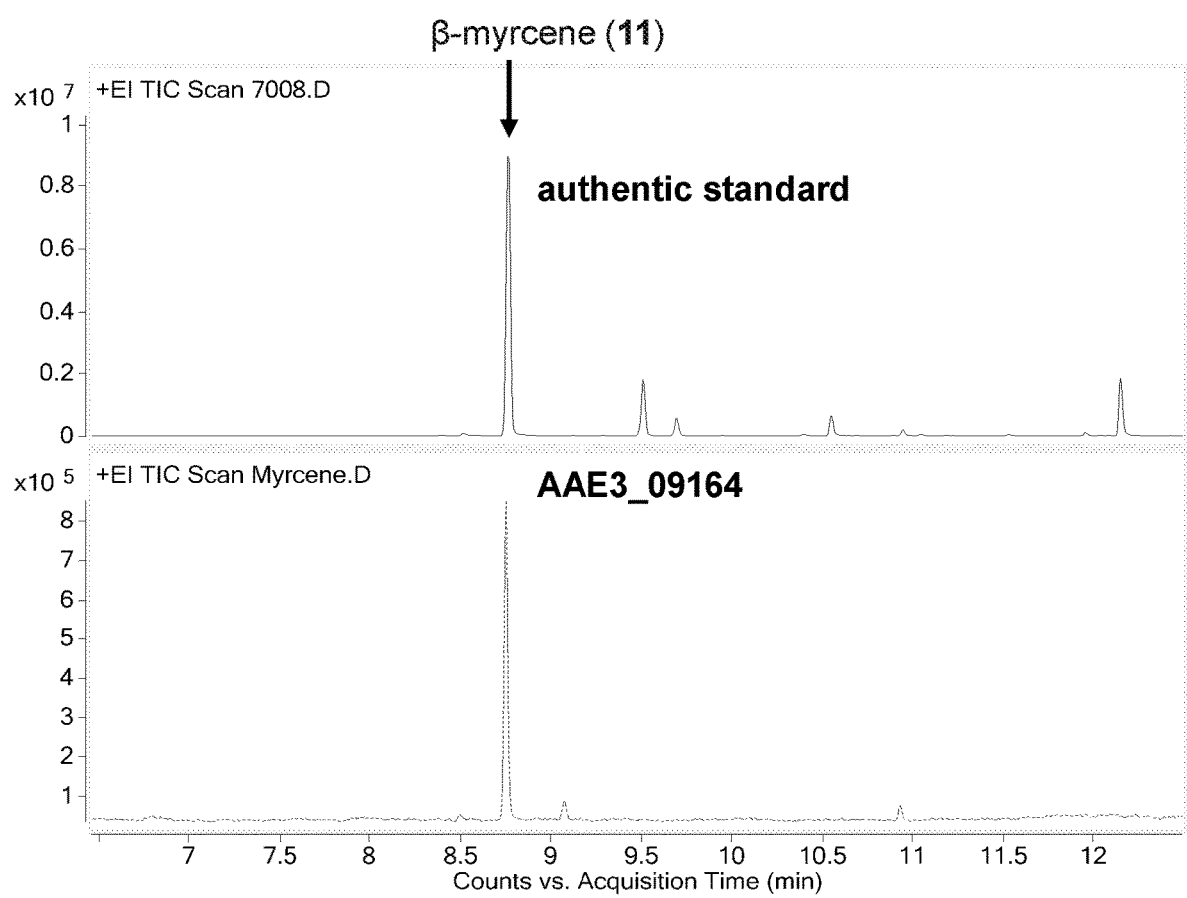
FIG. 12 shows the GC-MS profile of monoterpenes produced by AAE3_9164.
Figure 13:
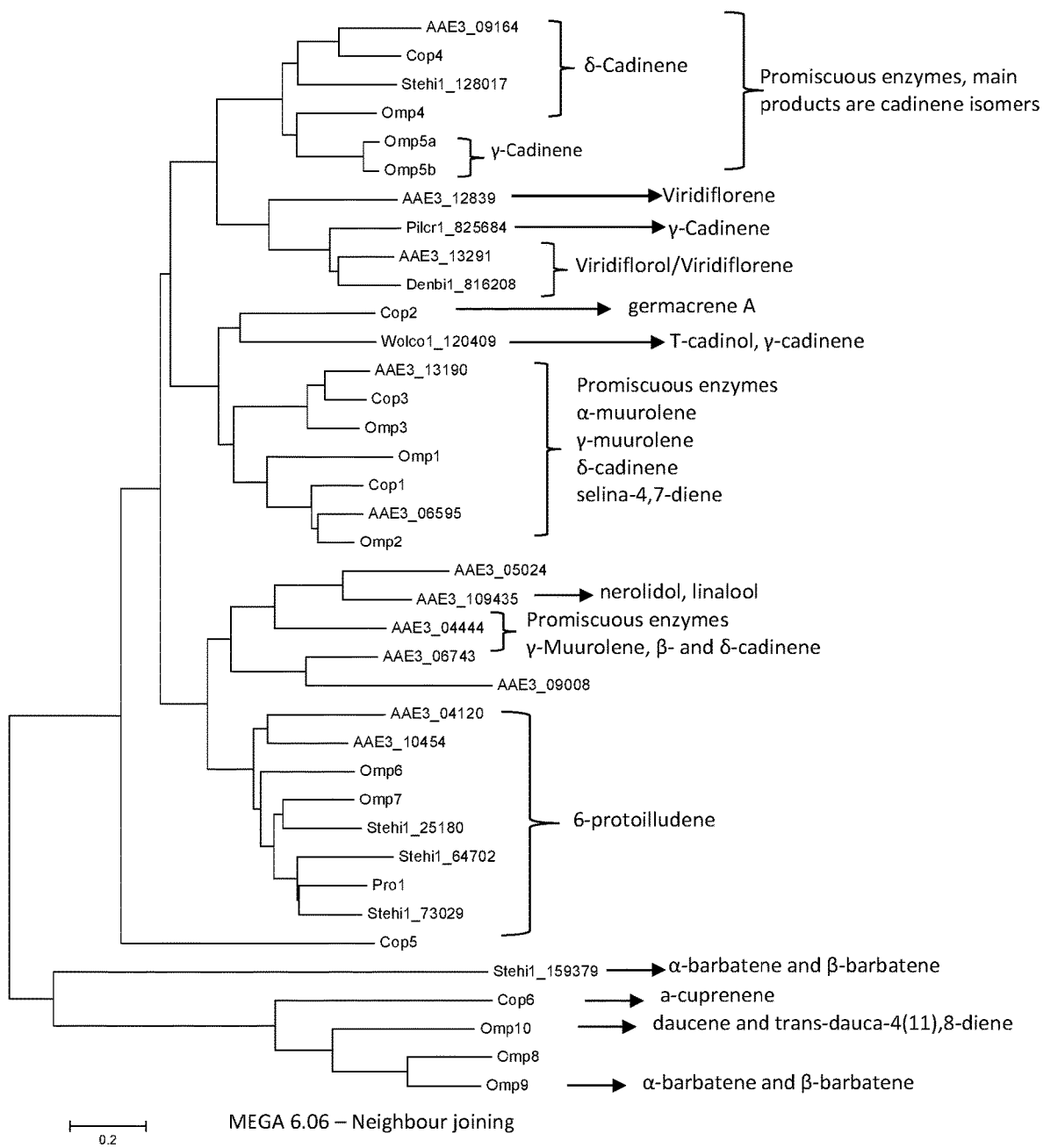
FIG. 13 shows the phylogenetics of characterized TPS homologues from four fungi. TPSs from *A. aegerita* (AAE3), *C. cinereus* (Cop), *O. olearius* (Omp), *Stereum hirsutum* (Stehi1) and the single TPS described from *Armillaria gallica* (Pro1). Sequences used in the final alignment can be found in Table 1. The TPSs highlighted with a square ("■") had no detected terpene products.

A wide variety of sesquiterpenes were detected for the *E. coli* culture expressing AAE3_09164 (SEQ ID NO: 30) (FIG. 7, FIG. 8 and Table 3). Among them, δ-cadinene 4 (37%) was main product, together with γ-muurolene 2 (15%), epizonarene[#](13%), epicubenol[#]10 (8%), α-cubebene[#](8%) and many uncharacterized minor products. In addition, cubebol (6.7%, Table 3) was detected by VFWAXms (but not by DB5 column) and verified by Cubeb essential oil (FIG. 10). Interesting, a noticeable amount of the monoterpene β-myrcene (10%, verified by authentic standard, FIG. 12) was detected in the headspace of AAE3_09164 culture, despite that the *E. coli* strain produced only little amount of the monoterpene precursor geranyl pyrophosphate (GPP). The results suggested AAE3_09164 could be a bi-functional enzyme that is able to use both FPP and GPP as substrates to synthesize sesquiterpenes and monoterpenes, respectively. Similar bi-functional TPSs were reported previously in the ascomycete family Hypoxylaceae, such as Hyp4, Hyp5 from *Hypoxylon* sp. and EC12-PGS from *Daldinia eschscholzii*. In the phylogenetic analysis of the deduced AAE3_09164 amino acid sequence clustered together with Cop4, Omp4 and Stehi1_128017 enzymes (FIG. 13). Indeed, all of these enzymes including AAE3_09164 are highly promiscuous enzymes with δ-cadinene 4 as a common major product.

The *E. coli* strain expressing AAE3_13190 (SEQ ID NO: 33) produced four major products, α-muurolene 5 (32%) and γ-muurolene 2 (22%), δ-cadinene 4 (24%) and δ-cadinol[#]8 (21%) (FIGS. 7, 8, 10 and 11 and Table 3). In addition, there were at least six other minor sesquiterpene products, including (−)-germacrene D (Table 3) and verified by verified by Cubeb essential oil (FIG. 10). According to phylogenetic clustering in FIG. 13, AAE3_13190 is closely related to Cop3 from *Coprinopsis cinerea* and Omp3 from *Omphalotus olearius*. Consistently, all of them produced α-muurolene 5 as the major product. The major product for the *E. coli* culture expressing AAE3_06595 (SEQ ID NO: 28) was δ-cadinene 4 (60% of total terpenes). In addition, a few minor sesquiterpene compounds were also detected for AAE3_06595 culture including γ-muurolene 2, β-selinene[#] and T-muurolor. The enzymes Cop1 and Omp2 are closely related to AAE3_06595. However, Omp2 was not functional in *E. coli*, and δ-cadinene 4 was only one minor product of Cop1 whose main product was β-elemene.

Figure 14:
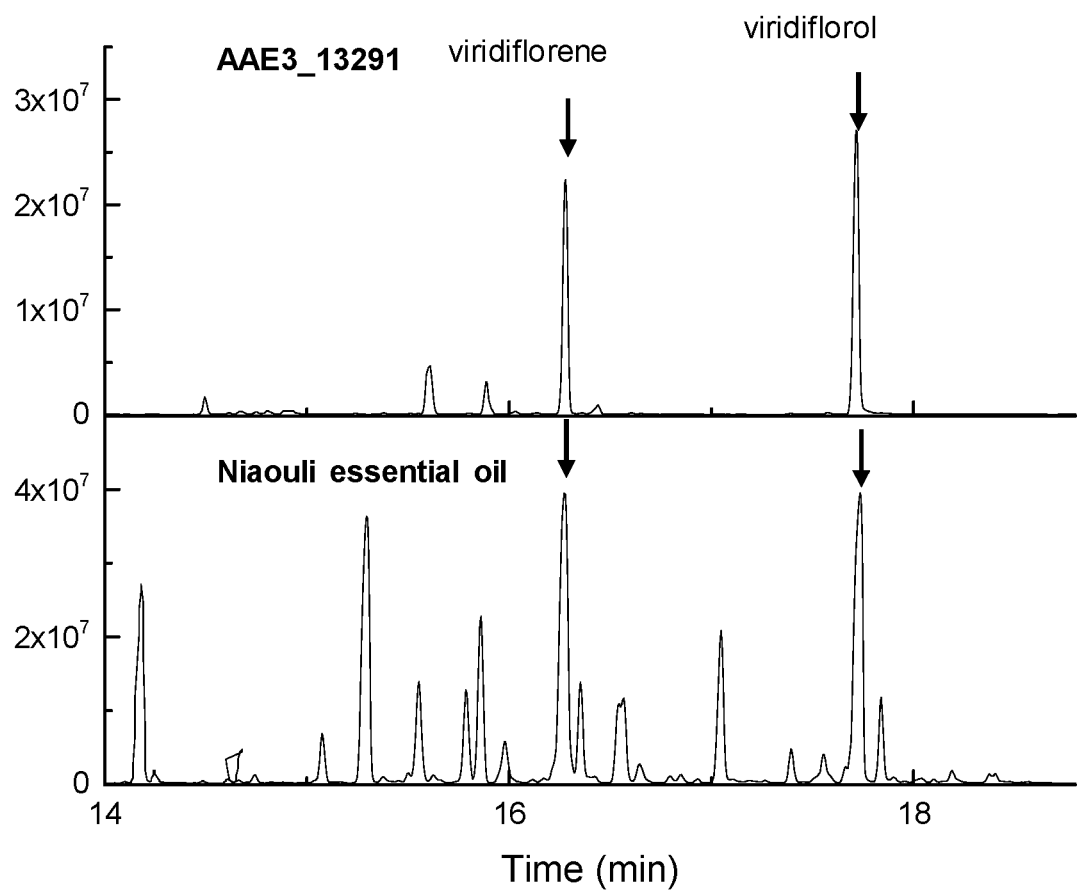
FIG. 14 shows the comparison of different GC columns for the analysis of terpenes. Niaouli essential oil was used as standards of viridiflorene 6 and viridiflorol 7. Viridiflorol 7 has relatively lower signal than viridiflorene 6 in DB-5 column as confirmed by authentic chemical standards from Santa Cruz Biotechnology (FIG. 17). The difference of relative intensity of viridiflorol and caryophyllene (structurally similar to viridiflorene) in DB-5 and VF-WAXms were further verified by authentic standards.
Figure 14:
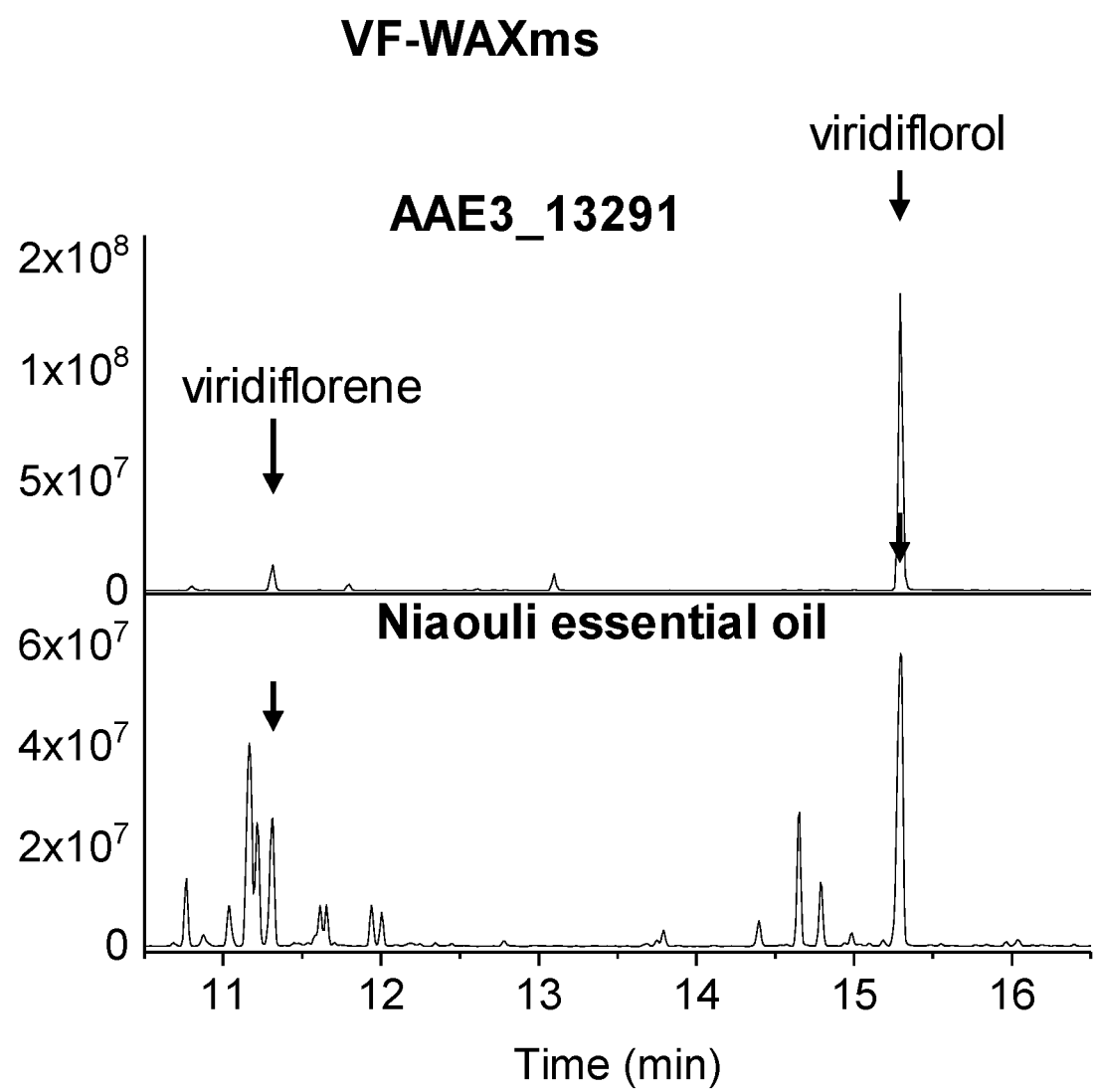

The major product of AAE3_12839 (SEQ ID NO: 34) was viridiflorene 6. In contrast, the *E. coli* strain expressing AAE3_13291 (SEQ ID NO: 32) produced viridiflorol 7 as the major product (viridiflorol 7 and viridiflorene 6 were confirmed by Niaouli essential oil, FIG. 14), with small amount of viridiflorene 6 (8.6% with VFWAXms in Table 3 and FIG. 8). Here, the data of VFWAXms column instead of DB5 column was used to quantify viridiflorol 7, as the quantification of viridiflorol 7 in DB5 was inaccurate with a significantly lower signal than viridiflorene 6 (FIG. 7 and Table 3). To our knowledge, no viridiflorene synthase or viridiflorol synthase has been reported in fungi. Even in plants, only six viridiflorene synthases were identified from *Solanum lycopersicum* and *Nicotiana tabacum* (Common tobacco). The alignment of AAE3_12839 and the tomato viridiflorene synthase indicated that there was limited sequence similarity (FIG. 15). Similarly, AAE3_13291 shares only 11% identity and less than 30% similarity with the viridiflorol synthase from *Melaleuca quinquenervia*, which is the only viridiflorol synthase reported so far (FIG. 16).

Figure 17:
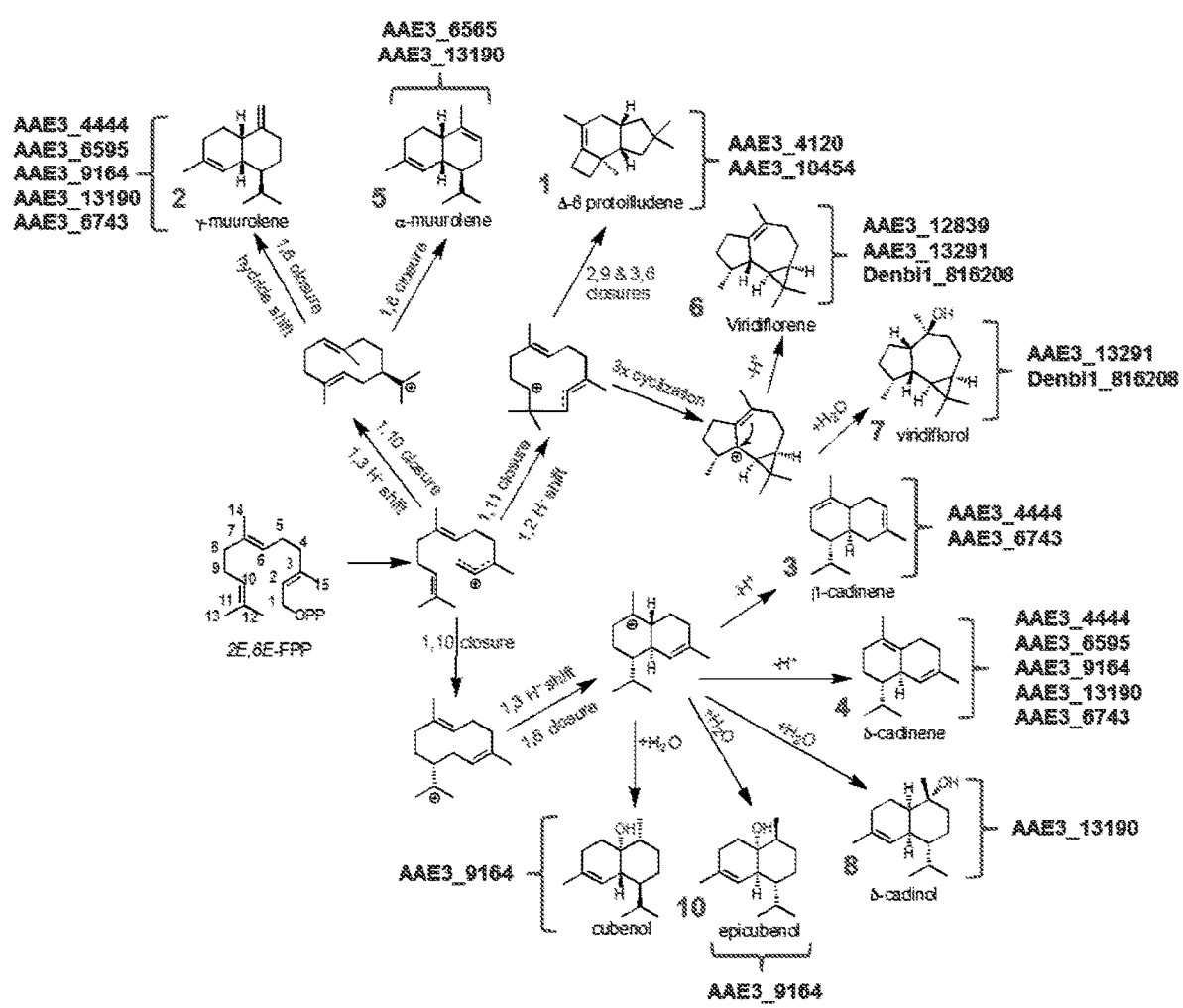
FIG. 17 shows the proposed reaction mechanisms for the formation of major products. The carbocation from FPP ionization undergoes two different primary ring closures (1,10 or 1,11 closure). Major compounds produced by recombinant *A. aegerita* TPSs are labelled by numbers, including Δ6-protolilludene 1, γ-muurolene 2, β-cadinene 3, δ-cadinene 4, α-muurolene 5, viridiflorene 6, viridiflorol 7, δ-cadinol 8 and epicubenol 10. See FIG. 5 for the mass spectra.

Furthermore, the identified TPSs in *A. aegerita* shared the same first cyclization step with TPSs in *C. cinerea* and *O. olearius*. For Δ-6-protoilludene synthase (AAE3_4120 (SEQ ID NO: 26) and AAE3_10454 (SEQ ID NO: 31)), viridiflorene synthase (AAE3_12839 (SEQ ID NO: 34)) and viridiflorol synthase (AAE3_13291 (SEQ ID NO: 32)), they all proceed through 1,11 cyclization of FPP to form tricyclic sesquiterpenes (FIG. 17). In contrast, other TPSs (AAE3_04444 (SEQ ID NO: 27), AAE3_6595 (SEQ ID NO: 28), AAE3_9164 (SEQ ID NO: 30), AAE3_13190 (SEQ ID NO: 33) and AAE3_6743 (SEQ ID NO: 29)) preferentially catalyze a 1,10 cyclization of FPP to form bicyclic sesquiterpenes.

Example 5

Analysis of Fungal Genome for TPS Functional Study

The results in FIGS. 7 and 13 reinforced that certain types of fungal TPSs have highly conserved sequences fortified by identical products, such as eight characterized Δ6-protoilludene synthases and four characterized δ-cadinene synthases. Thus, phylogenetic analysis provides a predictive framework to identify novel terpene synthases with novel or similar functions. The predictive accuracy of the model increases as the number of experimentally characterized TPSs accumulates. Previously, three of the Δ6-protoilludene synthases (Stehi1_25180, Stehi1_64702 and Stehi1_73029 from *S. hirsutum*) were correctly predicted and validated through bioinformatic analysis. Since then, the genomes of many new fungal species have been sequenced but their TPS genes have not been studied. Here, the aim was to establish a new predictive framework for the functional study of uncharacterized fungal TPSs with the new characterized *A. aegerita* TPSs and previously studied fungal TPSs. Through BLAST search in fungal genome database at the Joint Genome Institute (JGI, http://genome.jgi-psf.org/programs/fungi/index.jsf) and in The Universal Protein Resource (UniProt, http://www.uniprot.org/), about 2,000 putative TPS genes was uncovered. After a series of curation (as described in methods), a total of 1,408 putative TPSs from 85 Basidiomycota and 239 Ascomycota genomes were obtained (Table 4). On average, Basidiomycota have an average of 10-15 TPSs per genome (800 TPSs from 84 Basidiomycota) but about 80% Ascomycota have only 1-3 TPSs per genome (594 TPSs from 236 Ascomycota).

TABLE 4

The information about 1408 putative fungal TPSs in this study.

| Ascomycota | Basidiomycota |
|---|---|
| Aaosphaeria arxii | Agaricus bisporus |
| Aaoar1_459904 | Agabi_varbisH97_2_119105 |
| Acephala macrosclerotiorum | Agabi_varbisH97_2_144791 |
| Aciaci1_473652 | Agabi_varbisH97_2_149463 |
| Acremonium strictum | Agabi_varbisH97_2_195544 |
| Alternaria alternata | Agabi_varbisH97_2_73543 |
| Altal1_1080498 | Agabi_varbur_1_109605 |
| Alternaria brassicicola | Agabi_varbur_1_126555 |
| Altbr1_7288 | Agabi_varbur_1_130532 |
| Amniculicola lignicola | Agabi_varbur_1_46681 |
| Amnli1_450732 | Agabi_varbur_1_61902 |
| Amore1_23054 | Agabi_varbur_1_76352 |
| Ampelomyces quisqualis | Agabi_varbur_1_79290 |
| Ampqui1_550807 | Agrocybe aegerita |
| Anthostoma avocetta | AAE3_04120 |
| Antav1_377590 | AAE3_04444 |
| Antav1_383196 | AAE3_05024 |
| Antav1_400494 | AAE3_06595 |
| Antav1_445568 | AAE3_06743 |
| Antav1_446501 | AAE3_09008 |
| Antav1_453578 | AAE3_09164 |
| Antav1_468055 | AAE3_10454 |
| Antav1_472246 | AAE3_109435 |
| Antav1_476690 | AAE3_12839 |
| Antav1_484797 | AAE3_13190 |
| Antav1_504933 | AAE3_13291 |
| Apiospora montagnei | Agrocybe pediades |
| Apimo1_107765 | Agrped1_109003 |
| Apimo1_109481 | Agrped1_640059 |
| Aplosporella prunicola | Agrped1_665597 |
| Aplpr1_315168 | Agrped1_689671 |
| Arthrobotrys oligospora | Agrped1_689675 |
| Artol1_6616 | Agrped1_693394 |
| Arthroderma benhamiae | Agrped1_705454 |
| Artbe1_2427 | Agrped1_749682 |
| Ascocoryne sarcoides | Agrped1_804989 |
| Ascsa1_1273 | Agrped1_804996 |
| Ascsa1_6084 | Agrped1_820868 |
| Aspergillus aculeatinus | Amanita muscaria |
| Aspacu1_414218 | M378_161967 |
| Aspacu1_433825 | M378_167361 |
| Aspergillus brasiliensis | M378_181109 |
| Aspbr1_199648 | M378_186936 |
| Aspergillus brunneoviolaceus | M378_457656 |
| Aspbru1_469179 | M378_74452 |
| Aspergillus calidoustus | M378_78547 |
| Aspcal1_764165 | M378_9904 |
| Aspcal1_767797 | Armillaria gallica |
| Aspcal1_768162 | Pro1 |
| Aspcam1_281412 | Auricularia delicata |
| Aspcam1_337372 | Aurde1_106904 |
| Aspergillus carbonarius | Aurde1_129583 |
| Aspca3_517619 | Aurde1_138561 |
| Aspc11_4114 | Aurde1_166047 |
| Aspergillus costaricaensis | Aurde1_173663 |
| Aspcos1_212514 | Aurde1_56959 |
| Aspcos1_272862 | Aurde1_61813 |
| Aspergillus fijiensis | Aurde1_62781 |
| Aspfij1_393093 | Aurde1_73423 |
| Aspergillus flavus | Aurde1_73447 |
| Aspfl1_36410 | Aurde1_73578 |
| Aspergillus heteromorphus | Aurde1_75612 |
| Asphet1_431105 | Aurde1_81767 |
| Aspergillus homomorphus | Aurde1_90621 |
| Asphom1_411924 | Aurde1_97553 |
| Aspergillus ibericus | Auricularia subglabra |
| Aspibe1_454210 | AURDE_130623 |
| Aspergillus indologenus | Bjerkandera adusta |
| Aspind1_388535 | Bjead1_1_105488 |
| Aspergillus kawachii | Bjead1_1_117829 |
| Aspka1_1_17804 | Bjead1_1_156307 |
| Aspka1_1_20838 | Bjead1_1_158616 |
| Aspergillus lacticoffeatus | Bjead1_1_166045 |
| Asplac1_345547 | Bjead1_1_172777 |
| Asplac1_444313 | Bjead1_1_337295 |
| Aspergillus luchuensis | Bjead1_1_53082 |
| Aspfo1_40412 | Bjead1_1_54261 |
| Aspfo1_48364 | Bjead1_1_54262 |
| Aspfo1_701161 | Bjead1_1_64972 |
| Aspergillus neoniger | Botryobasidium botryosum |
| Aspneo1_451579 | Botbo1_115253 |
| Aspergillus niger | Botbo1_147563 |
| Aspni_bvT_1_291648 | Botbo1_150401 |
| Aspni_bvT_1_339193 | Botbo1_177898 |
| Aspni_DSM_1_158481 | Botbo1_189629 |
| Aspni_DSM_1_165991 | Botbo1_35044 |

TABLE 4-continued

The information about 1408 putative fungal TPSs in this study.

| | | | |
|---|---|---|---|
| Aspni_NRRL3_1_492 | Calocera cornea | Co1ac2_720284 | DAEQU_677968 |
| Aspni_NRRL3_1_8436 | CALC0_485200 | Co1ac2_722687 | DAEQU_696090 |
| Aspni_NRRL3_1_8732 | Calocera viscosa | Co1ac2_756572 | DAEQU_737681 |
| Aspni7_1085752 | CALVI_546272 | Colletotrichum caudatum | DAEQU_745062 |
| Aspni7_1155978 | CALVI_549316 | Colca1_582509 | DAEQU_769721 |
| Aspergillus nomius | CALVI_565570 | Colca1_613400 | DAEQU_811112 |
| Aspnom13137_1_4577 | Ceriporiopsis subvermispora | Colletotrichum cereale | Dendrothele bispora |
| Aspnom13137_1_5237 | Cersu1_100300 | Colce1_637756 | Denbi1_650172 |
| Aspnom13137_1_5921 | Cersu1_107906 | Colce1_710743 | Denbi1_654460 |
| Aspergillus novofumigatus | Cersu1_108146 | Colce1_751683 | Denbi1_659367 |
| Aspoch1432_1_2847 | Cersu1_113927 | Colce1_753190 | Denbi1_667929 |
| Aspergillus oryzae | Cersu1_114263 | Colletotrichum eremochloae | Denbi1_678334 |
| Aspor1_10090 | Cersu1_116249 | Coler1_553160 | Denbi1_689487 |
| Aspergillus phoenicis | Cersu1_126560 | Coler1_633162 | Denbi1_690253 |
| Aspph1_338445 | Cersu1_161387 | Coler1_645427 | Denbi1_692356 |
| Aspergillus piperis | Cersu1_162846 | Colletotrichum fioriniae | Denbi1_693874 |
| Asppip1_454731 | Cersu1_162851 | Colfi1_276541 | Denbi1_750040 |
| Aspergillus sclerotiicarbonarius | Cersu1_52233 | Colfi1_276864 | Denbi1_792287 |
| Aspscle1_371398 | Cersu1_71514 | Colfi1_283382 | Denbi1_816208 |
| Aspergillus steynii | Cersu1_78286 | Colfi1_285486 | Denbi1_818935 |
| Aspste1_453294 | Cersu1_83362 | Colfi1_288712 | Denbi1_824130 |
| Aspergillus terreus | Cersu1_85360 | Colletotrichum godetiae | Denbi1_855029 |
| Aspte1_5331 | Cersu1_95867 | Colgo1_546119 | Denbi1_866377 |
| Aspergillus udagawae | Cersu1_96486 | Colgo1_562331 | Denbi1_873510 |
| Aspuda1_1612 | Cersu1_98094 | Colgo1_645279 | Denbi1_896419 |
| Aspuda1_4266 | ter14 | Colgo1_696718 | Diaporthe helianthi |
| Aspergillus vadensis | Coniophora puteana | Colgo1_730749 | DHEL01_07884 |
| Aspvad1_340387 | Conpu1_102165 | Colletotrichum higginsianum | Dichomitus squalens |
| Aspvad1_341847 | Conpu1_102220 | Colhig2_12235 | Dicsq1_104353 |
| Aspwe1_186729 | Conpu1_118913 | Colhig2_13496 | Dicsq1_138476 |
| Aspwe1_691717 | Conpu1_137465 | Colhig2_6613 | Dicsq1_144469 |
| Aureobasidium pullulans | Conpu1_152083 | Colhig2_7207 | Dicsq1_146430 |
| Aurpu_var_mel1_89219 | Conpu1_155138 | Colhig2_9460 | Dicsq1_147637 |
| Baudoinia compniacensis | Conpu1_156845 | Collu1_212508 | Dicsq1_159719 |
| Bauco1_152112 | Conpu1_15871 | Collu1_590124 | Dicsq1_170641 |
| Bimuria novae-zelandiae | Conpu1_168606 | Collu1_79349 | Dicsq1_181048 |
| Biscogniauxia nummularia | Conpu1_170276 | Colletotrichum navitas | Dicsq1_57723 |
| Bisnum1_472611 | Conpu1_47697 | Colna1_600097 | Dicsq1_58025 |
| Bisnum1_480590 | Conpu1_50941 | Colna1_637650 | Dicsq1_63165 |
| Bisnum1_560481 | Conpu1_58009 | Colny1_1016018 | Dicsq1_80177 |
| Bisnum1_595288 | Conpu1_58901 | Colny1_1018170 | Dicsq1_80370 |
| Bisnum1_611126 | Conpu1_58994 | Colny1_1022050 | Dicsq1_86568 |
| Bisporella sp. | Conpu1_60451 | Colny1_1022440 | Exidia glandulosa |
| Bissp1_639301 | Conpu1_62719 | Colletotrichum orchidophilum | EXIGL_605329 |
| Bissp1_741721 | Conpu1_62911 | Color1_5151 | EXIGL_611671 |
| BcBOT2 | Conpu1_63003 | Color1_6973 | EXIGL_620059 |
| Bysci1_371003 | Conpu1_75631 | Color1_848 | EXIGL_664938 |
| Cadophora sp. | Conpu1_88505 | Colletotrichum phormii | EXIGL_673075 |
| Cadsp1_422591 | Conpu1_92191 | Colph1_306140 | EXIGL_673208 |
| Caloscypha fulgens | Coprinopsis cinerea | Colph1_417792 | EXIGL_677911 |
| Calful1_769187 | CC1G_03587 | Colph1_464784 | EXIGL_677941 |
| Capronia epimyces | Cop1 | Colph1_466218 | EXIGL_680198 |
| Capep1_3727 | Cop2 | Colph1_479875 | EXIGL_681577 |
| Chaetomium globosum | Cop3 | Colph1_516153 | EXIGL_688085 |
| CHGG_03509 | Cop4 | Colsa 1_939591 | EXIGL_713320 |
| Chalara longipes | Cop5 | Colsa 1_940033 | EXIGL_743228 |
| Chalo1_381634 | Cop6 | Colsa1_941201 | EXIGL_750528 |
| Chalo1_464358 | Cylindrobasidium torrendii | Colsa 1_942596 | EXIGL_767126 |
| Cladophialophora bantiana | CYLTO_347245 | Colsa 1_948955 | EXIGL_769607 |
| Claba1_132379 | CYLTO_369585 | Colsa 1_950600 | EXIGL_769609 |
| Cladophialophora psammophila | CYLTO_380537 | Colletotrichum simmondsii | EXIGL_770624 |
| Claps1_13034 | CYLTO_384541 | Colsi1_971930 | EXIGL_773846 |
| Cladorrhinum bulbillosum | CYLTO_400743 | Colsi1_972523 | EXIGL_831178 |
| Clabul1_1016528 | CYLTO_405471 | Colsi1_972624 | Fibroporia radiculosa |
| Clabul1_76434 | CYLTO_436484 | Colsi1_976172 | FIBRA_00633 |
| Clabul1_847239 | CYLTO_442632 | Colsi1_976953 | FIBRA_00800 |
| Clathrospora elynae | CYLTO_452977 | Colsi1_979039 | FIBRA_05385 |
| Clael1_510577 | CYLTO_453006 | Colsi1_981054 | FIBRA_05798 |
| Coccomyces strobi | Dacryopinax primogenitus | Colsi1_981282 | FIBRA_06228 |
| Cocst1_631366 | DACRY_34691 | Colsi1_983009 | FIBRA_06230 |
| CocheC4_1_36610 | Dacryopinax sp. | Colso1_559351 | FIBRA_06895 |
| CocheC5_3_10970 | Dacsp1_109687 | Colletotrichum sublineola | FIBRA_07171 |
| Cochliobolus miyabeanus | Dacsp1_81212 | Colsu1_648985 | FIBRA_07173 |
| Cocmi1_93348 | Dacsp1_96371 | Colsu1_724576 | Fibulorhizoctonia sp. |
| Cochliobolus sativus | Daedalea quercina | Colzo1_706815 | FIBSP_768030 |
| Cocsa1_348577 | DAEQU_261749 | Coniella sp | FIBSP_820394 |
| Colac2_589620 | DAEQU_662879 | Pilidi1_186199 | FIBSP_832548 |
| Co1ac2_693029 | DAEQU_663038 | Coniochaeta ligniaria | FIBSP_943511 |

TABLE 4-continued

The information about 1408 putative fungal TPSs in this study.

| | |
|---|---|
| Conli1_10674 | Fistulina hepatica |
| Conli1_1914 | FISHE_34696 |
| Conlig1_583628 | FISHE_45426 |
| Conlig1_658201 | FISHE_46267 |
| Coniochaeta sp. | FISHE_66255 |
| ConPMI546_932510 | Fomitiporia mediterranea |
| ConPMI546_934988 | Fomme1_105378 |
| Coniosporium apollinis | Fomme1_109318 |
| Conap1_98915 | Fomme1_112446 |
| Corollospora maritima | Fomme1_170128 |
| Corma2_707499 | Fomme1_17224 |
| Cryphonectria parasitica | Fomme1_27083 |
| Crypa2_343514 | Fomme1_80051 |
| Cryptodiaporthe populea | Fomme1_80204 |
| Crypo1_327771 | Fomme1_80444 |
| Crypo1_328559 | Fomme1_82079 |
| Crypo1_335598 | Fomme1_82792 |
| Crypo1_345542 | Fomme1_82811 |
| Crypo1_376330 | Fomme1_89798 |
| Crypo1_381328 | Fomme1_91806 |
| Crypo1_381563 | Fomme1_95393 |
| Crypo1_432491 | Fomme1_97061 |
| Crypo1_443797 | Fomitopsis pinicola |
| Crypo1_472123 | Fompi3_1017321 |
| Cucurbitaria berberidis | Fompi3_1017322 |
| Cucbe1_280026 | Fompi3_1023716 |
| Daldinia eschscholzii | Fompi3_1034271 |
| Da1EC12_1_12539 | Fompi3_110513 |
| Da1EC12_1_17536 | Fompi3_1118553 |
| Da1EC12_1_24646 | Fompi3_1118777 |
| Da1EC12_1_24764 | Fompi3_1120393 |
| Da1EC12_1_25458 | Fompi3_1137037 |
| Da1EC12_1_70183 | Fompi3_88169 |
| Decorospora gaudefroyi | Galerina marginata |
| Decga1_179458 | Galma_104215 |
| Delphinella strobiligena | Galma_1278404 |
| Delst1_202989 | Galma_1352301 |
| Delst1_230429 | Galma_137032 |
| Delst1_365307 | Galma_143861 |
| Diaporthe ampelina | Galma_222029 |
| Diaam1_7440 | Galma_223690 |
| Diaam1_7814 | Galma_225678 |
| Diaam1_8586 | Galma_229201 |
| Didymella zeae-maydis | Galma_245845 |
| Didma1_13214 | Galma_266794 |
| Didymocrea sadasivanii | Galma_62552 |
| Didsa1_432338 | Galma_63553 |
| Didsa1_459411 | Galma_63556 |
| Diplodia seriata | Galma_72334 |
| Dipse1_2018 | Galma_72397 |
| Dissoconium aciculare | Galma_78470 |
| Disac1_349444 | Ganoderma sp. |
| Dothidotthia symphoricarpi | Gansp1_106195 |
| Dotsy1_400389 | Gansp1_115598 |
| Endocarpon pusillum | Gansp1_116882 |
| EndpusZ1_8494 | Gansp1_118798 |
| EndpusZ1_8851 | Gansp1_119170 |
| Entoleuca mammata | Gansp1_126698 |
| Entma1_245693 | Gansp1_143866 |
| Entma1_278690 | Gansp1_147418 |
| Entma1_396117 | Gansp1_151250 |
| Entma1_410097 | Gansp1_151266 |
| Eutypa lata | Gansp1_151299 |
| Eutla1_2536 | Gansp1_155853 |
| Eutla1_3565 | Gansp1_164758 |
| Eutla1_5251 | Gansp1_166943 |
| Exophiala aquamarina | Gansp1_41036 |
| Exoaq1_8751 | Gansp1_57109 |
| Fonsecaea pedrosoi | Gansp1_57679 |
| Fonpe1_8054 | Gansp1_58158 |
| Fusarium fujikuroi | Gansp1_58881 |
| Ffsc4 | Gansp1_81688 |
| Ffsc6 | Gansp1_85736 |
| Fusfu1_1126 | Gloeophyllum trabeum |
| Fusfu1_11322 | Glotr1_1_103889 |
| Fusfu1_14268 | Glotr1_1_116237 |
| Fusfu1_2062 | Glotr1_1_117331 |
| Fusfu1_6471 | Glotr1_1_131990 |
| STC3 | Glotr1_1_47645 |
| STC5 | Glotr1_1_48290 |
| Fusarium graminearum | Glotr1_1_64172 |
| CLM1 | Glotr1_1_78472 |
| Fusgr1_10122 | Glotr1_1_79917 |
| Fusgr1_13217 | Glotr1_1_80390 |
| Fusgr1_2052 | Grifola frondosa |
| Fusgr1_4586 | COP3_0_A0H81_12697 |
| Fusgr1_548 | COP3_1_A0H81_08013 |
| Fusarium oxysporum | COP3_2_A0H81_10954 |
| Fusox2_10433 | COP3_5_A0H81_08017 |
| Fusox2_10434 | COP4_0_A0H81_07725 |
| Fusox2_10435 | COP4_1_A0H81_07728 |
| Fusox2_10673 | Gymnopus luxurians |
| Fusox2_10675 | Gymlu1_1012408 |
| Fusox2_8564 | Gymlu1_1024248 |
| Fusarium sporotrichioides | Gymlu1_152409 |
| FsTDS | Gymlu1_164402 |
| Fusarium verticillioides | Gymlu1_179557 |
| Fusve2_12377 | Gymlu1_181084 |
| Fusve2_1423 | Gymlu1_239618 |
| Fusve2_19 | Gymlu1_240529 |
| Fusve2_20 | Gymlu1_242070 |
| Fusve2_8588 | Gymlu1_249731 |
| Fusve2_8699 | Gymlu1_249732 |
| Glomerella acutata | Gymlu1_257858 |
| Gloac1_1349405 | Gymlu1_266288 |
| Gloac1_1383433 | Gymlu1_474275 |
| Gloac1_1413417 | Gymlu1_70394 |
| Gloac1_1624359 | Gymlu1_74039 |
| Gloac1_1638878 | Gymlu1_775187 |
| Glomerella cingulata | Hebeloma cylindrosporum |
| Gloci1_1722638 | M413_27416 |
| Gloci1_1750922 | M413_32803 |
| Gloci1_1755285 | M413_415200 |
| Gloci1_1819074 | M413_443011 |
| Gloci1_1825757 | M413_7659 |
| Gloci1_1830608 | M413_83524 |
| Gloci1_1835014 | Heterobasidion annosum |
| Gloci1_1852737 | Hetan2_115814 |
| Glonium stellatum | Hetan2_148791 |
| Glost2_424907 | Hetan2_167573 |
| Gremmeniella abietina | Hetan2_169607 |
| Greab1_222029 | Hetan2_172256 |
| Greab1_510929 | Hetan2_181194 |
| Grosmannia clavigera | Hetan2_34201 |
| CMQ_352 | Hetan2_382802 |
| Grocl1_2976 | Hetan2_382866 |
| Grocl1_8310 | Hetan2_42859 |
| Gymnascella aurantiaca | Hetan2_446121 |
| Gymau1_124723 | Hetan2_454193 |
| Gymau1_163306 | Hetan2_458479 |
| Gymnascella citrina | Hetan2_48772 |
| Gymci1_1_287288 | Hetan2_51706 |
| Gyromitra esculenta | Hydnomerulius pinastri |
| Gyresc1_452646 | HYDPI_175348 |
| Gyresc1_614921 | HYDPI_90513 |
| Hirsutella minnesotensis | HYDPI_93448 |
| HIM_03781 | HYDPI_95823 |
| Hymenoscyphus varicosporoides | Hypholoma sublateritium |
| Hymvar1_186372 | HYPSU_151315 |
| Hymvar1_433677 | Hypsu1_138166 |
| Hymvar1_527573 | Hypsu1_138665 |
| Hymvar1_530070 | Hypsu1_148365 |
| Hymvar1_530714 | Hypsu1_148385 |
| Hypoxylon sp. | Hypsu1_159396 |
| Hyp1 | Hypsu1_202683 |
| Hyp2 | Hypsu1_205915 |
| Hyp3 | Hypsu1_36467 |
| Hyp4 | Hypsu1_47068 |
| Hyp5 | Hypsu1_80866 |
| HypCI4A_1_20984 | Hypsu1_92421 |
| HypCI4A_1_216497 | Hypsizygus marmoreus |
| HypCI4A_1_322581 | COP3_1_Hypma_09878 |
| HypCI4A_1_59230 | COP3_2_Hypma_09820 |
| HypCI4A_1_6706 | COP4_Hypma_01074 |
| HypCI4A_1_69724 | Jaapia argillacea |
| HypCI4A_1_7067 | Jaaar1_125196 |

TABLE 4-continued

The information about 1408 putative fungal TPSs in this study.

| | |
|---|---|
| HypCO275_1_269219 | Jaaar1_129042 |
| HypCO275_1_31178 | Jaaar1_162104 |
| HypCO275_1_392541 | Jaaar1_191378 |
| HypCO275_1_397991 | Jaaar1_192672 |
| HypEC38_3_102477 | Jaaar1_206626 |
| HypEC38_3_372695 | Jaaar1_35337 |
| HypEC38_3_409185 | Jaaar1_453389 |
| HypEC38_3_424147 | Jaaar1_47108 |
| HypEC38_3_436214 | Jaaar1_487951 |
| Ilyonectria robusta | Jaaar1_62046 |
| Ilyrob1_438077 | Laccaria amethystina |
| Ilyrob1_458205 | K443_108732 |
| Ilyrob1_462532 | K443_126876 |
| Ilyonectria sp. | K443_309839 |
| Ilysp1_1486196 | K443_619353 |
| Ilysp1_1873426 | K443_681798 |
| Kalaharituber pfeilii | K443_99583 |
| Kalpfe1_784829 | Laccaria bicolor |
| Kalpfe1_789340 | LACBI_312850 |
| Karstenula rhodostoma | LACBI_326872 |
| Karrh1_427857 | Lacbi1_297082 |
| Karrh1_478359 | Lacbi1_307420 |
| Khuskia oryzae | Lacbi1_307559 |
| Khuory1_125966 | Lacbi1_307631 |
| Khuory1_156064 | Lacbi1_308775 |
| Khuory1_357319 | Lacbi1_310816 |
| Khuory1_456225 | Lacbi1_327169 |
| Khuory1_483548 | Lacbi1_331339 |
| Khuory1_495123 | Lacbi1_333748 |
| Lecythophora sp. | Laetiporus sulphureus |
| LecAK0013_1_225655 | LAESU_64487 |
| LecAK0013_1_337743 | LAESU_657286 |
| LecAK0013_1_358472 | LAESU_657700 |
| Lentithecium fluviatile | LAESU_682207 |
| Lenfl1_319520 | LAESU_706375 |
| Leptodontium sp. | LAESU_724692 |
| Leptod1_444196 | LAESU_736295 |
| Leptod1_455689 | LAESU_739029 |
| Leptod1_476038 | LAESU_754774 |
| Leptosphaeria maculans | LAESU_760769 |
| Lepmu1_308 | LAESU_760772 |
| Lindgomyces ingoldianus | LAESU_97217 |
| Linin1_380217 | Lentinula edodes |
| Lobaria pulmonaria | LENED_000675 |
| Lobpul1_1077425 | LENED_009785 |
| Lobpul1_1081061 | LENED_011156 |
| Lobpul1_1086700 | Leucoagaricus sp. |
| Lobpul1_1088690 | AN958_00679 |
| Lobpul1_1160659 | AN958_01976 |
| Lobpul1_1160823 | AN958_05697 |
| Lobpul1_1187714 | AN958_05837 |
| Lobpul1_1189558 | AN958_08196 |
| Lobpul1_1267101 | AN958_09576 |
| Lobpul1_1326505 | AN958_09577 |
| Lophiotrema nucula | AN958_11218 |
| Lopnu1_203111 | AN958_11219 |
| Lopnu1_576877 | AN958_12529 |
| Lopnu1_603805 | Moniliophthora perniciosa |
| Lophium mytilinum | MPER_03050 |
| Lopmy1_551480 | Moniliophthora roreri |
| Loramyces juncicola | Moror_10387 |
| Lorju1_472231 | Moror_10832 |
| Lorju1_513685 | Moror_11443 |
| Loramyces macrosporus | Moror_14186 |
| Lorma1_320020 | Moror_15644 |
| Lorma1_437337 | Moror_4213 |
| Lorma1_614065 | WG66_11919 |
| Macrophomina phaseolina | WG66_12445 |
| Macph1_8897 | WG66_17918 |
| Macroventuria anomochaeta | WG66_18074 |
| Macan1_446477 | WG66_18690 |
| Magnaporthe grisea | WG66_18985 |
| Maggr1_110458 | WG66_354 |
| Maggr1_111240 | WG66_8033 |
| Mariannaea sp. | Mycena chlorophos |
| MarPMI226_411544 | MCHLO_03985 |
| Marssonina brunnea | MCHLO_05513 |
| Marbr1_4753 | MCHLO_07787 |
| Massariosphaeria phaeospora | MCHLO_08688 |
| Masph1_606827 | MCHLO_13355 |
| Melanconium sp. | Neolentinus lepideus |
| Melsp1_127340 | NEOLE_1114180 |
| Melsp1_95914 | NEOLE_1127484 |
| Melanomma pulvis-pyrius | NEOLE_1129527 |
| Melpu1_277550 | NEOLE_1133313 |
| Melpu1_347683 | NEOLE_1153406 |
| Melanospora tiffanyae | NEOLE_1157631 |
| Melti1_461564 | NEOLE_1157743 |
| Meliniomyces bicolor | NEOLE_1180214 |
| Melbi2_645837 | NEOLE_1181640 |
| Meliniomyces variabilis | NEOLE_134104 |
| Melva1_455976 | NEOLE_318499 |
| Metarhizium robertsii | NEOLE_467896 |
| Metro1_2405 | NEOLE_632413 |
| Metro1_3595 | Omphalotus olearius |
| Metro1_6916 | Omp1 |
| Metro1_9225 | Omp10 |
| Microdochium bolleyi | Omp2 |
| Micbo1_128564 | Omp3 |
| Micbo1_13978 | Omp4 |
| Micbo1_151202 | Omp5a |
| Micbo1_158522 | Omp5b |
| Micbo1_181072 | Omp6 |
| Micbo1_186092 | Omp7 |
| Microdochium trichocladiopsis | Omp8 |
| Mictri1_125659 | Omp9 |
| Mictri1_260337 | Ophiostoma piceae |
| Mictri1_335184 | F503_01342 |
| Mictri1_375638 | Ophpic1_6625 |
| Mictri1_422579 | Paxillus involutus |
| Microsporum canis | Paxin1_101514 |
| Micca1_2230 | Paxin1_12806 |
| Myrothecium inundatum | Paxin1_137577 |
| Myrin1_398933 | Paxin1_167348 |
| Myrin1_546039 | Paxin1_176239 |
| Nectria haematococca | Paxin1_180528 |
| Necha2_74943 | Paxin1_181593 |
| Neofusicoccum parvum | Paxin1_18633 |
| Neopa1_3315 | Paxin1_77896 |
| Neopa1_4144 | Paxin1_83937 |
| Neopa1_7973 | Paxin1_86018 |
| Neosartorya fischeri | Paxillus rubicundulus |
| Neofi1_2116 | PAXRU_23853 |
| Niesslia exilis | PAXRU_642577 |
| Nieex1_76034 | Peniophora sp. |
| Oidiodendron maius | PENSP_572593 |
| OIDMA_107833 | PENSP_601208 |
| Oidma1_107833 | PENSP_625629 |
| Ophiobolus disseminans | PENSP_626963 |
| Ophdi1_289928 | PENSP_636610 |
| Ophdi1_418300 | PENSP_682634 |
| Ophdi1_58500 | PENSP_706592 |
| Ophiostoma novo-ulmi | PENSP_749173 |
| Ophnu1_1985851 | PENSP_755041 |
| Paracoccidioides brasiliensis | Phanerochaete chrysosporium |
| Parbr1_1519 | Phaca1_125341 |
| Parbra1_1841 | Phaca1_139052 |
| Paraconiothyrium sporulosum | Phaca1_197990 |
| Parsp1_1201140 | Phaca1_211240 |
| Parsp1_1217178 | Phaca1_211244 |
| Penicillium bilaiae | Phaca1_211256 |
| Penbi1_460541 | Phaca1_211257 |
| Penicillium brevicompactum | Phaca1_251936 |
| Penbr2_53488 | Phaca1_259972 |
| Penicillium canescens | Phaca1_89483 |
| Penca1_224374 | Phlebia brevispora |
| Penicillium chrysogenum | Phchr1_1815 |
| Pench1_25529 | Phchr1_3165 |
| Pench1_6764 | Phchr1_3229 |
| PenchWisc1_1_144631 | Phchr1_4239 |
| Penicillium digitatum | Phchr1_4445 |
| Pendi1_59 | Phlbr1_146388 |
| Pendi1_8028 | Phlbr1_146389 |
| Penicillium expansum | Phlbr1_148542 |
| Penex1_331919 | Phlbr1_152186 |
| Penex1_423287 | Phlbr1_153007 |

TABLE 4-continued

The information about 1408 putative fungal TPSs in this study.

| | | | |
|---|---|---|---|
| Penicillium janthinellum | Phlbr1_18034 | Rhizoscyphus ericae | Pospl1_95481 |
| Penja1_454093 | Phlbr1_27358 | Rhier1_616313 | Pospl1_97252 |
| Penicillium lanosocoeruleum | Phlbr1_71918 | Rhier1_704713 | Pospl1_98072 |
| Penla1_395992 | Phlbr1_75447 | Rhytidhysteron rufulum | Pospl1_99496 |
| Penicillium oxalicum | Phlbr1_83077 | Rhyru1_1_114183 | Punctularia strigosozonata |
| Penox1_1709 | Phlbr1_89160 | Rhyru1_1_114682 | Punst1_108886 |
| Penicillium roqueforti | Phlebia centrifuga | Rhyru1_1_116218 | Punst1_134752 |
| PrARS | PHLCEN_10709 | Sarcoscypha coccinea | Punst1_135766 |
| Penicillium thymicola | PHLCEN_10849 | Sarco1_413089 | Punst1_136240 |
| Penth1_227129 | PHLCEN_10850 | Sarco1_477087 | Punst1_138799 |
| Periconia macrospinosa | Phlebiopsis gigantea | Sarco1_533638 | Punst1_146877 |
| Perma1_640487 | Phlgi1_103744 | Septoria musiva | Punst1_45005 |
| Perma1_643878 | Phlgi1_114823 | Sepmu1_150980 | Punst1_61346 |
| Perma1_662832 | Phlgi1_12454 | Sepmu1_51031 | Punst1_62271 |
| Perma1_709192 | Phlgi1_126738 | Septoria populicola | Punst1_69007 |
| Pestalotiopsis fici | Phlgi1_157711 | Seppo1_112324 | Punst1_69869 |
| PFICI_04870 | Phlgi1_359064 | Seppo1_36729 | Pycnoporus cinnabarinus |
| Phaeosphaeriaceae sp. | Phlgi1_367715 | Setosphaeria turcica | BN946_scfl84637.g2 |
| PhaPMI808_630607 | Phlgi1_80906 | Settu1_155455 | BN946_scfl84747.g24 |
| PhaPMI808_701240 | Piloderma croceum | Sporothrix brasiliensis | BN946_scfl84790.g3 |
| PhaPMI808_718099 | Pilcr_14594 | SPBR_04258 | BN946_scfl84934.g16 |
| Phialocephala scopiformis | Pilcr_779936 | Sporothrix schenckii | BN946_scfl84940.g8 |
| LY89_757172 | Pilcr_810716 | HMPREF1624_08272 | BN946_scfl84945.g13 |
| Phisc1_722991 | Pilcr_81088 | Stagonospora nodorum | BN946_scfl84945.g9 |
| Phisc1_731760 | Pilcr_825684 | Stano2_10081 | Rhizoctonia solani |
| Phisc1_779859 | Pilcr_828668 | Stano2_10963 | RSOL_092870 |
| Phialocephala subalpina | Pilcr_98986 | Stagonospora sp. | RSOL_312180 |
| PAC_01018 | Pisolithus microcarpus | Stasp1_218798 | RSOL_403460 |
| Phoma tracheiphila | PISMI_111694 | Stasp1_378012 | RSOL_403680 |
| Photr1_393361 | PISMI_546554 | Symbiotaphrina kochii | RSOL_510110 |
| Phyllosticta capitalensis | PISMI_636067 | Symko1_913078 | RSOLAG22IIIB_02130 |
| Phycap1_294755 | PISMI_642487 | Talaromyces marneffei | RSOLAG22IIIB_06073 |
| Phycap1_350841 | PISMI_88043 | Talma1_2_9490 | RSOLAG22IIIB_08057 |
| Phyllosticta citriasiana | Pisolithus tinctorius | Talaromyces proteolyticus | RSOLAG22IIIB_09566 |
| Phycit1_361908 | M404_137874 | Talpro1_398870 | RSOLAG22IIIB_09570 |
| Phyllosticta citribraziliensis | M404_170039 | Talaromyces stipitatus | RSOLAG22IIIB_09739 |
| Phcit1_228662 | M404_29719 | Talst1_2_11311 | V565_056500 |
| Phcit1_230456 | M404_471194 | Teratosphaeria nubilosa | V565_214290 |
| Phyllosticta citricarpa | Pleurotus ostreatus | Ternu1_346415 | Rhizopogon vesiculosus |
| Phycitr1_625980 | PleosPC15_2_1039734 | Thielavia antarctica | AZE42_03256 |
| Phyllosticta sp. | PleosPC15_2_1041418 | Thian1_441220 | AZE42_03257 |
| Phy27169_293752 | PleosPC15_2_1046456 | Thielavia appendiculata | AZE42_03950 |
| Phy27169_350519 | PleosPC15_2_1047596 | Thiap1_653559 | AZE42_04671 |
| Phycpc1_413892 | PleosPC15_2_1048495 | Thielavia arenaria | AZE42_04965 |
| Phycpc1_489935 | PleosPC15_2_1060726 | Thiar1_832266 | AZE42_07544 |
| Plectania melastoma | PleosPC15_2_1061909 | Thielavia terrestris | AZE42_08339 |
| Plemel1_334852 | PleosPC15_2_1073415 | Thite2_2110120 | AZE42_08340 |
| Plemel1_353228 | PleosPC15_2_1098067 | Thozetella sp. | AZE42_08772 |
| Plemel1_396069 | PleosPC15_2_1106708_ | ThoPMI491_1_727832 | AZE42_08877 |
| Plemel1_527840 | PleosPC15_2_155013 | Trematosphaeria pertusa | AZE42_10031 |
| Plemel1_530055 | PleosPC15_2_160242 | Trepe1_605244 | AZE42_10033 |
| Plemel1_533333 | PleosPC15_2_161354 | Trichoderma asperellum | AZE42_12242 |
| Plectosphaerella cucumerina | PleosPC15_2_30147 | Trias1_142130 | Rhizopogon vinicolor |
| Plecu1_445621 | PleosPC15_2_50572 | Trias1_53311 | K503_537004 |
| Pleomassaria siparia | Plicaturopsis crispa | Triasp1_109551 | K503_537037 |
| Plesi1_495074 | PLICR_119075 | Triasp1_373402 | K503_696597 |
| Podospora anserina | Polyporus brumalis | Triasp1_382539 | K503_699336 |
| Podan2_5388 | TPS | Trichoderma atroviride | K503_740792 |
| Podan2_5672 | Postia placenta | Triat2_210728 | K503_767681 |
| Podospora curvicola | POSPL_38764 | Triat2_321366 | K503_783219 |
| Podcur1_279887 | Pospl1_101754 | Triat2_86577 | K503_790659 |
| Podcur1_310174 | Pospl1_105496 | Trichoderma citrinoviride | K503_791387 |
| Podcur1_326203 | Pospl1_106438 | Trici4_1108149 | K503_849799 |
| Podcur1_408089 | Pospl1_106440 | Trici4_66121 | Schizophyllum commune |
| Pseudographis elatina | Pospl1_125960 | Trichoderma guizhouense | Schco1_15679 |
| Pseel1_2508 | Pospl1_125961 | A0O28_0096870 | Schco1_17515 |
| Pseudomassariella vexata | Pospl1_128412 | Trichoderma harzianum | Schco1_55597 |
| Pseve2_338773 | Pospl1_130417 | THAR02_10331 | Schizopora paradoxa |
| Pseve2_344074 | Pospl1_24705 | Triha1_502236 | SCHPA_385230 |
| Pseve2_354204 | Pospl1_44163 | Triha1_523651 | SCHPA_600612 |
| Pseudovirgaria hyperparasitica | Pospl1_45581 | Triha1_74633 | SCHPA_600636 |
| Psehy1_445678 | Pospl1_46699 | Trihar1_48270 | SCHPA_626535 |
| Psehy1_496475 | Pospl1_59374 | Trihar1_691238 | SCHPA_825685 |
| Purpureocillium sp. | Pospl1_60326 | Trihar1_819783 | SCHPA_828532 |
| Pursp1_260473 | Pospl1_87954 | Trihar1_844963 | SCHPA_828604 |
| Pursp1_363397 | Pospl1_89105 | Trichoderma longibrachiatum | SCHPA_890331 |
| Pyrenochaeta sp. | Pospl1_91093 | Trilo3_1442452 | SCHPA_893708 |
| Pyrsp1_595056 | Pospl1_92799 | Trilo3_1456582 | SCHPA_894889 |

TABLE 4-continued

The information about 1408 putative fungal TPSs in this study.

| | |
|---|---|
| Trichoderma reesei | SCHPA_910670 |
| Trire2_112028 | SCHPA_931668 |
| Trire2_59597 | SCHPA_938296 |
| Trire2_68401 | SCHPA_940716 |
| TrireRUTC30_1_12695 | SCHPA_940718 |
| TrireRUTC30_1_75235 | SCHPA_940719 |
| Trichoderma virens | SCHPA_943858 |
| TriviGv29_8_2_187786 | SCHPA_944256 |
| TriviGv29_8_2_222187 | Scleroderma citrinum |
| TriviGv29_8_2_41289 | SCLCI_100351 |
| Trichophaea hybrida | SCLCI_1207283 |
| Trihyb1_876524 | SCLCI_12509 |
| Trichophyton rubrum | SCLCI_134791 |
| Triru1_8324 | Serendipita indica |
| Trichophyton verrucosum | PIIN_06735 |
| Triver1_4178 | Serendipita vermifera |
| Trypethelium eluteriae | M408_327964 |
| Tryvi1_496934 | Serpula lacrymans |
| Usnea florida | cyc6_SERLA_441878 |
| Usnflo1_55552 | SerlaS7_3_2_108414 |
| Usnflo1_574162 | SerlaS7_3_2_108585 |
| Usnflo1_877966 | SerlaS7_3_2_165924 |
| Usnflo1_901038 | SerlaS7_3_2_175395 |
| Usnflo1_955721 | SerlaS7_3_2_187364 |
| Venturia pirina | SerlaS7_3_2_61540 |
| Venpi1_211509 | SerlaS7_3_2_90456 |
| Venpi1_218661 | SerlaS7_3_2_94439 |
| Wilcoxina mikolae | Sistotremastrum niveocremeum |
| Wilmi1_425792 | SISNI_412344 |
| Xylaria hypoxylon | SISNI_413094 |
| Xylhyp1_472420 | SISNI_417792 |
| Xylhyp1_503745 | SISNI_419019 |
| Xylhyp1_529710 | SISNI_419037 |
| Xylhyp1_540106 | SISNI_420386 |
| Xylhyp1_540898 | SISNI_437403 |
| Xylhyp1_549956 | SISNI_445623 |
| Xylhyp1_569642 | SISNI_446492 |
| Xylhyp1_576955 | SISNI_455901 |
| Xylhyp1_588565 | SISNI_475911 |
| Xylhyp1_614361 | SISNI_482322 |
| Xylariales sp. | SISNI_486677 |
| XylPMI506_151792 | SISNI_490653 |
| XylPMI506_435412 | SISNI_511593 |
| XylPMI506_469434 | SISNI_511679 |
| XylPMI506_473008 | SISNI_534675 |
| XylPMI506_478051 | Sistotremastrum suecicum |
| Zymoseptoria ardabiliae | SISSU_1009262 |
| Zymar1_773224 | SISSU_1027225 |
| Zymoseptoria pseudotritici | SISSU_1035907 |
| Zymps1_798041 | SISSU_1035914 |
| | SISSU_1052084 |
| | SISSU_1061476 |
| | SISSU_1062338 |
| | SISSU_1062347 |
| | SISSU_1065756 |
| | SISSU_1067234 |
| | SISSU_1069491 |
| | SISSU_1132250 |
| | SISSU_138780 |
| | SISSU_221655 |
| | SISSU_992550 |
| | SISSU_993764 |
| | Sphaerobolus stellatus |
| | Sphst_181402 |
| | Sphst_184320 |
| | Sphst_192154 |
| | Sphst_255906 |
| | Sphst_255948 |
| | Sphst_266313 |
| | Sphst_266350 |
| | Sphst_47084 |
| | Sphst_55620 |
| | Sphst_68403 |
| | Sphst_785590 |
| | Stereum hirsutum |
| | STEHI_69906 |
| | Stehi1_111121 |
| | Stehi1_128017 |

| |
|---|
| Stehi1_146390 |
| Stehi1_155443 |
| Stehi1_159379 |
| Stehi1_161672 |
| Stehi1_167646 |
| Stehi1_25180 |
| Stehi1_45387 |
| Stehi1_50042 |
| Stehi1_52743 |
| Stehi1_64702 |
| Stehi1_70268 |
| Stehi1_73029 |
| Suillus luteus |
| CY34_184278 |
| CY34_23707 |
| CY34_71869 |
| CY34_799377 |
| CY34_801563 |
| CY34_80413 |
| CY34_81655 |
| Termitomyces sp. |
| J132_01558 |
| J132_02641 |
| J132_04009 |
| J132_04469 |
| J132_04694 |
| J132_04698 |
| J132_05842 |
| J132_07850 |
| J132_08389 |
| J132_09198 |
| J132_09201 |
| J132_09437 |
| J132_09567 |
| J132_09570 |
| J132_09647 |
| J132_09686 |
| J132_09687 |
| J132_10181 |
| J132_11041 |
| Thanatephorus cucumeris |
| BN14_00857 |
| BN14_03718 |
| RSOLAG1IB_02393 |
| RSOLAG1IB_05967 |
| RSOLAG1IB_05988 |
| RSOLAG1IB_06038 |
| Trametes pubescens |
| TRAPUB_14195 |
| TRAPUB_4416 |
| TRAPUB_4417 |
| TRAPUB_6039 |
| TRAPUB_6042 |
| TRAPUB_7379 |
| TRAPUB_9141 |
| Trametes versicolor |
| Trave1_118176 |
| Trave1_119121 |
| Trave1_122204 |
| Trave1_124930 |
| Trave1_125681 |
| Trave1_167198 |
| Trave1_169091 |
| Trave1_20994 |
| Trave1_30977 |
| Trave1_35003 |
| Trave1_44143 |
| Trave1_47002 |
| Trave1_47003 |
| Trave1_47026 |
| Trave1_75578 |
| Tulasnella calospora |
| M407_214286 |
| M407_214353 |
| M407_49795 |
| M407_51027 |
| M407_66752 |
| M407_70959 |

TABLE 4-continued

The information about 1408 putative fungal TPSs in this study.

M407_78466
Wolfiporia cocos
Wolco1_117435
Wolco1_120409
Wolco1_133798
Wolco1_134393
Wolco1_145847
Wolco1_150507
Wolco1_15395
Wolco1_162429
Wolco1_61127
Wolco1_62102
Wolco1_63709
Wolco1_70381
Wolco1_72514
Wolco1_72849
Wolco1_89832
Wolco1_95045
Wolco1_95361

Figure 18:
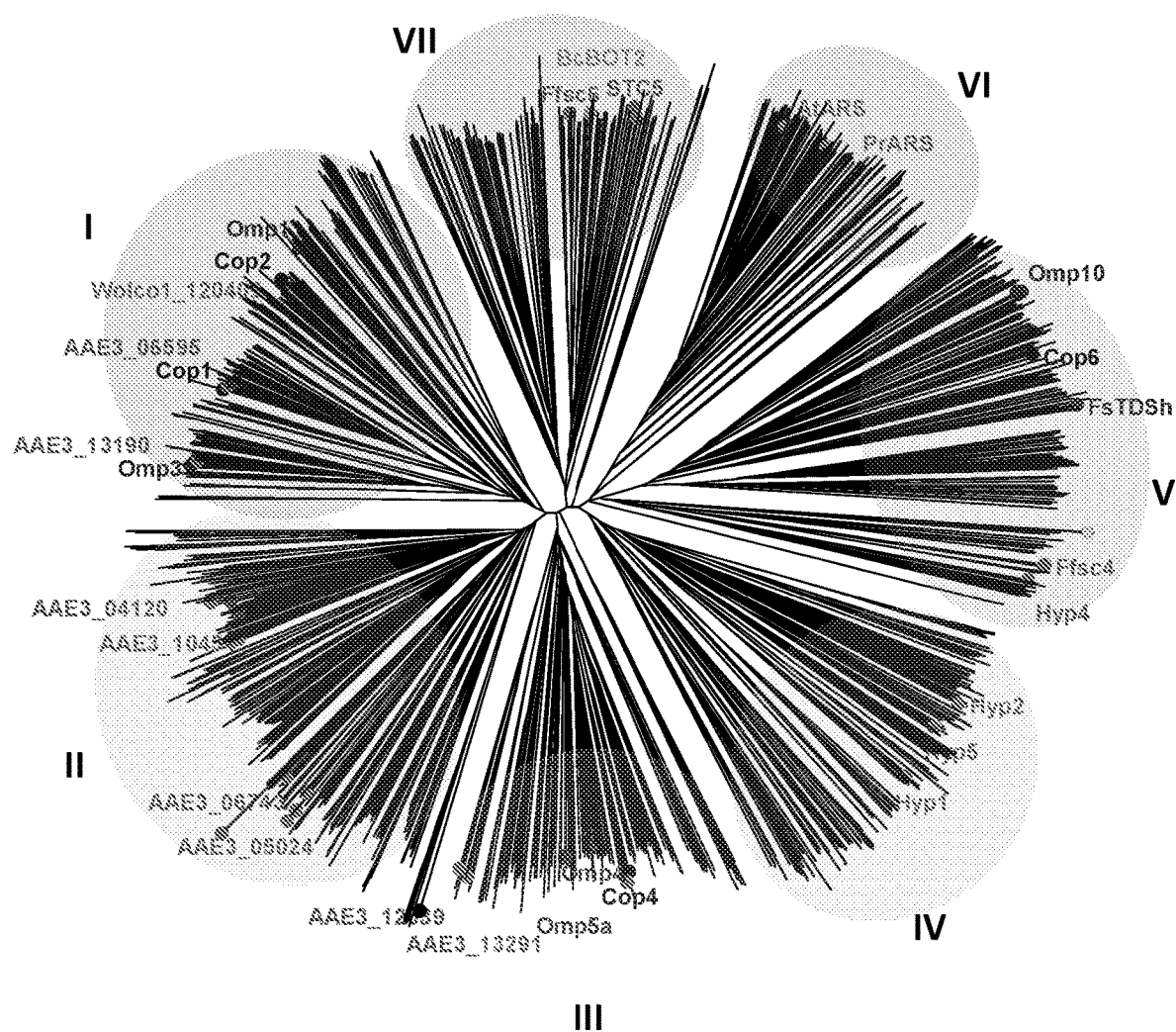
FIG. 18 shows the phylogenetic tree of TPS homologs identified in 85 Basidiomycota and 239 Ascomycota genomes. (A) shows all the fungal TPSs clustered into seven distinct clades. The characterized TPSs in this study and in literature were labelled in the figure. See more information in Table 1. In particular, these include *A. aegerita* (AAE3), *C. cinereus* (Cop), *O. olearius* (Omp), *Stereum hirsutum* (Stehi1), *Hypoxylon* sp (Hyp), *Fusarium fujikuroi* (Ffsc4, Ffsc6, STC3 and STC5) and a few aristolochene synthases (AtARS and PrARS). Most of Basidiomycota TPSs (including all the 11 *A. aegerita* TPSs) clustered in clade I, II and III, but Ascomycota TPSs scattered in clade IV, V, VI and VII. (B) shows potential Δ6-protoilludene synthases based on the phylogenetic analysis. The TPSs highlighted with a circle ("●") were characterized in this study or in literature.
Figure 19:
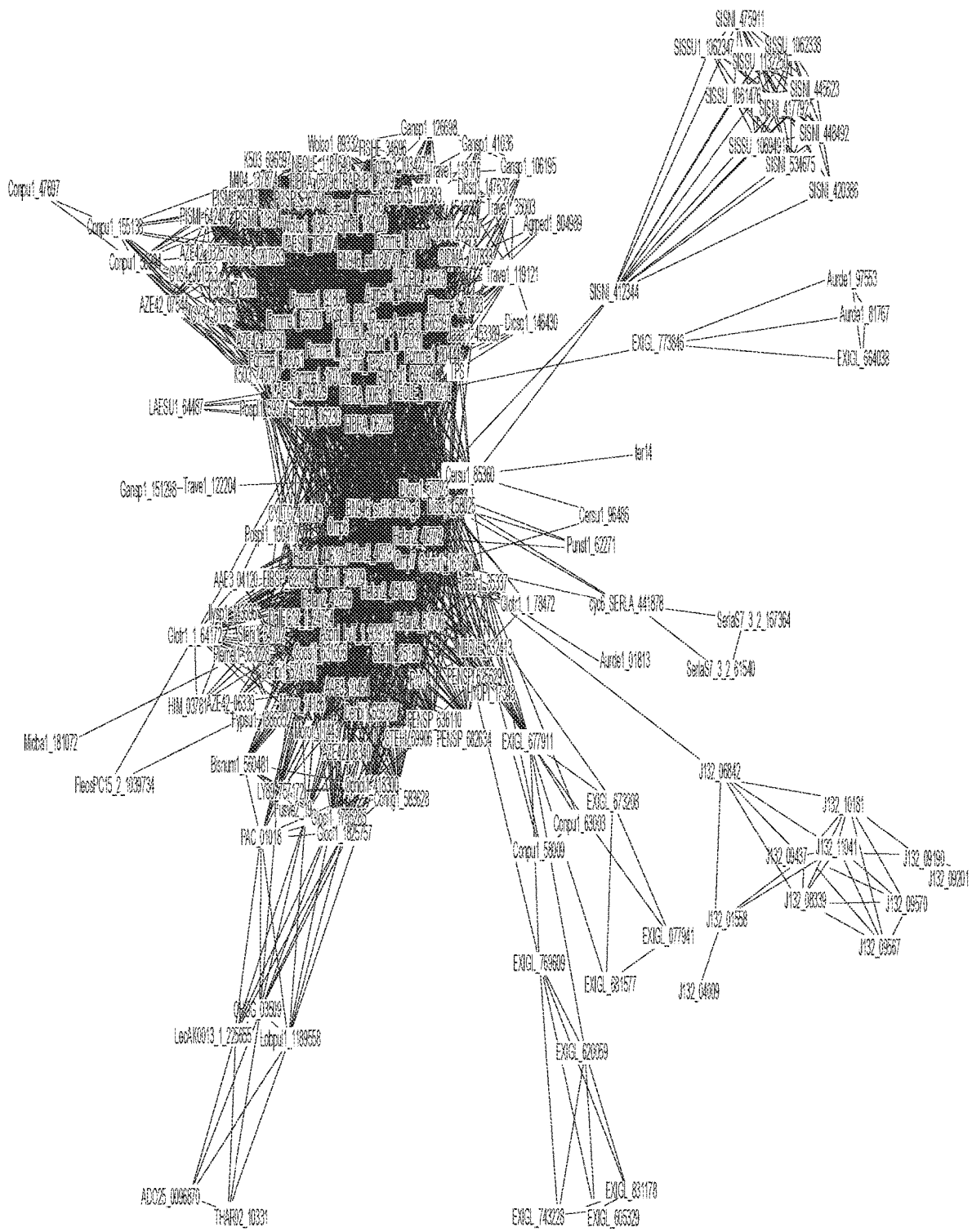
FIG. 19 shows a bioinformatics-guided predictive framework—all-by-all BLAST. The All-by-all BLAST of the 1408 putative TPS candidates was performed with enzyme function initiative (EFI)—enzyme similarity tool (EST). Sequence similarity networks (SSN) were generated by filtering the sequences into clusters at the alignment score of 100. SSNs were used for visualization by Cytoscape version 3.5.1. The model obtained here was used together with the phylogenetic tree in FIG. 13 to predict the TPS functions based on the sequence similarity and characterized TPS in this study and in literature.
Figure 19:
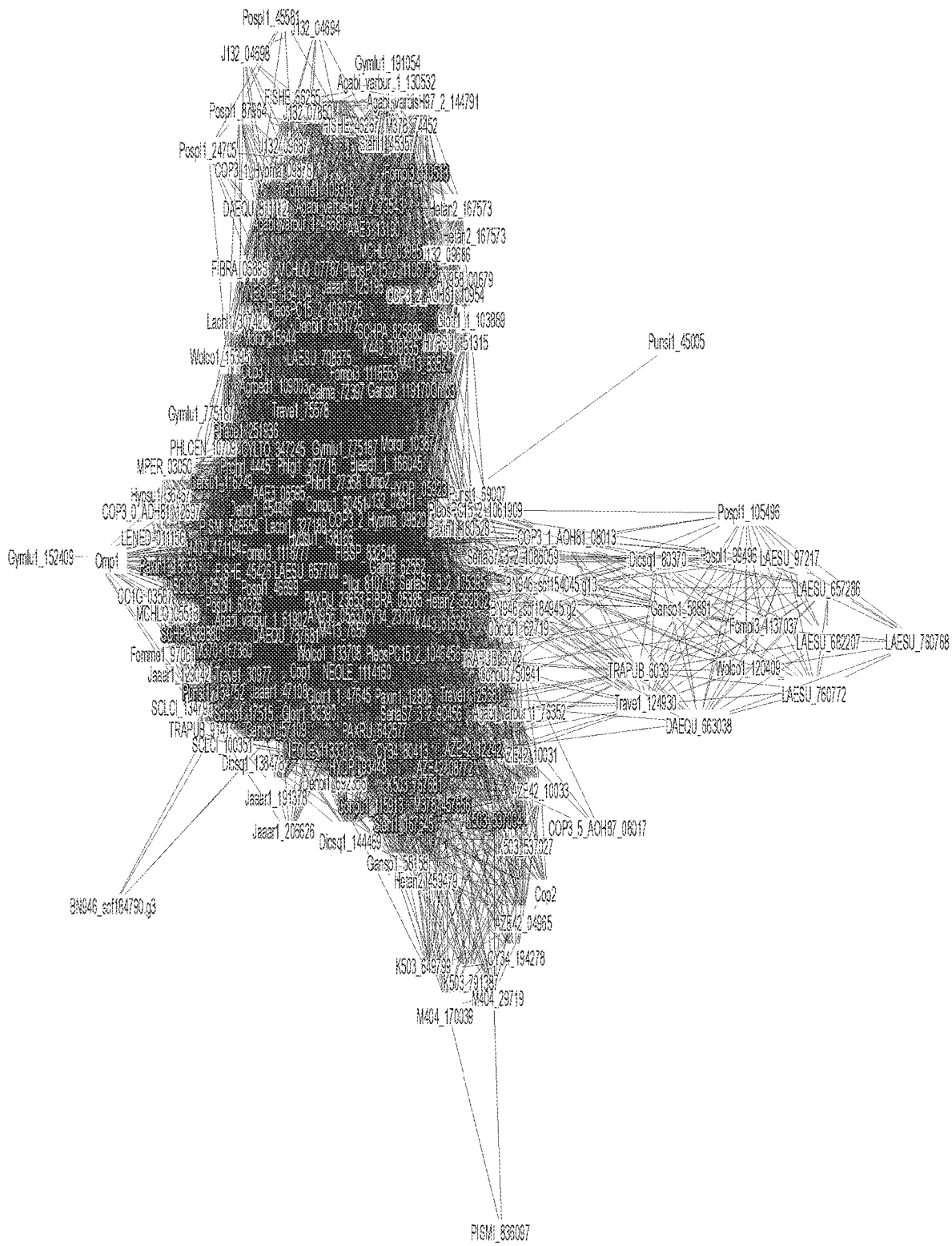
Figure 19:
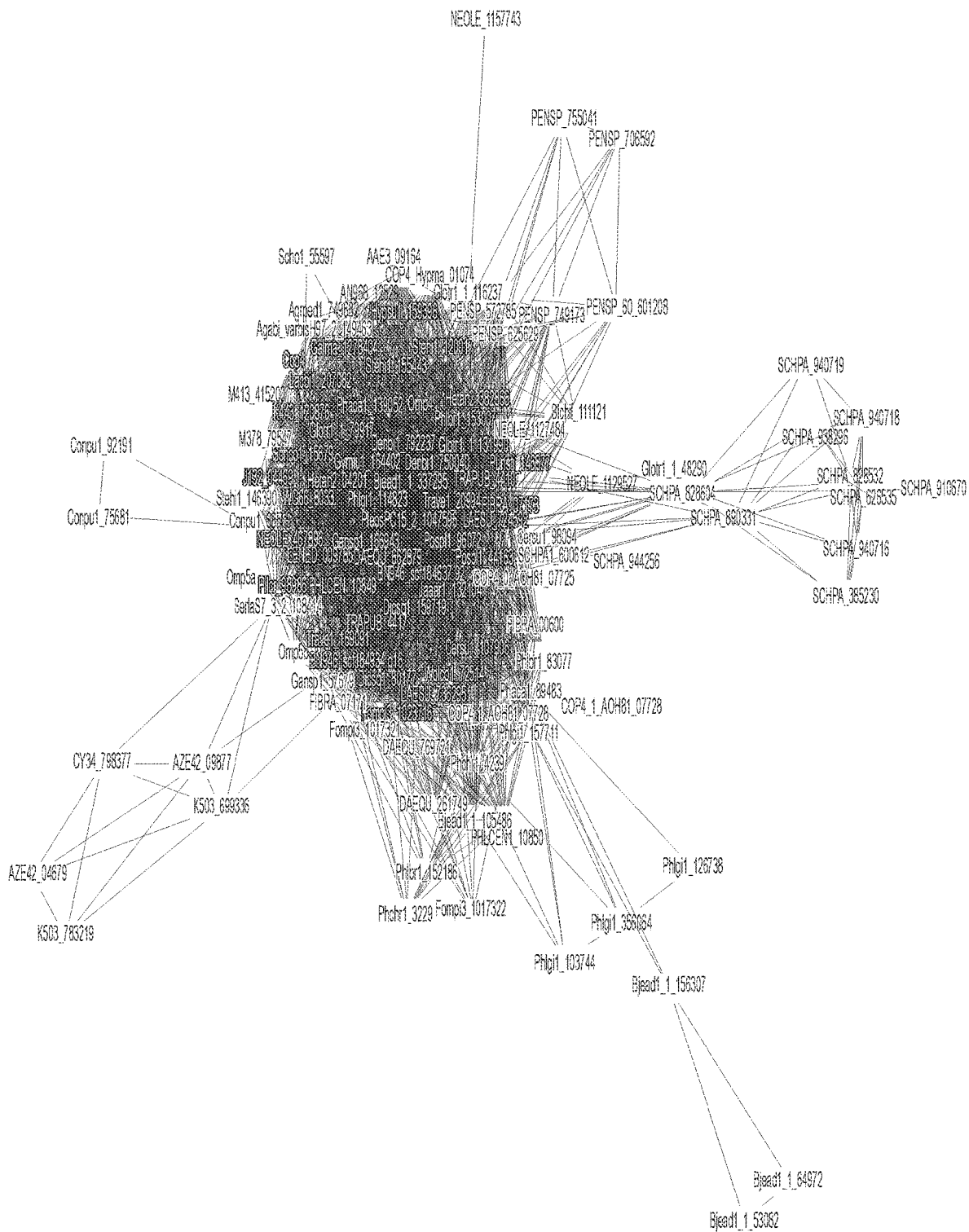
Figure 19:
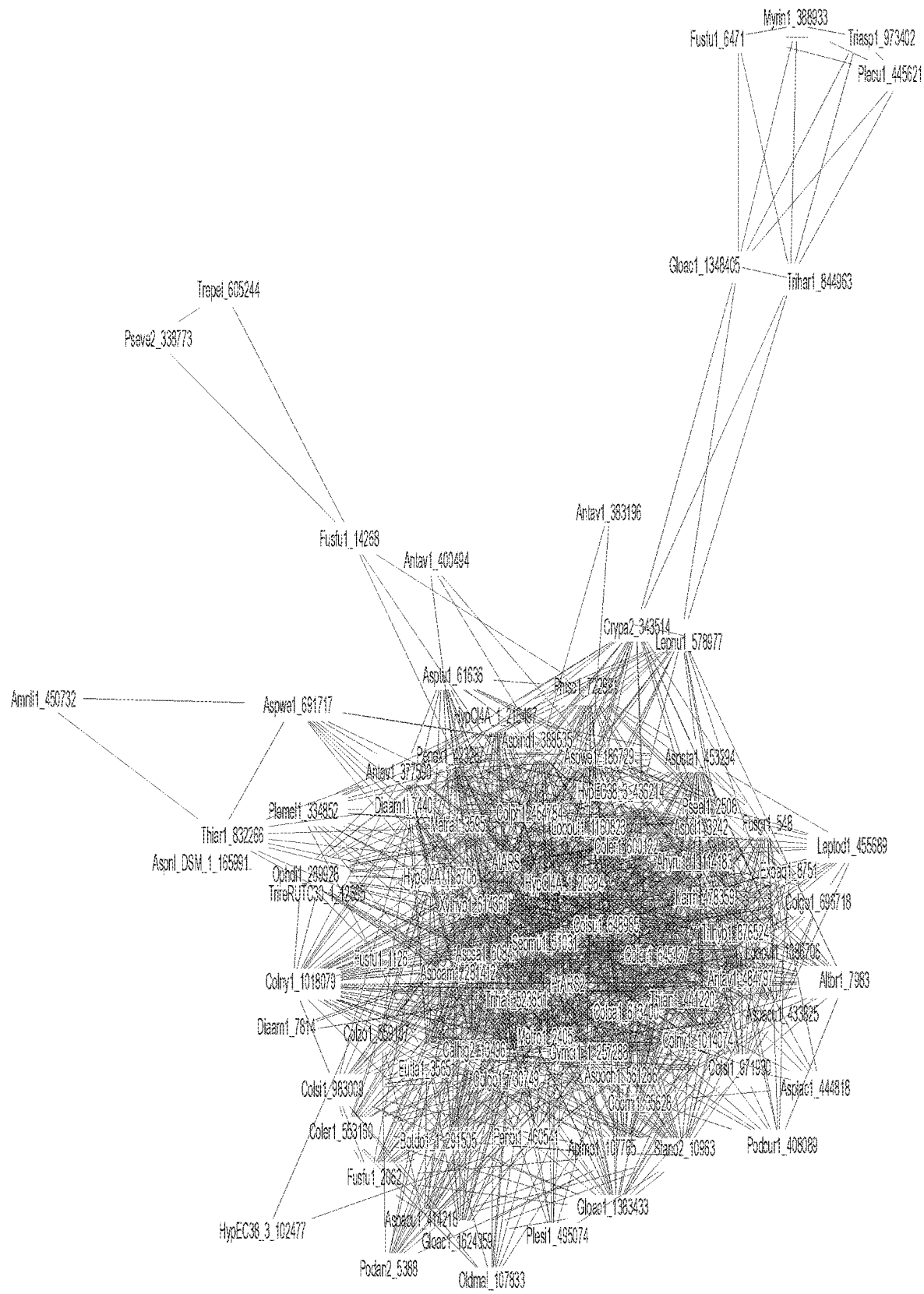
Figure 19:
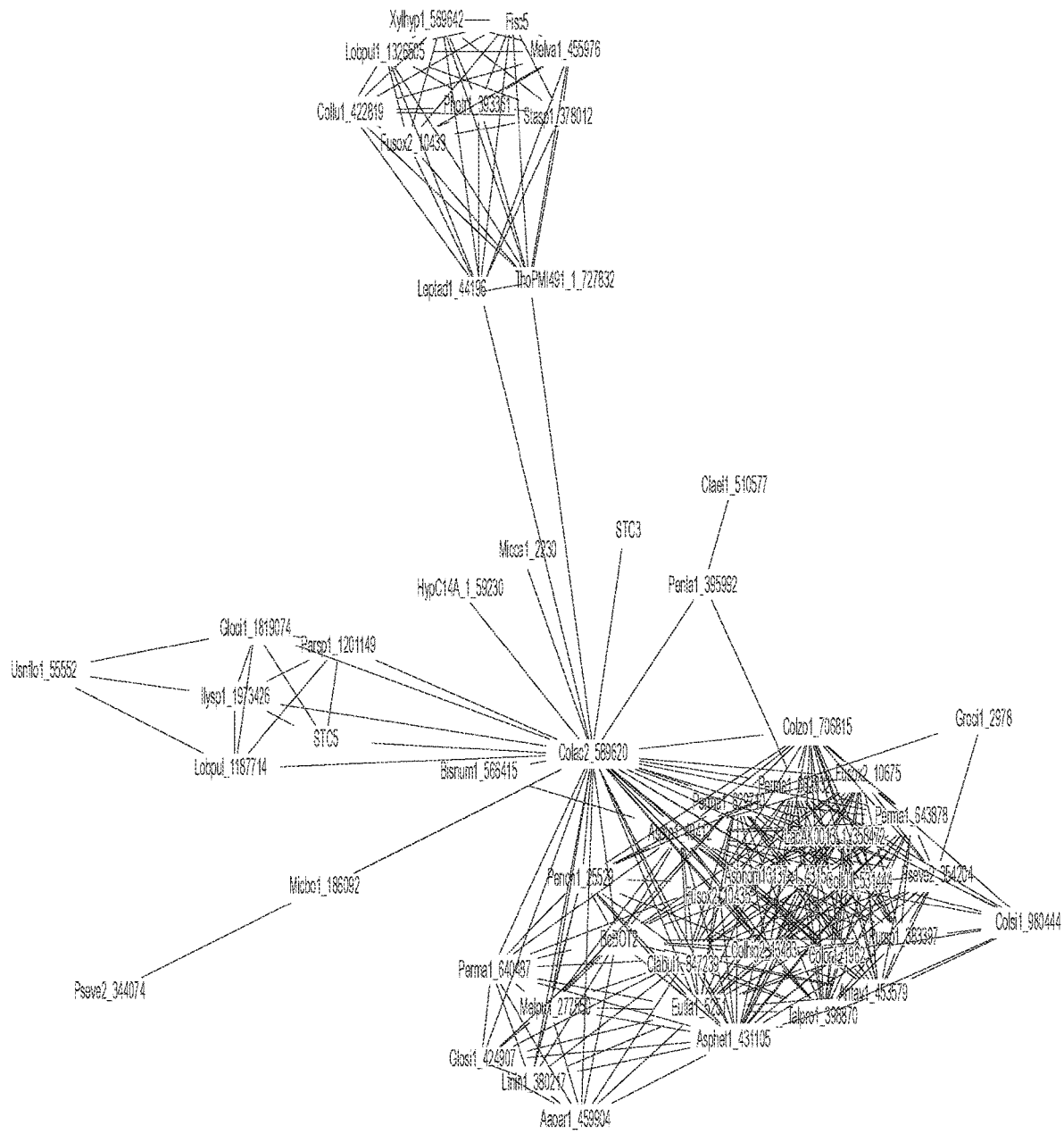
Figure 19:
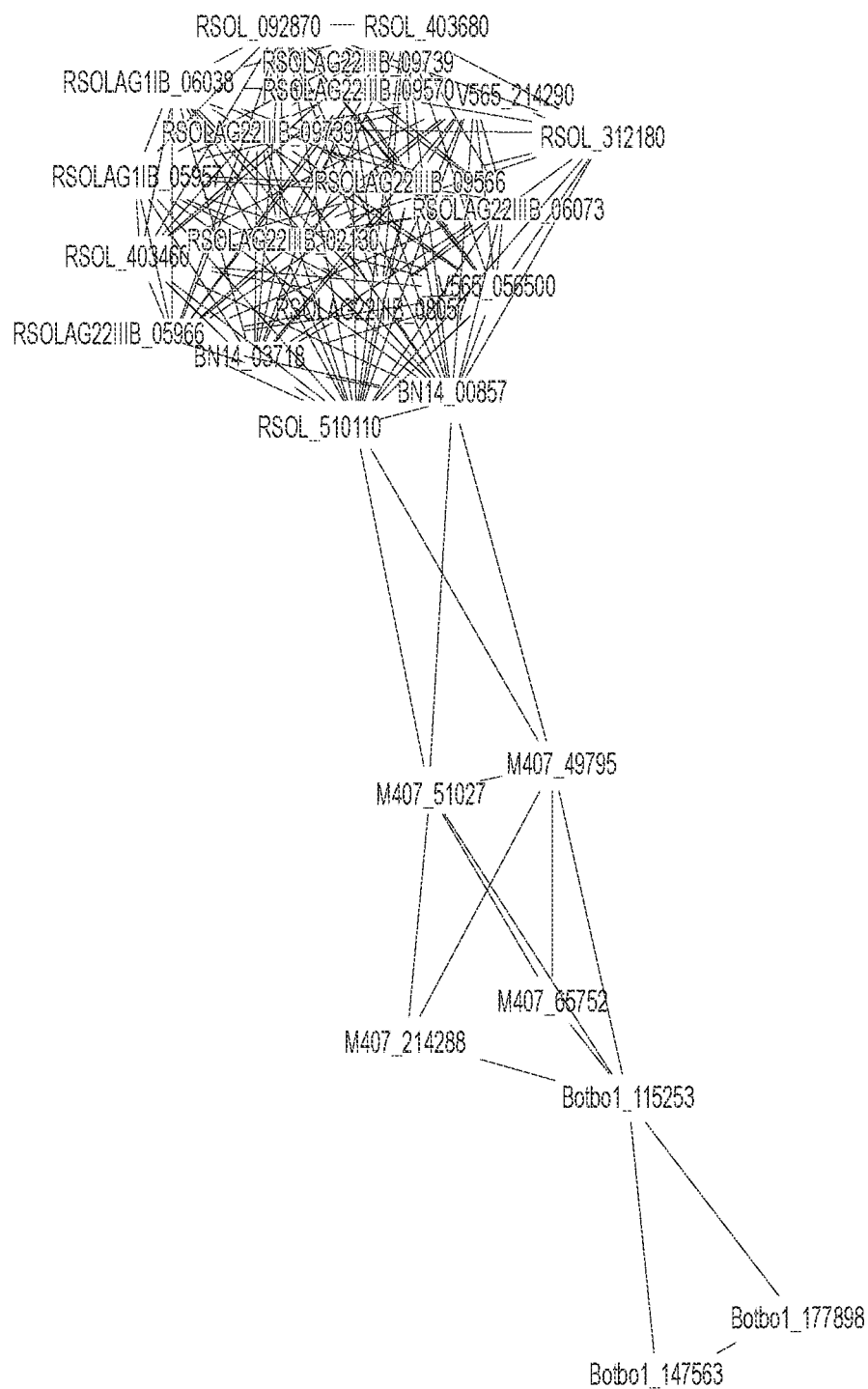
Figure 19:
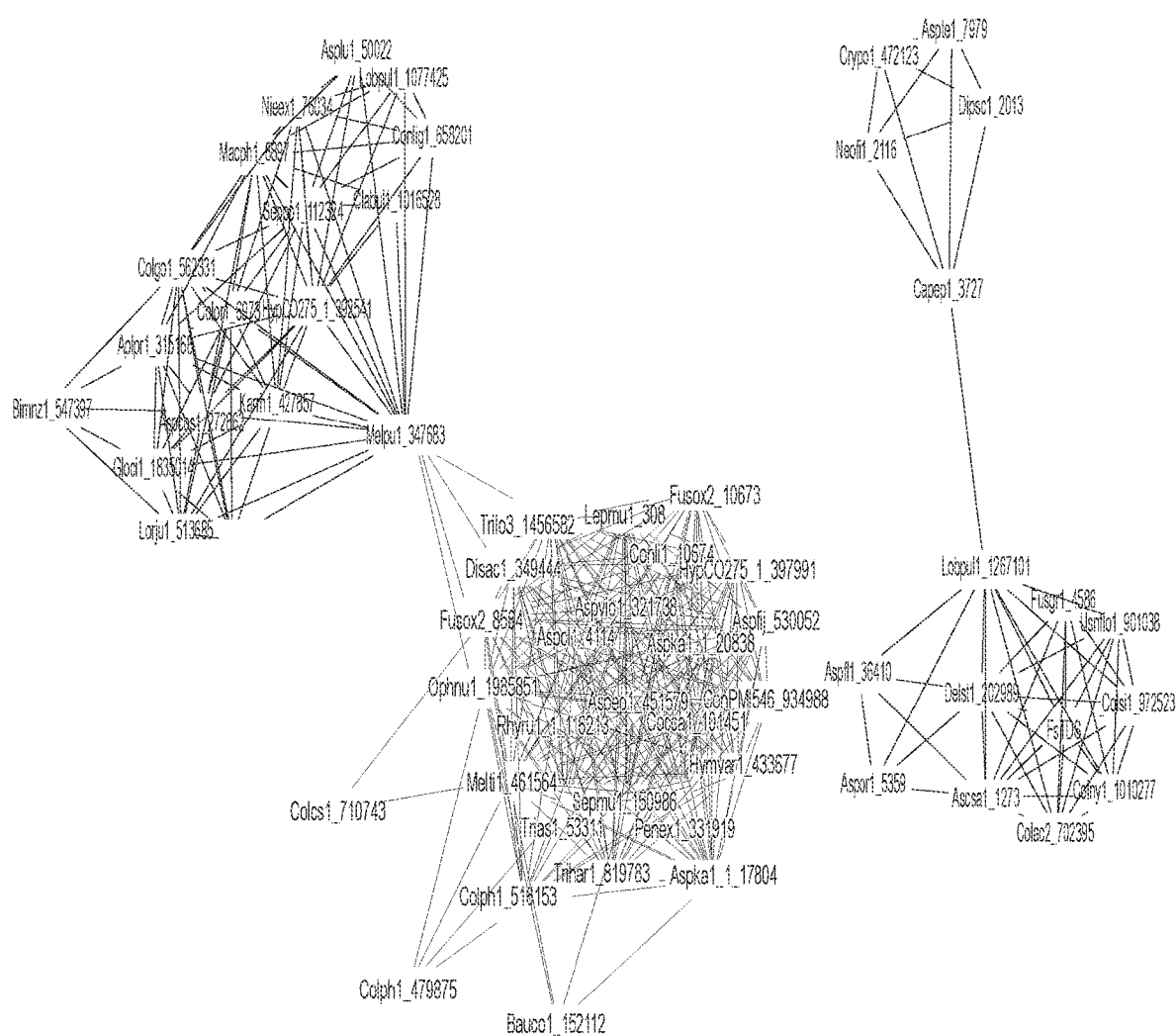
Figure 19:
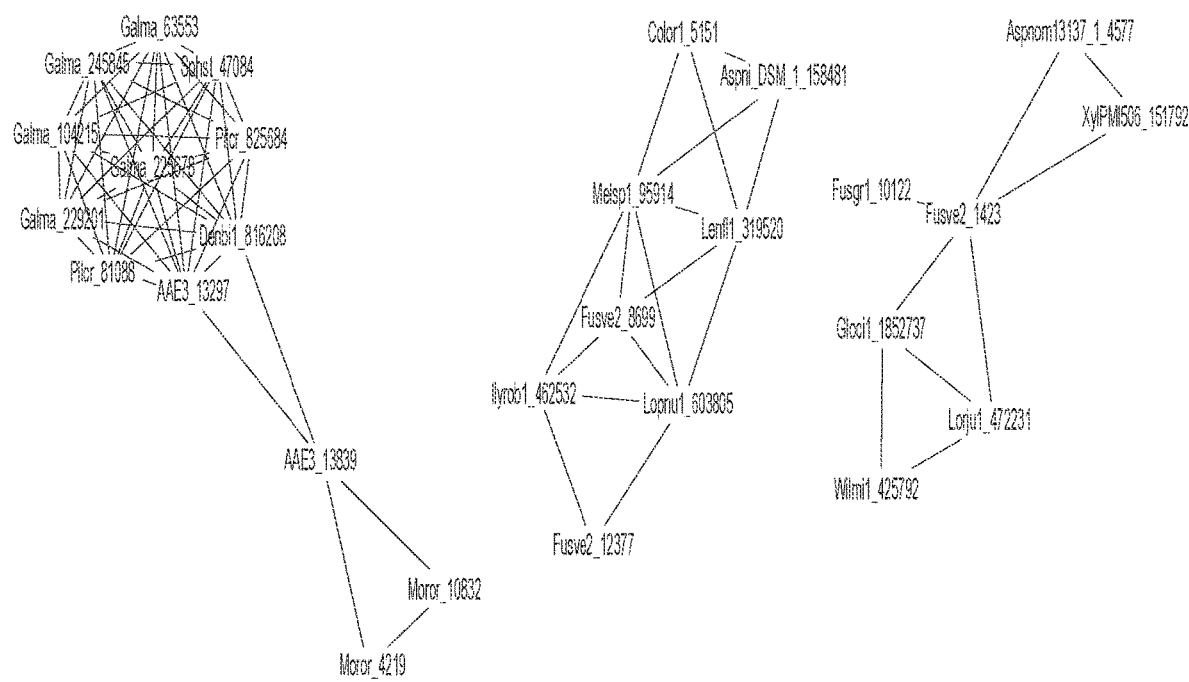
Figure 19:
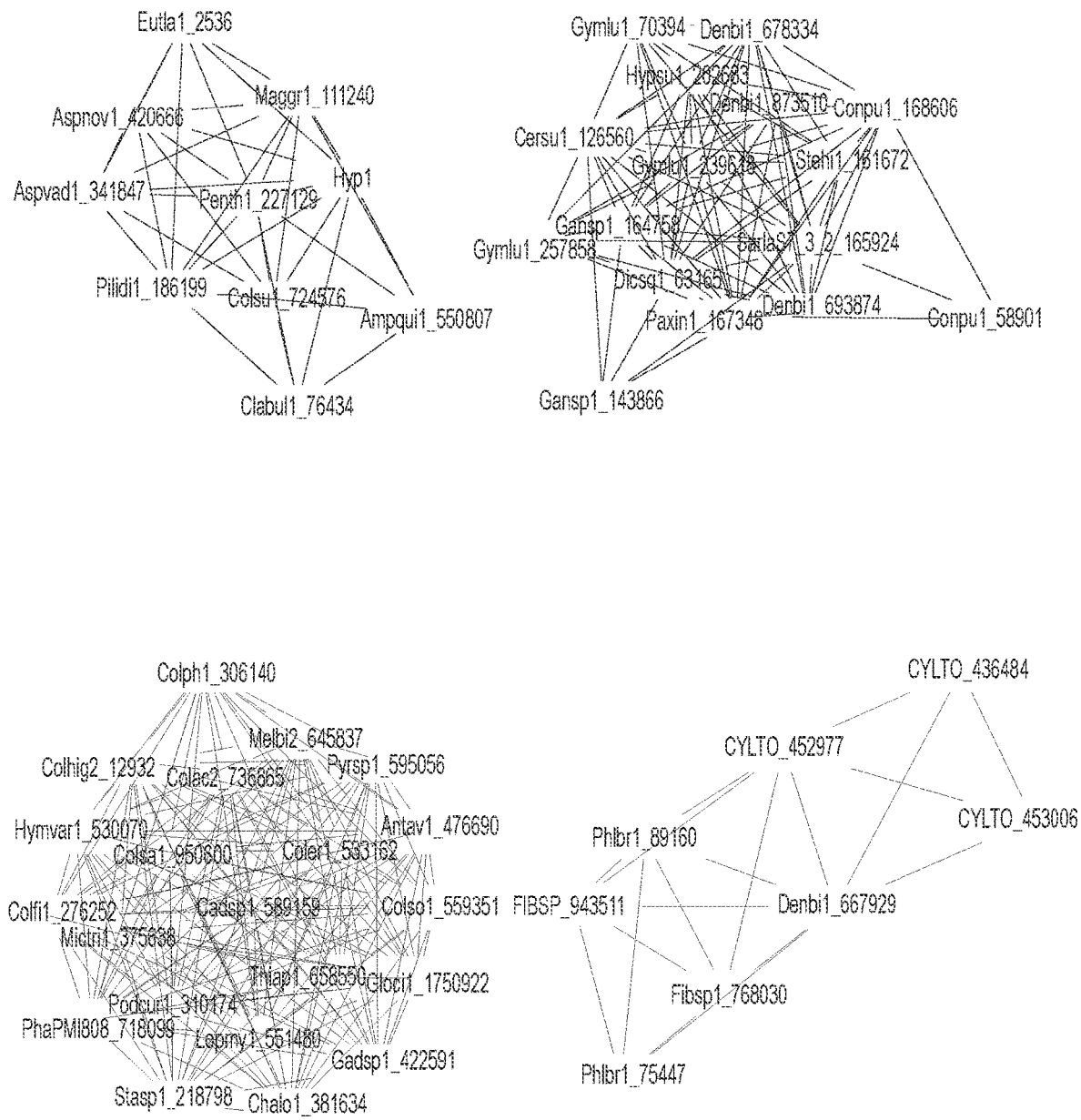
Figure 19:
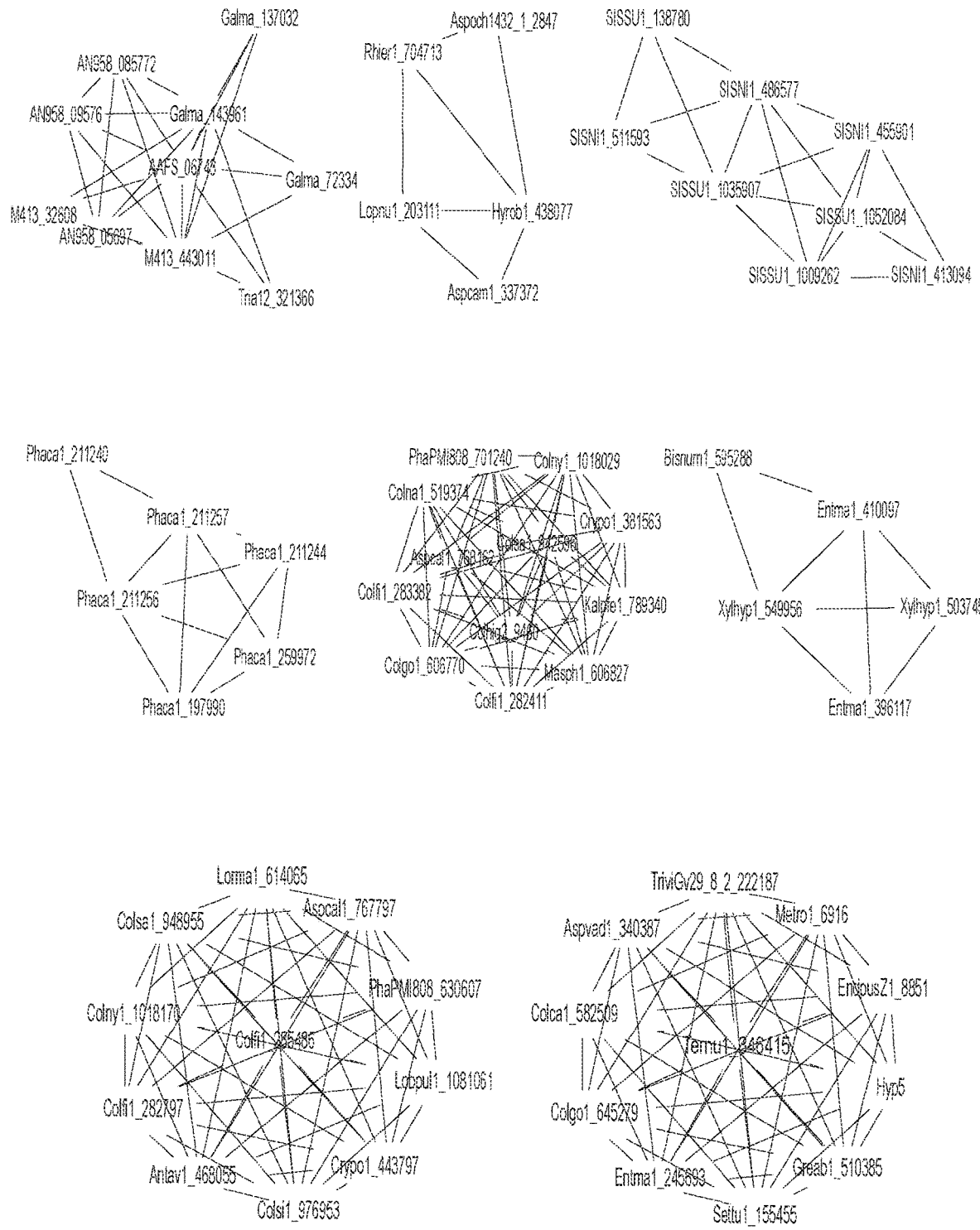
Figure 19:
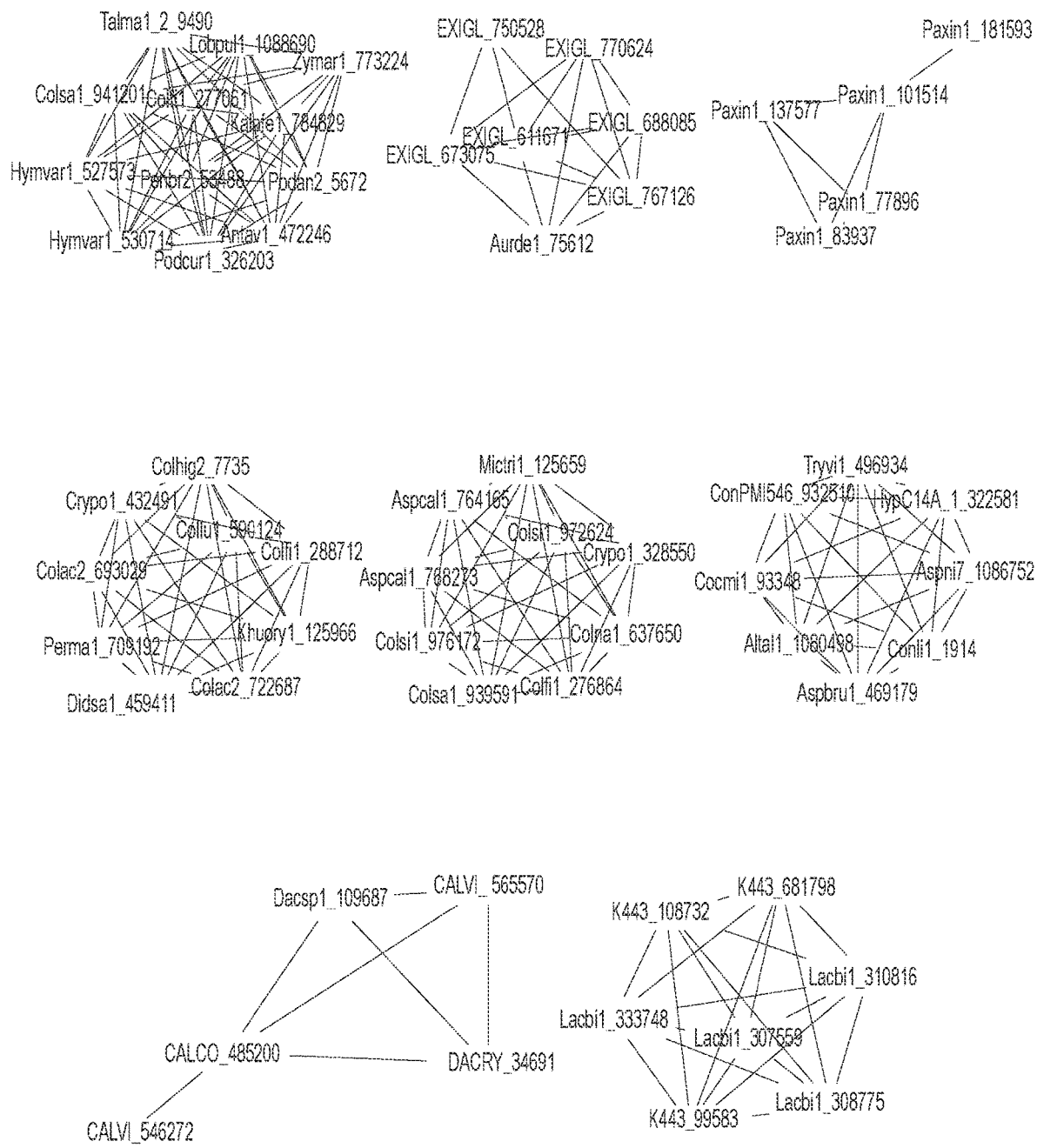
Figure 19:
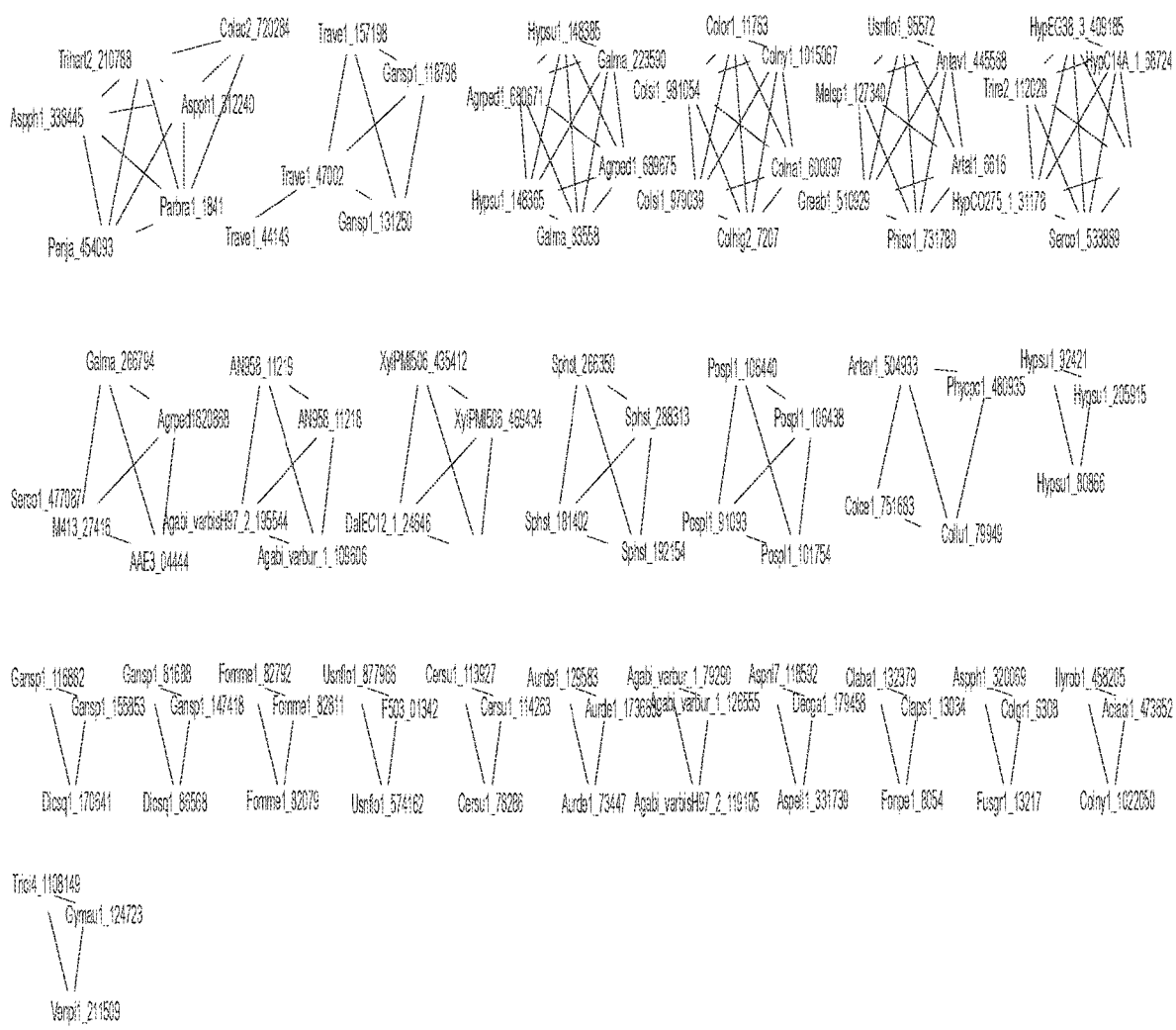
Figure 19:
Figure 19:
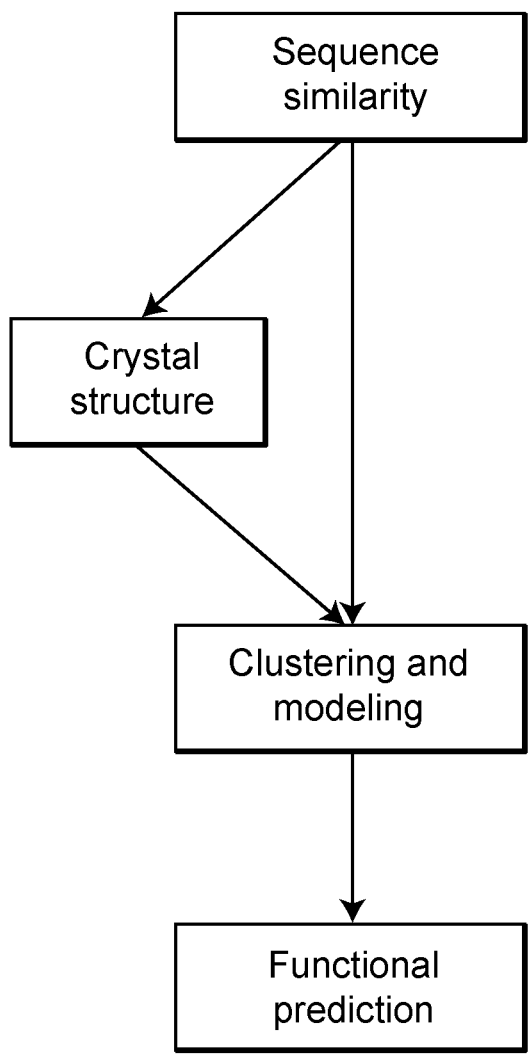

With the 1408 TPSs, a phylogenetic tree which has seven major distinct TPS clades (FIG. 18) was built and all-by-all BLAST analysis with enzyme function initiative (EFI)-enzyme similarity tool (EST) (FIG. 19) was carried out. All the clades have at least two characterized TPS enzymes. The promiscuous TPSs producing a series of muurolene and cadinene compounds (such as Omp1-3, Cop1-3, AAE3_13190 and AAE3_6595) clustered together in clade I (FIG. 18). Interestingly, all of the characterized TPS in clade I catalysed 1,10 cyclization of FPP (FIG. 17). All the eight characterized Δ6-protoilludene (1,11 cyclization of FPP, FIG. 17) synthases, together with other 32 putative TPSs, closely grouped in clade II. In addition, the four TPSs AAE3_9008, AAE3_6743, AAE3_0444, AAE3_5024 segmented closely in clade II, with multiple products including muurolene and cadinene (1,10 cyclization of FPP, FIG. 17). TPSs with cadinene as the major product (Cop4, Stehi1_128017, Omp4-5a,b and AAE3_9164) clustered together in clade III. Viridiflorene and viridiflorol synthases (AAE3_12839 and AAE3_13291, 1,11 cyclization of FPP, FIG. 17) were also in clade III but were distinct from cadiene synthases. Hyp1, 2 and 5 scattered loosely in clade IV as they have different products and different catalytic mechanisms. Hyp1 produces a linear terpene nerolidol, but Hyp2 and Hyp5 catalyze cadinene and bulnesene, respectively (1,10 cyclization of FPP). Ffsc4 (koraiol, 1,11 cyclization) and some TPSs responsible for 1,6 or 1,7 cyclization of FPP (Omp8-10, Cop6 and FsTDS (trichodiene)) clustered in clade V. Moreover, Hyp4 (unknown sesquiterpene products) and the monoterpene synthase Hyp3 (1,8-cineole) segmented in clade V. In clade VI, only two aristolochene (1,10 cyclization of FPP) synthases (AtARS (Cane and Kang, 2000) and PrARS (Hohn and Plattner, 1989)) were characterized. Lastly, a few characterized TPSs with different cyclization mechanisms, including STC3 ((+)-eremophilene, 1,10 cyclization of FPP), STC5 ((−)-guaia-6,10 (14)-diene, 1,10 cyclization of FPP), BcBOT2 (presilphiperfolan-8β-ol, 1,11 cyclization of FPP) and Ffsc6 ((−)-a-acorenol, 1,6 cyclization of FPP), scattered in clade VII. In sum, most of Basidiomycota TPSs (including all the 11 A. aegerita TPSs) grouped in clade I, II and III but Ascomycota TPSs mainly scattered in clade IV, V, VI and VII. Badisomycota TPSs, especially closely clustered ones, in each clade often share the similar cyclization mechanism. In contrast, Ascomycota TPSs in the same clade could have diverse cyclization mechanisms.

Example 6

Predictive Framework to Uncover Other Fungal Viridiflorol Synthases

Figure 24:
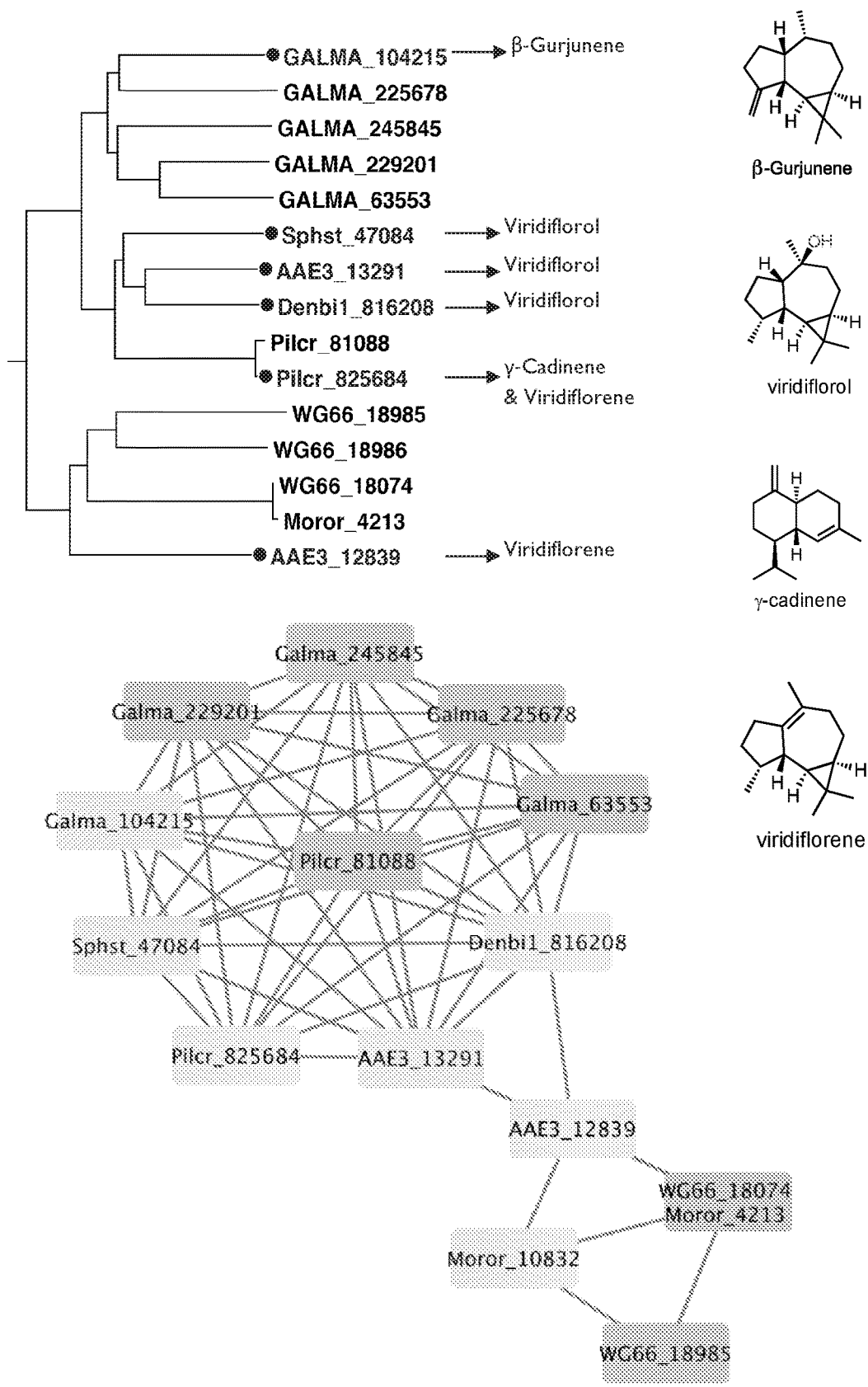
FIG. 24 shows a predictive example of the clustering and validation of putative fungal viridiflorol synthases. According to the phylogenetic tree in FIGS. 18 and 19, 15 fungal TPS homologs were closely clustered. Four of them (Sphst_47084 from *Sphaerobolus stellatus*, Denbi1_816208 from *Dendrothele bispora*, Galma_104215 from *Galerina marginata* and Pilcr_825684 from *Piloderma croceum*) were recombinantly expressed in *E. coli* and their products were analysed. Both phylogenetic analysis and EFI-EST analysis have very accurate prediction. The TPSs highlighted with a circle ("●") were characterized in this study.
Figure 24:
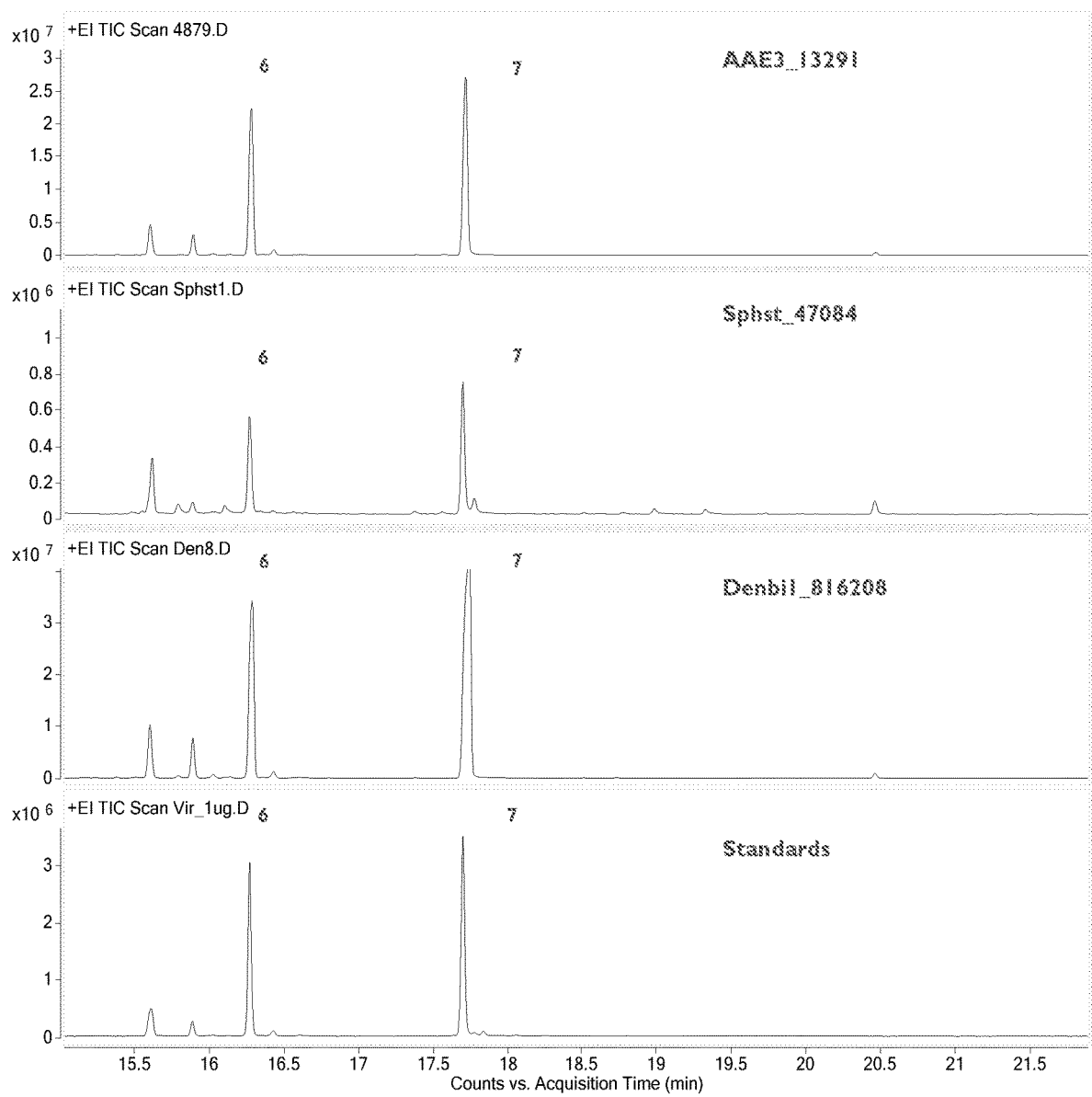
Figure 24:
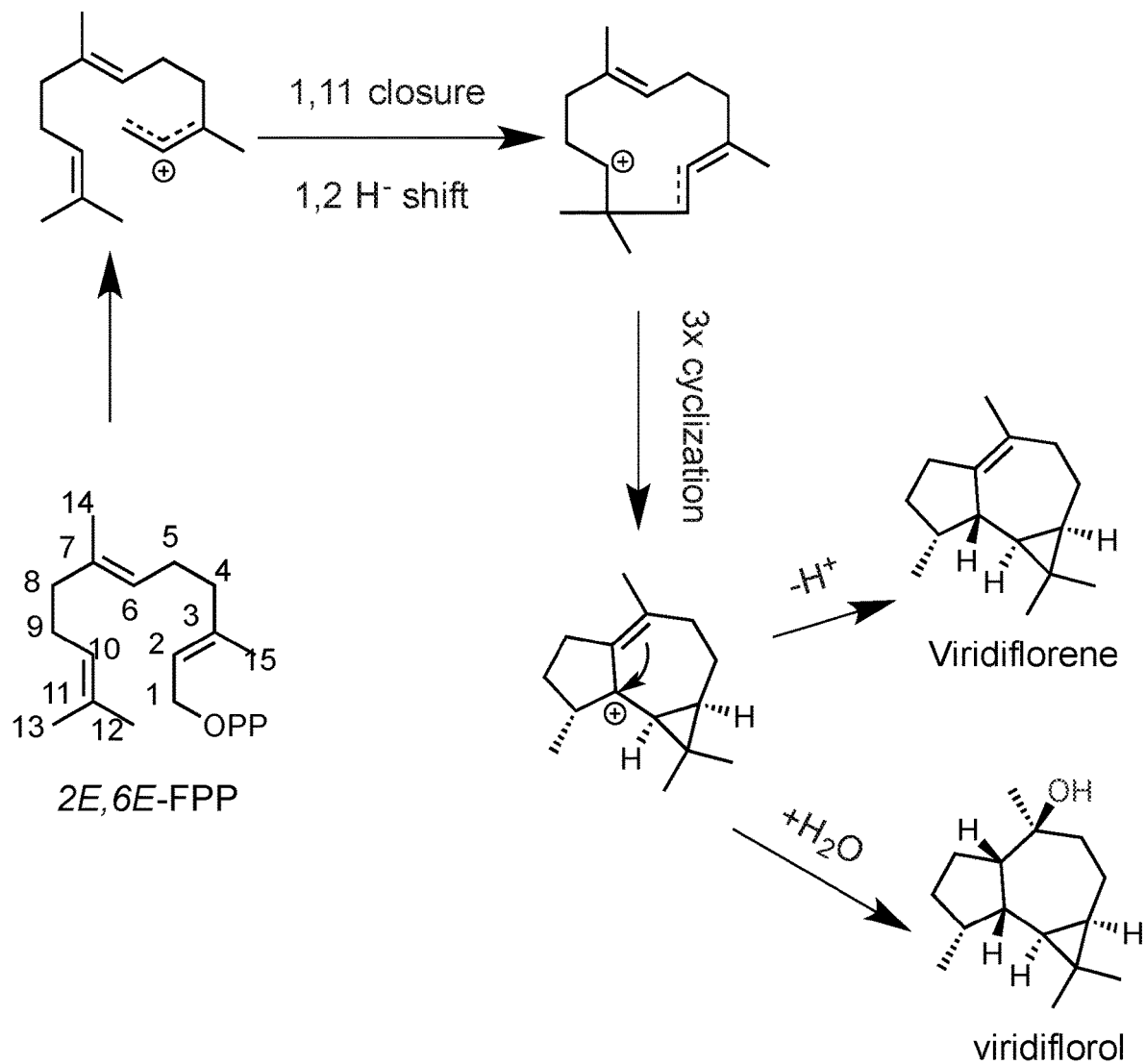

Knowledge acquired by studying the TPS products and the sequence conservation in each distinct clade provides a valuable basis for mechanistic understanding of the distinct activities. And it could be used to engineer and design more effective enzymes and to probe and even predict the functions of unknown TPSs. To test the predictive capability of the framework, identification of viridiflorol synthases in other species was carries out. The reason viridiflorol synthase was chosen is that there is only one type of plant viridiflorol synthase reported among all kinds of species. Analyzed by the phylogenetic tree in FIG. 18 and all-by-all BLAST in FIG. 19, 15 fungal TPS homologs were closely clustered. Four of them (Sphst_47084 from Sphaerobolus stellatus, Denbi1_816208 from Dendrothele bispora, Galma_104215 from Galerina marginata and Pilcr_825684 from Piloderma croceum) were recombinantly expressed in E. coli and their products were analysed. The TPSs highlighted with circle ("●") were characterized in this study. Among them, four TPSs (Sphst_47084 from Sphaerobolus stellatus, Denbi1_816208 from Dendrothele bispora, Galma_104215 from Galerina marginata and Pilcr_825684 from Piloderma croceum) were cloned and expressed in the chassis strain. The E. coli culture expressing Sphst_47084 and Denbi1_816208, the most closely related to AAE3_13291, produced identical products as AAE3_13291, viridiflorol 7 (~90%) and viridiflorene 6 (~10%) (FIG. 24). Interestingly, the main product of Galma_104215 was tentatively identified as β-gurjunene, a compound structurally similar to viridiflorene (FIG. 24). However, the cells expressing Pilcr_825684 produced γ-cadinene as the main product and a few minor sesquiterpenes including viridiflorene.

The results support that the phylogenetic tree could be used for identification of novel TPSs with similar functions.

Example 7

Prediction and Validation of Fungal Linalool and Nerolidol Synthases (LNSs)

Figure 20:
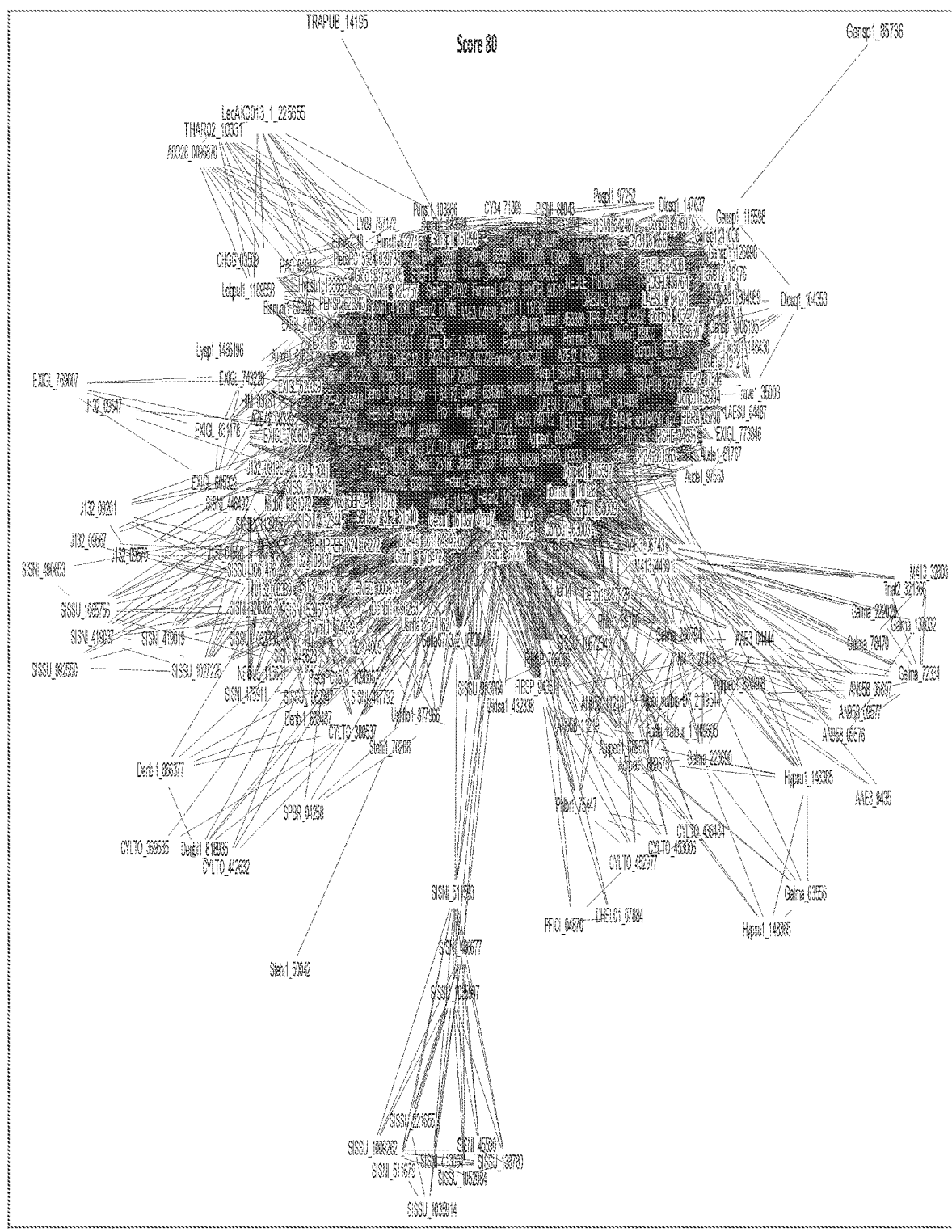
FIG. 20 shows a predictive example of the clustering of putative fungal linalool/nerolidol synthases (LNS). Based on EFI-EST analysis, a group of TPS homologues were clustered with AAE3_9435. By setting the alignment score to between 80 and 90, a smaller set of candidates were selected.
Figure 20:
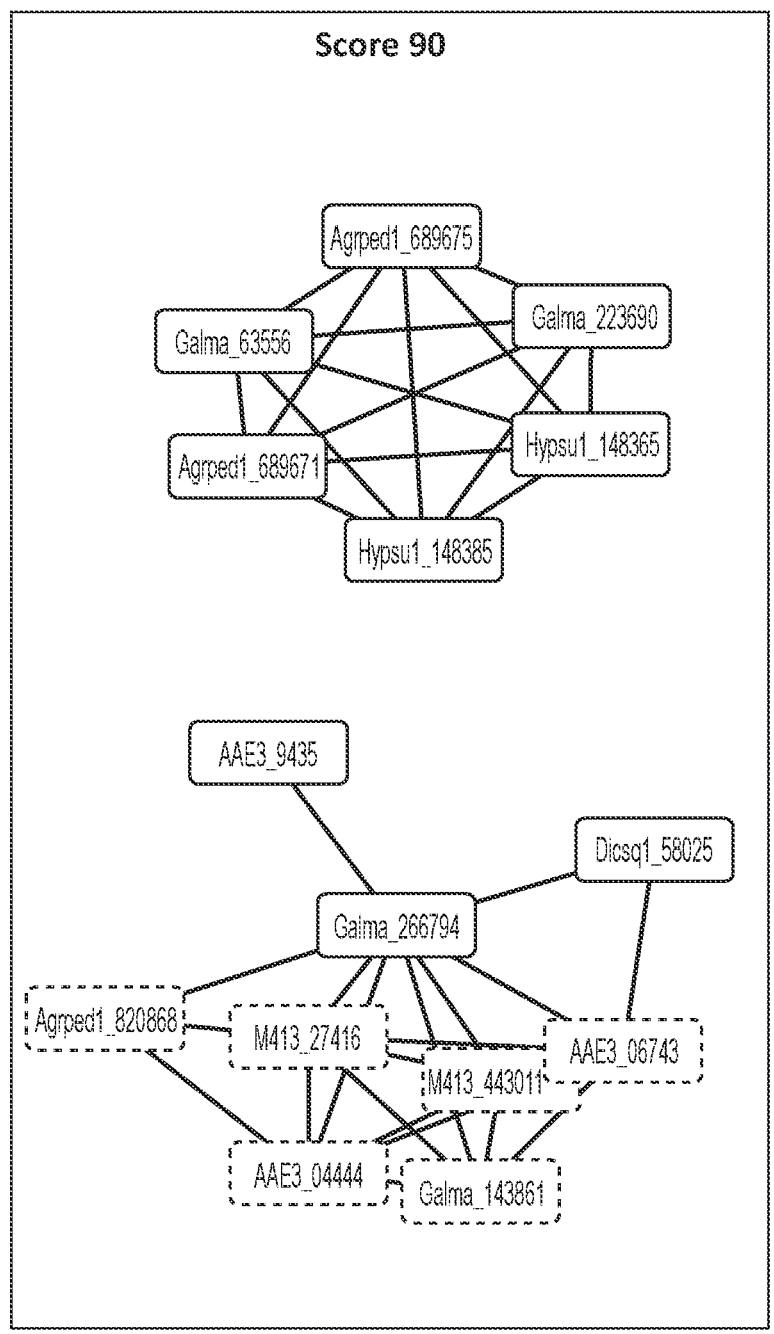
Figure 21A:
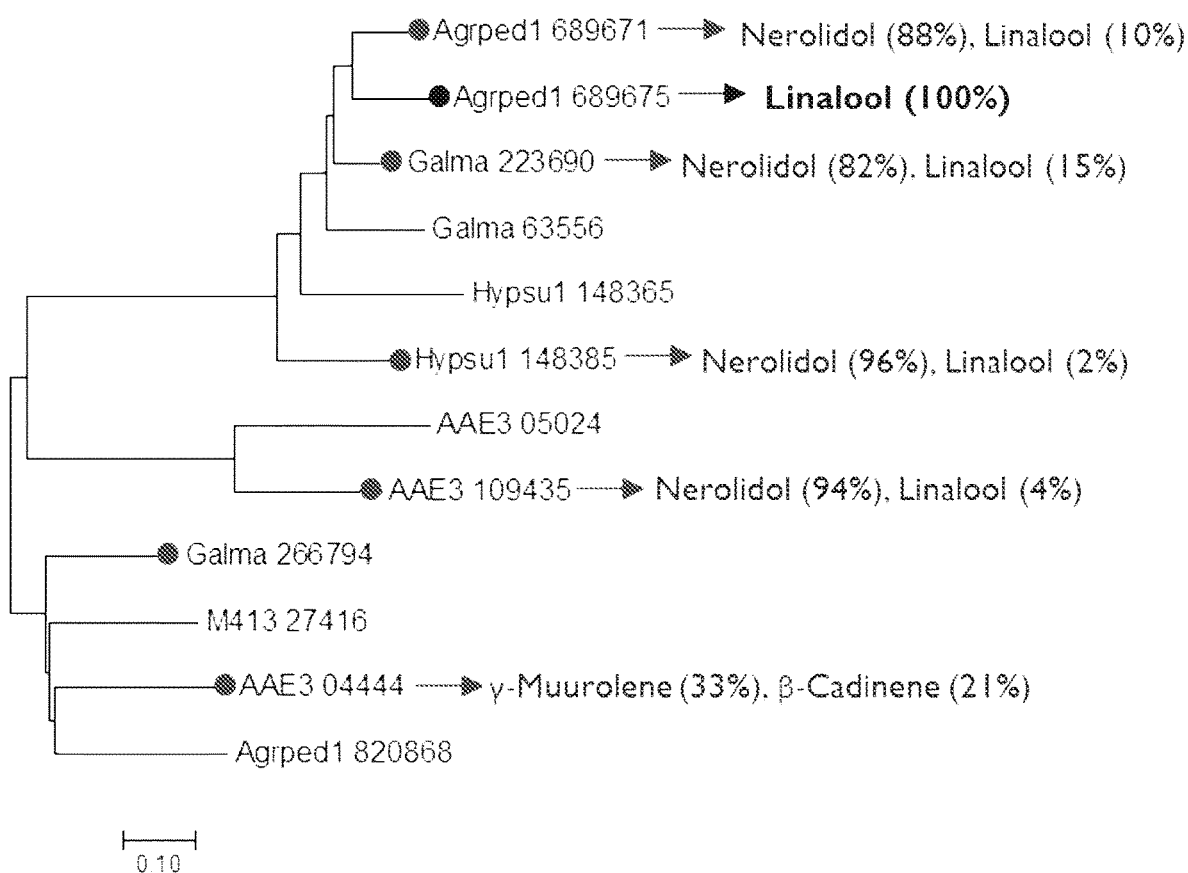
FIG. 21 shows a predictive example of the validation of putative fungal linalool/nerolidol synthases. Selected putative LNSs were expressed in the engineered *E. coli* strains. LNSs chosen here in the cluster are from *Agrocybe aegerita* (AAE3), *Agrocybe pediades* (Agrped1), *Galerina marginata* (Galma), *Hypholoma sublateritium* (Hypsu1), *Hebeloma cylindrosporum* (M413). Agrped1_689675 is found to a novel monoterpene synthase, linalool synthase (LS), while the others are bifunctional LNSs.
Figure 21B:
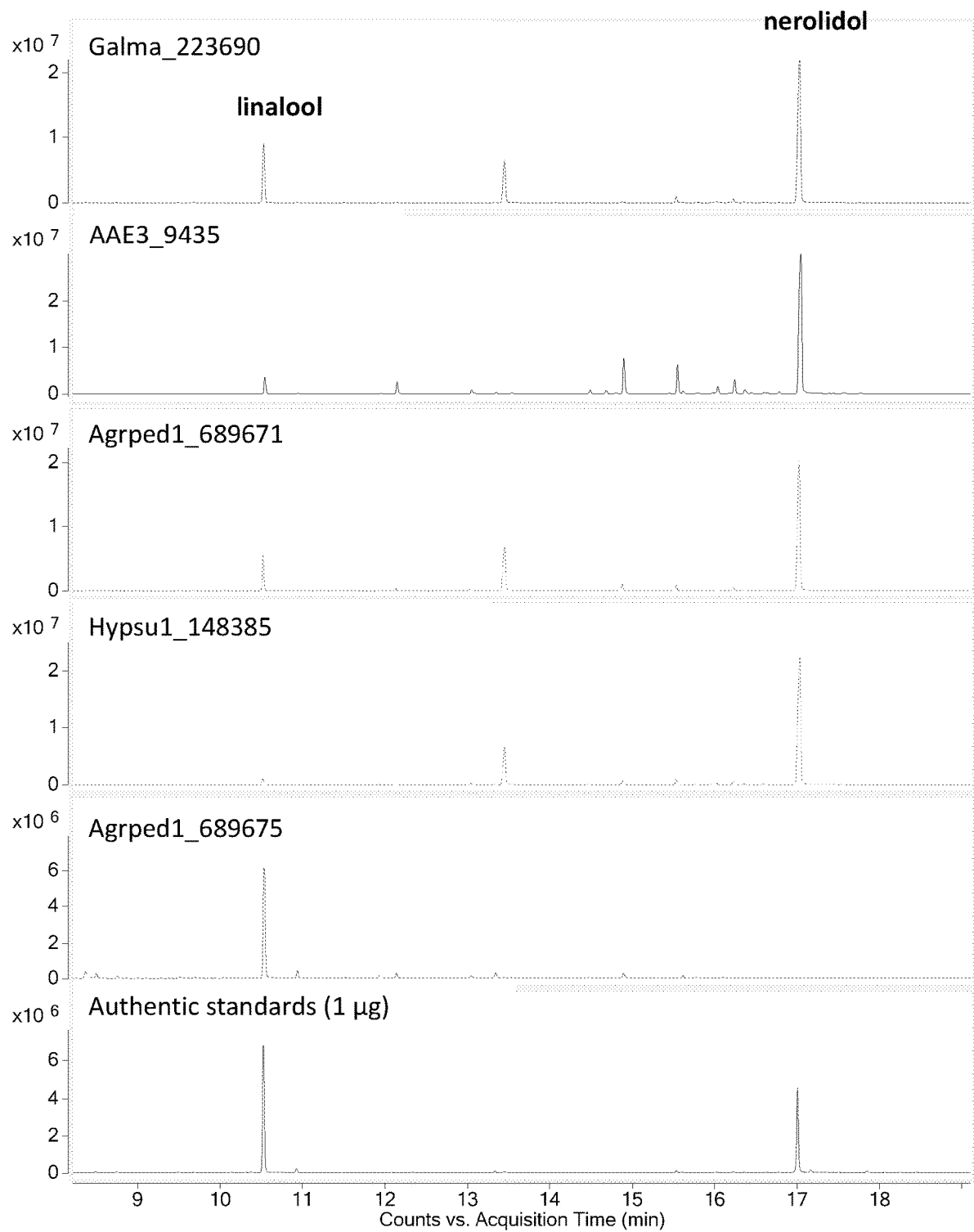
Figure 21C:
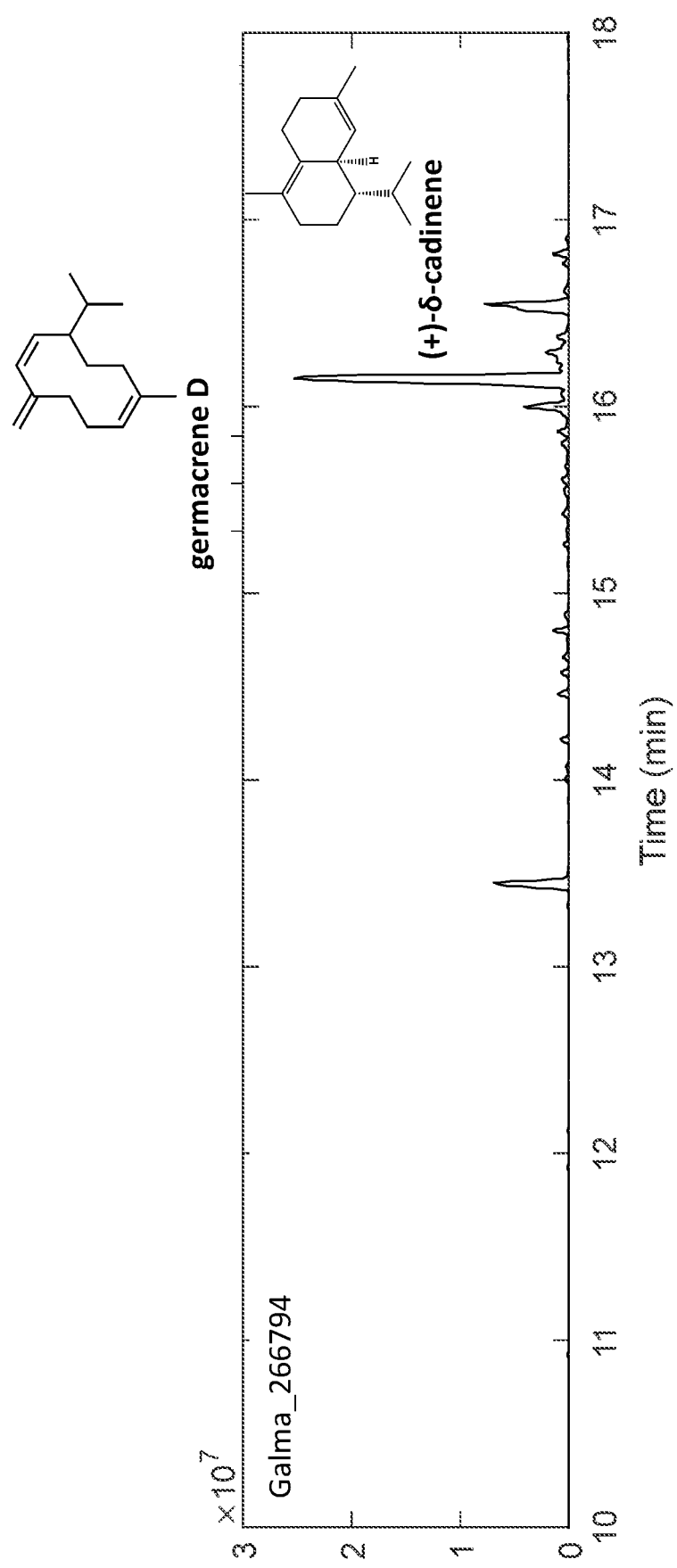
Figure 25:
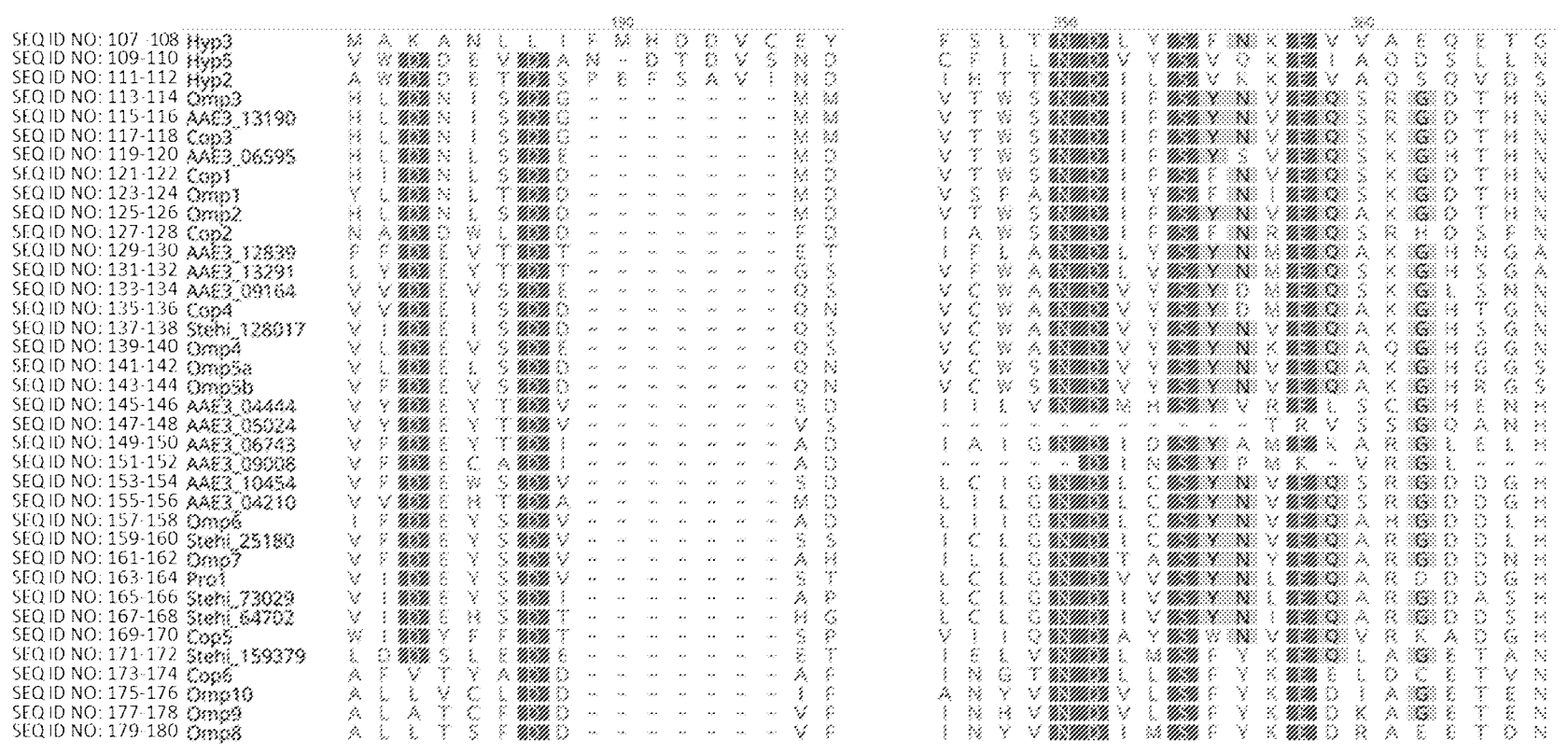

Starting with the sequence of AAE3_9435, identification of other NLSs in different fungal species was obtained by a BLAST search in databases of the Joint Genome Institute (JGI, http://jgi.doe.gov/fungi) and Universal Protein Resource (UniProt, http://www.uniprot.org/). EFI-EST analysis was carried out and a group of TPS homologues were shown to be clustered with AAE3_9435. By setting the alignment score to between 80 and 90, a smaller set of candidates were selected. With the selected cluster of TPSs in FIG. 20. A focused alignment indicated that 11 fungal TPSs were clustered closely with AAE3_9435 including two other TPSs from Agrocybe aegerita, AAE3_05024 and AAE3_04444 (SEQ ID NO: 27), three from Agrocybe pediades (Agrped1_689671 (SEQ ID NO: 2), Agrped1_689675 (SEQ ID NO: 3), Agrped1_820868), three from Galerina marginata (Galma_223690 (SEQ ID NO: 4), Galma_266794 (SEQ ID NO: 77), Galma_63556), two from Hypholoma sublateritium (Hypsu1_148365, Hypsu1_148385(SEQ ID NO: 5)) and M413_27416 from Hebeloma cylindrosporum (FIG. 20). Characterized in our previous study, AAE3_05024, the most closely related TPS to AAE3_9435, seems to be a pseudogene. The main products of AAE3_04444 were γ-muurolene (33%) and β-cadinene (21%). The other TPSs in FIG. 21 have not been functionally annotated. As a proof of concept, five out of the nine uncharacterized TPSs were chosen to test their functions. All five TPSs give rise to at least one terpene when expressed in the *E. coli* strain overproducing IPP and DMAPP. In *E. coli* strains expressing Agrped1_689675 only linalool was found in the headspace of the culture. Similar to AAE3_9435, Agrped1_689671, Galma_223690 and Hypsu1_148385 showed a bifunctional NLS function producing nerolidol and linalool (FIG. 21B). Galma_266794 clones leaded to the sesquiterpene germacrene D (62%, validated by Cubeb essential oil) as main product and a few other sesquiterpenes including δ-cadinene (17%), γ-muurolene (8%), but no monoterpene. Due to the lack of the GPP synthase in the *E. coli* strain, the concentration of intracellular FPP was much higher than that of intracellular GPP. Consequently, all the four TPSs (AAE3_9435, Agrped1_689671, Galma_223690 and Hypsu1_148385) produced nerolidol as the main product (88-96%) and linalool as the minor product (2-10%, FIG. 21). However, when expressed in the same *E. coli* strain, Agrped1_689675 produced only linalool but no sesquiterpenes. The data indicated that Agrped1_689675, is an exclusive monoterpene synthase and has no activity of sesquiterpene synthase thus this was named as 'Ape_LS'. Interestingly, despite with different products, all the six TPSs shared some very conserved regions in the metal-binding motif (such as 'DEYTD' and 'NDMHSYxxE' region). FIG. 25 shows the conserved regions for sesquiterpene and monoterpene synthases. The 2 conserved domains are DD(E/N/Y/S)XXD and NDSE. The two conserved domains served as an important pre-screening of terpene synthase homologues. Those homologues missing or having incomplete domains often have no activities and thus are excluded in our screening process.

Example 8

Mutating the LS for a Different Function

Figure 22:
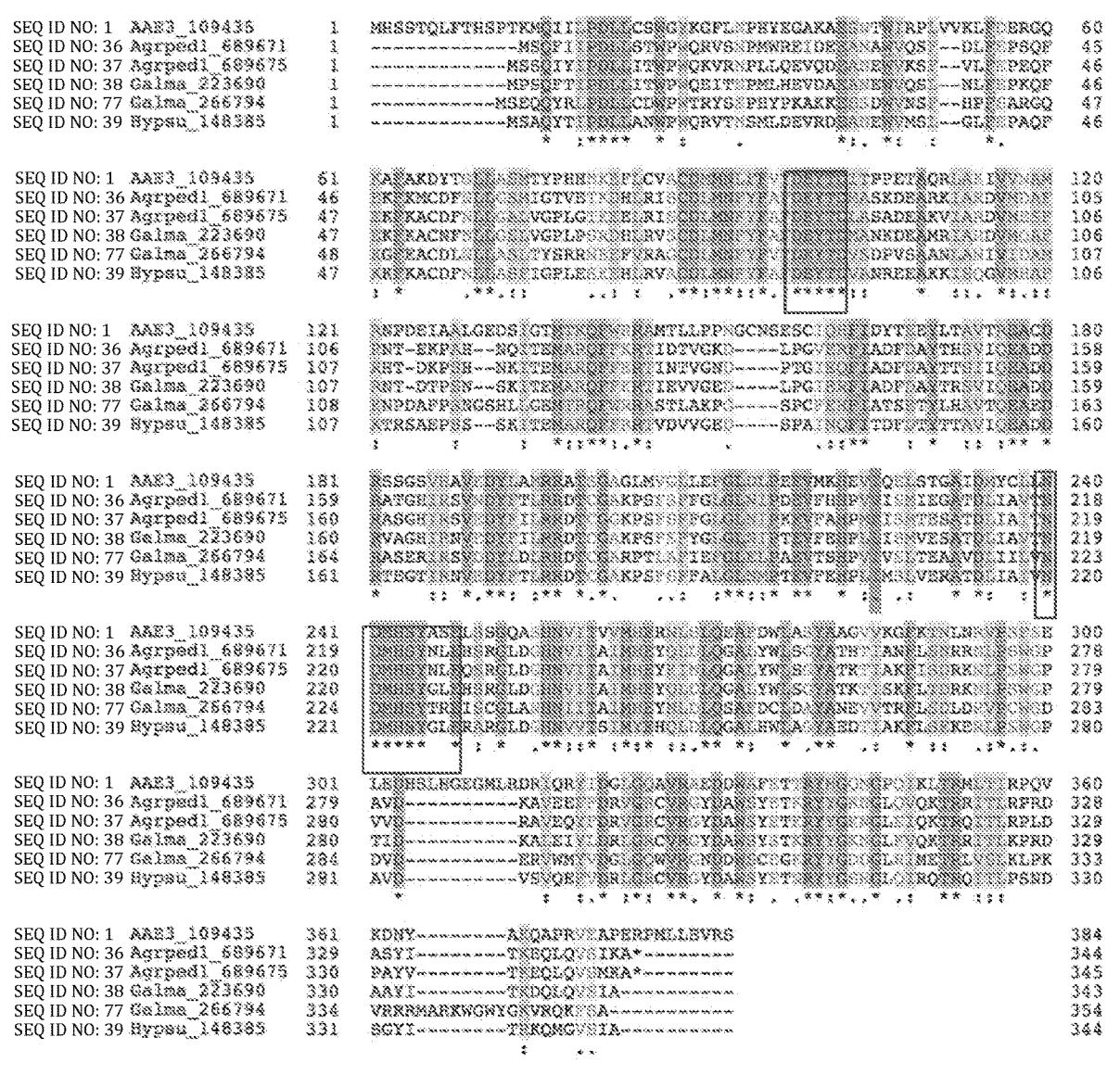
Figure 23A:
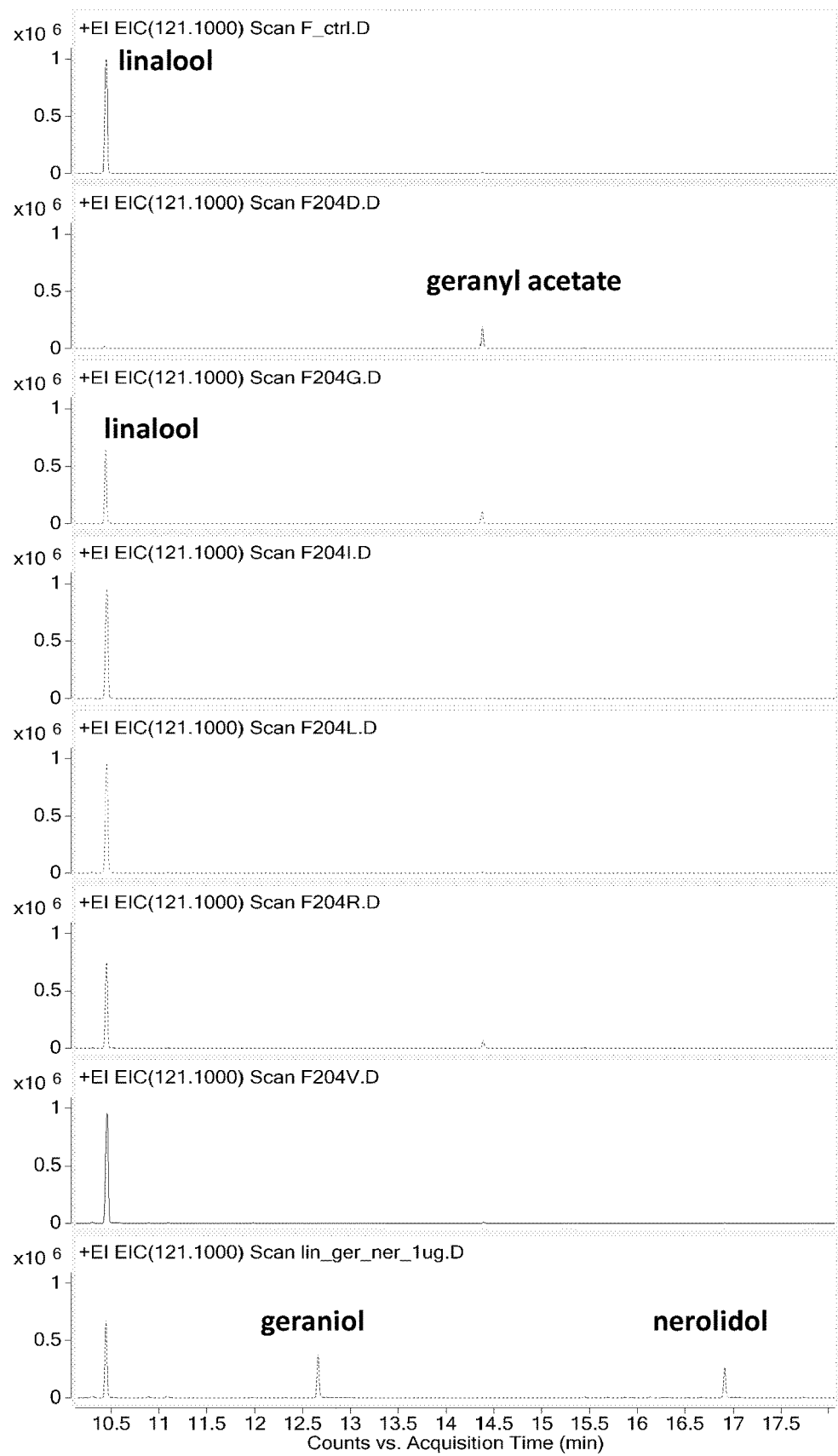
FIG. 23 shows the results of the engineering of the LS Agrped1_689675. The three mutants (F204D, F204G and F204R) have different product profiles to that of the wildtype enzyme. It produced both geranyl acetate (predicted by National Institute of Standards and Technology (NIST) library) and linalool. The other mutants (F204I, F204L and F204V) share the same product (linalool) with the wildtype Agrped1_689675.
Figure 23C:
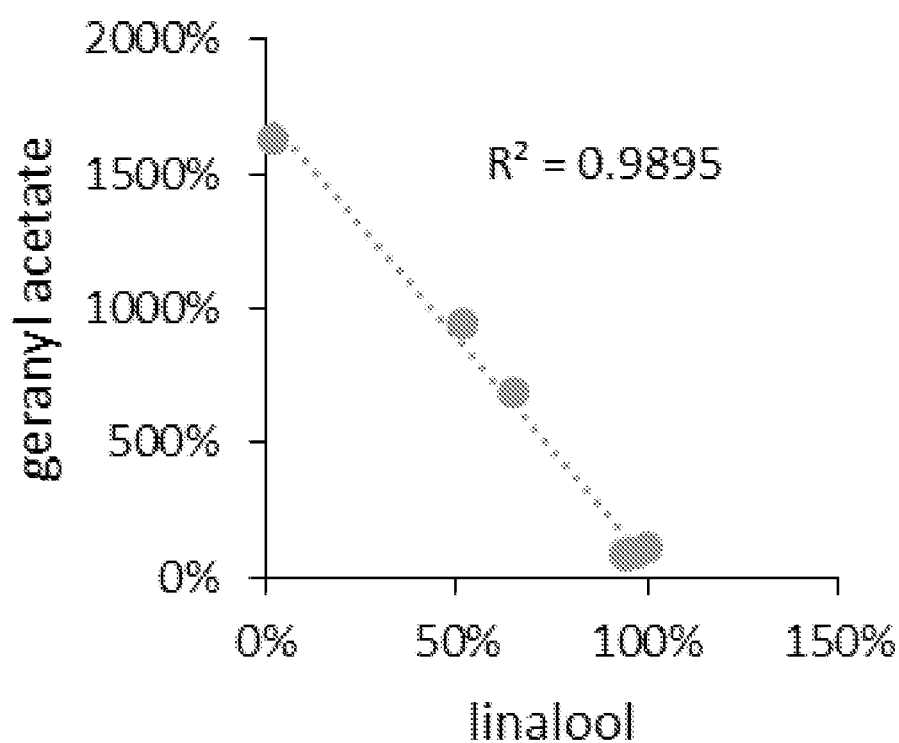
Figure 23D:

As an exclusive monoterpene synthase, it was hypothesized that a point mutation of Agrped1_689675 (SEQ ID NO: 3) could change its function and products. To test this hypothesis, a few positions where Agrped1_689675 and the rest are different were highlighted (FIG. 22). The crystal structure in FIG. 26 was used to guide the engineering of Agrped_689675. Among different amino acids, F204 was chosen as the first to mutate. It was found that 3 out of 6 mutants (F204D, F204G and F204R) had different product profiles. Unlike wild type produces only linalool, they produced both geranyl acetate (predicted by NIST library) and linalool (FIG. 23) while the other three mutants (F204I, F204L and F204V) had no significant effects on enzyme activity and functions. More interestingly, the production of geranyl acetate is inversely correlated with that of linalool (FIG. 23C).

The homologue model of Agr1 (Agrped1_689675) and Agr3 (Agrped1_689671) was built based on the structure of 1,8-cineole synthase from *Streptomyces clavuligerus* (PDB ID: 5nx5, 5nx6). The binding pocket, consisting of 15 residues within 6 Å from the substrate, was determined by PyMOL software v2.1.1 and highlighted here. The models were used to guide and understand the mutation of linalool/nerolidol synthases for improved selectivity or change of selectivity.

A summary of the sequence listing can be found in Table 5.

TABLE 5

Summary of sequence listing.

| Name | Description | SEQ ID NO |
|---|---|---|
| AAE3_109435 | Amino acid sequence of wild type *Agrocybe aegerita* FTPS | 1 |
| Agrped1_689671 | Amino acid sequence of wild type *Agrocybe pediades* FTPS | 2 |
| Agrped1_689675 | Amino acid sequence of wild type *Agrocybe pediades* FTPS | 3 |
| Galma_223690 | Amino acid sequence of wild type *Galerina marginata* FTPS | 4 |
| Hypsu_148385 | Amino acid sequence of wild type *Hypholoma sublateritium* FTPS | 5 |
| Ec.dxs | Amino acid sequence of wild type *Escherichia coli* DXS | 6 |
| Agrped1_689675_mut1 | Amino acid sequence of genetically modified Agrped1_689675, C-terminal truncation | 7 |
| Agrped1_689675_mut2 | Amino acid sequence of genetically modified Agrped1_689675, C-terminal truncation | 8 |
| Agrped1_689675_mut3 | Amino acid sequence of genetically modified Agrped1_689675, C-terminal truncation | 9 |
| Agrped1_689675_mut4 | Amino acid sequence of genetically modified Agrped1_689675, N-terminal truncation | 10 |
| Agrped1_689675_mut5 | Amino acid sequence of genetically modified Agrped1_689675, N-terminal truncation | 11 |
| Agrped1_689675_mut6 | Amino acid sequence of genetically modified Agrped1_689675, F204G | 12 |
| Agrped1_689675_mut7 | Amino acid sequence of genetically modified Agrped1_689675, F204V | 13 |
| Agrped1_689675_mut8 | Amino acid sequence of genetically modified Agrped1_689675, F204I | 14 |
| Agrped1_689675_mut9 | Amino acid sequence of genetically modified Agrped1_689675, F204D | 15 |
| Agrped1_689675_mut10 | Amino acid sequence of genetically modified Agrped1_689675, F204L | 16 |
| Agrped1_689675_mut11 | Amino acid sequence of genetically modified Agrped1_689675, F204R | 17 |
| Agrped1_689675_mut12 | Amino acid sequence of genetically modified Agrped1_689675, 1UP-3DW | 18 |
| Agrped1_689675_mut13 | Amino acid sequence of genetically modified Agrped1_689675, 3UP-1DW | 19 |
| AAE3_109435_mut1 | Amino acid sequence of genetically modified AAE3_109435, C-terminal truncation | 20 |
| Agrped1_689671_mut1 | Amino acid sequence of genetically modified Agrped1_689671, C-terminal truncation | 21 |
| Galma_223690_mut 1 | Amino acid sequence of genetically modified Galma_223690, C-terminal truncation | 22 |
| Hypsu_148385_mut1 | Amino acid sequence of genetically modified Hypsu_148385, C-terminal truncation | 23 |
| Ec.dxs_SL3 | Amino acid sequence of genetically modified *E. coli* DXS | 24 |
| Ec.dxs_SL5 | Amino acid sequence of genetically modified *E. coli* DXS | 25 |
| AAE3_04120 | Amino acid sequence of cDNA of wild type AAE3_04120 FTPS | 26 |
| AAE3_04444 | Amino acid sequence of cDNA of wild type AAE3_04444 FTPS | 27 |
| AAE3_06595 | Amino acid sequence of cDNA of wild type AAE3_06595 FTPS | 28 |
| AAE3_06743 | Amino acid sequence of cDNA of wild type AAE3_06743 FTPS | 29 |
| AAE3_09164 | Amino acid sequence of cDNA of wild type AAE3_09164 FTPS | 30 |
| AAE3_10454 | Amino acid sequence of cDNA of wild type AAE3_10454 FTPS | 31 |

TABLE 5-continued

Summary of sequence listing.

| Name | Description | SEQ ID NO |
|---|---|---|
| AAE3_13291 | Amino acid sequence of cDNA of wild type AAE3_13291 FTPS | 32 |
| AAE3_13190 | Amino acid sequence of cDNA of wild type AAE3_13190 FTPS | 33 |
| AAE3_12839 | Amino acid sequence of cDNA of wild type AAE3_12839 FTPS | 34 |
| AAE3_109435 | Nucleic acid sequence of cDNA of wild type AAE3_109435 FTPS | 35 |
| Agrped1_689671 | Nucleic acid sequence of cDNA of wild type Agrped1_689671 FTPS | 36 |
| Agrped1_689675 | Nucleic acid sequence of cDNA of wild type Agrped1_689675 FTPS | 37 |
| Galma_223690 | Nucleic acid sequence of cDNA of wild type Galma_223690 FTPS | 38 |
| Hypsu_148385 | Nucleic acid sequence of cDNA of wild type Hypsu_148385 FTPS | 39 |
| AAE3_04120 | Nucleic acid sequence of cDNA of wild type AAE3_04120 FTPS | 40 |
| AAE3_04444 | Nucleic acid sequence of cDNA of wild type AAE3_04444 FTPS | 41 |
| AAE3_06595 | Nucleic acid sequence of cDNA of wild type AAE3_06595 FTPS | 42 |
| AAE3_06743 | Nucleic acid sequence of cDNA of wild type AAE3_06743 FTPS | 43 |
| AAE3_09164 | Nucleic acid sequence of cDNA of wild type AAE3_09164 FTPS | 44 |
| AAE3_10454 | Nucleic acid sequence of cDNA of wild type AAE3_10454 FTPS | 45 |
| AAE3_12839 | Nucleic acid sequence of cDNA of wild type AAE3_12839 FTPS | 46 |
| AAE3_13190 | Nucleic acid sequence of cDNA of wild type AAE3_13190 FTPS | 47 |
| AAE3_13291 | Nucleic acid sequence of cDNA of wild type AAE3_13291 FTPS | 48 |
| AAE3_109435 | Nucleic acid sequence of cDNA of wild type AAE3_109435 FTPS | 49 |
| Ec.dxs | Nucleic acid sequence of wild type Escherichia coli DXS | 50 |
| Ec.dxs_SL3 | Nucleic acid sequence of genetically modified E. coli DXS | 51 |
| Ec.dxs_SL5 | Nucleic acid sequence of genetically modified E. coli DXS | 52 |
| AAE3_109435 | Nucleic acid sequence of wild type Agrocybe aegerita FTPS | 53 |
| Agrped1_689671 | Nucleic acid sequence of wild type Agrocybe pediades FTPS | 54 |
| Agrped1_689675 | Nucleic acid sequence of wild type Agrocybe pediades FTPS | 55 |
| Galma_223690 | Nucleic acid sequence of wild type Galerina marginata FTPS | 56 |
| Hypsu_148385 | Nucleic acid sequence of wild type Hypholoma sublateritium FTPS | 57 |
| Agrped1_689675_mut1 | Nucleic acid sequence of genetically modified Agrped1_689675, C-terminal truncation | 58 |
| Agrped1_689675_mut2 | Nucleic acid sequence of genetically modified Agrped1_689675, C-terminal truncation | 59 |
| Agrped1_689675_mut3 | Nucleic acid sequence of genetically modified Agrped1_689675, C-terminal truncation | 60 |
| Agrped1_689675_mut4 | Nucleic acid sequence of genetically modified Agrped1_689675, N-terminal truncation | 61 |
| Agrped1_689675_mut5 | Nucleic acid sequence of genetically modified Agrped1_689675, N-terminal truncation | 62 |
| Agrped1_689675_mut6 | Nucleic acid sequence of genetically modified Agrped1_689675, F204G | 63 |
| Agrped1_689675_mut7 | Nucleic acid sequence of genetically modified Agrped1_689675, F204V | 64 |
| Agrped1_689675_mut8 | Nucleic acid sequence of genetically modified Agrped1_689675, F204I | 65 |
| Agrped1_689675_mut9 | Nucleic acid sequence of genetically modified Agrped1_689675, F204D | 66 |
| Agrped1_689675_mut10 | Nucleic acid sequence of genetically modified Agrped1_689675, F204L | 67 |
| Agrped1_689675_mut11 | Nucleic acid sequence of genetically modified Agrped1_689675, F204R | 68 |
| Agrped1_689675_mut12 | Nucleic acid sequence of genetically modified Agrped1_689675, 1UP-3DW | 69 |
| Agrped1_689675_mut13 | Nucleic acid sequence of genetically modified Agrped1_689675, 3UP-1DW | 70 |
| AAE3_109435_mut1 | Nucleic acid sequence of genetically modified AAE3_109435, C-terminal truncation | 71 |
| Agrped1_689671_mut1 | Nucleic acid sequence of genetically modified Agrped1_689671, C-terminal truncation | 72 |
| Galma_223690_mut1 | Nucleic acid sequence of genetically modified Galma_223690, C-terminal truncation | 73 |
| Hypsu_148385_mut1 | Nucleic acid sequence of genetically modified Hypsu_148385, C-terminal truncation | 74 |
| TPS31 | Amino acid sequence of wild type Solanum lycopersicum FTPS | 75 |
| MqTPS1 | Amino acid sequence of wild type Melaleuca quinquenervia FTPS | 76 |
| Galma_266794 | Amino acid sequence of wild type Galerina marginata FTPS | 77 |
| Hyp3 | Amino acid sequence of Hyp3 FTPS | 78 |
| Hyp5 | Amino acid sequence of Hyp5 FTPS | 79 |
| Hyp2 | Amino acid sequence of Hyp2 FTPS | 80 |
| Omp3 | Amino acid sequence of Omp3 FTPS | 81 |
| Cop3 | Amino acid sequence of Cop3 FTPS | 82 |
| Cop1 | Amino acid sequence of Cop1 FTPS | 83 |
| Omp1 | Amino acid sequence of Omp4 FTPS | 84 |
| Omp2 | Amino acid sequence of Omp2 FTPS | 85 |
| Cop2 | Amino acid sequence of Cop2 FTPS | 86 |
| Cop4 | Amino acid sequence of Cop4 FTPS | 87 |
| Stehi_128017 | Amino acid sequence of Stehi_128017 FTPS | 88 |
| Omp4 | Amino acid sequence of Omp4 FTPS | 89 |
| Omp5a | Amino acid sequence of Omp5a FTPS | 90 |
| Omp5b | Amino acid sequence of Omp5b FTPS | 91 |
| AAE3_05024 | Amino acid sequence of AAE3_05024 FTPS | 92 |
| AAE3_09008 | Amino acid sequence of AAE3_09008 FTPS | 93 |
| AAE3_04210 | Amino acid sequence of AAE3_04210 FTPS | 94 |
| Omp6 | Amino acid sequence of Omp6 FTPS | 95 |
| Stehi_25180 | Amino acid sequence of Stehi_25180 FTPS | 96 |
| Omp7 | Amino acid sequence of Omp7 FTPS | 97 |
| Prol | Amino acid sequence of Prol FTPS | 98 |
| Stehi_73029 | Amino acid sequence of Stehi_73029 FTPS | 99 |
| Stehi_64702 | Amino acid sequence of Stehi_64702 FTPS | 100 |
| Cop5 | Amino acid sequence of Cop5 FTPS | 101 |
| Stehi_159379 | Amino acid sequence of Stehi_159379 FTPS | 102 |
| Cop6 | Amino acid sequence of Cop6 FTPS | 103 |
| Omp10 | Amino acid sequence of Omp10 FTPS | 104 |
| Omp9 | Amino acid sequence of Omp9 FTPS | 105 |
| Omp8 | Amino acid sequence of Omp8 FTPS | 106 |
| Hyp3 metal binding domain 1 | First metal binding domain of Hyp3 FTPS | 107 |
| Hyp3 metal binding domain 2 | Second metal binding domain of Hyp3 FTPS | 108 |
| Hyp5 metal binding domain 1 | First metal binding domain of Hyp5 FTPS | 109 |

TABLE 5-continued

Summary of sequence listing.

| Name | Description | SEQ ID NO |
|---|---|---|
| Hpy5 metal binding domain 2 | Second metal binding domain of Hyp5 FTPS | 110 |
| Hyp2 metal binding domain 1 | First metal binding domain of Hyp2 FTPS | 111 |
| Hyp2 metal binding domain 2 | Second metal binding domain of Hyp2 FTPS | 112 |
| Omp3 metal binding domain 1 | First metal binding domain of Omp3 FTPS | 113 |
| Omp3 metal binding domain 2 | Second metal binding domain of Omp3 FTPS | 114 |
| AAE3_13190 metal binding domain 1 | First metal binding domain of AAE3_13190 FTPS | 115 |
| AAE3_13190 metal binding domain 2 | Second metal binding domain of AAE3_13190 FTPS | 116 |
| Cop3 metal binding domain 1 | First metal binding domain of Cop3 FTPS | 117 |
| Cop3 metal binding domain 2 | Second metal binding domain of Cop3 FTPS | 118 |
| AAE3_06595 metal binding domain 1 | First metal binding domain of AAE3_06595 FTPS | 119 |
| AAE 06595 metal binding domain 2 | Second metal binding domain of AAE3_06595 FTPS | 120 |
| Cop1 metal binding domain 1 | First metal binding domain of Cop1 FTPS | 121 |
| Cop1 metal binding domain 2 | Second metal binding domain of Cop1 FTPS | 122 |
| Omp1 metal binding domain 1 | First metal binding domain of Omp1 FTPS | 123 |
| Omp1 metal binding domain 2 | Second metal binding domain of Omp1 FTPS | 124 |
| Omp2 metal binding domain 1 | First metal binding domain of Omp2 FTPS | 125 |
| Omp2 metal binding domain 2 | Second metal binding domain of Omp2 FTPS | 126 |
| Cop2 metal binding domain 1 | First metal binding domain of Cop2 FTPS | 127 |
| Cop2 metal binding domain 2 | Second metal binding domain of Cop2 FTPS | 128 |
| AAE3_12839 metal binding domain 1 | First metal binding domain of AAE3_12839 FTPS | 129 |
| AAE3_12839 metal binding domain 2 | Second metal binding domain of AAE3_12839 FTPS | 130 |
| AAE3_13291 metal binding domain 1 | First metal binding domain of AAE3_13291 FTPS | 131 |
| AAE3_13291 metal binding domain 2 | Second metal binding domain of AAE3_13291 FTPS | 132 |
| AAE3_09164 metal binding domain 1 | First metal binding domain of AAE3_09164 FTPS | 133 |
| AAE3_09164 metal binding domain 2 | Second metal binding domain of AAE3_09164 FTPS | 134 |
| Cop4 metal binding domain 1 | First metal binding domain of Cop4 FTPS | 135 |
| Cop4 metal binding domain 2 | Second metal binding domain of Cop4 FTPS | 136 |
| Stehi_128017 metal binding domain 1 | First metal binding domain of Stehi_128017 FTPS | 137 |
| Stehi_128017 metal binding domain 2 | Second metal binding domain of Stehi_128017 FTPS | 138 |
| Omp4 metal binding domain 1 | First metal binding domain of Omp4 FTPS | 139 |
| Omp4 metal binding domain 2 | Second metal binding domain of Omp4 FTPS | 140 |
| Omp5a metal binding domain 1 | First metal binding domain of Omp5a FTPS | 141 |
| Omp5a metal binding domain 2 | Second metal binding domain of Omp5a FTPS | 142 |
| Omp5b metal binding domain 1 | First metal binding domain of Omp5b FTPS | 143 |
| Omp5b metal binding domain 2 | Second metal binding domain of Omp5b FTPS | 144 |
| AAE3_04444 metal binding domain 1 | First metal binding domain of AAE3_04444 FTPS | 145 |
| AAE3_04444 metal binding domain 2 | Second metal binding domain of AAE3_04444 FTPS | 146 |
| AAE3_05024 metal binding domain 1 | First metal binding domain of AAE3_05024 FTPS | 147 |
| AAE3_05024 metal binding domain 2 | Second metal binding domain of AAE3_05024 FTPS | 148 |
| AAE3_06743 metal binding domain 1 | First metal binding domain of AAE3_06743 FTPS | 149 |
| AAE3_06743 metal binding domain 2 | Second metal binding domain of AAE3_06743 FTPS | 150 |
| AAE3_09008 metal binding domain 1 | First metal binding domain of AAE3_09008 FTPS | 151 |
| AAE3_09008 metal binding domain 2 | Second metal binding domain of AAE3_09008 FTPS | 152 |
| AAE3_10454 metal binding domain 1 | First metal binding domain of AAE3_10454 FTPS | 153 |
| AAE3_10454 metal binding domain 2 | Second metal binding domain of AAE3_10454 FTPS | 154 |
| AAE3_04210 metal binding domain 1 | First metal binding domain of AAE3_04210 FTP | 155 |
| AAE3_04210 metal binding domain 2 | Second metal binding domain of AAE3_04210 FTPS | 156 |
| Omp6 metal binding domain 1 | First metal binding domain of Omp6 FTPS | 157 |
| Omp6 metal binding domain 2 | Second metal binding domain of Omp6 FTPS | 158 |
| Stehi_25180 metal binding domain 1 | First metal binding domain of Stehi_25180 FTPS | 159 |
| Stehi_25180 metal binding domain 2 | Second metal binding domain of Stehi_25180 FTPS | 160 |
| Omp7 metal binding domain 1 | First metal binding domain of Omp7 FTPS | 161 |
| Omp7 metal binding domain 2 | Second metal binding domain of Omp7 FTPS | 162 |
| Pro1 metal binding domain 1 | First metal binding domain of Pro1 FTPS | 163 |
| Pro1 metal binding domain 2 | Second metal binding domain of Pro1 FTPS | 164 |
| Stehi_73029 metal binding domain 1 | First metal binding domain of Stehi_73029 FTPS | 165 |
| Stehi_73029 metal binding domain 2 | Second metal binding domain of Stehi_73029 FTPS | 166 |
| Stehi_64702 metal binding domain 1 | First metal binding domain of Stehi_64702 FTPS | 167 |
| Stehi_64702 metal binding domain 2 | Second metal binding domain of Stehi_64702 FTPS | 168 |
| Cop5 metal binding domain 1 | First metal binding domain of Cop5 FTPS | 169 |
| Cop5 metal binding domain 2 | Second metal binding domain of Cop5 FTPS | 170 |
| Stehi_159379 metal binding domain 1 | First metal binding domain of Stehi_159379 FTPS | 171 |
| Stehi_159379 metal binding domain 2 | Second metal binding domain of Stehi_159379 FTPS | 172 |
| Cop6 metal binding domain 1 | First metal binding domain of Cop6 FTPS | 173 |
| Cop6 metal binding domain 2 | Second metal binding domain of Cop6 FTPS | 174 |
| Omp10 metal binding domain 1 | First metal binding domain of Omp10 FTPS | 175 |
| Omp10 metal binding domain 2 | Second metal binding domain of Omp10 FTPS | 176 |
| Omp9 metal binding domain 1 | First metal binding domain of Omp9 FTPS | 177 |
| Omp9 metal binding domain 2 | Second metal binding domain of Omp9 FTPS | 178 |
| Omp8 metal binding domain 1 | First metal binding domain of Omp8 FTPS | 179 |
| Omp8 metal binding domain 2 | Second metal binding domain of Omp8 FTPS | 180 |

Equivalents

The foregoing examples are presented for the purpose of illustrating the invention and should not be construed as imposing any limitation on the scope of the invention. It will readily be apparent that numerous modifications and alterations may be made to the specific embodiments of the invention described above and illustrated in the examples without departing from the principles underlying the invention. All such modifications and alterations are intended to be embraced by this application.

The invention claimed is:

1. A bacterial strain comprising one or more vectors encoding
   a) one or more enzymes to produce one or more terpene precursors; and
   b) a fungal terpene synthase (FTPS), wherein the FTPS is an *Agrocybe aegerita* FTPS comprising an amino acid sequence selected from the group consisting of SEQ ID NO: 1, 20, 26, 27, 28, 29, 30, 31, 32, 33 and 34.

2. The bacterial strain according to claim 1, wherein the one or more vectors comprise one or more nucleotide sequences encoding the one or more enzymes and the FTPS, operably linked to an inducible or constitutive promoter.

3. The bacterial strain according to claim 1, wherein the one or more enzymes to produce the one or more terpene precursors is part of a 1-deoxy-D-xylulose 5-phosphate (DXP) pathway, optionally wherein the enzyme is 1-deoxyxylulose-5-phosphate synthase (DXS), isopentenyl diphosphate isomerase (IDI) or both, optionally wherein the DXS comprises the amino acid sequence set forth in SEQ ID NO: 6.

4. The bacterial strain according to claim 3, wherein the DXS is genetically modified, wherein the genetically modified DXS comprises an amino acid sequence comprising a mutation at one or more amino acid positions in the amino acid sequence set forth in SEQ ID NO: 6, optionally wherein the genetically modified DXS comprises the amino acid sequence set forth in SEQ ID NO: 24 or 25, optionally wherein the DXS is encoded by the nucleic acid sequence set forth in SEQ ID NO: 51 or 52.

5. The bacterial strain according to claim 1, wherein the one or more enzymes to produce the one or more terpene precursors is expressed at an elevated level compared to a wild-type enzyme, wherein the wild-type enzyme comprises the amino acid sequence set forth in SEQ ID NO: 6, optionally wherein the one or more terpene precursors is farnesyl pyrophosphate (FPP), geranyl pyrophosphate (GPP), geranylgeranyl pyrophosphate (GGPP), or combinations thereof.

6. The bacterial strain according to claim 1, wherein the FTPS is a monoterpene synthase or a sesquiterpene synthase, wherein the FTPS is encoded by a nucleic acid sequence selected from the group consisting of SEQ ID NO: 35, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, and SEQ ID NO: 71.

7. The bacterial strain according to claim 1, wherein the FTPS comprises the amino acid sequence set forth in SEQ ID NO: 1.

8. The bacterial strain according to claim 1, wherein the bacterial strain is *Escherichia coli*.

9. A method of producing a terpenoid comprising
   a) culturing the bacterial strain of claim 1 in an expression medium; and, b) isolating the terpenoid from said expression medium.

10. A bacterial strain comprising one or more vectors encoding
    a) one or more enzymes to produce one or more terpene precursors; and
    b) a fungal terpene synthase (FTPS) comprising an amino acid sequence having at least 90% identity to an amino acid sequence selected from the group consisting of SEQ ID NO: 1, 20, 26, 27, 28, 29, 30, 31, 32, 33 and 34.

11. The bacterial strain of claim 10, wherein the one or more vectors comprise one or more nucleotide sequences encoding the one or more enzymes and the FTPS, operably linked to an inducible or constitutive promoter.

12. The bacterial strain of claim 10, wherein the one or more enzymes to produce the one or more terpene precursors is part of a 1-deoxy-D-xylulose 5-phosphate (DXP) pathway, optionally wherein the enzyme is 1-deoxyxylulose-5-phosphate synthase (DXS), isopentenyl diphosphate isomerase (IDI) or both, optionally wherein the DXS comprises the amino acid sequence set forth in SEQ ID NO: 6.

13. The bacterial strain of claim 12, wherein the DXS is genetically modified, wherein the genetically modified DXS comprises an amino acid sequence comprising a mutation at one or more amino acid positions in the amino acid sequence set forth in SEQ ID NO: 6, optionally wherein the genetically modified DXS comprises the amino acid sequence set forth in SEQ ID NO: 24 or 25, optionally wherein the DXS is encoded by the nucleic acid sequence set forth in SEQ ID NO: 51 or 52.

14. The bacterial strain of claim 10, wherein the one or more enzymes to produce the one or more terpene precursors is expressed at an elevated level compared to a wild-type enzyme, wherein the wild-type enzyme comprises the amino acid sequence set forth in SEQ ID NO: 6, optionally wherein the one or more terpene precursors is farnesyl pyrophosphate (FPP), geranyl pyrophosphate (GPP), geranylgeranyl pyrophosphate (GGPP), or combinations thereof.

15. The bacterial strain of claim 10, wherein the FTPS is a monoterpene synthase or a sesquiterpene synthase, wherein the FTPS is encoded by a nucleic acid comprising a nucleotide sequence having at least 90% identity to a sequence selected from the group consisting of SEQ ID NO: 35, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, and SEQ ID NO: 71.

16. The bacterial strain of claim 10, wherein the bacterial strain is *Escherichia coli*.

17. The bacterial strain of claim 10, wherein the FTPS comprises an amino acid sequence having at least 95% identity to an amino acid sequence selected from the group consisting of SEQ ID NO: 1, 20, 26, 27, 28, 29, 30, 31, 32, 33 and 34.

18. A method of producing a terpenoid comprising
    a) culturing the bacterial strain of claim 10 in an expression medium; and
    b) isolating the terpenoid from said expression medium.

19. A genetically engineered 1-deoxyxylulose-5-phosphate synthase (DXS), wherein the genetically engineered DXS comprises an amino acid sequence comprising mutations E210D, Q459L and L415T in the amino acid sequence set forth in SEQ ID NO: 6, optionally wherein the genetically engineered DXS further comprises a mutation H105T.

20. The genetically engineered DXS according to claim 19, comprising the amino acid sequence set forth in SEQ ID NO: 25.

* * * * *